US011248048B2

(12) United States Patent
Park et al.

(10) Patent No.: US 11,248,048 B2
(45) Date of Patent: Feb. 15, 2022

(54) ANTIBODY TO PROGRAMMED CELL DEATH 1 (PD-1) AND USE THEREOF

(71) Applicant: Y-BIOLOGICS INC., Daejeon (KR)

(72) Inventors: Jae Eun Park, Daejeon (KR); Soo Young Kim, Daejeon (KR); Hyun Mi Lee, Daejeon (KR); Si Hyung Lee, Daejeon (KR); Hyun Kyung Lee, Daejeon (KR); Hye-Nan Kim, Daejeon (KR); Jin Chui Youn, Daejeon (KR); Bum-chan Park, Daejeon (KR); Jung Chae Lim, Daejeon (KR); Young-Gyu Cho, Daejeon (KR); Young Woo Park, Daejeon (KR)

(73) Assignee: Y-BIOLOGICS INC., Daejeon (KR)

( * ) Notice: Subject to any disclaimer, the term of this patent is extended or adjusted under 35 U.S.C. 154(b) by 515 days.

(21) Appl. No.: 16/321,124

(22) PCT Filed: Aug. 7, 2017

(86) PCT No.: PCT/KR2017/008494
§ 371 (c)(1),
(2) Date: Jan. 28, 2019

(87) PCT Pub. No.: WO2018/026248
PCT Pub. Date: Feb. 8, 2018

(65) Prior Publication Data
US 2019/0248900 A1 Aug. 15, 2019

(30) Foreign Application Priority Data

Aug. 5, 2016 (KR) .................. 10-2016-0100210
Aug. 7, 2017 (KR) .................. 10-2017-0099672

(51) Int. Cl.
C07K 16/28 (2006.01)
A61K 35/00 (2006.01)
C12N 15/85 (2006.01)
A61K 39/00 (2006.01)

(52) U.S. Cl.
CPC .......... C07K 16/2818 (2013.01); A61K 35/00 (2013.01); C07K 16/2827 (2013.01); C12N 15/85 (2013.01); A61K 2039/505 (2013.01); C07K 2317/33 (2013.01); C07K 2317/565 (2013.01); C07K 2317/622 (2013.01); C07K 2317/76 (2013.01); C07K 2317/92 (2013.01); C07K 2317/94 (2013.01); C12N 2015/8518 (2013.01)

(58) Field of Classification Search
None
See application file for complete search history.

(56) References Cited

U.S. PATENT DOCUMENTS

| 8,008,449 B2 | 8/2011 | Korman et al. |
| 2014/0294852 A1* | 10/2014 | Korman ................ C07K 16/28 424/143.1 |
| 2015/0203579 A1 | 7/2015 | Papadopoulos |
| 2016/0222113 A1 | 8/2016 | Buchanan et al. |

FOREIGN PATENT DOCUMENTS

| CA | 2920173 A1 | 2/2015 |
| CN | 105566496 A | 5/2016 |
| JP | 2006340714 A | 12/2006 |
| KR | 1020120002641 A | 1/2012 |
| RU | 2007145419 A | 6/2009 |
| WO | 8801649 A1 | 3/1988 |
| WO | 8806630 A1 | 9/1988 |
| WO | 8807085 A1 | 9/1988 |
| WO | 8807086 A1 | 9/1988 |
| WO | 8809344 A1 | 12/1988 |
| WO | WO2006121168 A1 | 11/2006 |
| WO | WO2008156712 A1 | 12/2008 |
| WO | WO2010032899 A2 | 3/2010 |
| WO | WO2013181634 A2 | 12/2013 |
| WO | WO2015036394 A1 | 3/2015 |
| WO | WO2016015685 A1 | 2/2016 |
| WO | WO2016069727 A1 | 5/2016 |

OTHER PUBLICATIONS

Panka, D., et al., "Variable region framework differences result in decreased or increased affinity of variant anti-digoxin antibodies", "Immunology", May 1988, pp. 3080-3084, vol. 85.
Xiang, J., et al., "Modification in Framework Region I Results in a Decreased Affinity of Chimeric ANTI-TAG72 Antibody", "Molecular Immunology", 1991, pp. 141-148, vol. 28, No. 1/2, Publisher: Pergamon Press plc.
Caldas, C., et al., "Humanization of the anti-CD18 Antibody 6.7: An Unexpected Effect of a Framework Residue in Binding to Antigen", "Molecular Immunology", 2003, pp. 941-952, vol. 39.
Du, J., et al., "Molecular Basis of Recognition of Human Osteopontin by 23C3, a Potential Therapeutic Antibody for Treatment of Rheumatoid Athritis", "J. Mol. Biol.", 2008, pp. 835-842, vol. 382.
Iwamoto, N., et al., "Validated LC-MS/MS Analysis of Immune Checkpoint Inhibitor Nivolumab in Human Plasma Using a Fab Peptide-Selective Quantitation Method: Nano-Surface and Molecular-Orientation Limited (nSMOL) Proteolysis", "Journal of Chromatography B", 2016, pp. 9-16, vol. 1023.

(Continued)

Primary Examiner — Gary B Nickol
Assistant Examiner — Jegatheesan Seharaseyon
(74) Attorney, Agent, or Firm — Hultquist, PLLC; Steven J. Hultquist

(57) ABSTRACT

Disclosed are an antibody to human programmed cell death 1 (PD-1) or an antigen-binding fragment thereof, a nucleic acid encoding the same, a vector including the nucleic acid, an isolated cell transformed with the vector, a method for producing the antibody or an antigen-binding fragment thereof, and a composition for preventing or treating cancer containing the same. The novel antibody binding to PD-1 or an antigen-binding fragment thereof can bind to PD-1 and inhibit the activity of PD-1, thus being useful for the development of immunotherapeutic agents for various diseases associated with PD-1.

12 Claims, 12 Drawing Sheets
(12 of 12 Drawing Sheet(s) Filed in Color)

Specification includes a Sequence Listing.

(56) References Cited

OTHER PUBLICATIONS

Chemnitz, J., et al., "SHP-1 and SHP-2 Associate with Immunoreceptor Tyrosine-Based Switch Motif of Programmed Death 1 Upon Primary Human T Cell Stimulation, but Only Receptor Ligation Prevents T Cell Activation", "The Journal of Immunology", 2004, pp. 945-954, vol. 173.

Ishida, Y., et al., "Induced Expression of PD-1, a Novel Member of the Immunoglobulin Gene Superfamily, Upon Programmed Cell Death", "The EMBO Journal", 1992, pp. 3887-3895, vol. 11, No. 11.

Riley, J.L., "PD-1 Signaling in Primary T Cells", "Immunological Reviews", 2009, pp. 114-125, vol. 229.

Shinohara, T., et al., "Structure and Chromosomal Localization of the Human PD-1 Gene (PDCD1)", "Genomics", 1994, pp. 704-706, vol. 23.

Vivier, E., et al., "Immunoreceptor Tyrosine-Based Inhibition Motifs", "Immunology Today", Jun. 1997, pp. 286-291, vol. 18, No. 6.

Khoja, L., et al., "Pembrolizumab", "Journal for ImmunoTherapy of Cancer", 2015, pp. 1-13, vol. 3, No. 36.

Wang, C., et al., "In Vitro Characterization of the Anti-PD-1 Antibody Nivolumab, BMS-936558, and In Vivo Toxicology in Non-Human Primates", "Cancer of Immunology Research", May 28, 2014, pp. 846-857.

\* cited by examiner

[Figure 1]
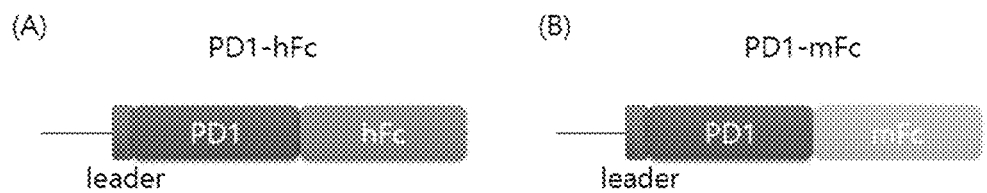
[Figure 2a]
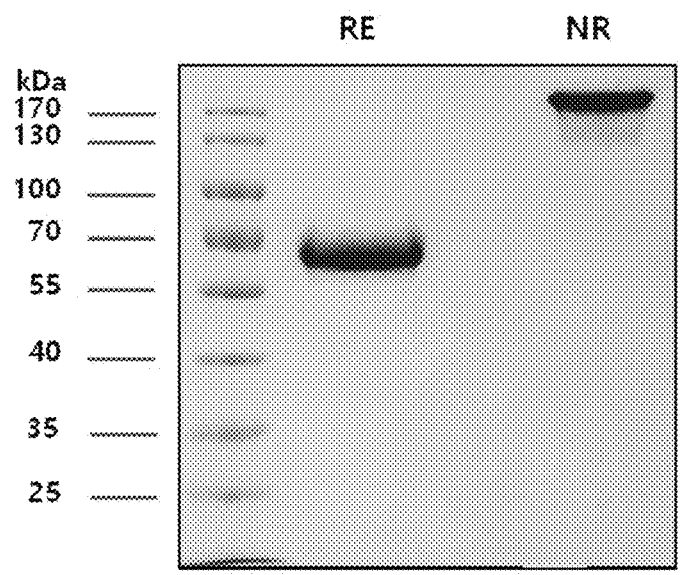
[Figure 2b]
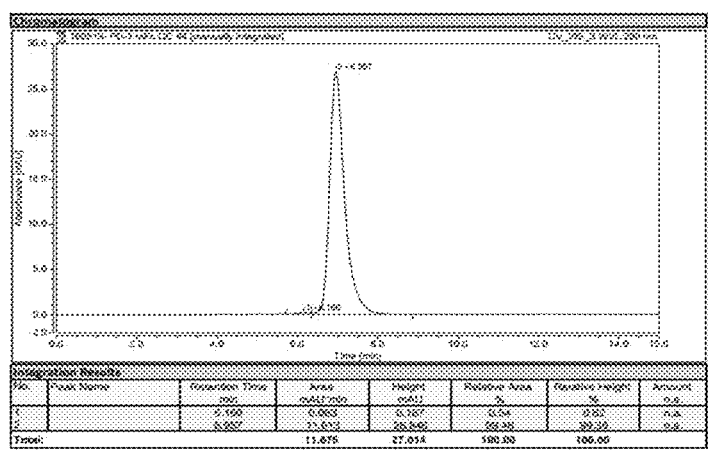

【Figure 2c】
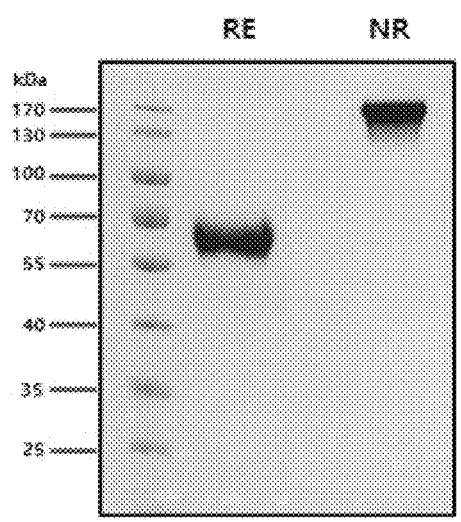
【Figure 2d】
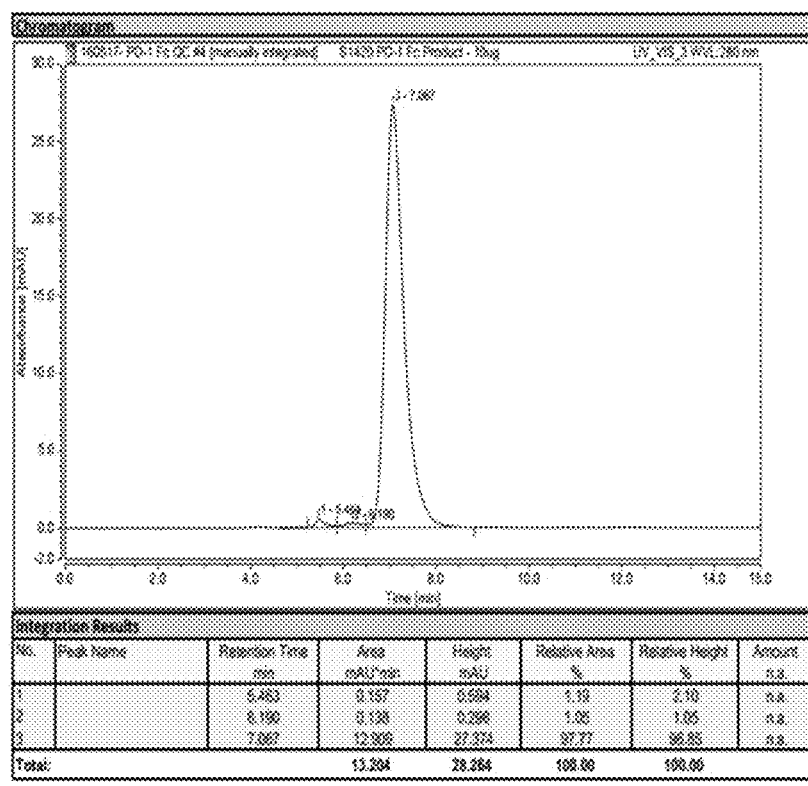

【Figure 3】
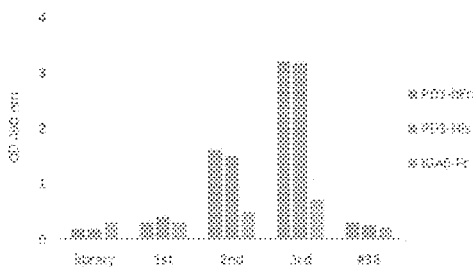
【Figure 4】
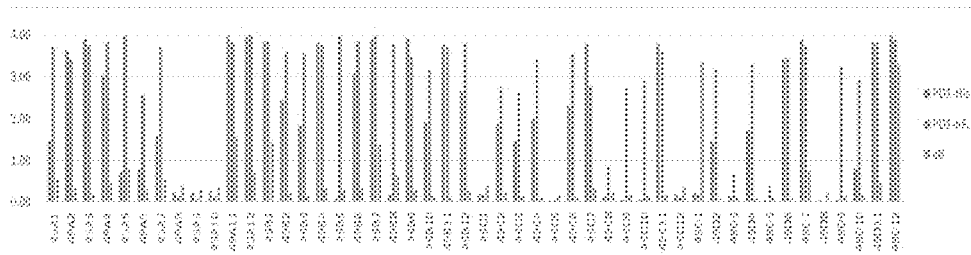
【Figure 5】
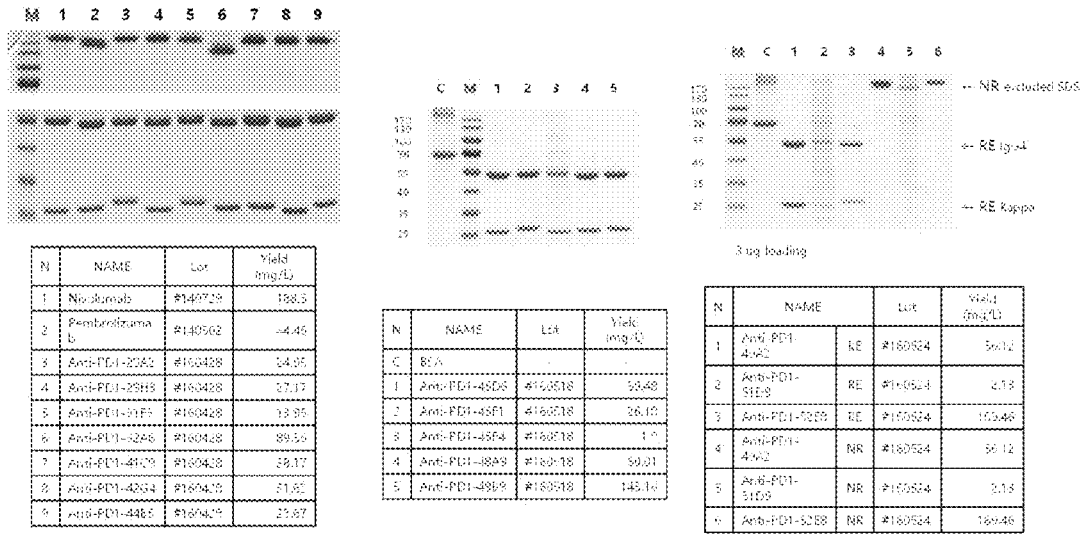

[Figure 6]
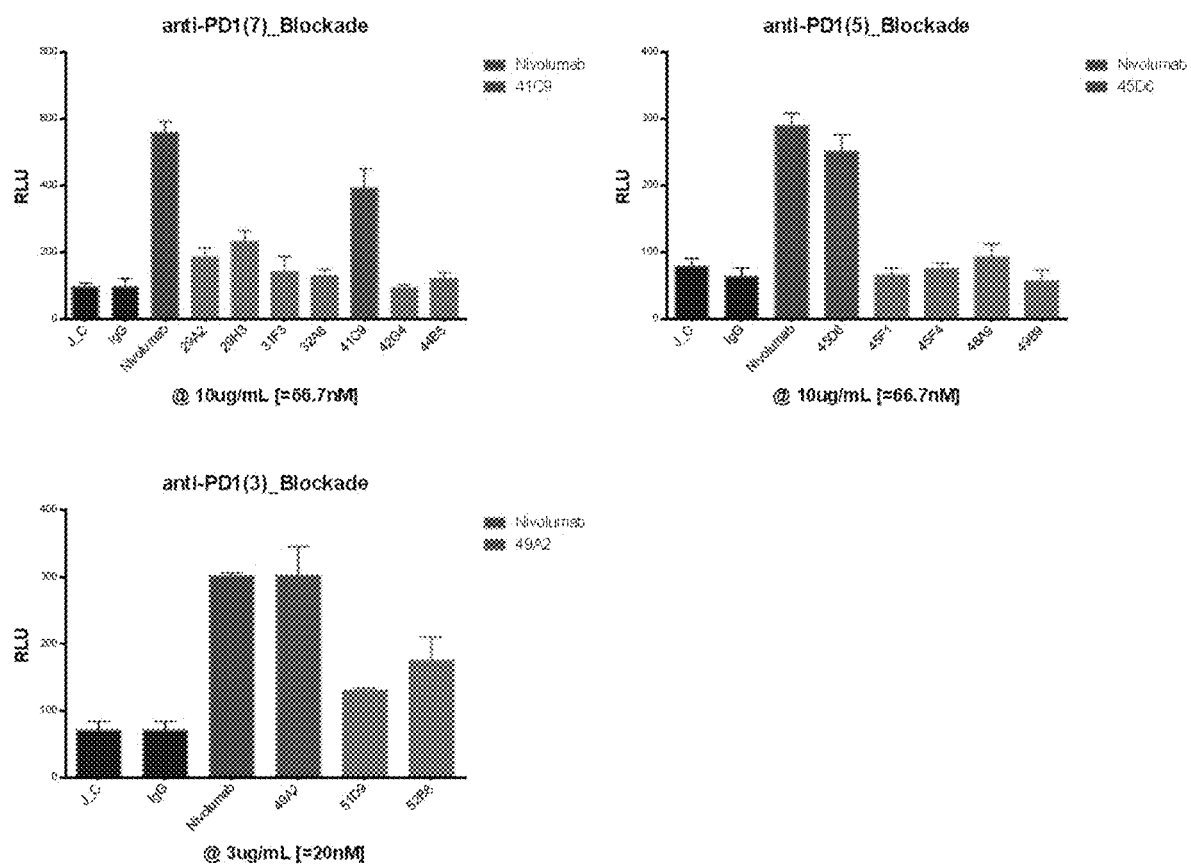

[Figure 7]
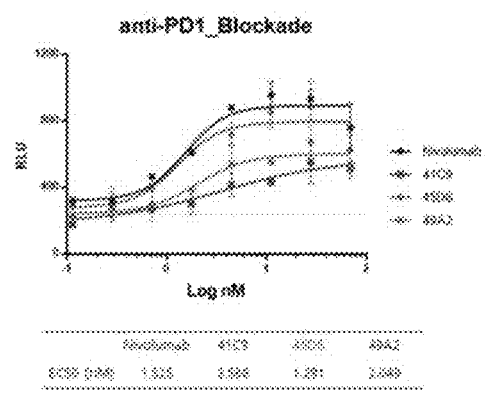
[Figure 8]
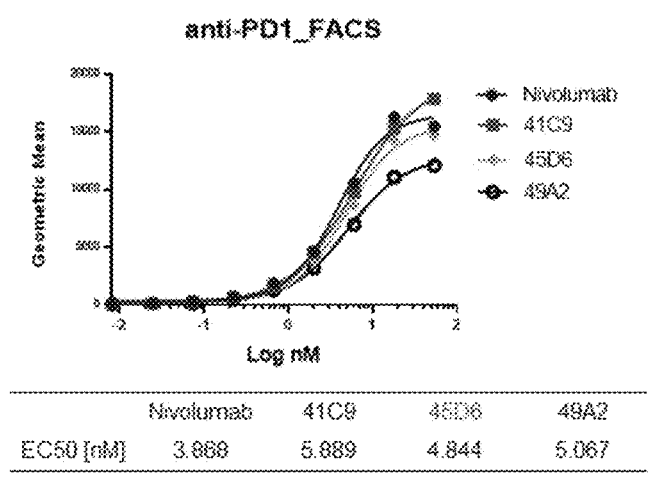

【Figure 9】
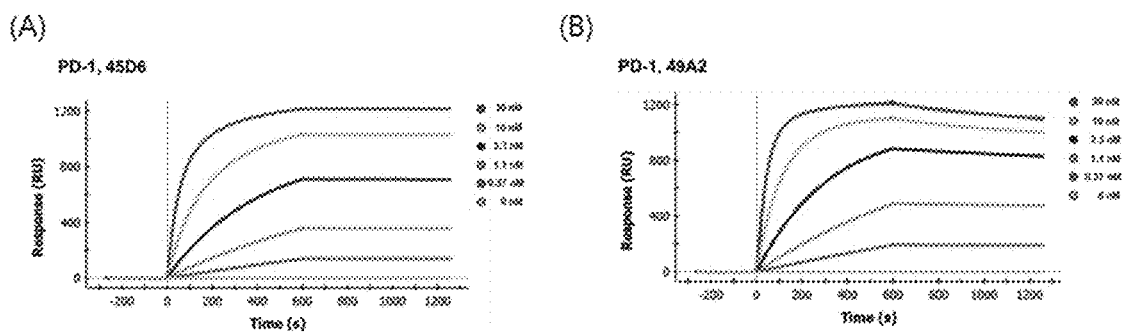
【Figure 10】
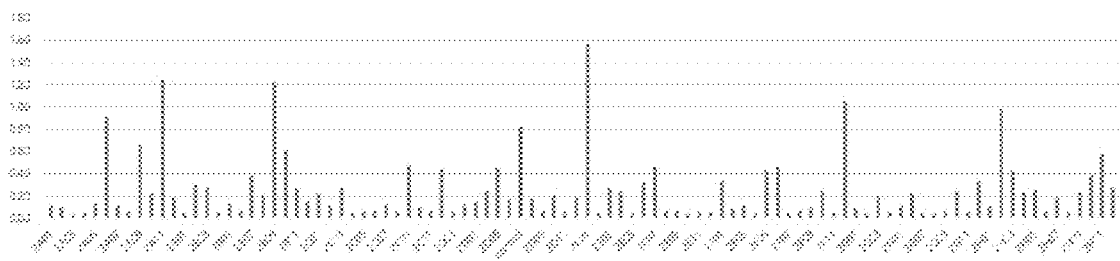
【Figure 11】
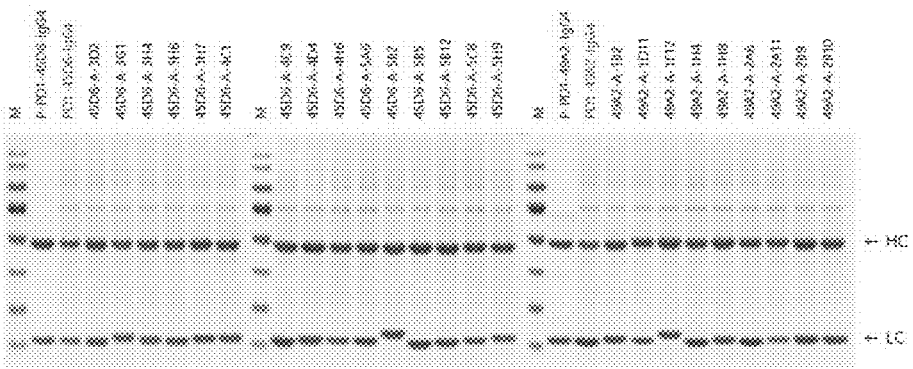

[Figure 12]
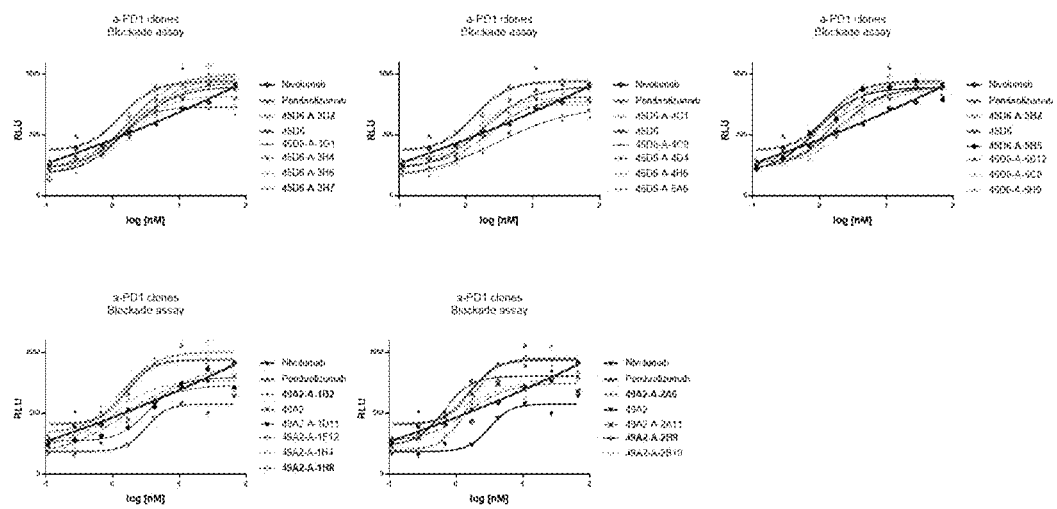
[Figure 13]
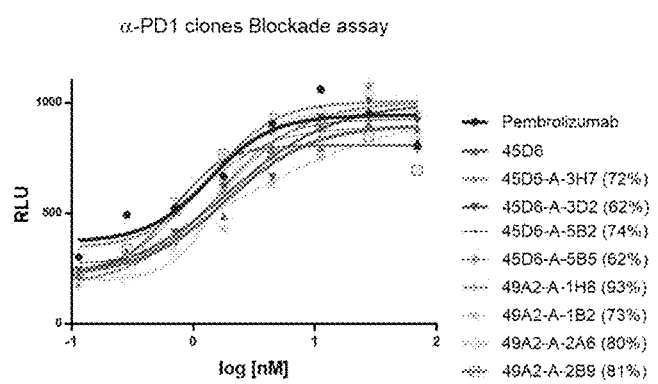
| | Pembrolizumab | 45D6 | 45D6-A-3D2 | 45D6-A-3H7 | 45D6-A-5B2 | 45D6-A-5B5 | 49A2-A-1B2 | 49A2-A-1H8 | 49A2-A-2A6 | 49A2-A-2B9 |
|---|---|---|---|---|---|---|---|---|---|---|
| Bottom | 370.3 | 218.1 | 138 | 167.1 | 270.5 | 193.6 | 121.5 | 341.3 | 196.8 | 236.5 |
| Top | 943.8 | 900.7 | 1002 | 1006 | 925.8 | 891.3 | 968.9 | 1006 | 957.3 | 807.4 |
| EC50 | 1.367 | 1.876 | 2.005 | 1.835 | 1.66 | 0.9064 | 2.033 | 1.454 | 1.669 | 0.6888 |
| R square | 0.8881 | 0.9796 | 0.9887 | 0.9702 | 0.9856 | 0.9583 | 0.928 | 0.8804 | 0.9708 | 0.9406 |
| productivity | | | 100.3 | 141 | 124.6 | 144.6 | 106.3 | 87.3 | 3.5 | 128 |

【Figure 14】
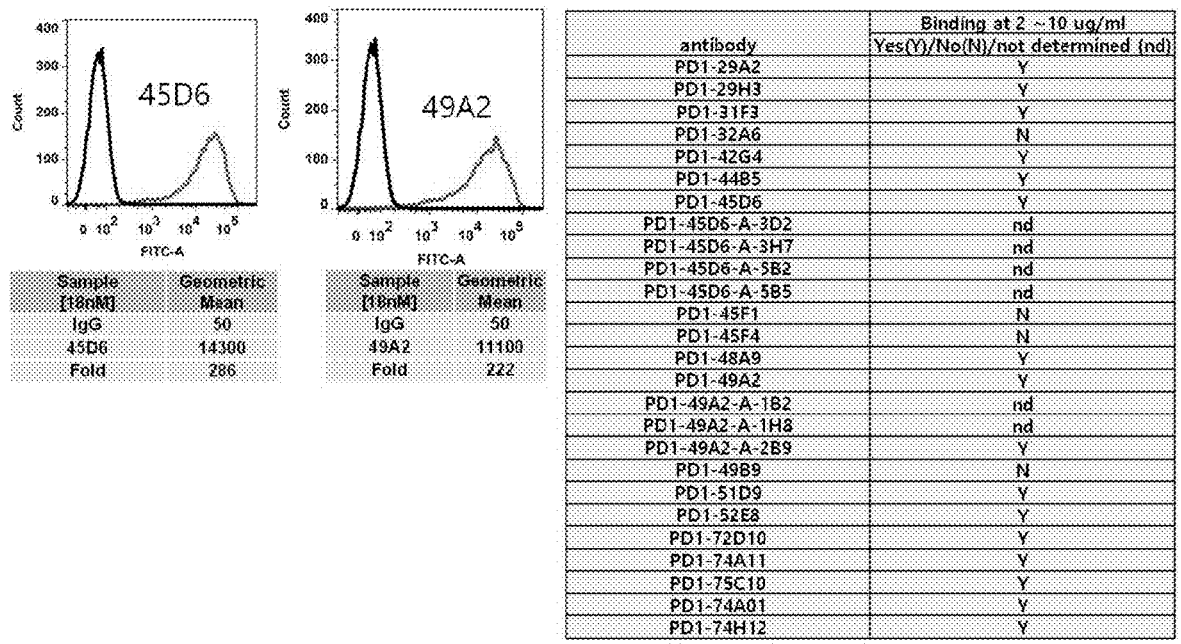
【Figure 15】
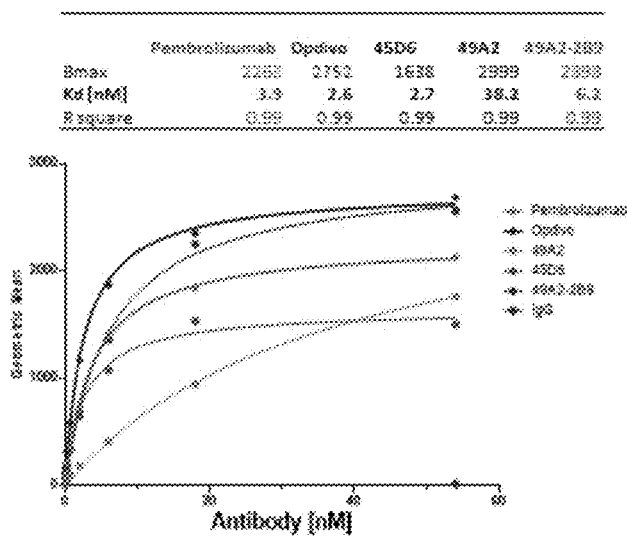

[Figure 16]
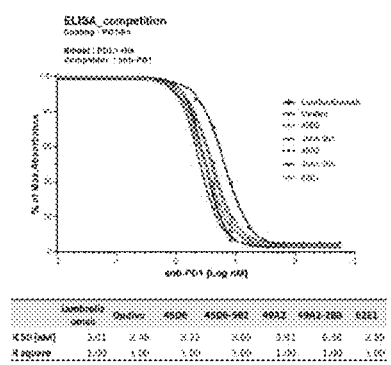
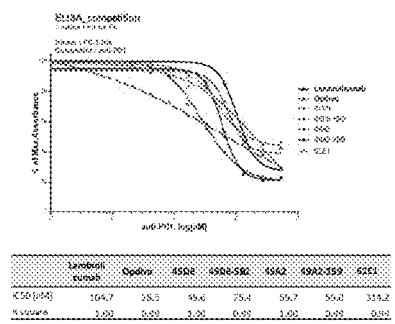
[Figure 17]
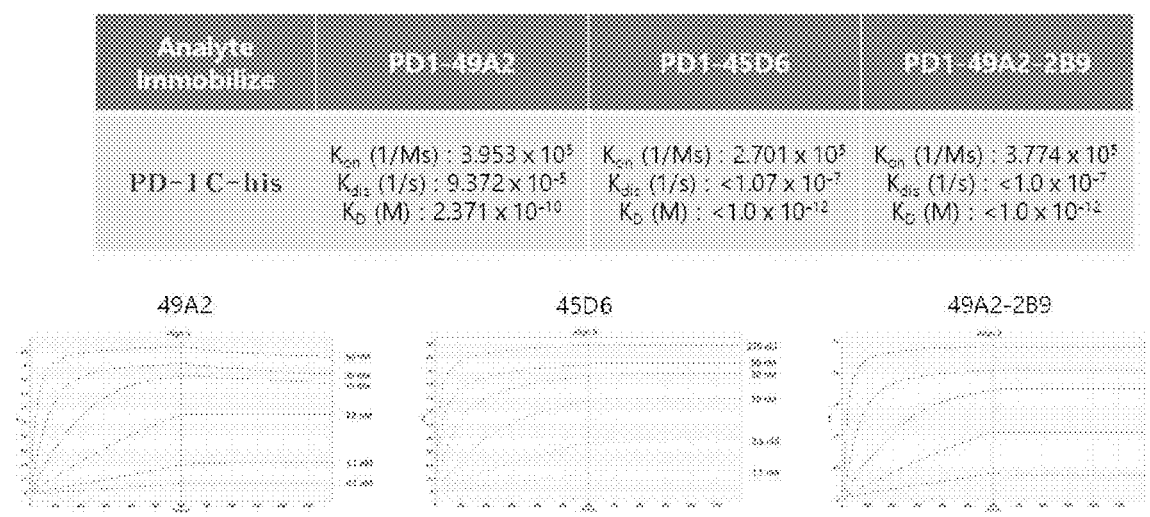

[Figure 18]

* Mutated Amino acid marked with Red

[Figure 19]

[Figure 20]
[Figure 21]
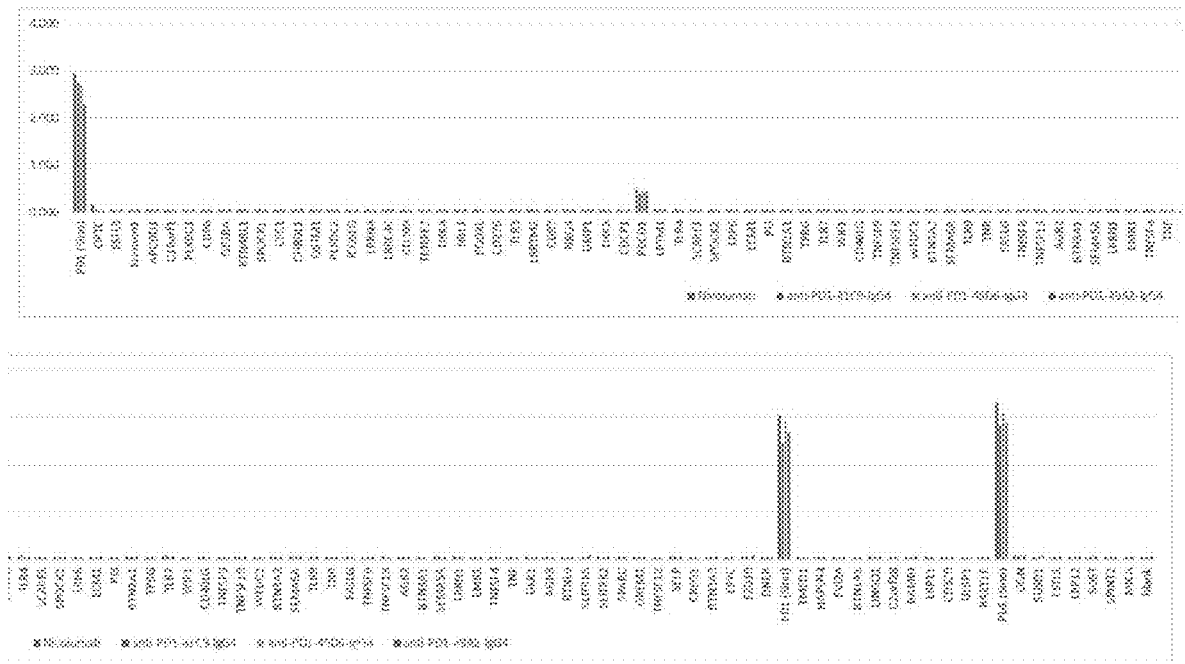

[Figure 22]
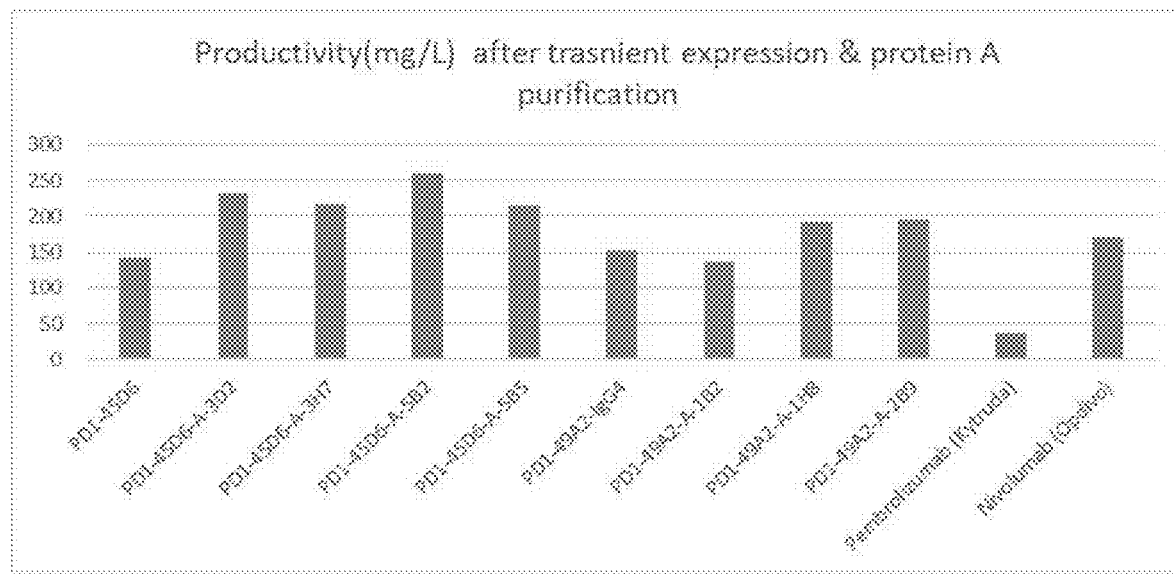
[Figure 23]
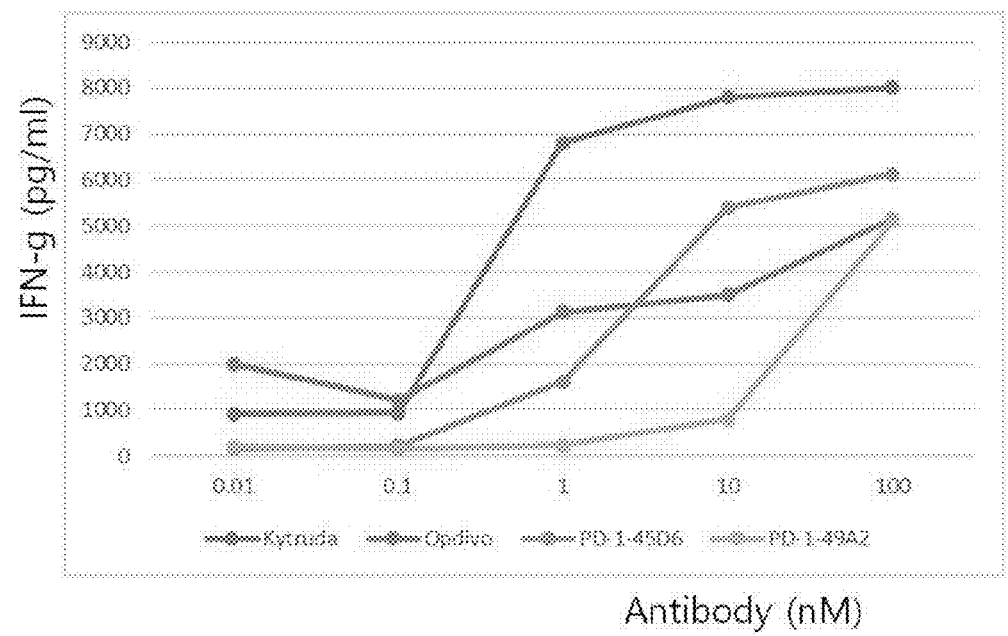

ANTIBODY TO PROGRAMMED CELL DEATH 1 (PD-1) AND USE THEREOF

CROSS-REFERENCE TO RELATED APPLICATIONS

This application is a U.S. national phase under 35 U.S.C. § 371 of International Patent Application No. PCT/KR17/08494 filed Aug. 7, 2017, which in turn claims the priorities under 35 U.S.C. § 119 of Korean Patent Application No. 10-2016-0100210 filed Aug. 5, 2016 and Korean Patent Application 10-2017-0099672 filed Aug. 7, 2017. The disclosures of such International Patent Application No. PCT/KR17/08494, Korean Patent Application No. 10-2016-0100210 filed Aug. 5, 2016 and Korean Patent Application 10-2017-0099672 are hereby incorporated herein by reference in their respective entireties, for all purposes.

TECHNICAL FIELD

The present disclosure relates to an antibody to human programmed cell death 1 (PD-1) or an antigen-binding fragment thereof, a nucleic acid encoding the same, a vector including the nucleic acid, an isolated cell transformed with the vector, a method for producing the antibody or an antigen-binding fragment thereof, and a composition for preventing or treating cancer containing the same.

BACKGROUND ART

First-generation chemotherapeutic anti-cancer drugs and second-generation targeted anti-cancer drugs, which are widely used at present, have problems of side effects due to the toxicity of anticancer drugs, high risk of drug resistance and the limitation that they can be administered only to patients having specific gene mutations. Immune anticancer drugs (immuno-oncology drugs) called "third-generation anticancer drugs", which overcome these problems, act on the signaling pathway of immune cells to activate immune cells and thereby attack cancer cells, thus providing therapeutic effects. Unlike conventional anticancer drugs, immune anticancer drugs can be applied to various diseases including cancer in a manner of treating diseases using the human immune system, and are reported to involve less side effects than conventional anticancer drugs.

PD-1 (also referred to as "CD279") is a 55 KD receptor protein associated with the CD28/CTLA4 co-stimulatory/inhibitory receptor family (Blank et al., 2005 Cancer Immunol Immunother 54: 307-314).

The characteristics in mice and humans are examined by cloning the gene and the cDNA encoding PD-1 (Ishida et al., 1992 EMBO J 11:3887-3395; Shinohara et al., 1994 Genomics 23:704-706). Whole-length PD-1 contains 288 amino acid residues (NCBI accession number: NP 005009). The extracellular domain consists of amino acid residues 1-167 and the cytoplasmic C-terminal tail contains amino acid residues 191-288, which contain two hypothetical immune-regulatory motifs, that is, an immunoreceptor tyrosine-based inhibitory motif (ITIM; Vivier et al., 1997 Immunol Today 18: 286-291) and an immunoreceptor tyrosine switch motif (ITSM; Chemnitz et al., 2004 J Immunol 173: 945-954).

To date, two sequence-related ligands, PD-L1 (B7-H1) and PD-L2 (B7-DC), have been known to specifically interact with PD-1 to induce intracellular signaling, and to inhibit CD3 and CD28-mediated T-cell activation (Riley, 2009 Immunol Rev 229: 114-125), which eventually regulates T-cell activity, for example, reduces secretion of other growth factors and cytokine, as well as cell growth, and secretion of IL-2 and IFN-γ.

The expression of PD-1 is frequently found in immune cells such as T-cells, B-cells, mononuclear cells and natural killer (NK) cells, and is almost not expressed in other human tissues such as muscle, epithelium and nervous tissue. In addition, high levels of PD-1 expression are often associated with the activity of immune cells. For example, when the human T-cell line, Jurkat is activated by PHA (phytohaemagglutinin) or 12-O-tetradecanoylphorbol-13-acetate or TPA, the expression of PD-1 is up-regulated, as can be seen from Weston blotting. Due to stimulation of the anti-CD3 antibody, the same phenomenon was observed in stimulated mouse T- and B-lymphocytes, and primary human $CD^{4+}$ T cells. The increased PD-1 expression causes stimulation of effector T cells and guides the activated effector T cells to the direction of depleted and reduced immune activation. Thus, PD-1-mediated inhibitory signals are known to play a key role in immune tolerance.

An increase in the expression of PD-1 of tumor-infiltrating lymphocytes (TILS) and the expression of PD-1 ligands in tumor cells has been reported in a variety of cancers and has been reported in other types of tissues and organs including the lungs, liver, stomach, breasts, ovaries, pancreas, melanocytes, and esophagus. More frequently, the expression of PD-1 and PD-L1 in such cancers is associated with a poor prognosis regarding patient survival results. The importance of PD-1 signaling on the regulation of the immune system for cancer removal or tolerance was described in more detail through transgenic mice that inhibit the growth of xenograft cancer cells by knocking out the PD-1 genes.

Up-regulation of PD-1 signaling leads to immune-tolerant cancer proliferation as well as to human viral infection and metastasis. Pandemic hepatitis B virus, HBV and HCV induce over-expression of PD-1 ligands in hepatocytes and activate PD-1 signaling in effector T cells, leading to T-cell depletion and tolerance for viral infection. Similarly, HIV infection frequently evades the human immune system through a similar mechanism. PD-1 signaling can be therapeutically modulated by antagonistic molecules so that immune cells can be recovered from tolerance and can be reactivated to eliminate cancer and chronic viral infections.

Nivolumab and pembrolizumab, which are monoclonal antibodies, are known as drugs targeting PD-1 and are used as therapeutic agents for malignant melanoma and non-small cell lung cancer. However, it is reported that these drugs put a huge financial burden on patients due to high production cost and accurate verification thereof is required. Therefore, there is an urgent need for developing new PD-1-targeting therapeutic agents that can overcome the limitations of conventional drugs.

Under this technical background, the present inventors have made efforts to develop antibodies for treating cancer that specifically bind to PD-L1. As a result, the present inventors have developed an anti-PD-L1 antibody that binds with a high affinity to PD-L1 using a phage display technology, and have found that such an anti-PD-L1 antibody can significantly inhibit the formation of the PD-1/PD-L1 complex, thus completing the present disclosure.

DISCLOSURE

Technical Problem

Therefore, it is one object of the present disclosure to provide a novel antibody to PD-1 or an antigen-binding fragment thereof.

It is another object of the present disclosure to provide a nucleic acid encoding the antibody or an antigen-binding fragment thereof.

It is another object of the present disclosure to provide a vector including the nucleic acid, a recombinant cell into which the vector is introduced, and a method for producing the same.

It is another object of the present disclosure to provide a composition for preventing or treating cancer, containing the antibody or an antigen-binding fragment thereof.

Technical Solution

In accordance with the present disclosure, the above and other objects can be accomplished by the provision of an antibody binding to PD-1 or an antigen-binding fragment thereof including: a heavy chain variable region including a heavy chain CDR1 including a sequence having a sequence identity of 90% or higher with a sequence selected from the group consisting of sequences as set forth in SEQ ID NOS: 1 to 30, a heavy chain CDR2 including a sequence having a sequence identity of 90% or higher with a sequence selected from the group consisting of sequences as set forth in SEQ ID NOS: 31 to 56, and a heavy chain CDR3 including a sequence having a sequence identity of 90% or higher with a sequence selected from the group consisting of sequences as set forth in SEQ ID NOS: 57 to 79; and a light chain variable region including a light chain CDR1 including a sequence having a sequence identity of 90% or higher with a sequence selected from the group consisting of sequences as set forth in SEQ ID NOS: 198 to 222, a light chain CDR2 including a sequence having a sequence identity of 90% or higher with a sequence selected from the group consisting of sequences: Gly Ala Ser; Lys Ile Ser; Ala Thr Ser; Lys Asp Thr; Tyr Asp Asp; Gly Asn Ser; Arg Ala Ser; Thr Leu Ser; Ala Ala Ser; Asn Tyr Asp; Gly Lys Asn; Gln Asp Thr; Asp Val Ser; Gly Asn Asn; Arg Asp Asp; Glu Val Ser; Leu Gly Ser; Lys Asp Ser; and Asp Ala Ser, and a light chain CDR3 including a sequence having a sequence identity of 90% or higher with a sequence selected from the group consisting of sequences as set forth in SEQ ID NOS: 223 to 250.

In accordance with another aspect of the present disclosure, provided is a nucleic acid encoding the antibody or an antigen-binding fragment.

In accordance with another aspect of the present disclosure, provided is an expression vector including the nucleic acid.

In accordance with another aspect of the present disclosure, provided is a cell transformed with the expression vector.

In accordance with another aspect of the present disclosure, provided is a method for producing the antibody or an antigen-binding fragment thereof, including (a) culturing the cell, and (b) recovering the antibody or an antigen-binding fragment thereof from the cultured cell.

In accordance with another aspect of the present disclosure, provided is a composition for preventing or treating cancer containing, as an active ingredient, the antibody or an antigen-binding fragment thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other objects, features and other advantages of the present disclosure will be more clearly understood from the following detailed description taken in conjunction with the accompanying drawings, in which:

FIG. 1 is a schematic diagram showing a PD-1 expression vector including human Fc or mouse Fc fused to a carboxyl terminal thereof;

FIGS. 2A-2D show a result of PD-1 protein purification; FIG. 2A shows a result of protein identification with regard to PD1-hFc on 10% SDS-PAGE gel under RE (reducing) and NR (non-reducing) conditions;

FIG. 2B shows a result of G-3000 SWXL SEC-HPLC at a flow rate of 1 ml/min and using PBS as a development solvent;

FIG. 2C shows a result of protein identification with regard to PD1-mFc on 10% SDS-PAGE gel under RE (reducing) and NR (non-reducing) conditions;

FIG. 2D shows a result of G-3000 SWXL SEC-HPLC at a flow rate of 1 ml/min and using PBS as a development solvent;

FIG. 3 shows a binding capacity of an antibody to PD-1 depending on the number of times of panning;

FIG. 4 shows a result of ELISA to measure a binding capacity of monophages to PD1-His;

FIG. 5 shows a result of SDS-PAGE analysis to identify purity of PD-1 antibodies;

FIG. 6 shows a result of evaluation of in vitro efficacy of PD-1 antibodies;

FIG. 7 shows a result of concentration-dependent in vitro efficacy evaluation of PD-1 antibodies;

FIG. 8 shows binding capacities of antibodies concentration-dependently bound to human PD-1 over-expressed on the cell surface, on the basis of mean fluorescence intensity (MFI);

FIG. 9 shows a result of measurement of kinetics between PD1-hFc and PD1-45D6, 49A2;

FIG. 10 shows a result of screening of optimization monoclones;

FIG. 11 shows comparative analysis of expression rates between the PD1 antibodies and a parent antibody;

FIG. 12 shows a result of evaluation of in vitro efficacy, with regard to the PD1 antibody according to the present disclosure;

FIG. 13 shows a result of concentration-dependent in vitro efficacy evaluation of the PD-1 antibody according to the present disclosure;

FIG. 14 shows a result of identification regarding binding of selected PD1 antibody variants to PD-1 expressed on cell surfaces of monoclonal antibodies;

FIG. 15 shows a result of measurement of binding capacities of selected PD1 antibody variants to PD-1 expressed on cell surfaces of monoclonal antibodies;

FIG. 16 shows a result of identification using enzyme immunoadsorption with regard to an inhibitory activity of selected antibodies to prevent formation of a PD-1/PD-L1 or PD-1/PD-L2 complex;

FIG. 17 shows a result of measurement of kinetics between PD1-hFc protein, and PD1-45D6, 49A2 and 49A2 (2B9);

FIG. 18 is a schematic diagram showing PD1 mutants;

FIG. 19 shows a result of identification using enzyme immunoadsorption with regard to binding capacities of selected phages to PD-1 mutants, wherein as binding capacity decreases, the corresponding value decreases;

FIG. 20 shows a result of identification using enzyme immunoadsorption with regard to binding capacities of selected antibodies to PD-1 mutants;

FIG. 21 shows a result of identification using enzyme immunoadsorption with regard to binding specificity;

FIG. 22 shows a result of comparison in productivity after transient expression in HEK-293 cells; and FIG. 23 shows a result of identification with regard to an increase in activity by PD1 monoclonal antibodies during heterogeneous MLR (mixed lymphocyte reaction).

DETAILED DESCRIPTION OF THE INVENTION

Unless defined otherwise, all technical and scientific terms used herein have the same meaning as those appreciated by those skilled in the field to which the present disclosure pertains. In general, nomenclature used herein is well-known in the art and is ordinarily used.

In one aspect, the present disclosure is directed to an antibody binding to PD-1 or an antigen-binding fragment thereof including: a heavy chain variable region including a heavy chain CDR1 including a sequence having a sequence identity of 90% or higher with a sequence selected from the group consisting of sequences as set forth in SEQ ID NOS: 1 to 30, a heavy chain CDR2 including a sequence having a sequence identity of 90% or higher with a sequence selected from the group consisting of sequences as set forth in SEQ ID NOS: 31 to 56, and a heavy chain CDR3 including a sequence having a sequence identity of 90% or higher with a sequence selected from the group consisting of sequences as set forth in SEQ ID NOS: 57 to 79; and a light chain variable region including a light chain CDR1 including a sequence having a sequence identity of 90% or higher with a sequence selected from the group consisting of sequences as set forth in SEQ ID NOS: 198 to 222, a light chain CDR2 including a sequence having a sequence identity of 90% or higher with a sequence selected from the group consisting of sequences: Gly Ala Ser; Lys Ile Ser; Ala Thr Ser; Lys Asp Thr; Tyr Asp Asp; Gly Asn Ser; Arg Ala Ser; Thr Leu Ser; Ala Ala Ser; Asn Tyr Asp; Gly Lys Asn; Gln Asp Thr; Asp Val Ser; Gly Asn Asn; Arg Asp Asp; Glu Val Ser; Leu Gly Ser; Lys Asp Ser; and Asp Ala Ser, and a light chain CDR3 including a sequence having a sequence identity of 90% or higher with a sequence selected from the group consisting of sequences as set forth in SEQ ID NOS: 223 to 250.

The present inventors have made efforts to develop an antibody for chemotherapy which binds to PD-1, which is known to be expressed in various cancers. As a result, the present inventors prepared an anti-PD-1 antibody that binds with high affinity to PD-1 using phage display technology and found that such an anti-PD-1 antibody can inhibit activity of PD-1.

As herein used, the term "programmed cell death 1 (PD-1)" is a signaling protein which is known to function to regulate activation and functions of T cells. The binding of PD-1 of T cells to PD-L1, which is a ligand expressed by cancer cells, under the tumor microenvironment activates the PD-1 signaling pathway and consequently induces inactivation of T cells. This phenomenon is found in various cancers such as malignant melanoma, non-small cell lung cancer and kidney cancer.

As used herein, the term "antibody" refers to an anti-PD-1 antibody that specifically binds to PD-1. The scope of the present disclosure includes not only a complete antibody specifically binding to PD-1, but also an antigen-binding fragment of the antibody molecule.

The complete antibody refers to a structure having two full-length light chains and two full-length heavy chains, wherein each light chain is linked to the corresponding heavy chain by a disulfide bond. The heavy chain constant region has gamma (γ), mu (μ), alpha (α), delta (δ) and epsilon (ε) types and is subclassed into gamma 1 (γ1), gamma 2 (γ2), gamma (γ3), gamma 4 (γ4), alpha 1 (α1) and alpha 2 (α2). The constant region of the light chain has kappa (κ) and lambda (λ) types.

The antigen-binding fragment of an antibody or the antibody fragment refers to a fragment that at least has an antigen-binding capacity and includes Fab, F(ab'), F(ab')2, and Fv. Among the antibody fragments, Fab refers to a structure including a variable region of each of the heavy chain and the light chain, the constant domain of the light chain, and the first constant domain (CH1) of the heavy chain, each having one antigen-binding site. Fab' is different from Fab in that it further includes a hinge region including at least one cysteine residue at a C-terminus of the CH1 domain of the heavy chain. F(ab')2 is created by a disulfide bond between cysteine residues in the hinge region of Fab'. Fv is the minimal antibody fragment having only a heavy chain variable region and a light chain variable region, and recombinant technology for producing Fv, is disclosed in PCT International Publications such as WO88/01649, WO88/06630, WO88/07085, WO88/07086, and WO88/09344. Two-chain Fv is a fragment wherein the variable region of the heavy chain and the variable region of the light chain are linked by a non-covalent bond, and single-chain Fv is a fragment wherein the variable region of the heavy chain and the variable region of the light chain are generally linked by a covalent bond via a peptide linker between, or are directly linked at the C-terminal, forming a dimer-like structure, like the two-chain Fv. Such antibody fragments may be obtained using proteases (e.g., Fabs can be obtained by restriction-cleaving the whole antibody with papain, and the F(ab') fragment can be obtained by restriction-cleaving the whole antibody with pepsin), and may be prepared by genetic recombination techniques.

In one embodiment, the antibody of the present disclosure is an Fv form (for example, scFv), Fab or a complete antibody form. In addition, the heavy chain constant region may be selected from the isotypes consisting of gamma (γ), mu (u), alpha (α), delta (δ) or epsilon (c). For example, the constant region may be gamma 1 (IgG1), gamma 3 (IgG3) or gamma 4 (IgG4). The light chain constant region may be kappa or lambda.

As used herein, the term "heavy chain" encompasses both a full-length heavy chain, which includes a variable domain (VH) containing an amino acid sequence having a sufficient variable region sequence for imparting a specificity to an antigen and three constant domains (CH1, CH2 and CH3), and a fragment thereof. As used herein, the term "light chain" encompasses both a full-length light chain, which includes a variable domain (VL) containing an amino acid sequence having a sufficient variable region sequence for imparting specificity to an antigen and a constant domain (CL), and a fragment thereof.

The antibody of the present disclosure includes, but is limited to, monoclonal antibodies, multispecific antibodies, human antibodies, humanized antibodies, chimeric antibodies, short chain Fvs (scFVs), short chain antibodies, Fab fragments, F(ab') fragments, disulfide-bond Fvs (sdFVs), anti-idiotypic (anti-Id) antibodies, or epitope-binding fragments of such antibodies, or the like.

The monoclonal antibody refers to the same antibody, excluding possible naturally occurring mutations where an antibody obtained from a population of substantially homogeneous antibodies, that is, each antibody constituting the population, may be present in a minor amount. Monoclonal antibodies are highly specific and are induced against a single antigenic site.

The non-human (e.g., murine) antibody of the "humanized" form is a chimeric antibody containing a minimal sequence derived from non-human immunoglobulin. In most cases, the humanized antibody is a human immunoglobulin (receptor antibody) wherein a residue from the hypervariable region of a receptor is replaced with a residue from the hypervariable region of non-human species (donor antibody), such as a mouse, rat, rabbit or non-human primate having the desired specificity, affinity and ability.

The term "human antibody" means a molecule derived from human immunoglobulin, wherein all the amino acid sequences constituting the antibody including a complementarity-determining region and a structural region are composed of human immunoglobulin.

Some of the heavy chain and/or light chain is identical to or homologous with the corresponding sequence in an antibody derived from a particular species or belonging to a particular antibody class or subclass, while the remaining chain(s) include "chimeric" antibodies (immunoglobulins) which are identical to or homologous with corresponding sequences in an antibody derived from another species or belonging to another antibody class or subclass as well as fragments of such antibody exhibiting the desired biological activity.

As used herein, the term "antibody variable domain" refers to the light and heavy chain regions of an antibody molecule including the amino acid sequences of a complementarity determining region (CDR; i.e., CDR1, CDR2, and CDR3) and a framework region (FR). VH refers to a variable domain of the heavy chain. VL refers to a variable domain of the light chain.

The term "complementarity determining region" (CDR; i.e., CDR1, CDR2, and CDR3) refers to an amino acid residue of the antibody variable domain, which is necessary for antigen binding. Each variable domain typically has three CDR regions identified as CDR1, CDR2, and CDR3.

In the present disclosure, the antibody binding to PD-1 or an antigen-binding fragment thereof includes:

a heavy chain variable region including:
a heavy chain CDR1 selected from the group consisting of SEQ ID NOS: 1 to 30;
a heavy chain CDR2 selected from the group consisting of SEQ ID NOS: 31 to 56; and
a heavy chain CDR3 selected from the group consisting of SEQ ID NOS: 57 to 79; and
a light chain variable region including:
a light chain CDR1 selected from the group consisting of SEQ ID NOS: 198 to 222;
a light chain CDR2 selected from the group consisting of: Gly Ala Ser; Lys Ile Ser; Ala Thr Ser; Lys Asp Thr; Tyr Asp Asp; Gly Asn Ser; Arg Ala Ser; Thr Leu Ser; Ala Ala Ser; Asn Tyr Asp; Gly Lys Asn; Gln Asp Thr; Asp Val Ser; Gly Asn Asn; Arg Asp Asp; Glu Val Ser; Leu Gly Ser; Lys Asp Ser; and Asp Ala Ser; and
a light chain CDR3 selected from the group consisting of SEQ ID NOS: 223 to 250.

Specifically, the antibody binding to PD-1 or an antigen-binding fragment thereof includes:

a heavy chain variable region including the heavy chain CDR1 of SEQ ID NO: 1, the heavy chain CDR2 of SEQ ID NO: 31 and the heavy chain CDR3 of SEQ ID NO: 57;

a heavy chain variable region including the heavy chain CDR1 of SEQ ID NO: 1, the heavy chain CDR2 of SEQ ID NO: 32 and the heavy chain CDR3 of SEQ ID NO: 58;

a heavy chain variable region including the heavy chain CDR1 of SEQ ID NO: 2, the heavy chain CDR2 of SEQ ID NO: 33 and the heavy chain CDR3 of SEQ ID NO: 59;

a heavy chain variable region including the heavy chain CDR1 of SEQ ID NO: 2, the heavy chain CDR2 of SEQ ID NO: 33 and the heavy chain CDR3 of SEQ ID NO: 60;

a heavy chain variable region including the heavy chain CDR1 of SEQ ID NO: 2, the heavy chain CDR2 of SEQ ID NO: 33 and the heavy chain CDR3 of SEQ ID NO: 61;

a heavy chain variable region including the heavy chain CDR1 of SEQ ID NO: 2, the heavy chain CDR2 of SEQ ID NO: 33 and the heavy chain CDR3 of SEQ ID NO: 62;

a heavy chain variable region including the heavy chain CDR1 of SEQ ID NO: 3, the heavy chain CDR2 of SEQ ID NO: 34 and the heavy chain CDR3 of SEQ ID NO: 63;

a heavy chain variable region including the heavy chain CDR1 of SEQ ID NO: 4, the heavy chain CDR2 of SEQ ID NO: 35 and the heavy chain CDR3 of SEQ ID NO: 64;

a heavy chain variable region including the heavy chain CDR1 of SEQ ID NO: 5, the heavy chain CDR2 of SEQ ID NO: 36 and the heavy chain CDR3 of SEQ ID NO: 65;

a heavy chain variable region including the heavy chain CDR1 of SEQ ID NO: 6, the heavy chain CDR2 of SEQ ID NO: 37 and the heavy chain CDR3 of SEQ ID NO: 66;

a heavy chain variable region including the heavy chain CDR1 of SEQ ID NO: 1, the heavy chain CDR2 of SEQ ID NO: 32 and the heavy chain CDR3 of SEQ ID NO: 67;

a heavy chain variable region including the heavy chain CDR1 of SEQ ID NO: 7, the heavy chain CDR2 of SEQ ID NO: 38 and the heavy chain CDR3 of SEQ ID NO: 68;

a heavy chain variable region including the heavy chain CDR1 of SEQ ID NO: 8, the heavy chain CDR2 of SEQ ID NO: 39 and the heavy chain CDR3 of SEQ ID NO: 69;

a heavy chain variable region including the heavy chain CDR1 of SEQ ID NO: 9, the heavy chain CDR2 of SEQ ID NO: 40 and the heavy chain CDR3 of SEQ ID NO: 70;

a heavy chain variable region including the heavy chain CDR1 of SEQ ID NO: 10, the heavy chain CDR2 of SEQ ID NO: 41 and the heavy chain CDR3 of SEQ ID NO: 71;

a heavy chain variable region including the heavy chain CDR1 of SEQ ID NO: 11, the heavy chain CDR2 of SEQ ID NO: 42 and the heavy chain CDR3 of SEQ ID NO: 72;

a heavy chain variable region including the heavy chain CDR1 of SEQ ID NO: 12, the heavy chain CDR2 of SEQ ID NO: 43 and the heavy chain CDR3 of SEQ ID NO: 73;

a heavy chain variable region including the heavy chain CDR1 of SEQ ID NO: 13, the heavy chain CDR2 of SEQ ID NO: 44 and the heavy chain CDR3 of SEQ ID NO: 74;

a heavy chain variable region including the heavy chain CDR1 of SEQ ID NO: 14, the heavy chain CDR2 of SEQ ID NO: 45 and the heavy chain CDR3 of SEQ ID NO: 75;

a heavy chain variable region including the heavy chain CDR1 of SEQ ID NO: 15, the heavy chain CDR2 of SEQ ID NO: 46 and the heavy chain CDR3 of SEQ ID NO: 76;

a heavy chain variable region including the heavy chain CDR1 of SEQ ID NO: 8, the heavy chain CDR2 of SEQ ID NO: 47 and the heavy chain CDR3 of SEQ ID NO: 77;

a heavy chain variable region including the heavy chain CDR1 of SEQ ID NO: 16, the heavy chain CDR2 of SEQ ID NO: 48 and the heavy chain CDR3 of SEQ ID NO: 78;

a heavy chain variable region including the heavy chain CDR1 of SEQ ID NO: 17, the heavy chain CDR2 of SEQ ID NO: 49 and the heavy chain CDR3 of SEQ ID NO: 58;

a heavy chain variable region including the heavy chain CDR1 of SEQ ID NO: 18, the heavy chain CDR2 of SEQ ID NO: 50 and the heavy chain CDR3 of SEQ ID NO: 58;

a heavy chain variable region including the heavy chain CDR1 of SEQ ID NO: 19, the heavy chain CDR2 of SEQ ID NO: 51 and the heavy chain CDR3 of SEQ ID NO: 58;

a heavy chain variable region including the heavy chain CDR1 of SEQ ID NO: 20, the heavy chain CDR2 of SEQ ID NO: 52 and the heavy chain CDR3 of SEQ ID NO: 58;

a heavy chain variable region including the heavy chain CDR1 of SEQ ID NO: 21, the heavy chain CDR2 of SEQ ID NO: 51 and the heavy chain CDR3 of SEQ ID NO: 58;

a heavy chain variable region including the heavy chain CDR1 of SEQ ID NO: 22, the heavy chain CDR2 of SEQ ID NO: 53 and the heavy chain CDR3 of SEQ ID NO: 58;

a heavy chain variable region including the heavy chain CDR1 of SEQ ID NO: 23, the heavy chain CDR2 of SEQ ID NO: 49 and the heavy chain CDR3 of SEQ ID NO: 58;

a heavy chain variable region including the heavy chain CDR1 of SEQ ID NO: 17, the heavy chain CDR2 of SEQ ID NO: 54 and the heavy chain CDR3 of SEQ ID NO: 58;

a heavy chain variable region including the heavy chain CDR1 of SEQ ID NO: 24, the heavy chain CDR2 of SEQ ID NO: 55 and the heavy chain CDR3 of SEQ ID NO: 58;

a heavy chain variable region including the heavy chain CDR1 of SEQ ID NO: 21, the heavy chain CDR2 of SEQ ID NO: 51 and the heavy chain CDR3 of SEQ ID NO: 58;

a heavy chain variable region including the heavy chain CDR1 of SEQ ID NO: 25, the heavy chain CDR2 of SEQ ID NO: 56 and the heavy chain CDR3 of SEQ ID NO: 57;

a heavy chain variable region including the heavy chain CDR1 of SEQ ID NO: 26, the heavy chain CDR2 of SEQ ID NO: 31 and the heavy chain CDR3 of SEQ ID NO: 57;

a heavy chain variable region including the heavy chain CDR1 of SEQ ID NO: 27, the heavy chain CDR2 of SEQ ID NO: 31 and the heavy chain CDR3 of SEQ ID NO: 57;

a heavy chain variable region including the heavy chain CDR1 of SEQ ID NO: 28, the heavy chain CDR2 of SEQ ID NO: 31 and the heavy chain CDR3 of SEQ ID NO: 57;

a heavy chain variable region including the heavy chain CDR1 of SEQ ID NO: 29, the heavy chain CDR2 of SEQ ID NO: 31 and the heavy chain CDR3 of SEQ ID NO: 57;

a heavy chain variable region including the heavy chain CDR1 of SEQ ID NO: 30, the heavy chain CDR2 of SEQ ID NO: 31 and the heavy chain CDR3 of SEQ ID NO: 57;

a heavy chain variable region including the heavy chain CDR1 of SEQ ID NO: 1, the heavy chain CDR2 of SEQ ID NO: 32 and the heavy chain CDR3 of SEQ ID NO: 79; or a heavy chain variable region including the heavy chain CDR1 of SEQ ID NO: 1, the heavy chain CDR2 of SEQ ID NO: 32 and the heavy chain CDR3 of SEQ ID NO: 57.

In addition, the antibody binding to PD-1 or an antigen-binding fragment thereof includes:

a light chain variable region including the light chain CDR1 of SEQ ID NO: 198, the light chain CDR2 of Gly Ala Ser and the light chain CDR3 of SEQ ID NO: 223;

a light chain variable region including the light chain CDR1 of SEQ ID NO: 199, the light chain CDR2 of Lys Ile Ser and the light chain CDR3 of SEQ ID NO: 224;

a light chain variable region including a light chain CDR1 of SEQ ID NO: 200, the light chain CDR2 of Ala Thr Ser and the light chain CDR3 of SEQ ID NO: 225;

a light chain variable region including the light chain CDR1 of SEQ ID NO: 201, the light chain CDR2 of Lys Asp Thr and the light chain CDR3 of SEQ ID NO: 226;

a light chain variable region including the light chain CDR1 of SEQ ID NO: 202, the light chain CDR2 of Tyr Asp Asp and the light chain CDR3 of SEQ ID NO: 227;

a light chain variable region including the light chain CDR1 of SEQ ID NO: 203, the light chain CDR2 of Gly Asn Ser and the light chain CDR3 of SEQ ID NO: 228;

a light chain variable region including the light chain CDR1 of SEQ ID NO: 204, the light chain CDR2 of Arg Ala Ser and the light chain CDR3 of SEQ ID NO: 229;

a light chain variable region including the light chain CDR1 of SEQ ID NO: 205, the light chain CDR2 of Thr Leu Ser and the light chain CDR3 of SEQ ID NO: 230;

a light chain variable region including the light chain CDR1 of SEQ ID NO: 206, the light chain CDR2 of Ala Ala Ser and the light chain CDR3 of SEQ ID NO: 231;

a light chain variable region including the light chain CDR1 of SEQ ID NO: 207, the light chain CDR2 of Asn Tyr Asp and the light chain CDR3 of SEQ ID NO: 232;

a light chain variable region including the light chain CDR1 of SEQ ID NO: 208, the light chain CDR2 of Thr Leu Ser and the light chain CDR3 of SEQ ID NO: 233;

a light chain variable region including the light chain CDR1 of SEQ ID NO: 209, the light chain CDR2 of Gly Lys Asn and the light chain CDR3 of SEQ ID NO: 234;

a light chain variable region including the light chain CDR1 of SEQ ID NO: 210, the light chain CDR2 of Gln Asp Thr and the light chain CDR3 of SEQ ID NO: 235;

a light chain variable region including the light chain CDR1 of SEQ ID NO: 211, the light chain CDR2 of Asp Val Ser and the light chain CDR3 of SEQ ID NO: 236;

a light chain variable region including the light chain CDR1 of SEQ ID NO: 212, the light chain CDR2 of Gly Asn Asn and the light chain CDR3 of SEQ ID NO: 237;

a light chain variable region including the light chain CDR1 of SEQ ID NO: 213, the light chain CDR2 of Thr Leu Ser and the light chain CDR3 of SEQ ID NO: 238, a light chain variable region including the light chain CDR1 of SEQ ID NO: 214, the light chain CDR2 of Arg Asp Asp and the light chain CDR3 of SEQ ID NO: 239;

a light chain variable region including the light chain CDR1 of SEQ ID NO: 215, the light chain CDR2 of Thr Leu Ser and the light chain CDR3 of SEQ ID NO: 230;

a light chain variable region including the light chain CDR1 of SEQ ID NO: 211, the light chain CDR2 of Glu Val Ser and the light chain CDR3 of SEQ ID NO: 240;

a light chain variable region including the light chain CDR1 of SEQ ID NO: 216, the light chain CDR2 of Glu Val Ser and the light chain CDR3 of SEQ ID NO: 241;

a light chain variable region including the light chain CDR1 of SEQ ID NO: 217, the light chain CDR2 of Leu Gly Ser and the light chain CDR3 of SEQ ID NO: 242;

a light chain variable region including the light chain CDR1 of SEQ ID NO: 218, the light chain CDR2 of Lys Asp Ser and the light chain CDR3 of SEQ ID NO: 243;

a light chain variable region including the light chain CDR1 of SEQ ID NO: 219, the light chain CDR2 of Asp Ala Ser and the light chain CDR3 of SEQ ID NO: 244;

a light chain variable region including the light chain CDR1 of SEQ ID NO: 220, the light chain CDR2 of Thr Leu Ser and the light chain CDR3 of SEQ ID NO: 233;

a light chain variable region including the light chain CDR1 of SEQ ID NO: 215, the light chain CDR2 of Thr Leu Ser and the light chain CDR3 of SEQ ID NO: 233;

a light chain variable region including the light chain CDR1 of SEQ ID NO: 205, the light chain CDR2 of Thr Leu Ser and the light chain CDR3 of SEQ ID NO: 245;

a light chain variable region including the light chain CDR1 of SEQ ID NO: 205, the light chain CDR2 of Thr Leu Ser and the light chain CDR3 of SEQ ID NO: 246;

a light chain variable region including the light chain CDR1 of SEQ ID NO: 221, the light chain CDR2 of Thr Leu Ser and the light chain CDR3 of SEQ ID NO: 247;

a light chain variable region including the light chain CDR1 of SEQ ID NO: 205, the light chain CDR2 of Thr Leu Ser and the light chain CDR3 of SEQ ID NO: 233;

a light chain variable region including the light chain CDR1 of SEQ ID NO: 205, the light chain CDR2 of Thr Leu Ser and the light chain CDR3 of SEQ ID NO: 248;

a light chain variable region including the light chain CDR1 of SEQ ID NO: 205, the light chain CDR2 of Thr Leu Ser and the light chain CDR3 of SEQ ID NO: 238;

a light chain variable region including the light chain CDR1 of SEQ ID NO: 220, the light chain CDR2 of Thr Leu Ser and the light chain CDR3 of SEQ ID NO: 248;

a light chain variable region including the light chain CDR1 of SEQ ID NO: 222, the light chain CDR2 of Thr Leu Ser and the light chain CDR3 of SEQ ID NO: 249; or a light chain variable region including the light chain CDR1 of SEQ ID NO: 220, the light chain CDR2 of Thr Leu Ser and the light chain CDR3 of SEQ ID NO: 250.

Specifically, the antibody or an antigen-binding fragment thereof according to the present disclosure may include the following heavy chain variable regions and light chain variable regions:

a heavy chain variable region including the heavy chain CDR1 of SEQ ID NO: 2, the heavy chain CDR2 of SEQ ID NO: 33 and the heavy chain CDR3 of SEQ ID NO: 62 and a light chain variable region including the light chain CDR1 of SEQ ID NO: 201, the light chain CDR2 of Lys Asp Thr and the light chain CDR3 of SEQ ID NO: 226;

a heavy chain variable region including the heavy chain CDR1 of SEQ ID NO: 3, the heavy chain CDR2 of SEQ ID NO: 34 and the heavy chain CDR3 of SEQ ID NO: 63 and a light chain variable region including the light chain CDR1 of SEQ ID NO: 202, the light chain CDR2 of Tyr Asp Asp and the light chain CDR3 of SEQ ID NO: 227;

a heavy chain variable region including the heavy chain CDR1 of SEQ ID NO: 4, the heavy chain CDR2 of SEQ ID NO: 35 and the heavy chain CDR3 of SEQ ID NO: 64, and a light chain variable region including the light chain CDR1 of SEQ ID NO: 203, the light chain CDR2 of Gly Asn Ser and the light chain CDR3 of SEQ ID NO: 228;

a heavy chain variable region including the heavy chain CDR1 of SEQ ID NO: 5, the heavy chain CDR2 of SEQ ID NO: 36 and the heavy chain CDR3 of SEQ ID NO: 65, and a light chain variable region including the light chain CDR1 of SEQ ID NO: 204, the light chain CDR2 of Arg Ala Ser and the light chain CDR3 of SEQ ID NO: 229;

a heavy chain variable region including the heavy chain CDR1 of SEQ ID NO: 1, the heavy chain CDR2 of SEQ ID NO: 32 and the heavy chain CDR3 of SEQ ID NO: 58, and a light chain variable region including the light chain CDR1 of SEQ ID NO: 205, the light chain CDR2 of Thr Leu Ser and the light chain CDR3 of SEQ ID NO: 230;

a heavy chain variable region including the heavy chain CDR1 of SEQ ID NO: 6, the heavy chain CDR2 of SEQ ID NO: 37 and the heavy chain CDR3 of SEQ ID NO: 66, and a light chain variable region including the light chain CDR1 of SEQ ID NO: 206, the light chain CDR2 of Ala Ala Ser and the light chain CDR3 of SEQ ID NO: 231;

a heavy chain variable region including the heavy chain CDR1 of SEQ ID NO: 1, the heavy chain CDR2 of SEQ ID NO: 32 and the heavy chain CDR3 of SEQ ID NO: 67, and a light chain variable region including the light chain CDR1 of SEQ ID NO: 207, the light chain CDR2 of Asn Tyr Asp and the light chain CDR3 of SEQ ID NO: 232;

a heavy chain variable region including the heavy chain CDR1 of SEQ ID NO: 1, the heavy chain CDR2 of SEQ ID NO: 31 and the heavy chain CDR3 of SEQ ID NO: 57, and a light chain variable region including the light chain CDR1 of SEQ ID NO: 208, the light chain CDR2 of Thr Leu Ser and the light chain CDR3 of SEQ ID NO: 233;

a heavy chain variable region including the heavy chain CDR1 of SEQ ID NO: 7, the heavy chain CDR2 of SEQ ID NO: 38 and the heavy chain CDR3 of SEQ ID NO: 68, and a light chain variable region including the light chain CDR1 of SEQ ID NO: 209, the light chain CDR2 of Gly Lys Asn and the light chain CDR3 of SEQ ID NO: 234;

a heavy chain variable region including the heavy chain CDR1 of SEQ ID NO: 8, the heavy chain CDR2 of SEQ ID NO: 39 and the heavy chain CDR3 of SEQ ID NO: 69, and a light chain variable region including the light chain CDR1 of SEQ ID NO: 210, the light chain CDR2 of Gln Asp Thr and the light chain CDR3 of SEQ ID NO: 235;

a heavy chain variable region including the heavy chain CDR1 of SEQ ID NO: 11, the heavy chain CDR2 of SEQ ID NO: 42 and the heavy chain CDR3 of SEQ ID NO: 72, and a light chain variable region including the light chain CDR1 of SEQ ID NO: 213, the light chain CDR2 of Thr Leu Ser and the light chain CDR3 of SEQ ID NO: 238;

a heavy chain variable region including the heavy chain CDR1 of SEQ ID NO: 1, the heavy chain CDR2 of SEQ ID NO: 3 and the heavy chain CDR3 of SEQ ID NO: 58, and a light chain variable region including the light chain CDR1 of SEQ ID NO: 215, the light chain CDR2 of Thr Leu Ser and the light chain CDR3 of SEQ ID NO: 230;

a heavy chain variable region including the heavy chain CDR1 of SEQ ID NO: 13, the heavy chain CDR2 of SEQ ID NO: 44 and the heavy chain CDR3 of SEQ ID NO: 74, and a light chain variable region including the light chain CDR1 of SEQ ID NO: 211, the light chain CDR2 of Glu Val Ser and the light chain CDR3 of SEQ ID NO: 240;

a heavy chain variable region including the heavy chain CDR1 of SEQ ID NO: 15, the heavy chain CDR2 of SEQ ID NO: 46 and the heavy chain CDR3 of SEQ ID NO: 76, and a light chain variable region including the light chain CDR1 of SEQ ID NO: 217, the light chain CDR2 of Leu Gly Ser and the light chain CDR3 of SEQ ID NO: 317; or a heavy chain variable region including the heavy chain CDR1 of SEQ ID NO: 8, the heavy chain CDR2 of SEQ ID NO: 47 and the heavy chain CDR3 of SEQ ID NO: 77, and a light chain variable region including the light chain CDR1 of SEQ ID NO: 218, the light chain CDR2 of Lys Asp Ser and the light chain CDR3 of SEQ ID NO: 318.

According to one embodiment of the present disclosure, the antibody is further screened through an optimization procedure, and the antibody or an antigen-binding fragment thereof according to the invention may include the following heavy chain variable regions and light chain variable regions:

a heavy chain variable region including the heavy chain CDR1 of SEQ ID NO: 17, the heavy chain CDR2 of SEQ ID NO: 49 and the heavy chain CDR3 of SEQ ID NO: 58, and a light chain variable region including the light chain CDR1 of SEQ ID NO: 220, the light chain CDR2 of Thr Leu Ser and the light chain CDR3 of SEQ ID NO: 233;

a heavy chain variable region including the heavy chain CDR1 of SEQ ID NO: 18, the heavy chain CDR2 of SEQ ID NO: 50 and the heavy chain CDR3 of SEQ ID NO: 58, and a light chain variable region including the light chain CDR1 of SEQ ID NO: 215, the light chain CDR2 of Thr Leu Ser and the light chain CDR3 of SEQ ID NO: 233;

a heavy chain variable region including the heavy chain CDR1 of SEQ ID NO: 19, the heavy chain CDR2 of SEQ ID NO: 51 and the heavy chain CDR3 of SEQ ID NO: 58, and a light chain variable region including the light chain CDR1 of SEQ ID NO: 218, the light chain CDR2 of Lys Asp Ser and the light chain CDR3 of SEQ ID NO: 318;

a heavy chain variable region including the heavy chain CDR1 of SEQ ID NO: 20, the heavy chain CDR2 of SEQ ID NO: 52 and the heavy chain CDR3 of SEQ ID NO: 58, and a light chain variable region including the light chain CDR1 of SEQ ID NO: 205, the light chain CDR2 of Thr Leu Ser and the light chain CDR3 of SEQ ID NO: 245;

a heavy chain variable region including the heavy chain CDR1 of SEQ ID NO: 21, the heavy chain CDR2 of SEQ ID NO: 51 and the heavy chain CDR3 of SEQ ID NO: 58, and a light chain variable region including the light chain CDR1 of SEQ ID NO: 205, the light chain CDR2 of Thr Leu Ser and the light chain CDR3 of SEQ ID NO: 246;

a heavy chain variable region including the heavy chain CDR1 of SEQ ID NO: 22, the heavy chain CDR2 of SEQ ID NO: 53 and the heavy chain CDR3 of SEQ ID NO: 58, and a light chain variable region including the light chain CDR1 of SEQ ID NO: 221, the light chain CDR2 of Thr Leu Ser and the light chain CDR3 of SEQ ID NO: 247;

a heavy chain variable region including the heavy chain CDR1 of SEQ ID NO: 23, the heavy chain CDR2 of SEQ ID NO: 49 and the heavy chain CDR3 of SEQ ID NO: 58, and a light chain variable region including the light chain CDR1 of SEQ ID NO: 205, the light chain CDR2 of Thr Leu Ser and the light chain CDR3 of SEQ ID NO: 233;

a heavy chain variable region including the heavy chain CDR1 of SEQ ID NO: 17, the heavy chain CDR2 of SEQ ID NO: 54 and the heavy chain CDR3 of SEQ ID NO: 58, and a light chain variable region including the light chain CDR1 of SEQ ID NO: 215, the light chain CDR2 of Thr Leu Ser and the light chain CDR3 of SEQ ID NO: 230;

a heavy chain variable region including the heavy chain CDR1 of SEQ ID NO: 24, the heavy chain CDR2 of SEQ ID NO: 55 and the heavy chain CDR3 of SEQ ID NO: 58, and a light chain variable region including the light chain CDR1 of SEQ ID NO: 205, the light chain CDR2 of Thr Leu Ser and the light chain CDR3 of SEQ ID NO: 248;

a heavy chain variable region including the heavy chain CDR1 of SEQ ID NO: 21, the heavy chain CDR2 of SEQ ID NO: 51 and the heavy chain CDR3 of SEQ ID NO: 58, and a light chain variable region including the light chain CDR1 of SEQ ID NO: 220, the light chain CDR2 of Thr Leu Ser and the light chain CDR3 of SEQ ID NO: 233;

a heavy chain variable region including the heavy chain CDR1 of SEQ ID NO: 1, the heavy chain CDR2 of SEQ ID NO: 31 and the heavy chain CDR3 of SEQ ID NO: 57, and a light chain variable region including the light chain CDR1 of SEQ ID NO: 221, the light chain CDR2 of Thr Leu Ser and the light chain CDR3 of SEQ ID NO: 247;

a heavy chain variable region including the heavy chain CDR1 of SEQ ID NO: 1, the heavy chain CDR2 of SEQ ID NO: 31 and the heavy chain CDR3 of SEQ ID NO: 57, and a light chain variable region including the light chain CDR1 of SEQ ID NO: 205, the light chain CDR2 of Thr Leu Ser and the light chain CDR3 of SEQ ID NO: 233;

a heavy chain variable region including the heavy chain CDR1 of SEQ ID NO: 1, the heavy chain CDR2 of SEQ ID NO: 31 and the heavy chain CDR3 of SEQ ID NO: 57, and a light chain variable region including and the light chain CDR1 of SEQ ID NO: 205, the light chain CDR2 of Thr Leu Ser and the light chain CDR3 of SEQ ID NO: 233;

a heavy chain variable region including the heavy chain CDR1 of SEQ ID NO: 1, the heavy chain CDR2 of SEQ ID NO: 31 and the heavy chain CDR3 of SEQ ID NO: 57, and a light chain variable region including the light chain CDR1 of SEQ ID NO: 215, the light chain CDR2 of Thr Leu Ser and the light chain CDR3 of SEQ ID NO: 233;

a heavy chain variable region including the heavy chain CDR1 of SEQ ID NO: 1, the heavy chain CDR2 of SEQ ID NO: 31 and the heavy chain CDR3 of SEQ ID NO: 57, and a light chain variable region including the light chain CDR1 of SEQ ID NO: 205, the light chain CDR2 of Thr Leu Ser and the light chain CDR3 of SEQ ID NO: 233;

a heavy chain variable region including the heavy chain CDR1 of SEQ ID NO: 1, the heavy chain CDR2 of SEQ ID NO: 31 and the heavy chain CDR3 of SEQ ID NO: 57, and a light chain variable region including the light chain CDR1 of SEQ ID NO: 220, the light chain CDR2 of Thr Leu Ser and the light chain CDR3 of SEQ ID NO: 233;

a heavy chain variable region including heavy chain CDR1 of SEQ ID NO: 1, heavy chain CDR2 of SEQ ID NO: 31 and heavy chain CDR3 of SEQ ID NO: 57, and a light chain variable region including the light chain CDR1 of SEQ ID NO: 205, the light chain CDR2 of Thr Leu Ser and the light chain CDR3 of SEQ ID NO: 233;

a heavy chain variable region including the heavy chain CDR1 of SEQ ID NO: 1, the heavy chain CDR2 of SEQ ID NO: 31 and the heavy chain CDR3 of SEQ ID NO: 57, and a light chain variable region including the light chain CDR1 of SEQ ID NO: 205, the light chain CDR2 of Thr Leu Ser and the light chain CDR3 of SEQ ID NO: 233;

a heavy chain variable region including the heavy chain CDR1 of SEQ ID NO: 1, the heavy chain CDR2 of SEQ ID NO: 31 and the heavy chain CDR3 of SEQ ID NO: 57, and a light chain variable region including the light chain CDR1 of SEQ ID NO: 215, the light chain CDR2 of Thr Leu Ser and the light chain CDR3 of SEQ ID NO: 233;

a heavy chain variable region including the heavy chain CDR1 of SEQ ID NO: 25, the heavy chain CDR2 of SEQ ID NO: 56 and the heavy chain CDR3 of SEQ ID NO: 57, and a light chain variable region including the light chain CDR1 of SEQ ID NO: 205, the light chain CDR2 of Thr Leu Ser and the light chain CDR3 of SEQ ID NO: 238;

a heavy chain variable region including the heavy chain CDR1 of SEQ ID NO: 26, the heavy chain CDR2 of SEQ ID NO: 31 and the heavy chain CDR3 of SEQ ID NO: 57, and a light chain variable region including the light chain CDR1 of SEQ ID NO: 220, the light chain CDR2 of Thr Leu Ser and the light chain CDR3 of SEQ ID NO: 248;

a heavy chain variable region including the heavy chain CDR1 of SEQ ID NO: 27, the heavy chain CDR2 of SEQ ID NO: 31 and the heavy chain CDR3 of SEQ ID NO: 57, and a light chain variable region including the light chain CDR1 of SEQ ID NO: 205, the light chain CDR2 of Thr Leu Ser and the light chain CDR3 of SEQ ID NO: 233;

a heavy chain variable region including the heavy chain CDR1 of SEQ ID NO: 28, the heavy chain CDR2 of SEQ ID NO: 31 and the heavy chain CDR3 of SEQ ID NO: 57, and a light chain variable region including the light chain CDR1 of SEQ ID NO: 205, the light chain CDR2 of Thr Leu Ser and the light chain CDR3 of SEQ ID NO: 233;

a heavy chain variable region including the heavy chain CDR1 of SEQ ID NO: 29, the heavy chain CDR2 of SEQ ID NO: 31 and the heavy chain CDR3 of SEQ ID NO: 57, and a light chain variable region including the light chain CDR1 of SEQ ID NO: 205, the light chain CDR2 of Thr Leu Ser and the light chain CDR3 of SEQ ID NO: 233; or a heavy chain variable region including the heavy chain CDR1 of SEQ ID NO: 30, the heavy chain CDR2 of SEQ ID NO: 31 and the heavy chain CDR3 of SEQ ID NO: 57, and a light chain variable region including the light chain CDR1 of SEQ ID NO: 220, the light chain CDR2 of Thr Leu Ser and the light chain CDR3 of SEQ ID NO: 248.

The term "framework region" (FR) refers to a variable domain residue other than a CDR residue. Each variable domain typically has four FRs identified as FR1, FR2, FR3, and FR4.

According to one embodiment of the present disclosure, the antibody or an antigen-binding fragment thereof may include:

a heavy chain variable region FR1 selected from the group consisting of SEQ ID NOS: 80 to 95;

a heavy chain variable region FR2 selected from the group consisting of SEQ ID NOS: 96 to 113;

a heavy chain variable region FR3 selected from the group consisting of SEQ ID NOS: 114 to 134; or a heavy chain variable region FR4 selected from the group consisting of SEQ ID NOS: 135 to 145.

In addition, the antibody or an antigen-binding fragment thereof may include:

a light chain variable region FR1 selected from the group consisting of SEQ ID NOS: 251 to 275;

a light chain variable region FR2 selected from the group consisting of SEQ ID NOS: 276 to 296;

a light chain variable region FR3 selected from the group consisting of SEQ ID NOS: 297 to 336; or a light chain variable region FR4 selected from the group consisting of SEQ ID NOS: 337 to 348.

The "Fv" fragment is an antibody fragment containing complete antibody recognition and binding sites. Such region includes a dimmer, for example, scFv, that consists of one heavy chain variable domain and one light chain variable domain substantially tightly covalently connected to each other.

A "Fab" fragment contains the variable and constant domains of the light chain, and a variable and first constant domain (CH1) of the heavy chain. A F(ab')2 antibody fragment generally includes a pair of Fab fragments covalently linked via a hinge cysteine located therebetween near the carboxyl end thereof.

The "single chain Fv" or "scFv" antibody fragment includes VH and VL domains of the antibody, wherein these domains are present in a single polypeptide chain. The Fv polypeptide may further include a polypeptide linker between the VH domain and the VL domain in order for the scFv to form a desired structure for antigen binding.

The PD-1 antibody is monovalent or divalent, and includes short or double chains. Functionally, the binding affinity of PD-1 antibody ranges from $10^{-3}$ M to $10^{-12}$ M. For example, the binding affinity of the PD-1 antibody is $10^{-6}$M to $10^{-12}$ M, $10^{-7}$ M to $10^{-12}$ M, $10^{-8}$ M to $10^{-12}$ M, $10^{-9}$ M to $10^{-12}$ M, $10^{-3}$ M to $10^{-11}$ M, $10^{-6}$ M to $10^{-11}$ M, $10^{-7}$ M to $10^{-11}$ M, $10^{-8}$ M to $10^{-11}$ M, $10^{-9}$ M to $10^{-11}$ M, $10^{-10}$ M to $10^{-11}$ M, $10^{-5}$ M to $10^{-10}$ M, $10^{-6}$ M to $10^{-10}$ M, $10^{-7}$ M to $10^{-10}$ M, $10^{-8}$ M to $10^{-10}$ M, $10^{-9}$ M to $10^{-10}$ M, $10^{-3}$ M to $10^{-9}$ M, $10^{-6}$ M to $10^{-9}$ M, $10^{-7}$ M to $10^{-9}$ M, $10^{-8}$ M to $10^{-9}$ M, $10^{-3}$ M to $10^{-8}$ M, $10^{-6}$ M to $10^{-8}$ M, $10^{-7}$ M to $10^{-8}$ M, $10^{-3}$ M to $10^{-7}$ M, $10^{-6}$ M to $10^{-7}$ M, or $10^{-3}$ M to $10^{-6}$ M.

The antibody binding to PD-1 or an antigen-binding fragment thereof may include a heavy chain variable region including a sequence having a sequence identity of 90% or higher with a sequence selected from the group consisting of sequences as set forth in SEQ ID NOS: 146 to 193. The antibody binding to PD-1 or an antigen-binding fragment thereof may include a heavy chain variable region selected from the group consisting of SEQ ID NOS: 146 to 193. In one embodiment of the present disclosure, the antibody or an antigen-binding fragment thereof may include a heavy chain variable region of SEQ ID NOS: 151, 152, 153, 154, 155, 156, 157, 158, 159, 160, 163, 165, 166, 168, 169, or 171 to 188.

In addition, the antibody binding to PD-1 or an antigen-binding fragment thereof may include a light chain variable region including a sequence having a sequence identity of 90% or higher with a sequence selected from the group consisting of sequences as set forth in SEQ ID NOS: 349 to 401. The antibody binding to PD-1 or an antigen-binding fragment thereof may include a light chain variable region selected from the group consisting of sequences as set forth in SEQ ID NOS: 349 to 401. In one embodiment of the present disclosure, the binding to PD-1 or an antigen-binding fragment thereof may include a light chain variable region of SEQ ID NOS: 352 to 361, 364, 366, 367, 369, 370, or 372 to 396.

In a specific embodiment according to the present disclosure, the antibody binding to PD-1 or an antigen-binding fragment thereof may include:

a heavy chain variable region of SEQ ID NO: 151 and a light chain variable region of SEQ ID NO: 352;

a heavy chain variable region of SEQ ID NO: 152 and a light chain variable region of SEQ ID NO: 353;

a heavy chain variable region of SEQ ID NO: 153 and a light chain variable region of SEQ ID NO: 354;

a heavy chain variable region of SEQ ID NO: 154 and a light chain variable region of SEQ ID NO: 355;

a heavy chain variable region of SEQ ID NO: 155 and a light chain variable region of SEQ ID NO: 356;

a heavy chain variable region of SEQ ID NO: 156 and a light chain variable region of SEQ ID NO: 357;

a heavy chain variable region of SEQ ID NO: 157 and a light chain variable region of SEQ ID NO: 358;

a heavy chain variable region of SEQ ID NO: 158 and a light chain variable region of SEQ ID NO: 359;

a heavy chain variable region of SEQ ID NO: 159 and a light chain variable region of SEQ ID NO: 360;

a heavy chain variable region of SEQ ID NO: 160 and a light chain variable region of SEQ ID NO: 361;

a heavy chain variable region of SEQ ID NO: 163 and a light chain variable region of SEQ ID NO: 364;

a heavy chain variable region of SEQ ID NO: 165 and a light chain variable region of SEQ ID NO: 366;

a heavy chain variable region of SEQ ID NO: 166 and a light chain variable region of SEQ ID NO: 367;

a heavy chain variable region of SEQ ID NO: 168 and a light chain variable region of SEQ ID NO: 369;

a heavy chain variable region of SEQ ID NO: 169 and a light chain variable region of SEQ ID NO: 370;

a heavy chain variable region of SEQ ID NO: 171 and a light chain variable region of SEQ ID NO: 372;

a heavy chain variable region of SEQ ID NO: 172 and a light chain variable region of SEQ ID NO: 373;

a heavy chain variable region of SEQ ID NO: 173 and a light chain variable region of SEQ ID NO: 374;

a heavy chain variable region of SEQ ID NO: 174 and a light chain variable region of SEQ ID NO: 375;

a heavy chain variable region of SEQ ID NO: 175 and a light chain variable region of SEQ ID NO: 376;

a heavy chain variable region of SEQ ID NO: 176 and a light chain variable region of SEQ ID NO: 377;

a heavy chain variable region of SEQ ID NO: 177 and a light chain variable region of SEQ ID NO: 378;
a heavy chain variable region of SEQ ID NO: 178 and a light chain variable region of SEQ ID NO: 379;
a heavy chain variable region of SEQ ID NO: 179 and a light chain variable region of SEQ ID NO: 380;
a heavy chain variable region of SEQ ID NO: 180 and a light chain variable region of SEQ ID NO: 381;
a heavy chain variable region of SEQ ID NO: 181 and a light chain variable region of SEQ ID NO: 382;
a heavy chain variable region of SEQ ID NO: 181 and a light chain variable region of SEQ ID NO: 383;
a heavy chain variable region of SEQ ID NO: 181 and a light chain variable region of SEQ ID NO: 384;
a heavy chain variable region of SEQ ID NO: 181 and a light chain variable region of SEQ ID NO: 385;
a heavy chain variable region of SEQ ID NO: 181 and a light chain variable region of SEQ ID NO: 386;
a heavy chain variable region of SEQ ID NO: 182 and a light chain variable region of SEQ ID NO: 387;
a heavy chain variable region of SEQ ID NO: 182 and a light chain variable region of SEQ ID NO: 388;
a heavy chain variable region of SEQ ID NO: 182 and a light chain variable region of SEQ ID NO: 389;
a heavy chain variable region of SEQ ID NO: 182 and a light chain variable region of SEQ ID NO: 390;
a heavy chain variable region of SEQ ID NO: 183 and a light chain variable region of SEQ ID NO: 391;
a heavy chain variable region of SEQ ID NO: 184 and a light chain variable region of SEQ ID NO: 392;
a heavy chain variable region of SEQ ID NO: 185 and a light chain variable region of SEQ ID NO: 393;
a heavy chain variable region of SEQ ID NO: 186 and a light chain variable region of SEQ ID NO: 394;
a heavy chain variable region of SEQ ID NO: 187 and a light chain variable region of SEQ ID NO: 395; or a heavy chain variable region of SEQ ID NO: 188 and a light chain variable region of SEQ ID NO: 396.

In a specific embodiment, the antibody binding to PD-1 or an antigen-binding fragment thereof may include:
a heavy chain variable region of SEQ ID NO: 155 and a light chain variable region of SEQ ID NO: 356;
a heavy chain variable region of SEQ ID NO: 158 and a light chain variable region of SEQ ID NO: 359;
a heavy chain variable region of SEQ ID NO: 165 and a light chain variable region of SEQ ID NO: 366;
a heavy chain variable region of SEQ ID NO: 171 and a light chain variable region of SEQ ID NO: 372;
a heavy chain variable region of SEQ ID NO: 175 and a light chain variable region of SEQ ID NO: 376;
a heavy chain variable region of SEQ ID NO: 176 and a light chain variable region of SEQ ID NO: 377;
a heavy chain variable region of SEQ ID NO: 178 and a light chain variable region of SEQ ID NO: 379;
a heavy chain variable region of SEQ ID NO: 181 and a light chain variable region of SEQ ID NO: 382; or
a heavy chain variable region of SEQ ID NO: 181 and a light chain variable region of SEQ ID NO: 386.

The part represented by X or Xaa in the sequence according to the present disclosure refers an unspecified amino acid and indicates that any amino acid can be included.

"Phage display" is a technique for displaying a mutant polypeptide as a fusion protein with at least a part of a coat protein, for example, on the surface of the particle of a phage, for example, a fibrous phage. The usefulness of phage display is to rapidly and efficiently classify sequences that bind to target antigens with high affinity in large libraries of randomized protein mutants. Displaying peptides and protein libraries on phages has been used to screen millions of polypeptides in order to identify polypeptides with specific binding properties.

Phage display technology has offered a powerful tool for generating and screening novel proteins that bind to specific ligands (e.g., antigens). Using the phage display technology, large libraries of protein mutants can be generated, and sequences binding with high affinity to target antigens can be rapidly classified. The nucleic acid encoding mutant polypeptides is fused with the sequence of nucleic acid encoding viral coat proteins, e.g., gene III proteins or gene VIII proteins. A monophasic phage display system, in which a nucleic acid sequence encoding protein or polypeptide is fused with a nucleic acid sequence encoding a part of the gene III protein, has been developed. In the monophasic display system, a fused gene is expressed at a low level, a wild-type gene III protein is also expressed, and thus particle infectivity is maintained.

It is important to demonstrate the expression of peptides on the fibrous phage surface and the expression of functional antibody fragments in the peripheral cytoplasm of E. coli for the development of antibody phage display libraries. Libraries of antibody- or antigen-binding polypeptides are prepared by a number of methods, for example, of modifying a single gene by inserting a random DNA sequence, or cloning a related gene sequence. The libraries can be screened for the expression of antibody- or antigen-binding proteins with desired characteristics.

Phage display technology has several advantages over conventional hybridomas and recombinant methods for producing antibodies with desired characteristics. This technique provides the generation of large antibody libraries with a variety of sequences within a short time without using animals. The production of hybridomas and the production of humanized antibodies may require a production time of several months. In addition, since no immunity is required, the phage antibody libraries can generate antibodies against antigens that are toxic or have low antigenicity. The phage antibody libraries can also be used to produce and identify novel therapeutic antibodies.

Techniques for generating human antibodies from non-immunized humans, germline sequences, or naive B cell Ig repertoires that have been immunized using phage display libraries can be used. Various lymphatic tissues can be used to prepare native or non-immunogenic antigen-binding libraries.

Techniques for identifying and separating high-affinity antibodies from phage display libraries are important for the separation of new therapeutic antibodies. The separation of high-affinity antibodies from the libraries can depend on the size of the libraries, the production efficiency in bacterial cells and the variety of libraries. The size of the libraries is reduced by inefficient folding of the antibody- or antigen-binding protein and inefficient production due to the presence of the stop codon. Expression in bacterial cells can be inhibited when the antibody- or antigen-binding domain is not properly folded. The expression can be improved by alternately mutating residues on the surface of the variable/constant interfaces or the selected CDR residues. The sequence of the framework region is an element to provide appropriate folding when generating antibody phage libraries in bacterial cells.

It is important to generate various libraries of antibody- or antigen-binding proteins in the separation of high-affinity antibodies. CDR3 regions have been found to often participate in antigen binding. Since the CDR3 region on the heavy chain varies considerably in terms of size, sequence and structurally dimensional morphology, various libraries can be prepared using the same.

Also, diversity can be created by randomizing the CDR regions of variable heavy and light chains using all 20 amino acids at each position. The use of all 20 amino acids results in antibody sequences with an increased diversity and an increased chance of identifying new antibodies.

The antibody or antibody fragment according to the present disclosure may include sequences of the anti-PD-1 antibody of the present disclosure described herein as well as biological equivalents thereto so long as the antibody or antibody fragment can specifically recognize PD-1. For example, an additional variation can be made to the amino acid sequence of the antibody in order to further improve the binding affinity and/or other biological properties of the antibody. Such a variation include, for example, deletion, insertion and/or substitution of amino acid sequence residues of the antibody. Such an amino acid variation are made, based on the relative similarity (identity) of amino acid side chain substituent, such as hydrophobicity, hydrophilicity, charge or size. Analysis of the size, shape and type of amino acid side chain substituent, demonstrates that all of arginine, lysine and histidine are positively charged residues, alanine, glycine and serine have similar sizes, and phenylalanine, tryptophan and tyrosine have similar shapes. Thus, based on these considerations, arginine, lysine and histidine; and alanine, glycine and serine; and phenylalanine, tryptophan and tyrosine are considered to be biologically functional equivalents.

In another aspect, the present disclosure relates to a nucleic acid encoding the antibody or an antigen-binding fragment thereof.

The antibody or antigen-binding fragment thereof can be recombinantly produced by isolating the nucleic acid encoding the antibody or antigen-binding fragment thereof according to the present disclosure. The nucleic acid is isolated and inserted into a replicable vector to conduct further cloning (amplification of DNA) or further expression. Based on this, in another aspect, the present disclosure is directed to a vector containing the nucleic acid.

The term "nucleic acid" is intended to encompass both DNA (gDNA and cDNA) and RNA molecules, and nucleotides, which are basic constituent units of the nucleic acid, include naturally derived nucleotides as well as analogues wherein sugar or base moieties are modified. The sequence of the nucleic acid encoding heavy and light chain variable regions of the present disclosure can be varied. Such a variation include addition, deletion, or non-conservative substitution or conservative substitution of nucleotides.

The amino acid sequence of the antibody or antigen-binding fragment thereof, or the nucleic acid encoding the same according to the present disclosure is also interpreted to include a sequence showing a substantial identity with the sequence set forth in the corresponding SEQ ID NO. The term "sequence showing a substantial identity" means a sequence that shows an identity of at least 90%, most preferably, at least 95%, 96% or more, 97% or more, 98% or more, or 99% or more, when aligning the sequence of the present disclosure so as to correspond to any other sequence as much as possible and analyzing the aligned sequence using an algorithm commonly used in the art.

Based on this, the antibody or antigen-binding fragment thereof according to the present disclosure can have a sequence identity of 90%, 91%, 92%, 93%, 94%, 95%, 96%, 97%, 98%, or 99% or more. Such an identity can be determined by the comparison and/or alignment of sequences by methods known in the art. For example, the percent sequence identity of the nucleic acid or protein according to the present disclosure can be determined using a sequence comparison algorithm (i.e., BLAST or BLAST 2.0), manual alignment or visual inspection.

The DNA encoding the antibody can be easily separated or synthesized using conventional procedures (for example, using an oligonucleotide probe specifically binding to DNA encoding heavy and light chains of the antibody). A variety of vectors are obtainable. Vector components generally include, but are not limited to, one or more of the following components: signal sequences, replication origins, one or more marker genes, enhancer elements, promoters and transcription termination sequences.

As used herein, the term "vector" refers to a means for expressing target genes in host cells and includes: plasmid vectors; cosmid vectors; and viral vectors such as bacteriophage vectors, adenovirus vectors, retroviral vectors and adeno-associated viral vectors. The nucleic acid encoding the antibody in the vector is operatively linked to a promoter.

The term "operatively linked" means a functional linkage between a nucleic acid expression regulation sequence (e.g., promoter, signal sequence or array of transcription regulator binding site) and another nucleic acid sequence, and is regulated by transcription and/or translation of the nucleic acid sequence.

When a prokaryotic cell is used as a host, the vector generally includes a potent promoter capable of conducting transcription (such as tac promoter, lac promoter, lacUV5 promoter, 1pp promoter, pLλ promoter, pRλ promoter, racy promoter, amp promoter, recA promoter, SP6 promoter, trp promoter, or T7 promoter), a ribosome binding site to initiate translation, and a transcription/translation termination sequence. In addition, for example, when a eukaryotic cell is used as a host, the vector includes a promoter (e.g., a metallothionein promoter, a β-actin promoter, a human hemoglobin promoter and a human muscle creatine promoter) derived from the genome of mammalian cells, or a promoter derived from animal virus such as adenovirus late promoter, vaccinia virus 7.5K promoter, SV40 promoter, cytomegalovirus (CMV) promoter, HSV tk promoter, mouse breast tumor virus (MMTV) promoter, HIV LTR promoter, Moloney virus promoter, Epstein Barr virus (EBV) promoter, and Rous sarcoma virus (RSV) promoter), and generally has a polyadenylation sequence as a transcription termination sequence.

Optionally, the vector may be fused with another sequence to facilitate purification of the antibody expressed therefrom. The sequence to be fused includes, for example, glutathione S-transferase (Pharmacia, USA), maltose-binding protein (NEB, USA), FLAG (IBI, USA), 6× His (hexahistidine; Quiagen, USA) and the like.

The vector includes antibiotic-resistant genes commonly used in the art as selectable markers and examples thereof include genes resistant to ampicillin, gentamycin, carbenicillin, chloramphenicol, streptomycin, kanamycin, geneticin, neomycin and tetracycline.

In another aspect, the present disclosure is directed to a cell transformed with the above-mentioned vector. The cell used to produce the antibody of the present disclosure may be a prokaryote, yeast or higher eukaryotic cell, but is not limited thereto.

Strains of the genus *Bacillus* such as *Escherichia coli*, *Bacillus subtilis* and *Bacillus tuligensis*, *Streptomyces*, *Pseudomonas* (for example, *Pseudomonas putida*), and prokaryotic host cells such as *Proteus mirabilis* and *Staphylococcus* (for example, *Staphylococcus carnosus*) can be used.

The interest in animal cells is the largest and examples of useful host cell lines include, but are not limited to, COS-7, BHK, CHO, CHOK1, DXB-11, DG-44, CHO/−DHFR, CV1, COS-7, HEK293, BHK, TM4, VERO, HELA, MDCK, BRL 3A, W138, Hep G2, SK-Hep, MMT, TRI, MRC 5, FS4, 3T3, RIN, A549, PC12, K562, PER.C6, SP2/0, NS-0, U20S, or HT1080.

In another aspect, the present disclosure is directed to a method for producing the antibody or an antigen-binding fragment thereof, including: (a) culturing the cells; and (b) recovering the antibody or an antigen-binding fragment thereof from the cultured cells.

The cells can be cultured in various media. Any commercially available medium can be used as a culture medium without limitation. All other essential supplements well-known to those skilled in the art may be included in appropriate concentrations. Culture conditions such as temperature and pH have already been used with selected host cells for expression, which will be apparent to those skilled in the art.

As used herein, the term "transformation" means introduction of a vector containing a nucleic acid encoding a target protein into a host cell so that protein encoded by the nucleic acid can be expressed in the host cell. The transformed nucleic acid includes both a transformed nucleic acid inserted into and positioned at the chromosome of the host cell, and a transformed nucleic acid positioned outside the chromosome, so long as it can be expressed in the host cell. In addition, the nucleic acid includes DNA and RNA encoding the target protein. The nucleic acid may be introduced in any form so long as it can be introduced into a host cell and expressed therein. For example, the nucleic acid can be introduced into the host cell in the form of an expression cassette, which is a gene construct containing all the elements necessary for self-expression. The expression cassette typically includes a promoter, a transcription termination signal, a ribosome binding site and a translation termination signal, which is operably linked to the nucleic acid. The expression cassette may take an expression vector allowing for self-replication. The nucleic acid may also be introduced into the host cell in its own form and be operably linked to the sequence necessary for expression in the host cell.

The recovery of the antibody or antigen-binding fragment thereof can be carried out, for example, by centrifugation or ultrafiltration to remove impurities, and purification of the resulting product, for example, using affinity chromatography. Additional other purification techniques such as anion or cation exchange chromatography, hydrophobic interaction chromatography, hydroxyl apatite chromatography and the like may be used.

In another aspect, the present disclosure is directed to a composition for preventing or treating cancer containing the antibody or antigen-binding fragment thereof as an active ingredient.

The present disclosure provides, for example, a composition for preventing or treating cancer containing: (a) a pharmaceutically effective amount of the antibody to PD-1 or an antigen-binding fragment thereof according to the invention; and (b) a pharmaceutically acceptable carrier. The present disclosure also relates to a method for preventing or treating cancer including administering the antibody to PD-1 or an antigen-binding fragment thereof according to the present disclosure in an effective amount required for a patient.

In the present disclosure, the cancer is preferably selected from the group consisting of melanoma, lung cancer, liver cancer, gliocytoma, ovarian cancer, colon cancer, head and neck cancer, bladder cancer, kidney cancer, stomach cancer, breast cancer, metastatic cancer, Hodgkin's lymphoma, prostate cancer and pancreatic cancer, but is not limited thereto.

As used herein, the term "treatment" means suppression or alleviation of cancer or one or more symptoms caused thereby, as well as prevention of the progress of cancer or the treatment of cancer, which reverses the symptoms of the disease, by administration of a composition and, as used herein, the term "prevention" means any action that inhibits or delays the progress of a cancer by administration of a composition. In the present disclosure, the prevention or treatment of cancer is carried out by binding between the antibody obtained according to the present disclosure, and PD-1. The antibody, which binds to PD-1, significantly inhibits activity of PD-1, thereby preventing or treating cancer.

The term "pharmaceutically acceptable carrier" as used herein refers to a carrier or diluent that does not impair biological activities or properties of an administered compound without irritating an organism. Acceptable pharmaceutical carriers for compositions, which are formulated into liquid solutions, are sterilized and biocompatible, and examples thereof include saline, sterile water, Ringer's solution, buffered saline, albumin injection solutions, dextrose solutions, maltodextrin solutions, glycerol, ethanol and mixtures of one or more thereof. If necessary, other conventional additives such as antioxidants, buffers and bacteriostatic agents may be added. In addition, diluents, dispersants, surfactants, binders and lubricants can be additionally added to formulate injectable solutions such as aqueous solutions, suspensions and emulsions, pills, capsules, granules or tablets.

The composition for preventing or treating cancer containing the antibody and the pharmaceutically acceptable carrier can be applied to any formulation containing the same as an active ingredient and can be prepared for oral or parenteral formulation. The pharmaceutical formulation may include formulations suitable for oral, rectal, nasal, topical (including under the cheek and tongue), subcutaneous, vaginal or parenteral (including intramuscular, subcutaneous and intravenous) administration, or inhalation or insufflation.

Examples of formulations for oral administration containing the composition of the present disclosure as an active ingredient include tablets, troches, lozenges, aqueous or oily suspensions, prepared powders or granules, emulsions, hard or soft capsules, syrups or elixirs. In order to prepare formulations such as tablets and capsules, a binder such as lactose, saccharose, sorbitol, mannitol, starch, amylopectin, cellulose or gelatin, an excipient such as dicalcium phosphate, a disintegrating agent such as corn starch or sweet potato starch, a lubricant such as calcium stearate, sodium stearyl fumarate or polyethyleneglycol wax can be incorporated, and capsule formulations may further contain a liquid carrier such as a fatty oil, in addition to the above-mentioned ingredients.

Examples of the formulations for parenteral administration containing the composition of the present disclosure as an active ingredient include injection forms such as subcutaneous injection, intravenous injection or intramuscular injection, suppository or spray forms such as aerosols inhalable through a breathing apparatus. For preparation into injectable formulations, the compositions of the present disclosure can be mixed in water with stabilizers or buffers to prepare solutions or suspensions and the solutions or suspensions can be formulated on the basis of an ampule or vial unit for administration. For suppository injection, compositions for rectal administration such as suppositories or enema preparations containing a conventional suppository base such as cocoa butter or other glycerides can be formulated. For spray formulation such as an aerosol, an additive such as a propellant may be mixed such that a water-dispersed concentrate or wet powder is dispersed.

In another aspect, the present disclosure is directed to a method for preventing or treating cancer including administering a composition for preventing or treating cancer containing the antibody.

As used herein, the term "administration" refers to introducing the pharmaceutical composition according to the present disclosure into a patient by any appropriate method. The route of administration of the composition of the present disclosure may be any route including oral or parenteral routes. Specifically, the pharmaceutical composition can be administered in a conventional manner via an oral, rectal, topical, intravenous, intraperitoneal, intramuscular, intraarterial, transdermal, intranasal, inhalation, ocular or intradermal route.

The treatment method of the present disclosure includes administering a pharmaceutically effective amount of the composition for preventing or treating cancer according to the present disclosure. It will be apparent to those skilled in the art that an appropriate total daily dose can be determined by a medical specialist's suitable judgment. The specific therapeutically effective amount for a certain patient preferably depends upon a variety of factors including the type and extent of the response to be achieved, as well as presence of other agents used, the specific composition, and age, body weight, general health conditions, gender and diet of the patient, administration time, administration route and the secretion rate of the composition, treatment period, and drugs used in conjunction with or concurrently with the specific composition, and upon similar factors well-known in the pharmaceuticals field. Therefore, the effective amount of the composition for preventing or treating cancer, which is suitable for the object of the present disclosure, is preferably determined in consideration of the aforementioned factors.

In addition, the treatment method of the present disclosure can be applied to any animal that may develop diseases such as tumor development and neovascularization due to excessive activity of PD-1, and the animal includes humans and primates as well as livestock such as cows, pigs, sheep, horses, dogs and cats.

In another aspect, the present disclosure is directed to a composition for diagnosing cancer containing the PD-1 antibody or an antigen-binding fragment thereof according to the present disclosure. Also, the present disclosure is directed to a method for diagnosing cancer by treatment with the PD-1 antibody or an antigen-binding fragment thereof according to the present disclosure.

Cancer can be diagnosed by measuring the level of PD-1 expression in a sample through the antibody to PD-1 according to the present disclosure. The level of expression can be measured by a conventional immunoassay method that includes, but is not limited to, radioimmunoassay, radioimmunoprecipitation, immunoprecipitation, immunohistochemical staining, enzyme-linked immunosorbent assay (ELISA), captured-ELISA, inhibition or competition analysis, sandwich analysis, flow cytometry, immunofluorescent staining and immunoaffinity purification using the antibody to PD-1.

Cancer can be diagnosed by analyzing the intensity of the final signal by the immunoassay process. That is, when protein of a marker according to the present disclosure is highly expressed in a biological sample and thus the signal of biological sample is stronger than that of a normal biological sample (for example, normal stomach tissue, blood, plasma or serum), cancer is diagnosed.

In another aspect, the present disclosure is directed to a kit for diagnosing cancer containing the composition for diagnosing cancer. The kit according to the present disclosure includes the antibody to PD-1 according to the present disclosure and can diagnose cancer by analyzing a signal generated upon reaction between a sample and the antibody. The signal may include, but is not limited to, an enzyme coupled to an antibody such as alkaline phosphatase, β-galactosidase, horseradish peroxidase, luciferase or cytochrome P450. In this case, when alkaline phosphatase is used as an enzyme, as a substrate for the enzyme, a chromogenic reaction substrate such as bromochloroindole phosphate (BCIP), nitroblue tetrazolium (NBT), naphthol-AS-B1-phosphate and ECF (enhanced chemifluorescence) are used, and when horseradish peroxidase is used, a substrate such as chloronaphthol, aminoethylcarbazole, diaminobenzidine, D-luciferin, lucigenin (Bis-N-methyl acridinium nitrate), resorufin benzyl ether, luminol, Amplex Red reagent (10-acetyl-3,7-dihydroxy phenoxazine), HYR (p-phenylenediamine-HCl and pyrocatechol), TMB (tetramethylbenzidine), ABTS (2,2'-Azine-di[3-ethylbenzthiazoline sulfonate]), o-phenylenediamine (OPD) and naphthol/pyronin, glucose oxidase, t-NBT (nitroblue tetrazolium) or m-PMS (phenzaine methosulfate) is used, but the present disclosure is not limited thereto.

In addition, the kit according to the present disclosure may also include a label for generating a detectable signal and the label may include a chemical (e.g., biotin), an enzyme (alkaline phosphatase, β-galactosidase, horseradish peroxidase and cytochrome P450), a radioactive substance (such as C14, I125, P32 and S35), a fluorescent substance (such as fluorescein), a luminescent substance, a chemiluminescent substance and FRET (fluorescence resonance energy transfer), but is not limited thereto.

Measurement of the activity of the enzyme used for cancer diagnosis or measurement of the signal can be carried out by a variety of methods known in the art. Thus, PD-1 expression can be qualitatively or quantitatively analyzed.

Hereinafter, the present disclosure will be described in more detail with reference to examples. However, it is obvious to those skilled in the art that these examples are provided only for illustration of the present disclosure and should not be construed as limiting the scope of the present disclosure.

Example 1: Expression and Purification of PD-1 Antigen

1. Production of PD-1 Protein Expression Vectors

For cloning of PD-1, amplification was conducted through polymerase chain reaction (PCR) using primers for PD1 containing restriction enzyme SfiI sites at 5' and 3' (Table 1) in order to obtain only an extracellular domain using Jurkat cell cDNA libraries (Stratagene, USA). The amplified PCR product was prepared by fusing human Fc (SEQ ID NO: 196) and mouse Fc (SEQ ID NO: 197) to a carboxyl terminal using N293F vector (FIG. 1).

TABLE 1

| Name | 5'→3' sequence | SEQ ID NO. |
|---|---|---|
| PD1-F | ccaggatggttcttagactcccc | 194 |
| PD1-R | caccagggtttggaactggc | 195 |

2. Expression and Purification of PD-1 Antigen

In order to express an antigen in animal cells, HEK-293F cells were transfected with plasmid DNA. The polyplex reaction solution for transfection was prepared by mixing 25 μg of plasmid DNA with 3 ml of a Freestyle 293 expression medium and further mixing 2 mg/ml of PET (polyethylenimine, polyplusA-transfection, USA) with the resulting mixture again. The polyplex reaction solution was reacted at room temperature for 15 minutes and then cultured in 40 ml of the culture medium having a concentration of 1×10$^6$ cells/ml for 24 hours at 37° C. and 8% $CO_2$ at 120 rpm. After 24 hours of transfection, Soytone (BD, USA), as a supplement, is added to a final concentration of 10 g/L. Antibodies were produced using a transient expression system using HEK-293F for 7 days. Affinity chromatography was performed to obtain the antigen from the culture solution. The supernatant was obtained by centrifugation at 5,000 rpm for 10 minutes to remove cells and cell debris from the culture medium recovered on the 7th day. The supernatant was reacted with a recombinant protein A agarose resin washed with DPBS at 4° C. for 16 hours.

When the recombinant protein A agarose resin was used, the protein was eluted with 0.1M glycine and neutralized with 500 μl of 1M Tris-HCl to perform primary purification. The primarily purified protein was secondarily purified using Superdex 200 (1.5 cm*100 cm) gel filtration chromatography.

The purity of the purified protein was identified by SDS-PAGE gel and size exclusion chromatography [TSK-GEL G-3000 SWXL size-exclusion chromatography (SEC) (Tosoh)].

As a result, it was confirmed that the purified PD1 protein had a purity of 95% or more, as shown in FIGS. 2A to 2D.

Example 2: Screening of PD-1 Human Antibodies

1. Antigen Preparation

PD1-hFc and PD1-mFc prepared in Example 1 and PD1-his (Catalog Number, 10377-H08H) purchased from Sino Biological Inc. as protein antigens were coated in a dose of 50 ug on an immunosorbent tube and then blocked.

2. Bio-Panning

A human antibody library phage was obtained by infecting a human scFv library with a variety of 2.7×10$^{10}$ with bacteria and then culturing at 30° C. for 16 hours. After culturing, the culture solution was centrifuged, and the supernatant was concentrated with PEG, and then dissolved in PBS buffer to prepare a human antibody library. The human antibody library phage was charged into an immune tube, followed by reaction at room temperature for 2 hours. After washing with 1×PBS/T and 1×PBS, only the scFv-phages specifically bound to the antigen were eluted.

The eluted phages were infected with E. coli again and amplified (panning process) to obtain a pool of positive phages. The second and third round panning processes were conducted using the phages amplified in the first round of panning in the same manner as above, except that only the number of times of the PBST washing step was increased.

As a result, as shown in Table 2, it was seen that the number of phages bound to the antigen (output) during the third round panning was slightly increased, as compared to the input phages.

TABLE 2

| Number of (times) of panning | Number of input phages | Number of output phages |
|---|---|---|
| 1 | 2 × 10$^{13}$ | 3.6 × 10$^7$ |
| 2 | 1.2 × 10$^{13}$ | 7 × 10$^7$ |
| 3 | 2 × 10$^{13}$ | 2 × 10$^9$ |

3. Polyphage ELISA

Polyphage ELISA (enzyme linked immunoassay) was conducted to investigate specificity to an antigen of the positive poly scFv-phage antibody pool obtained by each round of the panning process in Example 2.

The cell stock frozen after the first to third panning processes was added to a medium containing 5 ml of 2×YTCM, 2% glucose and 5 mM $MgCl_2$ to $OD_{600}$ of 0.1 and then cultured at 37° C. for 2 to 3 hours ($OD_{600}$=0.5 to 0.7). M1 helper phages were infected and cultured in a medium containing 2×YTCMK, 5 mM $MgCl_2$, and 1 mM IPTG at 30° C. for 16 hours. The cultured cells were centrifuged (4,500 rpm, 15 min, 4° C.), and the supernatant was transferred to a new tube (first to third-panned poly scFv-phages). Two kinds of antigens were each coated at a density of 100 ng/well on 96-well immuno-plates (NUNC 439454) with coating buffer at 4° C. for 16 hours, and each well was blocked using 4% skim milk dissolved in PBS.

Each well was washed with 0.2 ml of PBS/T, and 100 μl of the first to third-panned poly scFv-phage was added to each well, followed by reaction at room temperature for 2 hours. Again, each well was washed 4 times with 0.2 ml of PBS/T, and the secondary antibody, anti-M13-HRP (Amersham 27-9421-01) was diluted at 1:2000 and reacted at room temperature for 1 hour. After washing with PBS/T, OPD tablets (Sigma. 8787-TAB) were dissolved in PC buffer, and the resulting solution was added at a concentration of 100 μl/well to induce color development for 10 minutes. Then, absorbance was measured at 490 nm with a spectrophotometer (Molecular Device).

The results are shown in FIG. 3. As can be seen from FIG. 3, ELISA showed that binding capacity to two PD-1 antigens was enriched in the third poly scFv-phages.

4. Screening of Positive Phages

Colonies obtained from the polyclonal phage antibody group (third panning) with high binding capacity were cultured in a 1 ml 96-deep well plate (Bioneer 90030) at 37° C. for 16 hours. 100 to 200 μl of the cells grown thus were added to a medium containing 2×YTCM, 2% glucose and 5 mM $MgCl_2$, to $OD_{600}$ of 0.1, and were added to a medium containing 1 ml of 2×YTCM, 2% glucose and 5 mM $MgCl_2$, and then cultured in a 96-deep well plate at 37° C. for 2 to 3 hours to $OD_{600}$ of 0.5 to 0.7. M1 helper phages were infected at an MOI of 1:20 and cultured in a medium containing 2×YTCMK, 5 mM $MgCl_2$, 1 mM IPTG at 30° C. for 16 hours.

The antigen PD1 was coated at a density of 100 ng/well on a 96-well immunoplate at 4° C. for 16 hours and each well was blocked using 4% skim milk dissolved in PBS. Each monoclonal scFv-phage (100 scFv-phage) washed with 0.2 ml PBS/T and cultured for 16 hours was added in a dose of 100 μl to each well and reacted at room temperature for 2 hours. Again, each well was washed 4 times with 0.2 ml of PBS/T, and the secondary antibody, anti-M13-

HRP, was diluted to 1/2000 and reacted at room temperature for 1 hour. After washing with 0.2 ml of PBS/T, color development was performed and absorbance was measured at 490 nm.

As a result, as shown in FIG. 4, a total of several tens of single-phage clones for PD1 were obtained as single-phage clones having high binding capacity to each antigen.

5. Base Sequence Analysis of Positive Phage Antibodies

The selected single clones were subjected to DNA-prep using a DNA purification kit (Qiagen, Germany) to obtain DNAs, and sequence analysis for DNAs was requested (Solgent). The CDR regions of VH and VL of the selected antibodies were identified, based on results of sequence analysis and the similarity (identity) between these antibodies and germ line antibody groups was investigated using an Ig BLAST program on the NCBI website at http://www.ncbi.nlm.nih.gov/igblast/. As a result, 15 species of phage antibodies specific to PD1 were obtained and are summarized in Table 3 below.

TABLE 3

Characteristics of PD1 monoclones

| Clone name | VH | Identity | VL | Identity | Group |
|---|---|---|---|---|---|
| Nivolumab | VH3-33 | 91.80% | L6 | 98.90% | |
| Pembrolizumab | VH1-2 | 79.60% | L25 | 80.80% | |

TABLE 3-continued

Characteristics of PD1 monoclones

| Clone name | VH | Identity | VL | Identity | Group |
|---|---|---|---|---|---|
| PD1-29A2 | VH3-9 | 91.80% | V2-17 | 86.50% | 1 |
| PD1-29H3 | VH3-9 | 90.80% | V1-11 | 88.50% | 2 |
| PD1-31F3 | VH1-69 | 92.90% | V1-13 | 93.90% | 3 |
| PD1-32A6 | VH1-69 | 87.80% | L5 | 91.60% | 4 |
| PD1-41C9 | VH3-30 | 95.80% | O1 | 92.10% | 5 |
| PD1-42G4 | VH3-11 | 93.80% | O2 | 93.80% | 6 |
| PD1-44B5 | VH3-30 | 99.00% | V1-16 | 85.60% | 7 |
| PD1-45D6 | VH3-30 | 95.80% | O1 | 93.10% | 8 |
| PD1-45F1 | VH1-46 | 91.80% | V2-13 | 93.80% | 9 |
| PD1-45F4 | VH3-9 | 90.80% | V2-1 | 77.70% | 10 |
| PD1-48A9 | VH1-69 | 79.60% | O1 | 96.00% | 11 |
| PD1-49B9 | VH3-9 | 88.70% | V1-2 | 93.90% | 12 |
| PD1-49A2 | VH3-30 | 97.90% | O1 | 93.10% | 13 |
| PD1-51D9 | VH1-3 | 82.70% | A3 | 94.00% | 14 |
| PD1-52E8 | VH3-9 | 91.80% | V2-17 | 90.50% | 15 |

Antibodies including the heavy and light-chain CDRs and FR sequences of the selected antibodies, and the heavy chain variable regions and light chain variable regions including the same are shown in Tables 4 and 5 below.

TABLE 4

Heavy chain variable regions of PD1 clones

| NAME | FR1 | CDR1 | FR2 | CDR2 | FR3 | CDR3 | FR4 |
|---|---|---|---|---|---|---|---|
| PD1-45D6 | QVQLVES GGGVVQP GRSLRLSC AAS | GFT FSS YA | MHWVRQ VPGKGLE WVAV | ISY DGN DK | YYADSVKGRFTISRDN SKNTLYLQMNSLRAE DTAVYYC | VPTTFEY | WGQG SQVT VSS |
| SEQ ID NO | 80 | 1 | 96 | 31 | 114 | 57 | 135 |
| PD1-49A2 | QVQLVES GGGVVQP GRSLRLSC AAS | GFT FSS YA | MHWVRQ APGKGLE WVAV | ISY DGS NK | YYADSVKGRFTISRDN PKNTLYLQMNSLRAE DTAVYYC | TTTTFDS | WGRG TLVT VSS |
| SEQ ID NO | 80 | 1 | 97 | 32 | 115 | 58 | 136 |
| PD1-27A12 | QVQLVES GGGLVQP GRSLRLSC AAS | GFT FND YA | MHWVRQ VPGKGLE WVSG | ISW NSG RI | VYADSMKGRFTISRDN AKNSLYLQMNSLRAE DTAVYYC | ARSQQQIL DY | WGQG TLVT VSS |
| SEQ ID NO | 81 | 2 | 98 | 33 | 116 | 59 | 137 |
| PD1-27B1 | QVQLVES GGGLVKP GGSLRLSC AAS | GFT FND YA | MHWVRQ VPGKGLE WVSG | ISW NSG RI | VYADSMKGRFTISRDN AKNSLYLQMNSLRAE DTAVYYC | ARSIRQILD Y | WGQG TLVT VSS |
| SEQ ID NO | 82 | 2 | 98 | 33 | 116 | 60 | 137 |
| PD1-28D12 | QVQLVES GGGLVQP GRSLRLSC AAS | GFT FND YA | MHWVRQ VPGKGLE WVSG | ISW NSG RI | VYADSMKGRFTISRDN AKNSLYLQMNSLRAE DTAVYYC | ARSLPXSR SRLDV | WGQG TLVT VSS |
| SEQ ID NO | 81 | 2 | 98 | 33 | 116 | 61 | 137 |
| PD1-29A2 | QVQLVES GGGLVQP GRSLRLSC AAS | GFT FND YA | MHWVRQ VPGKGLE WVSG | ISW NSG RI | VYADSMKGRFTISRDN AKNSLYLQMNSLRAE DTAVYYC | ARAXTSPL DMSLDY | WGQG TLVT VSS |
| SEQ ID NO | 81 | 2 | 98 | 33 | 116 | 62 | 137 |

TABLE 4-continued

Heavy chain variable regions of PD1 clones

| NAME | FR1 | CDR1 | FR2 | CDR2 | FR3 | CDR3 | FR4 |
|---|---|---|---|---|---|---|---|
| PD1-29H3 | QMQLVES GGNLVQP GRSLRLSC AAS | GFT FDD YG | MHWVRQ APGKGLE WVSS | ISW NSG TI | GYADSVKGRFTISRDN AKNSLYLQMNSLRSE DTAVYYC | ARLLHQM NEHEFMD V | WGQG TTVT VSS |
| SEQ ID NO | 83 | 3 | 99 | 34 | 117 | 63 | 138 |
| PD1-31F3 | QVQLVQS GAEVKKP GSSVKVSC KAS | GGT FSS YA | ISWVRQA PGQGLEW MGG | IIPL FST A | HSAQKFQGRVTITADE SSSTAYMELSSLRSED TAVYYC | AKHKGLPF DWSPDGFD T | WGQG TMVT VSS |
| SEQ ID NO | 84 | 4 | 100 | 35 | 118 | 64 | 139 |
| PD1-32A6 | QVQLVQS GAEVKKP GSSVKVSC KAS | GDT FTR NA | VSWVRQA PGEGLEW MAD | IIPIF GSA | NYAQKFQGRLTLTAD VSTSTAYMELSSLRSE DTAVYYC | ARTIEGAF DI | WGQG TMVT VSS |
| SEQ ID NO | 84 | 5 | 101 | 36 | 119 | 65 | 139 |
| PD1-41C9 | QMQLVES GGGVVQP GRSLRLSC AAS | GFT FSS YA | MHWVRQ APGKGLE WVAV | ISY DGS NK | YYADSVKGRFTISRDN SKNTLYLQMNRLRSE DTAVYYC | TTTTFDS | WGQG TLITV SS |
| SEQ ID NO | 85 | 1 | 97 | 32 | 120 | 58 | 140 |
| PD1-42G4 | QVQLVES GGGLVKP GGSLRLSC AAS | GFT FSD YY | MSWIRQA PGKGLEW VSD | ISAS GNS I | YYADSVKRRFTISRDN SKNSLYLQMNSLRAE DTAVYYC | VTSGPFGE FRN | WGLG TLVT VSS |
| SEQ ID NO | 82 | 6 | 102 | 37 | 121 | 66 | 141 |
| PD1-44B5 | QVQLVES GGGVVQP GRSLRLSC AAS | GFT FSS YA | MHWVRQ APGKGLE WVAV | ISY DGS NK | YYADSVKGRFTISRDN SKNTLYLQMNSLRAE DTAVYYC | ARLMHTFS VQYFLDV | WGQG TTVT VSS |
| SEQ ID NO | 80 | 1 | 97 | 32 | 114 | 67 | 138 |
| PD1-45D6 | QVQLVES GGGVVQP GRSLRLSC AAS | GFT FSS YA | MHWVRQ VPGKGLE WVAV | ISY DGN DK | YYADSVKGRFTISRDN SKNTLYLQMNSLRAE DTAVYYC | VPTTFEY | WGQG SQVT VSS |
| SEQ ID NO | 80 | 1 | 96 | 31 | 114 | 57 | 135 |
| PD1-45F1 | QVQLVQS GAEVKKP GASVKLSC KAS | GYT FNS YY | VHWVRQ APGQGLE WMGI | INPS DGS A | TYAQKFQGRVTMTSD TSTSSVYMELSSLRSE DTAVYYC | ARDGNYY DSRGYYY DTFDM | WGQG TLITV SS |
| SEQ ID NO | 86 | 7 | 103 | 38 | 122 | 68 | 140 |
| PD1-45F4 | QMQLVES GGGLVQP GRSLRLSC AAS | GFT FDD YA | MHWVRQ APGQGLE WVSG | ISW NSN NI | KYADSVKGRFTISRDN SKNSLYLQMNSLRAE DTAVYYC | ARGALTPL DV | WGQG TPVT VSS |
| SEQ ID NO | 87 | 8 | 104 | 39 | 123 | 69 | 142 |
| PD1-47B8 | QMQLVQS GAEVKKP GASVKVS CKAS | GYT FTS YD | INWVRQA SGQAPEW MGW | LHA DSG KT | GYAQTFQGRVTMTRD TSIDTAYLELSSLRSED TAVYYC | ARGTHWL DS | WGQG TLVT VSS |
| SEQ ID NO | 88 | 9 | 105 | 40 | 124 | 70 | 137 |
| PD1-48A6 | QVQLVQS GGGLIQPG GSLRLSCA AS | GFT VSR NS | MNWVRQ TPGKGPE WVSL | IFSG GTT K | YKDSVKGRFTISRDNS KNTLYLQMNSLRAED TAVYYCA | AREEQFLI ALAGRYFD Y | WGQG TLVT VSS |
| SEQ ID NO | 89 | 10 | 106 | 41 | 125 | 71 | 138 |

TABLE 4-continued

Heavy chain variable regions of PD1 clones

| NAME | FR1 | CDR1 | FR2 | CDR2 | FR3 | CDR3 | FR4 |
|---|---|---|---|---|---|---|---|
| PD1-48A9 | QMQLVQSGAEVKKPGSSVKVSCKAS | GDTFTRYI | INWVRQAPGQGLEWMGR | VIPTLGLT | TYAQNFQDTVTIIADKSTNTAYMELKNLRSEDTAVYYC | ARGYGSGAFDI | WGQGTMITVSS |
| SEQ ID NO | 90 | 11 | 107 | 42 | 126 | 72 | 143 |
| PD1-48G6 | QMQLVESGGGVVQPGRSLRLSCAAS | GFTFSHYA | MHWVRQAPGKGLEWVAV | ISYDGSKI | YYADSVKGRFTVSRDNSKNTLYLQMNSLRAEDTAVYYC | ARIGYKDAFDI | WGQGTMVTVSS |
| SEQ ID NO | 85 | 12 | 97 | 43 | 127 | 73 | 139 |
| PD1-49A2 | QVQLVESGGGVVQPGRSLRLSCAAS | GFTFSSYA | MHWVRQAPGKGLEWVAV | ISYDGSNK | YYADSVKGRFTISRDNPKNTLYLQMNSLRAEDTAVYYC | TTTTFDS | WGRGTLVTVSS |
| SEQ ID NO | 80 | 1 | 97 | 32 | 115 | 58 | 136 |
| PD1-49B9 | QMQLVESGGGLVQPGRSLRLSCAAS | GFTFEDYA | MHWVRQPPGKGLEWVSS | ISWNSHNI | AYADSVKGRFTISRDNSKNSLYLQMNSLRAEDTAVYYC | STSGLGVHA | WGQGTMVTVSS |
| SEQ ID NO | 87 | 13 | 108 | 44 | 128 | 74 | 139 |
| PD1-51A6 | QVQLVESGGGLVQPGGSLRLSCAAS | GLSFSSYW | MTWVRQAPGKGLEWVAN | IKQDGSEK | YYVDSVKGRFTISRDNAKNSLYLQMNSLRAEDTAVYYC | ARDSFGGHLDL | WGQGTLVTVSS |
| SEQ ID NO | 91 | 14 | 109 | 45 | 129 | 75 | 137 |
| PD1-51D9 | QVQLVESGAEVKKPGASVKLSCKAS | GYTFSSYW | MHWVRQAPGQRLEWMGE | INPNGNGHT | NYNEKFKSRVTITVDKSASTAYMELSSLRSEDTAVYYC | AREGDGSYWGYFDS | WGQGTPITVSS |
| SEQ ID NO | 92 | 15 | 110 | 46 | 130 | 76 | 144 |
| PD1-52E8 | QVQLVQSGGNLVQPGRSLRLSCAAS | GFTFDDYA | MHWVRQAPGKGLEWVSG | ISWNSGTP | GYADSVQGRFTISRDNAKNSLYLQMNSLRAEDTAVYYC | ARGHNYLDSSYYDY | WGQGTLVTVSS |
| SEQ ID NO | 93 | 8 | 111 | 47 | 131 | 77 | 137 |
| PD1-62E1 | QVQLVESGGDLVKPGRSLRLSCTGS | GFTFGDHP | LTWVRQIPGKGLEWVGF | IRSKAYGE | TTEYAASVKGRFTISRDDSKSIAYLQMNSLRAEDTAVY | ASVSYCSGGSCYQGTFDY | WGQGTLVTVSS |
| SEQ ID NO | 94 | 16 | 112 | 48 | 132 | 78 | 137 |
| PD1-72D10 | QVQLVESGGGVVQPGRSLRLSCAAS | GFTFSSYA | MHWVRQAPGKGLEWVAV | ISYDGSNK | YYADSVKGRFTISRDNSKNTLYLQMNSLRAEDTAVYYC | TTTTFDS | WGQGTLVTVSS |
| SEQ ID NO | 80 | 1 | 97 | 32 | 114 | 58 | 137 |
| PD1-74A11 | QVQLVQSGGGVVQPGRSLRLSCAAS | GFTFSSYA | MHWVRQAPGKGLEWVAV | ISYDGSNK | YYADSVKGRFTISRDNSKNTLYLQMNSLRAEDTAVYYC | ARTTFDY | WGQGTLITVSS |
| SEQ ID NO | 95 | 1 | 97 | 32 | 114 | 79 | 140 |
| PD1-75C10 | QVQLVESGGGVVQPGRSLRLSCAAS | GFTFSSYA | MHWVRQAPGKGLEWVAV | ISYDGSNK | YYADSVKGRFTISRDNSKNTLYLQMNSLRAE | VPTTFEY | WGQGSQVT |

TABLE 4-continued

Heavy chain variable regions of PD1 clones

| NAME | FR1 | CDR1 | FR2 | CDR2 | FR3 | CDR3 | FR4 |
|---|---|---|---|---|---|---|---|
| | GRSLRLSC AAS | YA | WVAV | NK | DTAVYYC | | VSS |
| SEQ ID NO | 80 | 1 | 97 | 32 | 114 | 57 | 135 |
| PD1-74A01 | QVQLVES GGGVVQP GRSLRLSC AAS | GFT FSS YA | MHWVRQ APGKGLE WVAV | ISY DGS NK | YYADSVKGRFTISRDN SKNTLYLQMNSLRSED TAVYYC | VPTTFEY | WGQG SQVT VSS |
| SEQ ID NO | 80 | 1 | 97 | 32 | 133 | 57 | 135 |
| PD1-74H12 | QVQLVES GGGVVQP GRSLRLSC AAS | GFT FSS YA | MHWVRQ APGKGLE WVAV | ISY DGS NK | YYADSVKGRFTISRDN SKNMLYLEMNSLRAE DTAVYYC | VPTTFEY | WGQG SQVT VSS |
| SEQ ID NO | 80 | 1 | 97 | 32 | 134 | 57 | 135 |

TABLE 5

Light chain variable regions of PD1 clones

| NAME | FR1 | CDR1 | FR2 | CDR2 | FR3 | CDR3 | FR4 |
|---|---|---|---|---|---|---|---|
| PD1-27A12 | DIQMTQSPSSV SASVGDRVTIT CRAS | RDISR W | LAWYQQKP GEAPKLLIY | GAS | SLRSGVSSRFSGSGS GTDFTLTISSLQPEDF ATYFC | QQGKS FPYT | FGQGT KVDIK |
| SEQ ID NO | 251 | 198 | 276 | | 297 | 223 | 337 |
| PD1-27B1 | DIVMTQTPLSS PVTLGQPASISC RSS | QSLVH | LNWFHQRP GQPPRLLIH | KIS | NRVSGVPDRFSGSG AGTDFTLKISRVEAE DVGVYYC | MQSTQ FPYT | FGQGT KVDIK |
| SEQ ID NO | 252 | 199 | 277 | | 298 | 224 | 337 |
| PD1-28D12 | DIQMTQSPSSV SASLGDRVTIT CRAS | QAISN W | LTWYQQKP GKAPKLLIY | ATS | SLQSGVPSRFSGSGS GTDFTLTISSLQPED VATYYC | QQTDSF PLT | FGGGT KVDIK |
| SEQ ID NO | 272 | 200 | 297 | 225 | 318 | 244 | 357 |
| PD1-29A2 | SYELTQSPSVS MSPGQTARITC SGD | ALSKQ Y | ASWYQLKP GQAPVVVM Y | KDT | ERPSGIPDRFSGSSSG TTVTLTISGVQAEDG ADYYC | QSITDK SGTDVI | FGGGT KLTVL |
| SEQ ID NO | 254 | 201 | 279 | | 300 | 226 | 339 |
| PD1-29H3 | QLVLTQPSSMS EAPGQRVTISC SGG | TSNIGT NA | VNWYQQPP GKAPTLLIY | YDD | RLTSGVSDRFSGSKS GTSASLAISRLQSED EADYYC | AAWDD SLNGW V | FGGGT KLTVL |
| SEQ ID NO | 255 | 202 | 280 | | 301 | 227 | 339 |
| PD1-31F3 | QFVLTQPPSVS GAPGQRVIISCT GS | SSNIGA GYD | VHWYQQLP GTAPKVLIY | GNS | DRPSGVPDRFSASKS ATSASLAITGLQAED EADYYC | QSYDSS LSGYV | FGTGT KVTV L |
| SEQ ID NO | 256 | 203 | 281 | | 302 | 228 | 340 |
| PD1-32A6 | DIQMTQSPSSV SASVGDRVTIT CRAS | QGIVS W | LAWYQQKP GKAPRLLIY | RAS | DLETGVPSRFSGSGS GTDFTLTISSLQPED VATYYC | QQADS FPLT | FGGGT KVEIK |
| SEQ ID NO | 251 | 204 | 282 | | 303 | 229 | 341 |
| PD1-41C9 | DIVMTQTPLSL PVTPGEAASISC RSS | QSLLD SEDGN TY | LDWYLQKP GQSPQLLIY | TLS | HRASGVPDRFSGSG SGTDFTLKISRVEAE DVGLYYC | LQRMG FPYT | FGQGT KLDIK |

TABLE 5-continued

Light chain variable regions of PD1 clones

| NAME | FR1 | CDR1 | FR2 | CDR2 | FR3 | CDR3 | FR4 |
|---|---|---|---|---|---|---|---|
| SEQ ID NO | 257 | 205 | 283 | | 304 | 230 | 342 |
| PD1-42G4 | DIQMTQSPSSL SASVGDRVTTT CRAS | QGISSY | LAWYQQKP GKAPKLLIY | AAS | TLQSGVPSRFSGSGS GTDFTLTISSLQPEDF ATYFC | QQSYTS PRT | FGQGT KLDIK |
| SEQ ID NO | 258 | 206 | 284 | | 305 | 231 | 342 |
| PD1-44B5 | QFVLTQSPSAS GTPGQNIVISCS AS | TFNIGT TT | VNWYQRLP GTAPKLLIY | NYD | QRPSGVPDRFSGSKS GTSASLAISGLQSED EADYYC | AAWDD SLNAW L | FGGGT KLTVL |
| SEQ ID NO | 259 | 207 | 285 | | 306 | 232 | 339 |
| PD1-45D6 | DIVMTQTPLSL PVTPGEAASISC RSS | QSLLD SDDGK TY | LDWYLQKP GQSPQLLIY | TLS | YRASGVPDRFSGSG SGTEFNLRISRVEAE DVGIYYC | MQRVE FPFT | FGQGT KLDIK |
| SEQ ID NO | 257 | 208 | 283 | | 307 | 233 | 342 |
| PD1-45F1 | SYELTQDPAVS VALGQTVRITC QGD | SLRTY Y | ASWYQQKP GQAPILVIY | GKN | NRPSGIPDRFSGSSS GNTASLTITAAQAE DEADYYC | NSRDSS GKSLV | FGGGT KLTVL |
| SEQ ID NO | 260 | 209 | 286 | | 308 | 234 | 339 |
| PD1-45F4 | SYELTQAPSLS VSPGQTANIICS GD | NLRTK Y | VSWYQQKP GQSPLLVIY | QDT | RRPSGIPARFSGSNS GNTATLTISGTQTRD ESTYYC | MTWDV DTTSMI | FGGGT KLTVL |
| SEQ ID NO | 261 | 210 | 287 | | 309 | 235 | 339 |
| PD1-47B8 | QSALTQPASVS GSPGQSITISCT GT | SSDVG GYNY | VSWYQQHP GKAPKLMI Y | DVS | KRPSGVSNRFSGSKS GNTASLTISGLQAED EADYYC | SSFTSSS TVV | FGGGT KLTVL |
| SEQ ID NO | 262 | 211 | 288 | | 310 | 236 | 339 |
| PD1-48A6 | QFVLTQPPSVS GAPGQRVTISC TGS | RSNFG AGHD | VHWCQQLP GTAPKLLIY | GNN | NRPSGVPDRFSGSKS GTSASLAITGLQAED EAEYYC | QSYDSS LSAWG | VRRR DQAD RP |
| SEQ ID NO | 263 | 212 | 289 | | 311 | 237 | 343 |
| PD1-48A9 | DIVMTQTPLSL PVTPGEPASISC RSS | QSLLD SHDGN TY | LDWYLQKP GQSPQLLIY | TLS | HRASGVPDRFSGSG SGTDFTLKISRVEAE DVGLYYC | MQRIDF PYT | FGQGT KVEIK |
| SEQ ID NO | 264 | 213 | 283 | | 312 | 238 | 344 |
| PD1-48G6 | NFMLTQPPSTS GTPGQRVTISC SGR | SSNIGI NT | VTWYQQLP GTAPKVLM Y | RDD | QRPSGVPDRFSGSRS GISASLAISGLQSEDE ADYYC | ASWDD TLNGW V | FGGGT KLTVL |
| SEQ ID NO | 265 | 214 | 290 | | 313 | 239 | 339 |
| PD1-49A2 | DIVMTQSPLSL PVTPGEPASISC RSS | QSLFD SDDGN TY | LDWYLQKP GQSPQLLIY | TLS | HRASGVPDRFSGSG SGTDFTLKISRVEAE DVGIYYC | LQRMG FPYT | FGQGT KVEIK |
| SEQ ID NO | 266 | 215 | 283 | | 314 | 230 | 344 |
| PD1-49B9 | QSALTQPPSAS GSPGQSVTISCT GT | SSDVG GYNY | VSWYQQHP GKAPKLMI Y | EVS | KRPSGVPDRFSGSKS GNTASLTVSGLQPE DEADYYC | SSFARN SNYV | FGTGT KVTV L |
| SEQ ID NO | 267 | 211 | 288 | | 315 | 240 | 340 |
| PD1-51A6 | DIVMTQTPLSL SVTPGQPASISC KSS | QSLLYI DGETY | LFWYLQKP GQSPQLLIY | EVS | SRFSGVPDRFSGSGS GTDFTLKISRVEAED VGVYYC | MQGIH LPLT | FGQGT RLE1K |
| SEQ ID NO | 268 | 216 | 291 | | 316 | 241 | 345 |

TABLE 5-continued

Light chain variable regions of PD1 clones

| NAME | FR1 | CDR1 | FR2 | CDR2 | FR3 | CDR3 | FR4 |
|---|---|---|---|---|---|---|---|
| PD1-51D9 | DIVMTQTPLSL PVTPGEPASISC RSS | QSLLH SNGNN Y | LDWYLQKP GQSPQLLIY | LGS | YRASGVPDRFSGSG SGTDFTLKISRVEAE DVGLYYC | MQGLQ IPST | FGPGT KVDIK |
| SEQ ID NO | 264 | 217 | 283 | | 317 | 242 | 346 |
| PD1-52E8 | SYELTQPLSLS VAPGQTARITC SGD | ALSKE Y | SYWYQQKP GQAPVLVM Y | KDS | ERPSGIPERFSGSSSG TTVTLTISGVQAEDE ADYYC | QSVDSS DTSVV | FGGGT KLTVL |
| SEQ ID NO | 269 | 218 | 292 | | 318 | 243 | 339 |
| PD1-62E1 | DIQMTQSPAILS LSPGERATLSC RAS | QSVTS D | VAWYQHIR GQAPRLLIY | DAS | NRASGIPARFSGGGS GTEFTLTISSLEPEDF AVYYC | QQYNN WPLT | FGGGT KVEIK |
| SEQ ID NO | 270 | 219 | 293 | | 319 | 244 | 341 |
| PD1-72D10 | DIVMTQTPLSL PVTPGEAASISC RSS | QSLLD SEDGN TY | LDWYLQKP GQSPQLLIY | TLS | HRASGVPDRFSGSG SGTDFTLKISRVEAE DVGIYYC | MQRVE FPFT | FGQGT KLEIK |
| SEQ ID NO | 257 | 205 | 283 | | 314 | 233 | 347 |
| PD1-74A11 | DIVMTQTPLSL PVTPGEPASISC RSS | QSLFD SDDGN TY | LDWYLQKP GQSPQLLIY | TLS | YRASGVPDRFSGSG SGTDFTLKISRVAAE DVGIYYC | MQRVE FPFT | FGQGT KVDIK |
| SEQ ID NO | 264 | 215 | 283 | | 334 | 233 | 337 |
| PD1-75C10 | DIVMTQTPLSL PVTPGEAASISC RSS | QSLLD SEDGN TY | LDWYLQKP GQSPQLLIY | TLS | HRASGVPDRFSGSG SGTDFTLKITRVEAE DVGVYYC | MQRIEF PYT | FGQGT KLEIK |
| SEQ ID NO | 257 | 205 | 283 | | 335 | 245 | 347 |
| PD1-74A01 | DIVMTQTPLSL PVTPGEPASISC RSS | QSLLD RGGGH TY | LDWYLQKP GQSPQLLIY | TLS | HRASGVPDRFSGSG SGTDFTLKISRVEAE DVGIYYC | MQRKE FPLT | FGPGT KLEIK |
| SEQ ID NO | 264 | 222 | 283 | | 314 | 249 | 348 |
| PD1-74H12 | DIVMTQTPLSL SVTPGEPASISC RSS | QSLLD SDDGN TY | LDWYLQKP GQSPQLLIY | TLS | HRASGVPDRFSGRG SHTDFTLTISSVEAE DVGVYYC | MQRIHF PLT | FGQGT RLEIK |
| SEQ ID NO | 275 | 220 | 283 | | 336 | 250 | 345 |

Example 3: Production of PD-1 Human Antibody

1. Conversion of scFv Form to IgG Form

PCR (iCycler iQ, BIO-RAD) was performed on the heavy and light chains to convert the selected 15 species of monoclonal phage antibodies to PD1 from phages to IgG whole vector. As a result, heavy and light chains were obtained, and the vectors and the heavy and light chains of each of the clones were cut (digested) with restriction enzymes. DNAs were eluted from each of the vector and heavy chain with a DNA-gel extraction kit (Qiagen). Ligation was performed by mixing 1 µl (10 ng) of the vector, 15 µl (100-200 ng) of the heavy chain, 2 µl of 10× buffer, 1 µl of ligase (1 U/µl) and distilled water, allowing the mixture to stand at room temperature for 1 to 2 hours, injecting the resulting mixture into transformed cells (competent cells, XL1-blue), placing the cells on ice for 5 minutes and subjecting the cells to heat-shock at 42° C. for 90 seconds.

After the heat shock, 1 ml of the medium was added to the cells, and then the cells were grown at 37° C. for 1 hour, spread on an LB Amp plate and incubated at 37° C. for 16 hours. The colony thus obtained was inoculated with 5 ml of LB Amp medium, cultured at 37° C. for 16 hours and subjected to DNA-prep using a DNA-prep kit (Nuclogen). Sequence analysis of the obtained DNAs was requested (Solgent).

As a result, it was confirmed that the sequences of heavy chains and light chains of 15 clones for PD1 converted into the whole IgG corresponded to the sequences of phage antibodies of 15 clones shown in Table 3. In order to transfect into HEK 293F cells, the heavy and light chains of respective clones converted into whole IgG were grown in 100 ml of LB Amp medium, and DNAs were obtained using a Midi-prep kit (QIAgen).

2. Human Antibody Production

The cloned pNATVH and pNATVL vectors were co-transfected at a ratio of 6:4 into HEK293F cells and the supernatant was collected on the 7th day, the cells and debris were removed through centrifugation and a 0.22 µm top filter, and the supernatant was collected and subjected to protein A affinity chromatography to purify the IgG antibody. After purification, the antibody was separated through a glycine buffer, and buffer was changed such that the final resuspension buffer was PBS. Purified antibodies were quantitated by BCA and nano drop, and each of 15 species of antibodies was loaded in a dose of 5 ug under reducing and non-reducing conditions, and analyzed by SDS-PAGE to determine purity and mobility of the purified protein (FIG. 5).

As a result, as shown in FIG. 5, all of the 15 antibodies were detected at a molecular weight of 150 kDa or more under non-reducing conditions, and Nivolumab was produced as a control antibody.

Example 4: Characteristics of PD-1 Monoclonal Antibody

1. Evaluation of Antibody Activity

Testing for activity of the selected antibodies was carried out using a PD1/PD-L1 blockade bioassay kit (promega, J1250). A CHO cell line highly expressing PD-L1 was spread on a 96-well plate, cultured for 16 hours or longer, treated with each antibody serially diluted at a constant concentration and then cultured together with a Jurkat cell line highly expressing human PD-1, for 6 hours. The degree of recovery of the inhibition of the antibody was determined with a spectrophotometer (SpectraMax M5 spectrophotometer, Molecular Devices, USA), which was determined from a luminescent intensity resulting from degradation of the substrate by luciferase. The activity of 16 species of PD-1 antibodies including the control antibody was found based on the value to recover a reduced signal by formation of a PD-1/PD-L1 complex, and 41C9, 45D6 and 49A2 exhibited similar activity to the control antibody (FIG. 6).

In order to measure activity of PD-1 antibodies, 41C9, 45D6 and 49A2 in a concentration-dependent manner, serial dilution and PD1/PD-L1 blockade bioassay were performed again to recover the reduced signal in a concentration gradient dependent manner. The degree of recovery can be expressed as EC50 (effective concentration of mAb at 50% level of recovery signal), analyzed using Graphpad Prism6, and in vitro efficacy inhibition recovery ability of EC50 is shown in FIG. 7.

2. Affinity of PD1 Antibody to Overexpressed Cells

Regarding transformation cell pools highly expressing PD-1, HEK293E was transformed with a plasmid pcDNA3.1 containing human PD-1 (NM_005018.2) and screened in a selective medium containing 150 ug/ml Zeocin (#R25001, Thermo Fisher). Each cell pool was identified and selected by fluorescence activated cell sorting (FACS) analysis using anti-PD-1 (#557860, BD) and used for functional assays such as FACS binding assays or FACS competition assays.

0.5 to 1×10⁶ cells per sample were each prepared from the transformation cell pools highly expressing human PD-1, and antibodies were serially diluted at a constant dilution rate and reacted with the prepared cells at 4° C. for 20 minutes. Then, the cells were washed three times with PBS (#LB001-02, Welgene) containing 2% fetal bovine serum and reacted at 4° C. for 20 minutes with an anti-human IgG antibody (#FI-3000, Vectorlabs) conjugated with a FITC (fluorescein isothiocyanate) fluorescent substance. Then, the cells were subjected to the same washing process as above and then suspended in 0.5 ml of PBS containing 2% FBS (#26140-079, Thermo Fisher) with an FACSCanto II flow cytometer (BD Biosciences, USA) as a flow cytometer. As a result, all three PD-1 antibodies were specifically bound and the binding capacity thereof was determined from an equilibrium dissociation constant (Kd) obtained through an analysis function of Graphpad Prism6.

As a result, as can be seen from FIG. 8, the binding capacity of antibody bound in a concentration-dependent manner to human PD-1 over-expressed on the cell surface can be found by MFI (mean fluorescence intensity).

3. Screening of Positive Phage Antibodies Having Similar Sequence to PD1-45D6 and 49A2

Additional antibody screening was conducted for 45D6 and 49A2 in addition to 41C9, which was considered to have excellent activity and binding capacity in FACS.

Antibodies having a similar sequence to PD1-45D6 and 49A2 were further screened by the same procedure as in Example 2. The characteristics thereof are summarized in Table 6 below.

TABLE 6

Characteristics of additionally screened 45D6 and 49A2-like antibody clones

| Clone name | VH | Identity | VL | Identity 2 | Group |
|---|---|---|---|---|---|
| PD1-72D10 | VH3-30 | 96.90% | O1 | 94.10% | 1 |
| PD1-74A11 | VH3-30 | 97.96% | O1 | 95.05% | 2 |
| PD1-75C10 | VH3-30 | 96.94% | O1 | 95.05% | 3 |
| PD1-74A01 | VH3-30 | 95.92% | O1 | 92.08% | 4 |
| PD1-74H12 | VH3-30 | 94.90% | O1 | 92.08% | 5 |

4. Affinity of PD1 Antibody Using ProteOn XPR36

A ProteOn XPR36 (BioRad) instrument was used. The GLC sensor chip (BioRad) was mounted on the instrument and washed with PBST buffer, and the carboxymethyldextran surface was activated with an EDC/sulfo-NHS mixed solution. PD1-hFc dissolved at a concentration of 5 ug/ml in a 10 mM sodium acetate buffer solution (pH 5.0) was injected and immobilized on the GLC sensor chip.

In order to deactivate the activated carboxyl groups that remain unreacted with the PD1 protein, 1 M ethanolamine was flowed and 10 mM glycine (pH 2.0) was injected in order to wash proteins that remain unbound to the sensor chip. Then, sensogram data were collected during binding and dissociation over time while allowing the antibodies to flow at a flow rate of 30 μL/min (30 nM to 0.123 nM) for 10 min using PBST buffer.

The equilibrium dissociation constant (KD) was calculated by plotting and fitting the sensogram data in the equilibrium state depending on concentration. As a result, 45D6 and 49A2 exhibited KD of 0.001 nM and 0.019 nM, respectively, indicating high affinity to PD1 antigen (FIG. 9).

Example 5: Antibody Optimization for PD1 Antibodies, 45D and 49A2

1. Production of libraries for Optimization of PD1-45D6 and 49A2 Antibodies

For antibody optimization, new LC shuffling libraries were produced by immobilizing the heavy chain and injecting a 10³-10⁶ light chain (LC) pool owned by Ybiologics, Inc. Also, antibody optimization was conducted by the following three methods: LC shuffling; core packing+LC shuffling including comparatively analyzing the residues of structurally important sites such as hydrophobic cores of heavy chains, exposed residues, charge clusters, salt bridges, mutating the same into conserved residues and then conducting LC shuffling; and CDR hotspot+LC shuffling, in the case of DNAs in antibody variable regions, including randomly mutating mutational hot spots that can be mutated frequently in the process of in vivo affinity maturation and then conducting LC shuffling.

In order to produce LC shuffling libraries, LC genes of 45D6 and 49A2 antibodies were cut (digested) with BstX I and then used as vectors and the library pools owned by Ybiologics, Inc. were cut (digested) into BstX I and used as inserts. After ligation with a ligase, transformation was carried out using cells for electroporation transformation. The antibody libraries were produced by collecting the transformed cells on a square plate. As a result, about $1.5 \times 10^7$ various libraries were obtained. The result of sequence analysis showed that all HC sequences were identical and LC sequences were different from each other.

In order to produce the core packing+LC shuffling libraries, the framework (FR) sites of the 45D6 and 49A2 antibodies were replaced with conserved amino acid sequences, the LC genes were cut with BstX I and then used as vectors, and the library pools owned by Ybiologics, Inc. were cut with BstX I and then used as inserts. After ligation with a ligase, transformation was carried out using cells for electroporation transformation. The antibody libraries were produced by collecting the transformed cells on a square plate. As a result, about $8.4 \times 10^6$ various libraries were obtained. The result of sequence analysis showed that the FR sites of HC were replaced with conserved amino acid sequences and LC sequences were different from each other.

In order to produce the core hot spot+LC shuffling libraries, the framework (FR) sites of the 45D6 antibodies were replaced with conserved amino acid sequences, the hot spot libraries of CDR1 were cut with Sfi I and used as inserts, and the library pools owned by Ybiologics, Inc. were cut with Sfi I and then used as vectors. After ligation with a ligase, transformation was carried out using cells for electroporation transformation. The antibody libraries were produced by collecting the transformed cells on a square plate. As a result, about $5.6 \times 10^6$ various libraries were obtained. The result of sequence analysis showed that the FR sites of HC were replaced with conserved amino acid sequences, the hot spot sequences of CDR1 were randomly mutated and LC sequences were different from each other.

Example 6: Screening of PD-1 Human Antibodies

1. Antigen Preparation

PD1-hFc and PD1-mFc produced by Ybiologics, Inc. and PD1-his (Catalog Number, 10377-H08H) purchased from Sino Biological Inc. as protein antigens were coated in a dose of 50 ug on an immunosorbent tube and then blocked.

2. Bio-panning

A human antibody library phage was obtained by infecting a human scFv library with a variety of $2.7 \times 10^{10}$ with bacteria and then culturing at 30° C. for 16 hours. After culturing, the culture solution was centrifuged, and the supernatant was concentrated with PEG, and then dissolved in PBS buffer to prepare a human antibody library. The human antibody library phage was charged into an immune tube, followed by reaction at room temperature for 2 hours. After washing with 1×PBS/T and 1×PBS, only the scFv-phages specifically bound to the antigen were eluted.

The eluted phages were infected with E. coli again and amplified (panning process) to obtain a pool of positive phages. For antibody optimization, only the first round of panning was conducted. As a result, as shown in Table 7, it was seen that the number of phages bound to the antigen (output) during the first round of panning was slightly increased, as compared to the input phages.

TABLE 7

Comparison in titer of antibodies in optimization panning

| Sample | Number of input phages | Number of output phages |
|---|---|---|
| 45D6 (LS) | $1.3 \times 10^{13}$ | $2.8 \times 10^7$ |
| 45D6 (Core packing + LS) | $1.1 \times 10^{13}$ | $4.8 \times 10^7$ |
| 45D6 (CDR hotspot + LS) | $1.1 \times 10^{13}$ | $3.6 \times 10^6$ |
| 49A2 (LS) | $1.3 \times 10^{13}$ | $1.8 \times 10^7$ |
| 49A2 (CDR hotspot + LS) | $1.1 \times 10^{13}$ | $1.6 \times 10^6$ |

3. Screening of Positive Phages

Colonies obtained from panning were cultured in a 1 ml 96-deep well plate (Bioneer 90030) at 37° C. for 16 hours. 100 to 200 µl of the cells grown thus were added to a medium containing 2×YTCM, 2% glucose and 5 mM $MgCl_2$, to $OD_{600}$ of 0.1, and were added to a medium containing 1 ml of 2×YTCM, 2% glucose and 5 mM $MgCl_2$, and then cultured in a 96-deep well plate at 37° C. for 2 to 3 hours to $OD_{600}$ of 0.5 to 0.7. M1 helper phages were infected at an MOI of 1:20 and cultured in a medium containing 2×YTCMK, 5 mM $MgCl_2$, and 1 mM IPTG at 30° C. for 16 hours.

The antigen PD1 was coated at a density of 100 ng/well on a 96-well immunoplate at 4° C. for 16 hours and each well was blocked using 4% skim milk dissolved in PBS. Each monoclonal scFv-phage (100 scFv-phage) washed with 0.2 ml of PBS/T and cultured for 16 hours was added in a dose of 1 j to each well and reacted at room temperature for 2 hours. Again, each well was washed 4 times with 0.2 ml of PBS/T, and the secondary antibody, anti-M13-HRP, was diluted to 1/2000 and reacted at room temperature for 1 hour. After washing with 0.2 ml of PBS/T, color development was performed and absorbance was measured at 490 nm.

As a result, single-phage clones having higher binding capacity to each antigen than the parent antibody (49A2 or 45D6) were obtained and results are shown in FIG. 10.

4. Base Sequence Analysis of Positive Phage Antibodies

The selected single clones were subjected to DNA-prep using a DNA purification kit (Qiagen, Germany) to obtain DNA, and sequence analysis for DNA was requested (Solgent). The CDR regions of VH and VL of the selected antibodies were identified, based on results of sequence analysis and the similarity (identity) between these antibodies and germ line antibody groups was investigated using an Ig BLAST program on the NCBI website at http://www.ncbi.nlm.nih.gov/igblast/. As a result, 25 species of phage antibodies (49A2: 10 species, 45D6: 15 species) having higher binding capability than the parent antibody were obtained and are summarized in Table 8 below.

TABLE 8

Characteristics of monoclones of PD1 antibody variants selected by optimization

| Clone name | VH | Identity | VL | Identity 2 | Group |
|---|---|---|---|---|---|
| PD1-49A2(A/1B2) | VH3-30 | 92.86% | O1 | 93.07% | 1 |
| PD1-49A2(A/1D11) | VH3-30 | 91.84% | O1 | 97.03% | 2 |
| PD1-49A2(A/1F12) | VH3-30 | 92.86% | O1 | 93.07% | 3 |
| PD1-49A2(A/1H4) | VH3-30 | 92.86% | O1 | 92.08% | 4 |
| PD1-49A2(A/1H8) | VH3-30 | 92.86% | O1 | 90.10% | 5 |
| PD1-49A2(A/2A6) | VH3-30 | 91.84% | O1 | 89.11% | 6 |
| PD1-49A2(A/2A11) | VH3-30 | 93.88% | O1 | 90.10% | 7 |
| PD1-49A2(A/2B9) | VH3-30 | 92.86% | O1 | 93.07% | 8 |
| PD1-49A2(A/2B10) | VH3-30 | 93.88% | O1 | 95.05% | 9 |

TABLE 8-continued

Characteristics of monoclones of PD1 antibody variants selected by optimization

| Clone name | VH | Identity | VL | Identity 2 | Group |
|---|---|---|---|---|---|
| PD1-45D6(A/3D2) | VH3-30 | 93.88% | O1 | 94.06% | 10 |
| PD1-45D6(A/3G1) | VH3-30 | 93.88% | O1 | 95.05% | 11 |
| PD1-45D6(A/3H4) | VH3-30 | 93.88% | O1 | 93.07% | 12 |
| PD1-45D6(A/3H6) | VH3-30 | 93.88% | O1 | 95.05% | 13 |
| PD1-45D6(A/3H7) | VH3-30 | 93.88% | O1 | 92.08% | 14 |
| PD1-45D6(A/4C1) | VH3-30 | 94.90% | O1 | 96.04% | 15 |
| PD1-45D6(A/4C9) | VH3-30 | 94.90% | O1 | 93.07% | 16 |
| PD1-45D6(A/4D4) | VH3-30 | 94.90% | O1 | 92.08% | 17 |
| PD1-45D6(A/4H6) | VH3-30 | 94.90% | O1 | 95.05% | 18 |
| PD1-49A2(A/2D7) | VH3-30 | 92.86% | O1 | 95.05% | 19 |
| PD1-45D6(A/5A6) | VH3-30 | 91.84% | O1 | 96.04% | 20 |
| PD1-45D6(A/5B2) | VH3-30 | 93.88% | O1 | 94.06% | 21 |
| PD1-45D6(A/5B5) | VH3-30 | 92.86% | O1 | 92.08% | 22 |
| PD1-45D6(A/5B12) | VH3-30 | 93.88% | O1 | 94.06% | 23 |
| PD1-45D6(A/5C8) | VH3-30 | 92.86% | O1 | 95.05% | 24 |
| PD1-45D6(A/5H9) | VH3-30 | 92.86% | O1 | 94.06% | 25 |

Antibodies including the heavy and light-chain CDRs and FR sequences of selected antibodies and heavy chain variable regions and light chain variable regions including the same are shown in Tables 9 and 10 below.

TABLE 9

Heavy chain variable regions of PD1 human antibodies

| NAME | FR1 | CDR1 | FR2 | CDR2 | FR3 | CDR3 | FR4 |
|---|---|---|---|---|---|---|---|
| PD1-49A2 (A/1B2) SEQ ID NO | QVQLVESGGGVVQPGRSLRLSCAAS 80 | GFTFLRYA 17 | MHWVRQAPGKGLEWVAV 97 | ISYDGQDK 49 | YYADSVKGRFTISRDNSKNTLYLQMNSLRAEDTAVYYC 114 | TTTTFDS 58 | WGRGTLVTVSS 136 |
| PD1-49A2 (A/1D11) SEQ ID NO | QVQLVESGGGVVQPGRSLRLSCAAS 80 | GFTFKNNA 18 | MHWVRQAPGKGLEWVAV 97 | ISYDGRHK 50 | YYADSVKGRFTISRDNSKNTLYLQMNSLRAEDTAVYYC 114 | TTTTFDS 58 | WGQGTLVTVSS 137 |
| PD1-49A2 (A/1F12) SEQ ID NO | QVQLVESGGGVVQPGRSLRLSCAAS 80 | GFTFRNYA 19 | MHWVRQAPGKGLEWVAV 97 | ISYDGQHK 51 | YYADSVKGRFTISRDNSKNTLYLQMNSLRAEDTAVYYC 114 | TTTTFDS 58 | WSQGTLVTVSS 145 |
| PD1-49A2 (A/1H4) SEQ ID NO | QVQLVESGGGVVQPGRSLRLSCAAS 80 | GFTFPIYA 20 | MHWVRQAPGKGLEWVAV 97 | ISYDGAHK 52 | YYADSVKGRFTISRDNSKNTLYLQMNSLRAEDTAVYYC 114 | TTTTFDS 58 | WGQGTLVTVSS 137 |
| PD1-49A2 (A/1H8) SEQ ID NO | QVQLVESGGGVVQPGRSLRLSCAAS 80 | GFTFKTYA 21 | MHWVRQAPGKGLEWVAV 97 | ISYDGQHK 51 | YYADSVKGRFTISRDNSKNTLYLQMNSLRAEDTAVYYC 114 | TTTTFDS 58 | WGQGTLVTVSS 137 |
| PD1-49A2 (A/2A6) SEQ ID NO | QVQLVESGGGVVQPGRSLRLSCAAS 80 | GFTFKYYA 22 | MHWVRQAPGKGLEWVTV 113 | ISYDGQYK 53 | YYADSVKGRFTISRDNSKNTLYLQMNSLRAEDTAVYYC 114 | TTTTFDS 58 | WGQGTLVTVSS 137 |
| PD1-49A2 (A/2A1) SEQ ID NO | QVQLVESGGGVVQPGRSLRLSCAAS 80 | GFTFRSYA 23 | MHWVRQAPGKGLEWVAV 97 | ISYDGQDK 49 | YYADSVKGRFTISRDNSKNTLYLQMNSLRAEDTAVYYC 114 | TTTTFDS 58 | WGQGTLVTVSS 137 |
| PD1-49A2 (A/2B9) SEQ ID NO | QVQLVESGGGVVQPGRSLRLSCAAS 80 | GFTFLRYA 17 | MHWVRQAPGKGLEWVAV 97 | ISYDGRYK 54 | YYADSVKGRFTISRDNSKNTLYLQMNSLRAEDTAVYYC 114 | TTTTFDS 58 | WGQGTLVTVSS 137 |
| PD1-49A2 (A/2B10) SEQ ID NO | QVQLVESGGGVVQPGRSLRLSCAAS 80 | GFTFLVYA 24 | MHWVRQAPGKGLEWVAV 97 | ISYDGSHK 55 | YYADSVKGRFTISRDNSKNTLYLQMNSLRAEDTAVYYC 114 | TTTTFDS 58 | WGQGTLVTVSS 137 |

TABLE 9-continued

Heavy chain variable regions of PD1 human antibodies

| NAME | FR1 | CDR1 | FR2 | CDR2 | FR3 | CDR3 | FR4 |
|---|---|---|---|---|---|---|---|
| PD1-49A2 (A/2D7) | QVQLVESGGGV VQPGRSLRLSC AAS | GFTF KTY | MHWVRQA PGKGLEWV A | ISYD GQH K | YYADSVKGRFTISRDNSK NTLYLQMNSLRAEDTAV YYC | TTT TFD S | WGQG TLVTV SS |
| SEQ ID NO | 80 | 21 | 97 | 51 | 114 | 58 | 137 |
| PD1-45D6 (A/3D2) | QVQLVESGGGV VQPGRSLRLSC AAS | GFTF SSY | MHWVRQV PGKGLEWV A AV | ISYD GND K | YYADSVKGRFTISRDNSK NTLYLQMNSLRAEDTAV YYC | VPT TFE Y | WGQG SQVTV SS |
| SEQ ID NO | 80 | 1 | 96 | 31 | 114 | 57 | 135 |
| PD1-45D6 (A/3G1) | QVQLVESGGGV VQPGRSLRLSC AAS | GFTF SSY | MHWVRQV PGKGLEWV A AV | ISYD GND K | YYADSVKGRFTISRDNSK NTLYLQMNSLRAEDTAV YYC | VPT TFE Y | WGQG SQVTV SS |
| SEQ ID NO | 80 | 1 | 96 | 31 | 114 | 57 | 135 |
| PD1-45D6 (A/3H4) | QVQLVESGGGV VQPGRSLRLSC AAS | GFTF SSY | MHWVRQV PGKGLEWV A AV | ISYD GND K | YYADSVKGRFTISRDNSK NTLYLQMNSLRAEDTAV YYC | VPT TFE Y | WGQG SQVTV SS |
| SEQ ID NO | 80 | 1 | 96 | 31 | 114 | 57 | 135 |
| PD1-45D6 (A/3H6) | QVQLVESGGGV VQPGRSLRLSC AAS | GFTF SSY | MHWVRQV PGKGLEWV A AV | ISYD GND K | YYADSVKGRFTISRDNSK NTLYLQMNSLRAEDTAV YYC | VPT TFE Y | WGQG SQVTV SS |
| SEQ ID NO | 80 | 1 | 96 | 31 | 114 | 57 | 135 |
| PD1-45D6 (A/3H7) | QVQLVESGGGV VQPGRSLRLSC AAS | GFTF SSY | MHWVRQV PGKGLEWV A AV | ISYD GND K | YYADSVKGRFTISRDNSK NTLYLQMNSLRAEDTAV YYC | VPT TFE Y | WGQG SQVTV SS |
| SEQ ID NO | 80 | 1 | 96 | 31 | 114 | 57 | 135 |
| PD1-45D6 (A/4C1) | QVQLVESGGGV VQPGRSLRLSC AAS | GFTF SSY | MHWVRQA PGKGLEWV A AV | ISYD GND K | YYADSVKGRFTISRDNSK NTLYLQMNSLRAEDTAV YYC | VPT TFE Y | WGQG TLVTV SS |
| SEQ ID NO | 80 | 1 | 97 | 31 | 114 | 57 | 137 |
| PD1-45D6 (A/4C9) | QVQLVESGGGV VQPGRSLRLSC AAS | GFTF SSY | MHWVRQA PGKGLEWV A AV | ISYD GND K | YYADSVKGRFTISRDNSK NTLYLQMNSLRAEDTAV YYC | VPT TFE Y | WGQG TLVTV SS |
| SEQ ID NO | 80 | 1 | 97 | 31 | 114 | 57 | 137 |
| PD1-45D6 (A/4D4) | QVQLVESGGGV VQPGRSLRLSC AAS | GFTF SSY | MHWVRQA PGKGLEWV A AV | ISYD GND K | YYADSVKGRFTISRDNSK NTLYLQMNSLRAEDTAV YYC | VPT TFE Y | WGQG TLVTV SS |
| SEQ ID NO | 80 | 1 | 97 | 31 | 114 | 57 | 137 |
| PD1-45D6 (A/4H6) | QVQLVESGGGV VQPGRSLRLSC AAS | GFTF SSY | MHWVRQA PGKGLEWV A AV | ISYD GND K | YYADSVKGRFTISRDNSK NTLYLQMNSLRAEDTAV YYC | VPT TFE Y | WGQG TLVTV SS |
| SEQ ID NO | 80 | 1 | 97 | 31 | 114 | 57 | 137 |
| PD1-45D6 (A/5A6) | QVQLVESGGGV VQPGRSLRLSC AAS | GFTF RLY | MHWVRQA PGKGLEWV A AV | ISHD GND K | YYADSVKGRFTISRDNSK NTLYLQMNSLRAEDTAV YYC | VPT TFE Y | WGQG TLVTV SS |
| SEQ ID NO | 80 | 25 | 97 | 56 | 114 | 57 | 137 |
| PD1-45D6 (A/5B2) | QVQLVESGGGV VQPGRSLRLSC AAS | GFTF SFY | MHWVRQA PGKGLEWV A AV | ISYD GND K | YYADSVKGRFTISRDNSK NTLYLQMNSLRAEDTAV YYC | VPT TFE Y | WGQG TLVTV SS |
| SEQ ID NO | 80 | 26 | 97 | 31 | 114 | 57 | 137 |
| PD1-45D6 (A/5B5) | QVQLVESGGGV VQPGRSLRLSC AAS | GFTF RTY | MHWVRQA PGKGLEWV A AV | ISYD GND K | YYADSVKGRFTISRDNSK NTLYLQMNSLRAEDTAV YYC | VPT TFE Y | WGQG TLVTV SS |

TABLE 9-continued

Heavy chain variable regions of PD1 human antibodies

| NAME | FR1 | CDR1 | FR2 | CDR2 | FR3 | CDR3 | FR4 |
|---|---|---|---|---|---|---|---|
| SEQ ID NO | 80 | 27 | 97 | 31 | 114 | 57 | 137 |
| PD1-45D6 (A/5B12) | QVQLVESGGGV VQPGRSLRLSC AAS | GFTF SVY A | MHWVRQA PGKGLEWV AV | ISYD GND K | YYADSVKGRFTISRDNSK NTLYLQMNSLRAEDTAV YYC | VPT TFE Y | WGQG TLVTV SS |
| SEQ ID NO | 80 | 28 | 97 | 31 | 114 | 57 | 137 |
| PD1-45D6 (A/5C8) | QVQLVESGGGV VQPGRSLRLSC AAS | GFTF MRY A | MHWVRQA PGKGLEWV AV | ISYD GND K | YYADSVKGRFTISRDNSK NTLYLQMNSLRAEDTAV YYC | VPT TFE Y | WGQG TLVTV SS |
| SEQ ID NO | 80 | 29 | 97 | 31 | 114 | 57 | 137 |
| PD1-45D6 (A/5H9) | QVQLVESGGGV VQPGRSLRLSC AAS | GFTF WTY A | MHWVRQA PGKGLEWV AV | ISYD GND K | YYADSVKGRFTISRDNSK NTLYLQMNSLRAEDTAV YYC | VPT TFE Y | WGQG TLVTV SS |
| SEQ ID NO | 80 | 30 | 97 | 31 | 114 | 57 | 137 |

TABLE 10

Light chain variable regions of PD1 human antibodies

| NAME | FR1 | CDR1 | FR2 | CDR2 | FR3 | CDR3 | FR4 |
|---|---|---|---|---|---|---|---|
| PD1-49A2 (A/1B2) | DIVMTQTPLSLPV TPGEPASISCRSS | QSLLDS DDGNT Y | LDWYLQKP GQSPQLLIY | TLS | HRASGVPDRFSGSGSGT EFNLRISRVEAEDVGIY YC | MQRV EFPFT | FGQGT KLEIK |
| SEQ ID NO | 264 | 220 | 283 | | 320 | 233 | 347 |
| PD1-49A2 (A/1D11) | DIVMTQTPLSLPV TPGEPASISCRSS | QSLFDS DDGNT Y | LDWYLQKP GQSPQLLIY | TLS | YRASGVPDRFSGSGSGT DFTLKISRVEAEDVGVY YC | MQRV EFPFT | FGQGT KVEIK |
| SEQ ID NO | 264 | 215 | 283 | | 321 | 233 | 347 |
| PD1-49A2 (A/1F12) | DIVMTQTPHSLPV TPGEPASISCRSS | QSLLDS EDGNTY | LDWYLQKP GQSPQLLIY | TLS | HRALGVPDRFSGSGSGT DFTLKISRVEAEDSGIYY C | MQRI EFPYT | FGQGT KLEIK |
| SEQ ID NO | 271 | 205 | 283 | | 322 | 245 | 347 |
| PD1-49A2 (A/1H4) | DIVMTQSPLSLPV TPGEAASISCRSS | QSLLDS EDGNTY | LDWYLQKP GQSPQLLIY | TLS | HRASGVPDRFSGSGSGT DFTLKISRVEAEDSGIYY C | MQRV EFPYT | FGQGT KLDIK |
| SEQ ID NO | 272 | 205 | 283 | | 323 | 246 | 342 |
| PD1-49A2 (A/1H8) | DIVMTQTPLSLPV TPGEPASISCRSS | QSLLDR DGGHT Y | VDWYLQKP GQSPRLLIY | TLS | HRALGVPDRFSGSGSGT DFTLKISRVEADDVGLY YC | MQRI EFPFT | FGQGT KVEIK |
| SEQ ID NO | 264 | 221 | 294 | | 324 | 247 | 344 |
| PD1-49A2 (A/2A6) | DIVMTQTPLSLPV TPGEAASISCRSS | QSLLDS EDGNTY | LDWYLQRP GQSPQLLIY | TLS | HRASGVPGRFSGSGSGT EFNLRISRVEAEDVGIY YC | MQRV EFPFT | FGQGT KVEIK |
| SEQ ID NO | 257 | 205 | 295 | | 325 | 233 | 344 |
| PD1-49A2 (A/2A11) | DIVMTQTPLSLPV TPGEPASISCRSS | QSLFDS DDGNT Y | LDWYLQKP GQSPRLLIY | TLS | HRALGVPDRFSGSGSGT DFTLKISRVAAEDVGLY YC | LQRM GFPY T | FGQGT KLEIK |
| SEQ ID NO | 264 | 215 | 296 | | 326 | 230 | 347 |

TABLE 10-continued

Light chain variable regions of PD1 human antibodies

| NAME | FR1 | CDR1 | FR2 | CDR2 | FR3 | CDR3 | FR4 |
|---|---|---|---|---|---|---|---|
| PD1-49A2 (A/2B9) | DIVMTQTPLSLPV TPGEAASISCRSS | QSLLDS EDGNTY | LDWYLQKP GQSPQLLIY | TLS | HRASGVPDRFSGSGSGT DFTLEISRVEAEDVGVY YC | MQRR DFPFT | FGQGT KVDIK |
| SEQ ID NO | 257 | 205 | 283 | | 327 | 248 | 337 |
| PD1-49A2 (A/2B10) | DIVMTQTPLSLPV TPGEPASISCRSS | QSLLDS DDGNTY | LDWYLQKP GQSPQLLIY | TLS | HRASGVPDRFSGSGSGT DFTLKISRVAAEDVGLY YC | MQRV EFPFT | FGQGT KLDIK |
| SEQ ID NO | 264 | 220 | 283 | | 304 | 233 | 342 |
| PD1-49A2 (A/2D7) | DIVMTQTPLSLPV TPGEPASISCRSS | QSLLDR DGGHTY | VDWYLQKP GQSPRLLIY | TLS | HRALGVPDRFSGSGSGT DFTLKISRVEADNVGLY YC | MQRI EFPFT | FGQGT KVEIK |
| SEQ ID NO | 264 | 221 | 294 | | 328 | 266 | 344 |
| PD1-45D6 (A/3D2) | DIVMTQTPLSLPV TPGEAASISCRSS | QSLLDS EDGNTY | LDWYLQKP GQSPQLLIY | TLS | HRASGVPDRFSGSGSGT DFTLKISRVEAEDVGIY YC | MQRV EFPFT | FGQGT KVEIK |
| SEQ ID NO | 257 | 205 | 283 | | 314 | 233 | 344 |
| PD1-45D6 (A/3G1) | DIVMTQTPLSLPV TPGEPASISCRSS | QSLLDS EDGNTY | LDWYLQKP GQSPQLLIY | TLS | HRASGVPDRFSGSGSGT DFTLEISRVEAEDVGVY YC | MQRV EFPFT | FGQGT KLDIK |
| SEQ ID NO | 264 | 205 | 283 | | 327 | 233 | 342 |
| PD1-45D6 (A/3H4) | DIVMTQTPLSLPV TPGEPASISCRSS | QSLFDS DDGNTY | LDWYLQKP GQSPQLLIY | TLS | HRASGVSDRFSGSGSGT DFTLKISRVEAEDSGIYY C | MQRV EFPFT | FGQGT KLDIK |
| SEQ ID NO | 264 | 215 | 283 | | 329 | 233 | 342 |
| PD1-45D6 (A/3H6) | DIVMTQTPLSLPV TPGEAASISCRSS | QSLLDS EDGNTY | LDWYLQKP GQSPQLLIY | TLS | HRASGVPDRFSGSGSGT DFTLKISRVEAEDVGVY YC | MQRV EFPFT | FGQGT KLEIK |
| SEQ ID NO | 257 | 205 | 283 | | 330 | 233 | 347 |
| PD1-45D6 (A/3H7) | DIVMTQTPLSLPV TPGEPASISCRSS | QSLLDS DDGNTY | LDWYLQKP GQSPQLLIY | TLS | HRASGVPGRFSGSGSGT EFNLRISRVEAEDVGIY YC | MQRV EFPFT | FGQGT KLEIK |
| SEQ ID NO | 264 | 220 | 283 | | 325 | 233 | 347 |
| PD1-45D6 (A/4C1) | DIVMTQTPLSLPV TPGEPASISCRSS | QSLLDS DDGNTY | LDWYLQKP GQSPQLLIY | TLS | HRASGVPDRFSGSGSGT DFTLKISRVEAEDVGIY YC | MQRV EFPFT | FGQGT KLDIK |
| SEQ ID NO | 264 | 220 | 283 | | 314 | 233 | 342 |
| PD1-45D6 (A/4C9) | DIVMTQTPLSLPV TPGEAASISCRSS | QSLLDS EDGNTY | LDWYLQKP GQSPQLLIY | TLS | HRASGVPDRFSGSGSGT DFTLKISRVAAEDVGIY YC | MQRV EFPFT | FGQGT KLEIK |
| SEQ ID NO | 257 | 205 | 283 | | 331 | 233 | 347 |
| PD1-45D6 (A/4D4) | DIVMTQTPLSLPV TPGEPASISCRSS | QSLLDS EDGNTY | LDWYLQKP GQSPQLLIY | TLS | HRASGVPDRFSGSGSGT EFNLRISRVEAEDVGIY YC | MQRV EFPFT | FGQGT KVDIK |
| SEQ ID NO | 264 | 205 | 283 | | 320 | 233 | 337 |
| PD1-45D6 (A/4H6) | DIVMTQTPLSLPV TPGEPASISCRSS | QSLFDS DDGNTY | LDWYLQKP GQSPQLLIY | TLS | HRASGVPDRFSGSGSGT DFTLKISRVEAEDVGLY YC | MQRV EFPFT | FGQGT KLEIK |
| SEQ ID NO | 264 | 215 | 283 | | 312 | 233 | 347 |
| PD1-45D6 (A/5A6) | DIVMTQTPLSLPV TPGEPASISCRSS | QSLLDS EDGNTY | LDWYLQKP GQSPQLLIY | TLS | HRASGVPDRFSGSGSGT DFTLKISRVEAEDVGVY YC | MQRI DFPYT | FGQGT KLDIK |

TABLE 10-continued

Light chain variable regions of PD1 human antibodies

| NAME | FR1 | CDR1 | FR2 | CDR2 | FR3 | CDR3 | FR4 |
|------|-----|------|-----|------|-----|------|-----|
| SEQ ID NO | 264 | 205 | 283 | | 330 | 238 | 342 |
| PD1-45D6 (A/5B2) | DIVMTQTPLSPPV TPGEPASISCRSS | QSLLDS DDGNTY | LDWYLQKP GQSPQLLIY | TLS | HRASGVPDRFSGSGSGT DFTLEISRVEAEDVGVY YC | MQRR DFPFT | FGQGT KLDIK |
| SEQ ID NO | 273 | 220 | 283 | | 327 | 248 | 342 |
| PD1-45D6 (A/5B5) | DIVMTQTPLSLPV MPGEAASISCRSS | QSLLDS EDGNTY | LDWYLQKP GQSPQLLIY | TLS | HRASGVPDRFSGSGSGT DFTLKISRVEADDVGIY YC | MQRV EFPFT | FGQGT KVEIK |
| SEQ ID NO | 274 | 205 | 283 | | 332 | 233 | 344 |
| PD1-45D6 (A/5B12) | DIVMTQTPLSLPV TPGEAASISCRSS | QSLLDS EDGNTY | LDWYLQKP GQSPQLLIY | TLS | HRASGVPDRFSGSGSGT DFTLKISRVEAEDVGIY YC | MQRV EFPFT | FGQGT KVEIK |
| SEQ ID NO | 257 | 205 | 283 | | 314 | 233 | 344 |
| PD1-45D6 (A/5C8) | DIVMTQSPLSLPV TPGEPASISCRSS | QSLLDS EDGNTY | LDWYLQKP GQSPQLLIY | TLS | HRASGVPDRFSGSGSGT DFTLKISRVEAEDVGVY YC | MQRV EFPFT | FGQGT KLDIK |
| SEQ ID NO | 266 | 205 | 283 | | 330 | 233 | 342 |
| PD1-45D6 (A/5H9) | DIVMTQTPLSLPV TPGEPASISCRSS | QSLLDS DDGNTY | LDWYLQKP GQSPQLLIY | TLS | HRASGVSDRFSGSGSGT DFTLEISRVEAEDVGVY YC | MQRR DFPFT | FGQGT KVEIK |
| SEQ ID NO | 264 | 220 | 283 | | 333 | 248 | 344 |

Example 7: Production of PD-1 Human Antibody

1. Conversion of scFv Form to IgG Form

PCR (iCycler iQ, BIO-RAD) was performed on the heavy and light chains to convert the selected 25 species of monoclonal phage antibodies to PD1 from phages to IgG whole vector. As a result, heavy and light chains were obtained, and the vectors and the heavy and light chains of each of the clones were cut (digested) with restriction enzymes. DNAs were eluted from each of the vector and heavy chain with a DNA-gel extraction kit (Qiagen). Ligation was performed by mixing 1 µl (10 ng) of the vector, 15 µl (100-200 ng) of the heavy chain, 2 µl of 10× buffer, 1 µl of ligase (1 U/µl) and distilled water, allowing the mixture to stand at room temperature for 1 to 2 hours, injecting the resulting mixture into transformed cells (competent cells, XL1-blue), placing the cells on ice for 5 minutes and subjecting the cells to heat-shock at 42° C. for 90 seconds.

After the heat shock, 1 ml of the medium was added to the cells, and then the cells were grown at 37° C. for 1 hour, spread on an LB Amp plate and incubated at 37° C. for 16 hours. The colony thus obtained was inoculated with 5 ml of LB Amp medium, cultured at 37° C. for 16 hours and subjected to DNA-prep using a DNA-prep kit (Nuclogen). Sequence analysis of the obtained DNAs was requested (Solgent).

As a result, it was confirmed that the sequences of heavy chains and light chains of 25 clones for PD1 converted into the whole IgG corresponded to the sequences of the phage antibodies. In order to transfect into HEK 293F cells, the heavy and light chains of respective clones converted into whole IgG were grown in 100 ml of LB Amp medium, and DNAs were obtained using a Midi-prep kit (QIAgen).

2. Human Antibody Production

The cloned pNATVH and pNATVL vectors were co-transfected at a ratio of 6:4 into HEK293F cells and the supernatant was collected on the 7th day, the cells and debris were removed through centrifugation and a 0.22 µm top filter, and the supernatant was collected and subjected to protein A affinity chromatography to purify the IgG antibody. After purification, the antibody was separated through a glycine buffer, and buffer was changed such that the final resuspension buffer was PBS. Purified antibodies were quantitated by BCA and nano drop, and each of 25 species of antibodies was loaded in a dose of 5 ug under reducing and non-reducing conditions, and analyzed by SDS-PAGE to determine purity and mobility of the purified protein. In addition, some of the supernatants were loaded on SDS-PAGE to compare the expression rates with the parent antibody, the majority of the antibodies were more expressed than the parent antibody and the results can be seen from FIG. 11.

Example 8: Characteristics of PD-1 Monoclonal Antibody

1. Evaluation of Antibody Activity

Testing for activity of the selected antibodies was carried out using a PD1/PD-L1 blockade bioassay kit (promega, J1250). A CHO cell line highly expressing PD-L1 was spread on a 96-well plate, cultured for 16 hours or longer, treated with each antibody serially diluted at a constant concentration, and then cultured together with a Jurkat cell line highly expressing human PD-1, for 6 hours. The degree of recovery of the inhibition of the antibody was determined with a spectrophotometer (SpectraMax M5 spectrophotometer, Molecular Devices, USA), which was determined from a luminescent intensity resulting from degradation of the substrate by luciferase. The activity of 24 species of PD-1 antibodies was found based on the value to recover a reduced signal by formation of a PD-1/PD-L1 complex, and among 45D6 antibodies, 45D6-3D2, 45D6-3H7, 45D6-5B2, and 45D6-5B5 and, among 49A2 antibodies, 49A2-1B2, 49A2-1H8, 49A2-2A6, and 49A2-2B9 exhibited higher activity than the parent antibody and similar activity to the control antibody (FIG. 12).

In order to measure activity of 8 species of PD-1 antibodies (45D6-3D2, 45D6-3H7, 45D6-5B2, 45D6-5B5, 49A2-1B2, 49A2-1H8, 49A2-2A6, 49A2-2B9) in a concentration-dependent manner, serial dilution and PD1/PD-L1 blockade bioassay were performed again to recover the reduced signal in a concentration gradient dependent manner. The degree of recovery can be expressed as EC50 (effective concentration of mAb at 50% level of recovery signal), analyzed using Graphpad Prism6, and 49A2-1B2 exhibited the highest in vitro efficacy inhibition recovery ability of EC50 (FIG. 13, Table 11).

TABLE 11

Activity of monoclones of selected PD1 antibody variants

| Antibody | EC50 [nM] |
| --- | --- |
| PD-1-41C9 | 3.91 |
| PD-1-45D6 | 2 |
| PD-1-45D6-A-3D2 | 2.16 |
| PD-1-45D6-A-3G1 | 0.98 |
| PD-1-45D6-A-3H4 | 1.67 |
| PD-1-45D6-A-3H6 | 1.49 |
| PD-1-45D6-A-3H7 | 1.98 |
| PD-1-45D6-A-4C1 | 1.76 |
| PD-1-45D6-A-4C9 | 2.72 |
| PD-1-45D6-A-4D4 | 1.74 |
| PD-1-45D6-A-4H6 | 1.19 |
| PD-1-45D6-A-5A6 | 0.92 |
| PD-1-45D6-A-5B12 | 0.8 |
| PD-1-45D6-A-5B2 | 1.48 |
| PD-1-45D6-A-5B5 | 1.68 |
| PD-1-45D6-A-5C8 | 1.44 |
| PD-1-45D6-A-5H9 | 2 |
| PD-1-48A9 | 8.64 |
| PD-1-49A2 | 3.78 |
| PD-1-49A2-A-1B2 | 1.3 |
| PD-1-49A2-A-1D11 | 2.89 |
| PD-1-49A2-A-1F12 | 1.03 |
| PD-1-49A2-A-1H4 | 0.84 |
| PD-1-49A2-A-1H8 | 1.21 |
| PD-1-49A2-A-2A11 | 0.79 |
| PD-1-49A2-A-2A6 | 1.51 |
| PD-1-49A2-A-2B10 | 0.65 |
| PD-1-49A2-A-2B9 | 1.23 |
| PD-1-51D9 | ~4.695e+010 |
| PD-1-52E8 | 8.43 |
| PD-1-62E1 | 2.73 |
| PD1-72D10 | 1.21 |
| PD1-74A11 | 1.31 |
| PD1-75C10 | 0.81 |
| PD1-74A01 | 1.01 |
| PD1-74H12 | 0.98 |

2. Affinity of PD1 Antibody to Overexpressed Cells

Regarding transformation cell pools highly expressing human PD-1, HEK293E was transformed with a pcDNA3.1 plasmid containing human PD-1 (NM_005018.2) or human PD-L1 (NM_014143.2) and screened in a selective medium containing 400 ug/ml Zeocin (#R25001, Thermo Fisher). Each cell pool was identified and selected by fluorescence activated cell sorting (FACS) analysis using anti-PD-1 (#557860, BD) and used for functional assays such as FACS binding assays or FACS competition assays. 0.5 to 1×10⁶ cells per sample were prepared from the transformation cell pools highly expressing human PD-1, and antibodies were serially diluted at a constant dilution rate and reacted with the prepared cells at 4° C. for 20 minutes. Then, the cells were washed three times with PBS (#LB001-02, Welgene) containing 2% fetal bovine serum and reacted at 4° C. for 20 minutes with an anti-human IgG antibody (#FI-3000, Vectorlabs) conjugated with a FITC (fluorescein isothiocyanate) fluorescent substance. Then, the cells were subjected to the same washing process as above and then suspended in 0.5 ml of PBS containing 2% FBS (#26140-079, Thermo Fisher) with an FACSCanto II flow cytometer (BD Biosciences, USA) as a flow cytometer.

0.5 to 1×10⁶ cells per sample were each prepared from the transformation cell pools highly expressing human PD-1, and antibodies were serially diluted at a constant dilution rate and reacted with the prepared cells at 4° C. for 20 minutes. Then, the cells were washed three times with PBS (#LB001-02, Welgene) containing 2% fetal bovine serum and reacted at 4° C. for 20 minutes with an anti-human IgG antibody (#FI-3000, Vectorlabs) conjugated with a FITC (fluorescein isothiocyanate) fluorescent substance. Then, the cells were subjected to the same washing process as above and then suspended in 0.5 ml of PBS containing 2% FBS (#26140-079, Thermo Fisher) with an FACSCanto II flow cytometer (BD Biosciences, USA) as a flow cytometer. The binding capacity was determined from an equilibrium dissociation constant ($K_d$) obtained through an analysis function of Graphpad Prism6. As a result, as can be seen from FIG. 15, the binding capacity of antibody bound in a concentration-dependent manner to human PD-1 over-expressed on the cell surface can be found by MFI (mean fluorescence intensity). As can be seen from FIGS. 14 and 15, antibodies excluding 49A2 (Parent 49A2) exhibited similar binding capability.

3. Inhibitory Ability of Antibody Against Formation of PD-1/PD-L1 or PD-1/PD-L2 Complex by Enzyme Immunoadsorption Human PD-1-Fc (S1420, Y-Biologics) or PD-L2-Fc (#10292-H02H, Sino) was added to wells of a 96-well immuno microplate (#439454, Thermo) and then washed three times with PBS containing 0.05% tween-20 (#P9416, Sigma-Aldrich), followed by allowing to stand in a cleaning solution containing 4% skim milk (#232120, Becton, Dickinson and Company) at room temperature for 1 hour to block non-specific binding. At the same time, human PD-L1-His (51479, Y-Biologics) or PD-1-His (S1352, Y-Biologics) was reacted with antibodies serially diluted at a constant dilution rate at room temperature for hour, followed by allowing to stand in the prepared microplate at room temperature for 1 hour. After the resulting product was subjected to the same washing method as above, the anti-Biotin-His antibody (#MA1-21315-BTIN, Thermo) diluted to 1:2000 was added to the well of the microplate, allowed to react at room temperature for 1 hour, streptavidin poly-HRP antibody (#21140, Pierce) diluted to 1:5000 was added to the well of microplate, reacted at room temperature for 1 hour and then washed in the same manner. 100 ul of a TMB substrate solution (#T0440, Sigma-Aldrich) was added to the reaction product, light was shielded, and the reaction product was allowed to stand at room temperature for 3 minutes, 50 μL of 2.5 M sulfuric acid (#S1478, Samchun) was added to stop the reaction, and absorbance was measured at 450 nm using a spectrophotometer (*GM3000, Glomax® Discover System Promega). The results are shown in FIG. 16.

4. Affinity of PD1 Antibody Using ProteOn XPR36

A ProteOn XPR36 (BioRad) instrument was used. The GLC sensor chip (BioRad) was mounted on the instrument and washed with PBST buffer, and the carboxymethyldextran surface was activated with an EDC/sulfo-NHS mixed solution. PD1-hFc dissolved at a concentration of 5 ug/ml in a 10 mM sodium acetate buffer solution (pH 5.0) was injected and immobilized on the GLC sensor chip.

In order to deactivate the activated carboxyl groups that remain unreacted with the PD1 protein, 1 M ethanolamine was flowed and 10 mM glycine (pH 2.0) was injected in order to wash proteins that remain unbound to the sensor chip. Then, sensogram data were collected during binding and dissociation over time while allowing the antibodies to flow at a flow rate of 30 μL/min (30 nM to 0.123 nM) for 10 min using PBST buffer.

The equilibrium dissociation constant ($K_D$) was calculated by plotting and fitting the sensogram data in the equilibrium state depending on concentration. As a result, 49A2 (2B9) exhibited $K_D$ of 0.001 nM, indicating high affinity to PD1 antigen (FIG. 17).

The affinity of other antibodies to the human PD-1 protein, the affinity to monkey PD-1 proteins, and the affinity to rat PD-1 proteins are as shown in Tables 12 to 14.

TABLE 12

Binding kinetics between human PD1 protein and selected antibody

| Ab | KD(M) | Ka(1/Ms) | Kd(1/s) |
|---|---|---|---|
| PD1 49A2 | $2.371 \times 10^{-10}$ | $3.953 \times 10^5$ | $9.372 \times 10^{-5}$ |
| PD1 49A2 1H8 | $1.245 \times 10^{-11}$ | $2.201 \times 10^5$ | $2.741 \times 10^{-6}$ |
| PD1 49A2 1B2 | $1.659 \times 10^{-10}$ | $3.853 \times 10^5$ | $6.390 \times 10^{-5}$ |
| PD1 49A2 2A6 | $6.907 \times 10^{-11}$ | $3.101 \times 10^5$ | $2.142 \times 10^{-5}$ |
| PD1 49A2 2B9 | $1.0 \times 10^{-12}$ | $3.774 \times 10^5$ | $1.0 \times 10^{-7}$ |
| PD1 45D6 | $1.0 \times 10^{-12}$ | $2.701 \times 10^5$ | $1.07 \times 10^{-7}$ |
| PD1 45D6 3D2 | $1.0 \times 10^{-12}$ | $1.81 \times 10^5$ | $1.0 \times 10^{-7}$ |
| PD1 45D6 3H7 | $2.53 \times 10^{-11}$ | $3.076 \times 10^5$ | $7.781 \times 10^{-6}$ |
| PD1 45D6 5B2 | $5.818 \times 10^{-11}$ | $3.315 \times 10^5$ | $1.928 \times 10^{-5}$ |
| PD1 45D6 5B5 | $4.773 \times 10^{-11}$ | $2.96 \times 10^5$ | $1.413 \times 10^{-5}$ |

TABLE 13

Binding kinetics between monkey PD1 protein and selected antibody

| Ab | KD (M) | Ka(1/Ms) | Kd(1/s) |
|---|---|---|---|
| PD-1-49A2 | $1.0 \times 10^{-12}$ | $1.683 \times 10^5$ | $1.0 \times 10^{-7}$ |
| PD-1-49A2-2B9 | $1.0 \times 10^{-12}$ | $1.853 \times 10^5$ | $1.0 \times 10^{-7}$ |
| PD-1-45D6 | $1.0 \times 10^{-12}$ | $1.535 \times 10^5$ | $1.0 \times 10^{-7}$ |
| PD-1-45D6-5B2 | $1.0 \times 10^{-12}$ | $2.078 \times 10^5$ | $1.0 \times 10^{-7}$ |

TABLE 14

Binding kinetics between rat PD1 protein and selected antibody

| Ab | KD(M) | Ka(1/Ms) | Kd(1/s) |
|---|---|---|---|
| PD-1-49A2-2B9 | $4.231 \times 10^{-9}$ | $1.478 \times 10^5$ | $6.252 \times 10^{-4}$ |
| PD-1-45D6 | $2.391 \times 10^{-9}$ | $5.544 \times 10^4$ | $1.326 \times 10^{-4}$ |
| PD-1-45D6-5B2 | $4.590 \times 10^{-9}$ | $1.879 \times 10^5$ | $8.626 \times 10^{-4}$ |

Example 9: Determination of Epitope of PD1 Monoclonal Antibody

The monoclonal scFv-phage binding to the PD1 antigen was cultured in a medium containing 2×YTCM, 2% glucose and 5 mM $MgCl_2$ at 37° C. for 16 hours. The cells thus grown were cultured in a medium containing 2×YTCM, 2% glucose and 5 mM $MgCl_2$ to $OD_{600}$ of 0.1, and then cultured at 37° C. for 2 to 3 hours at $OD_{600}$ of 0.5 to 0.7. M1 helper phages were infected at an MOI of 1:20 and cultured in a medium containing 2×YTCMK, 5 mM $MgCl_2$, and 1 mM IPTG at 30° C. for 16 hours.

Figures 18, 19:
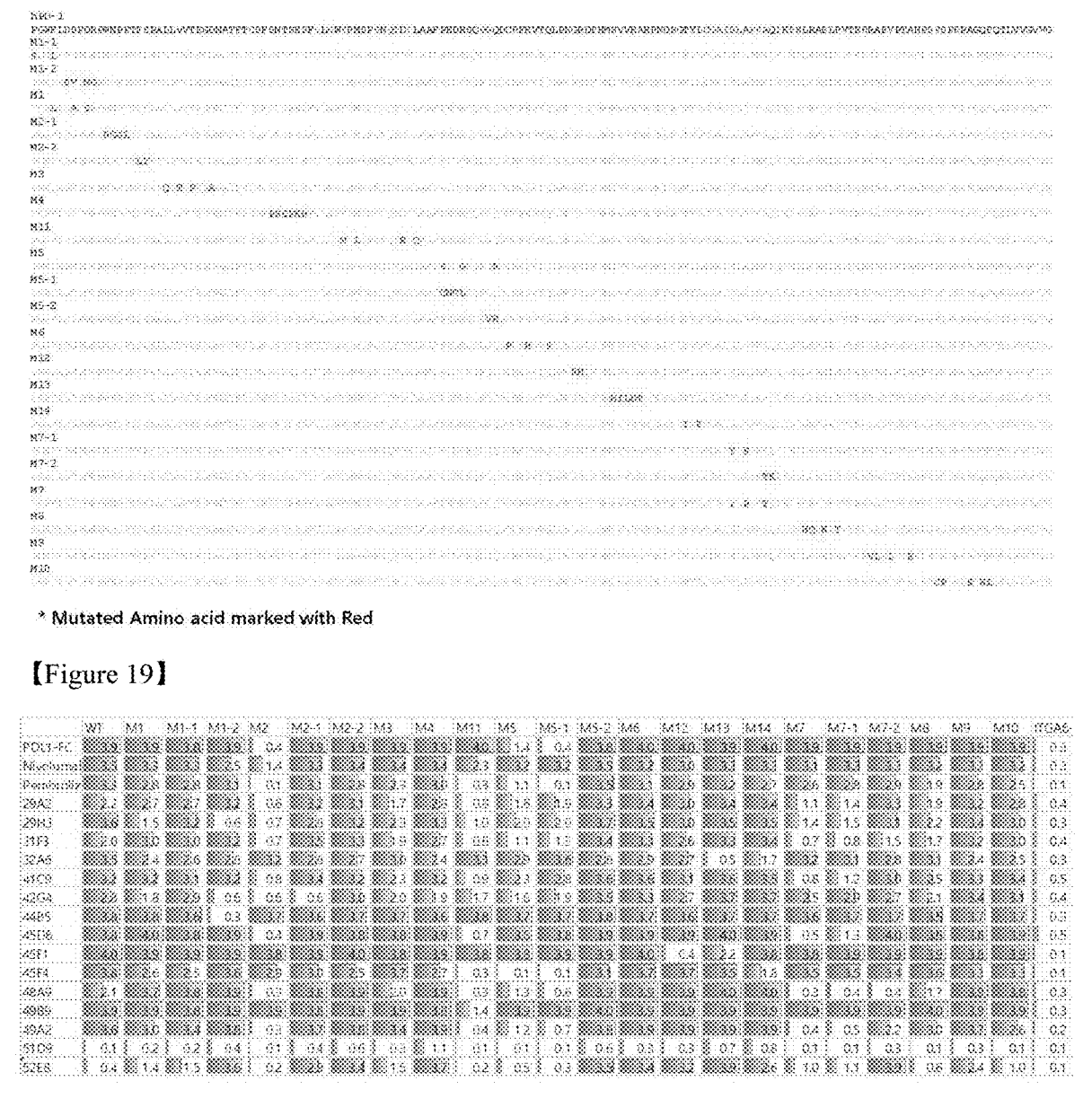

The antigen PD1 wild type (WT) or several variants (FIG. 18) were coated at a density of 100 ng/well on a 96-well immunoplate at 4° C. for 16 hours and the wells were blocked with 4% skim milk dissolved in PBS. Each well was washed with 0.2 ml of PBS/T, and then a single clone scFv-phage (each 100 scFv-phage) cultured for 16 hours was added in a dose of 100 μl to each well and reacted at room temperature for 2 hours. Again, each well was washed 4 times with 0.2 ml of PBS/T, and then the second antibody, anti-M13-HRP, was diluted to 1/2000 and reacted at room temperature for 1 hour. After washing with 0.2 ml of PBS/T, color development was performed and absorbance was measured at 490 nm.

As a result, it was confirmed that the selected single clone scFv-phage, control scFv-phage and PD-1 variants showed different binding behaviors and thus had different epitopes (FIG. 19).

The antigen PD1 wild type (WT) or several variants (FIG. 18) were coated at a density of 100 ng/well on a 96-well immunoplate at 4° C. for 16 hours and the wells were blocked with 4% skim milk dissolved in PBS. Each well was washed with 0.2 ml of PBS/T, and then a single clone scFv-phage cultured for 16 hours was added in a dose of 100 μl (1 ug/ml) to each well and reacted at room temperature for 2 hours. Again, each well was washed 4 times with 0.2 ml of PBS/T, and then the second antibody, anti-Fab, was diluted to 1/2000 and reacted at room temperature for 1 hour. After washing with 0.2 ml of PBS/T, color development was performed and absorbance was measured at 490 nm.

As a result, it was confirmed that control scFv-phage and PD-1 variants showed different binding behaviors and thus had different epitopes (FIG. 20).

Example 10: Specific Binding of PD1 Parent Antibody

To identify binding capacities of the PD1 parent antibody and the control antibody (Nivolumab) to various antigens other than the PD1 antigen (Table 15), about 90 non-specific antigens coated at a density of at 100 ng/well on 96-well immuno-plates at 4° C. for 16 hours and respective wells were blocked using 4% skim milk dissolved in PBS. Each well was washed with 0.2 ml of PBS/T, and then the parent antibody and control antibody were added in a dose of 100 μl (1 ug/ml) to each well and reacted at room temperature for 2 hours. Again, each well was washed 4 times with 0.2 ml of PBS/T, and then the second antibody, anti-kappa-HRP, was diluted to 1/2000 and reacted at room temperature for 1 hour. After washing with 0.2 ml of PBS/T, color development was performed and absorbance was measured at 490 nm.

TABLE 15

| Fc | GP1BA | LRRN4 | TLR3 | LRTM1 | TPBG | SEMA6A | SEMA5A | SLITRK5 | EPYC | LINGO1 | OGN |
| --- | --- | --- | --- | --- | --- | --- | --- | --- | --- | --- | --- |
| OPTC | RTN4RL1 | LRRC4C | LRRTM2 | TLR4 | TLR7 | TLR9 | LRRN1 | SLITRK2 | FZD10 | C2orf28 | SUSD1 |
| FSTL3 | SPOCK1 | CD209 | CD97 | SCARF1 | WIF1 | TNR | EMR1 | SPARC | DNER | BAMBI | FSTL1 |
| Kremen1 | CFC1 | TMEFF2 | NRG4 | SPOCK2 | CD40LG | FASLG | TNFSF4 | GREM1 | Fc | LRP11 | LRP12 |
| APCDD1 | CHRDL1 | DKK4 | DMP1 | LRP6 | TNFSF9 | TNFSF8 | TNF | TNFSF12 | TMED1 | CD320 | SOST |
| C18orf1 | OSTM1 | NBL1 | DKK3 | ECM1 | TNFSF18 | TNFSF13 | DKK1 | SELP | HAPLN4 | ULBP1 | SPINT2 |
| PLXDC1 | PLXDC2 | PODXL | CDCP1 | P13 | WFDC2 | AGR2 | AGR3 | CREG1 | EV12A | RAET1E | MICA |
| CD86 | ICOSLG | CD276 | PDCD1 | BTN2A1 | BTN3A2 | BTN3A1 | BTNL9 | BTN3A3 | BTN1A1 | Fc | blank |

As a result, it was confirmed that both the control antibody and the parent antibody specifically bind only to the PD1 antigen without binding to the unspecified antigen (FIG. 21).

Example 11: Comparison of Productivity in Transient Expression System of PD1 Monoclonal Antibodies It can be seen that the optimized antibody has relatively uniform and high productivity due to excellent physical properties upon production and purification through the temporary expression system. Some antibodies have higher productivity than conventionally commercially available antibodies (FIG. 22).

Example 12: Activity Increase of PD1 Monoclonal Antibody in Allogenic MLR Reaction T cells were mixed with monocyte-derived dendritic cells separated from different humans at a ratio of 1:10 and cultured for 5 days, and the amount of interferon gamma in the culture medium was measured. As a result, culture media containing parent antibodies of 45D6 and 49A2 exhibited a concentration-dependent increase in amount of interferon gamma (FIG. 23).

Example 13: Thermal Stability Test of PD1 Monoclonal Antibody

The antibody protein was diluted in DPBS to 3 uM, 45 ul, mixed with 5 ul of 200× Sypro orange dye (#S6650, Thermo) and then aliquoted in a dose of 50 ul into a qPCR Tube (#B77009, B57651, bioplastics). QPCR was performed using a Biorad CFX96 real time PCR system. The qPCR conditions were given as follows: reaction at 25° C. for 30 seconds, elevation of the temperature by 1° C. up to 99° C. and at the same time, reaction at each temperature for 1 min, and final reaction at 25° C. for 10 seconds. Tm (melting temperature) was used as a rate constant at which the antibody structure was un-bound. The results are shown in Table 16 below.

TABLE 16

| Sample | Tm |
| --- | --- |
| Pembrolizumab | 63 |
| Opdivo | 64 |
| 45D6 | 63 |
| 49A2 | 63 |
| 49A2-2B9 | 64 |

INDUSTRIAL AVAILABILITY

The novel antibodies that bind to PD-1 or antigen-binding fragments thereof according to the present disclosure can bind to PD-1 and inhibit the activity of PD-1, thus being useful for the development of immunotherapeutic agents for various diseases associated with PD-1.

Although specific configurations of the present disclosure have been described in detail, those skilled in the art will appreciate that this description is provided as preferred embodiments for illustrative purposes and should not be construed as limiting the scope of the present disclosure. Therefore, the substantial scope of the present disclosure is defined by the accompanying claims and equivalents thereto.

---

The invention claimed is:

1. An antibody binding to PD-1 or an antigen-binding fragment thereof, comprising:

(A) a heavy chain variable region comprising a heavy chain CDR1 comprising the sequence of SEQ ID NO: 1, a heavy chain CDR2 comprising the sequence of SEQ ID NO: 32, and a heavy chain CDR3 comprising the sequence of SEQ ID NO: 58; and a light chain variable region comprising a light chain CDR1 comprising the sequence of SEQ ID NO: 215, a light chain CDR2 comprising the sequence of Thr Leu Ser, and a light chain CDR3 comprising the sequence of SEQ ID NO: 230, (B) a heavy chain variable region comprising a heavy chain CDR1 comprising the sequence of SEQ ID NO: 1, a heavy chain CDR2 comprising the sequence of SEQ ID NO: 31, a and heavy chain CDR3 comprising the sequence of SEQ ID NO: 57; and a light chain variable region comprising a light chain CDR1 comprising the sequence of SEQ ID NO: 208, a light chain CDR2 comprising the sequence of Thr Leu Ser, and a light chain CDR3 comprising the sequence of SEQ ID NO: 233, (C) a heavy chain variable region comprising a heavy chain CDR1 comprising the sequence of SEQ ID NO: 21, a heavy chain CDR2 comprising the sequence of SEQ ID NO: 51, a and heavy chain CDR3 comprising the sequence of SEQ ID NO: 58; and a light chain variable region comprising a light chain CDR1 comprising the sequence of SEQ ID NO: 221, a light chain CDR2 comprising the sequence of Thr Leu Ser, and a light chain CDR3 comprising the sequence of SEQ ID NO: 247, (D) a heavy chain variable region comprising a heavy chain CDR1 comprising the sequence of SEQ ID NO: 17, a heavy chain CDR2 comprising the sequence of SEQ ID NO: 49, a and heavy chain CDR3 comprising the sequence of SEQ ID NO: 58; and a light chain variable region comprising a light chain CDR1 comprising the sequence of SEQ ID NO: 220, a light chain CDR2 comprising the sequence of Thr Leu Ser, and a light chain CDR3 comprising the sequence of SEQ ID NO: 233, (E) a heavy chain variable region comprising a heavy chain CDR1 comprising the sequence of SEQ ID NO: 22, a heavy chain CDR2 comprising the sequence of SEQ ID NO: 53, a and heavy chain CDR3 comprising the sequence of SEQ ID NO: 58; and a light chain variable region comprising a light chain CDR1 comprising the sequence of SEQ ID NO: 205, a light chain CDR2 comprising the sequence of Thr Leu Ser, and a light chain CDR3 comprising the sequence of SEQ ID NO: 233, (F) a heavy chain variable region comprising a heavy chain CDR1 comprising the sequence of SEQ ID NO: 17, a heavy chain CDR2 comprising the sequence of SEQ ID NO: 54, a and heavy chain CDR3 comprising the sequence of SEQ ID NO: 58; and a light chain variable region comprising a light chain CDR1 comprising the sequence of SEQ ID NO: 205, a light chain CDR2 comprising the sequence of Thr Leu Ser, and a light chain CDR3 comprising the sequence of SEQ ID NO: 248, (G) a heavy chain variable region comprising a heavy chain CDR1 comprising the sequence of SEQ ID NO: 1, a heavy chain CDR2 comprising the sequence of SEQ ID NO: 31, a and heavy chain CDR3 comprising the sequence of SEQ ID NO: 57, a light chain variable region comprising a light chain CDR1 comprising the sequence of SEQ ID NO: 205, a light chain CDR2 comprising the sequence of Thr Leu Ser, and a light chain CDR3 comprising the sequence of SEQ ID NO: 233, (H) a heavy chain variable region comprising a heavy chain CDR1 comprising the sequence of SEQ ID NO: 1, a heavy chain CDR2 comprising the sequence of SEQ ID NO: 31, a and heavy chain CDR3 comprising the sequence of SEQ ID NO: 57; and a light chain variable region comprising a light chain CDR1 comprising the sequence of SEQ ID NO: 220, a light chain CDR2 comprising the sequence of Thr Leu Ser, and a light chain CDR3 comprising the sequence of SEQ ID NO: 233, (I) a heavy chain variable region comprising a heavy chain CDR1 comprising the sequence of SEQ ID NO: 26, a heavy chain CDR2 comprising the sequence of SEQ ID NO: 31, a and heavy chain CDR3 comprising the sequence of SEQ ID NO: 57; and a light chain variable region comprising a light chain CDR1 comprising the sequence of SEQ ID NO: 220, a light chain CDR2 comprising the sequence of Thr Leu Ser, and a light chain CDR3 comprising the sequence of SEQ ID NO: 248, or (J) a heavy chain variable region comprising a heavy chain CDR1 comprising the sequence of SEQ ID NO: 27, a heavy chain CDR2 comprising the sequence of SEQ ID NO: 31, a and heavy chain CDR3 comprising the sequence of SEQ ID NO: 57; and a light chain variable region comprising a light chain CDR1 comprising the sequence of SEQ ID NO: 205, a light chain CDR2 comprising the sequence of Thr Leu Ser, and a light chain CDR3 comprising the sequence of SEQ ID NO: 233.

2. The antibody or an antigen-binding fragment thereof according to claim 1, comprising:
a heavy chain variable region FR1 selected from the group consisting of SEQ ID NOS: 80 to 95;
a heavy chain variable region FR2 selected from the group consisting of SEQ ID NOS: 96 to 113;
a heavy chain variable region FR3 selected from the group consisting of SEQ ID NOS: 114 to 134; or
a heavy chain variable region FR4 selected from the group consisting of SEQ ID NOS: 135 to 145.

3. The antibody or an antigen-binding fragment thereof according to claim 1, comprising:
a light chain variable region FR1 selected from the group consisting of SEQ ID NOS: 251 to 275;
a light chain variable region FR2 selected from the group consisting of SEQ ID NOS: 276 to 296;
a light chain variable region FR3 selected from the group consisting of SEQ ID NOS: 297 to 336; or
a light chain variable region FR4 selected from the group consisting of SEQ ID NOS: 337 to 348.

4. The antibody or an antigen-binding fragment thereof according to claim 1, comprising:
a heavy chain variable region comprising a sequence selected from the group consisting of sequences as set forth in SEQ ID NOS: 146, 147, 171, 175, 176, 178, 181, 184, and 185.

5. The antibody or an antigen-binding fragment thereof according to claim 1, comprising:
a light chain variable region comprising a sequence selected from the group consisting of sequences as set forth in SEQ ID NOS: 359, 366, 372, 376, 377, 379, 382, 386, 392, and 393.

6. A nucleic acid encoding the antibody or an antigen-binding fragment thereof according to claim 1.

7. An expression vector comprising the nucleic acid according to claim 6.

8. A cell transformed with the expression vector according to claim 7.

9. A method for producing an antibody binding to PD-1 or an antigen-binding fragment thereof, comprising:
(a) culturing the cell according to claim 8; and
(b) recovering the antibody or an antigen-binding fragment thereof from the cell culture.

10. A composition for preventing or treating cancer comprising, as an active ingredient, the antibody or an antigen-binding fragment thereof according to claim 1.

11. The composition according to claim 10, wherein the cancer is selected from the group consisting of melanoma, lung cancer, liver cancer, gliocytoma, ovarian cancer, colon cancer, head and neck cancer, bladder cancer, kidney cancer, stomach cancer, breast cancer, metastatic cancer, prostate cancer and pancreatic cancer.

12. An antibody binding to PD-1 or an antigen-binding fragment thereof, comprising:
a heavy chain variable region comprising
a heavy chain CDR1 comprising the sequence of SEQ ID NO: 17,
a heavy chain CDR2 comprising the sequence of SEQ ID NO: 54,
a heavy chain CDR3 comprising the sequence of SEQ ID NO: 58,
a light chain variable region comprising
a light chain CDR1 comprising the sequence of SEQ ID NO: 205,
a light chain CDR2 comprising the sequence of Thr Leu Ser,
a light chain CDR3 comprising the sequence of SEQ ID NO: 248.

* * * * *

UNITED STATES PATENT AND TRADEMARK OFFICE
CERTIFICATE OF CORRECTION

PATENT NO. : 11,248,048 B2  
APPLICATION NO. : 16/321124  
DATED : February 15, 2022  
INVENTOR(S) : Park et al.

Page 1 of 1

It is certified that error appears in the above-identified patent and that said Letters Patent is hereby corrected as shown below:

In the Specification

Column 2, Line 21, "(TILS)" should be -- (TILs) --.

Column 20, Line 30, "racy" should be -- rac5 --.

Column 54, Line 46, "51479" should be -- S1479 --.

Column 54, Line 63, "*GM3000" should be -- #GM3000 --.

Signed and Sealed this  
Twelfth Day of April, 2022

Drew Hirshfeld  
*Performing the Functions and Duties of the  
Under Secretary of Commerce for Intellectual Property and  
Director of the United States Patent and Trademark Office*

SEQUENCE LISTING

```
<160> NUMBER OF SEQ ID NOS: 401

<210> SEQ ID NO 1
<211> LENGTH: 8
<212> TYPE: PRT
<213> ORGANISM: Artificial Sequence
<220> FEATURE:
<223> OTHER INFORMATION: synthetic construct heavy chain CDR1

<400> SEQUENCE: 1

Gly Phe Thr Phe Ser Ser Tyr Ala
1               5

<210> SEQ ID NO 2
<211> LENGTH: 8
<212> TYPE: PRT
<213> ORGANISM: Artificial Sequence
<220> FEATURE:
<223> OTHER INFORMATION: synthetic construct heavy chain CDR1
```

```
<400> SEQUENCE: 2

Gly Phe Thr Phe Asn Asp Tyr Ala
1               5

<210> SEQ ID NO 3
<211> LENGTH: 8
<212> TYPE: PRT
<213> ORGANISM: Artificial Sequence
<220> FEATURE:
<223> OTHER INFORMATION: synthetic construct heavy chain CDR1

<400> SEQUENCE: 3

Gly Phe Thr Phe Asp Asp Tyr Gly
1               5

<210> SEQ ID NO 4
<211> LENGTH: 8
<212> TYPE: PRT
<213> ORGANISM: Artificial Sequence
<220> FEATURE:
<223> OTHER INFORMATION: synthetic construct heavy chain CDR1

<400> SEQUENCE: 4

Gly Gly Thr Phe Ser Ser Tyr Ala
1               5

<210> SEQ ID NO 5
<211> LENGTH: 8
<212> TYPE: PRT
<213> ORGANISM: Artificial Sequence
<220> FEATURE:
<223> OTHER INFORMATION: synthetic construct heavy chain CDR1

<400> SEQUENCE: 5

Gly Asp Thr Phe Thr Arg Asn Ala
1               5

<210> SEQ ID NO 6
<211> LENGTH: 8
<212> TYPE: PRT
<213> ORGANISM: Artificial Sequence
<220> FEATURE:
<223> OTHER INFORMATION: synthetic construct heavy chain CDR1

<400> SEQUENCE: 6

Gly Phe Thr Phe Ser Asp Tyr Tyr
1               5

<210> SEQ ID NO 7
<211> LENGTH: 8
<212> TYPE: PRT
<213> ORGANISM: Artificial Sequence
<220> FEATURE:
<223> OTHER INFORMATION: synthetic construct heavy chain CDR1

<400> SEQUENCE: 7

Gly Tyr Thr Phe Asn Ser Tyr Tyr
1               5

<210> SEQ ID NO 8
<211> LENGTH: 8
<212> TYPE: PRT
<213> ORGANISM: Artificial Sequence
<220> FEATURE:
<223> OTHER INFORMATION: synthetic construct heavy chain CDR1

<400> SEQUENCE: 8
```

```
Gly Phe Thr Phe Asp Asp Tyr Ala
1               5

<210> SEQ ID NO 9
<211> LENGTH: 8
<212> TYPE: PRT
<213> ORGANISM: Artificial Sequence
<220> FEATURE:
<223> OTHER INFORMATION: synthetic construct heavy chain CDR1

<400> SEQUENCE: 9

Gly Tyr Thr Phe Thr Ser Tyr Asp
1               5

<210> SEQ ID NO 10
<211> LENGTH: 8
<212> TYPE: PRT
<213> ORGANISM: Artificial Sequence
<220> FEATURE:
<223> OTHER INFORMATION: synthetic construct heavy chain CDR1

<400> SEQUENCE: 10

Gly Phe Thr Val Ser Arg Asn Ser
1               5

<210> SEQ ID NO 11
<211> LENGTH: 8
<212> TYPE: PRT
<213> ORGANISM: Artificial Sequence
<220> FEATURE:
<223> OTHER INFORMATION: synthetic construct heavy chain CDR1

<400> SEQUENCE: 11

Gly Asp Thr Phe Thr Arg Tyr Ile
1               5

<210> SEQ ID NO 12
<211> LENGTH: 8
<212> TYPE: PRT
<213> ORGANISM: Artificial Sequence
<220> FEATURE:
<223> OTHER INFORMATION: synthetic construct heavy chain CDR1

<400> SEQUENCE: 12

Gly Phe Thr Phe Ser His Tyr Ala
1               5

<210> SEQ ID NO 13
<211> LENGTH: 8
<212> TYPE: PRT
<213> ORGANISM: Artificial Sequence
<220> FEATURE:
<223> OTHER INFORMATION: synthetic construct heavy chain CDR1

<400> SEQUENCE: 13

Gly Phe Thr Phe Glu Asp Tyr Ala
1               5

<210> SEQ ID NO 14
<211> LENGTH: 8
<212> TYPE: PRT
<213> ORGANISM: Artificial Sequence
<220> FEATURE:
<223> OTHER INFORMATION: synthetic construct heavy chain CDR1

<400> SEQUENCE: 14
```

Gly Leu Ser Phe Ser Ser Tyr Trp
1               5

<210> SEQ ID NO 15
<211> LENGTH: 8
<212> TYPE: PRT
<213> ORGANISM: Artificial Sequence
<220> FEATURE:
<223> OTHER INFORMATION: synthetic construct heavy chain CDR1

<400> SEQUENCE: 15

Gly Tyr Thr Phe Ser Ser Tyr Trp
1               5

<210> SEQ ID NO 16
<211> LENGTH: 8
<212> TYPE: PRT
<213> ORGANISM: Artificial Sequence
<220> FEATURE:
<223> OTHER INFORMATION: synthetic construct heavy chain CDR1

<400> SEQUENCE: 16

Gly Phe Thr Phe Gly Asp His Pro
1               5

<210> SEQ ID NO 17
<211> LENGTH: 8
<212> TYPE: PRT
<213> ORGANISM: Artificial Sequence
<220> FEATURE:
<223> OTHER INFORMATION: synthetic construct heavy chain CDR1

<400> SEQUENCE: 17

Gly Phe Thr Phe Leu Arg Tyr Ala
1               5

<210> SEQ ID NO 18
<211> LENGTH: 8
<212> TYPE: PRT
<213> ORGANISM: Artificial Sequence
<220> FEATURE:
<223> OTHER INFORMATION: synthetic construct heavy chain CDR1

<400> SEQUENCE: 18

Gly Phe Thr Phe Lys Asn Asn Ala
1               5

<210> SEQ ID NO 19
<211> LENGTH: 8
<212> TYPE: PRT
<213> ORGANISM: Artificial Sequence
<220> FEATURE:
<223> OTHER INFORMATION: synthetic construct heavy chain CDR1

<400> SEQUENCE: 19

Gly Phe Thr Phe Arg Asn Tyr Ala
1               5

<210> SEQ ID NO 20
<211> LENGTH: 8
<212> TYPE: PRT
<213> ORGANISM: Artificial Sequence
<220> FEATURE:
<223> OTHER INFORMATION: synthetic construct heavy chain CDR1

<400> SEQUENCE: 20

Gly Phe Thr Phe Pro Ile Tyr Ala

```
<210> SEQ ID NO 21
<211> LENGTH: 8
<212> TYPE: PRT
<213> ORGANISM: Artificial Sequence
<220> FEATURE:
<223> OTHER INFORMATION: synthetic construct heavy chain CDR1

<400> SEQUENCE: 21

Gly Phe Thr Phe Lys Thr Tyr Ala
1               5

<210> SEQ ID NO 22
<211> LENGTH: 8
<212> TYPE: PRT
<213> ORGANISM: Artificial Sequence
<220> FEATURE:
<223> OTHER INFORMATION: synthetic construct heavy chain CDR1

<400> SEQUENCE: 22

Gly Phe Thr Phe Lys Tyr Tyr Ala
1               5

<210> SEQ ID NO 23
<211> LENGTH: 8
<212> TYPE: PRT
<213> ORGANISM: Artificial Sequence
<220> FEATURE:
<223> OTHER INFORMATION: synthetic construct heavy chain CDR1

<400> SEQUENCE: 23

Gly Phe Thr Phe Arg Ser Tyr Ala
1               5

<210> SEQ ID NO 24
<211> LENGTH: 8
<212> TYPE: PRT
<213> ORGANISM: Artificial Sequence
<220> FEATURE:
<223> OTHER INFORMATION: synthetic construct heavy chain CDR1

<400> SEQUENCE: 24

Gly Phe Thr Phe Leu Val Tyr Ala
1               5

<210> SEQ ID NO 25
<211> LENGTH: 8
<212> TYPE: PRT
<213> ORGANISM: Artificial Sequence
<220> FEATURE:
<223> OTHER INFORMATION: synthetic construct heavy chain CDR1

<400> SEQUENCE: 25

Gly Phe Thr Phe Arg Leu Tyr Ala
1               5

<210> SEQ ID NO 26
<211> LENGTH: 8
<212> TYPE: PRT
<213> ORGANISM: Artificial Sequence
<220> FEATURE:
<223> OTHER INFORMATION: synthetic construct heavy chain CDR1

<400> SEQUENCE: 26

Gly Phe Thr Phe Ser Phe Tyr Ala
1               5
```

<210> SEQ ID NO 27
<211> LENGTH: 8
<212> TYPE: PRT
<213> ORGANISM: Artificial Sequence
<220> FEATURE:
<223> OTHER INFORMATION: synthetic construct heavy chain CDR1

<400> SEQUENCE: 27

Gly Phe Thr Phe Arg Thr Tyr Ala
1               5

<210> SEQ ID NO 28
<211> LENGTH: 8
<212> TYPE: PRT
<213> ORGANISM: Artificial Sequence
<220> FEATURE:
<223> OTHER INFORMATION: synthetic construct heavy chain CDR1

<400> SEQUENCE: 28

Gly Phe Thr Phe Ser Val Tyr Ala
1               5

<210> SEQ ID NO 29
<211> LENGTH: 8
<212> TYPE: PRT
<213> ORGANISM: Artificial Sequence
<220> FEATURE:
<223> OTHER INFORMATION: synthetic construct heavy chain CDR1

<400> SEQUENCE: 29

Gly Phe Thr Phe Met Arg Tyr Ala
1               5

<210> SEQ ID NO 30
<211> LENGTH: 8
<212> TYPE: PRT
<213> ORGANISM: Artificial Sequence
<220> FEATURE:
<223> OTHER INFORMATION: synthetic construct heavy chain CDR1

<400> SEQUENCE: 30

Gly Phe Thr Phe Trp Thr Tyr Ala
1               5

<210> SEQ ID NO 31
<211> LENGTH: 8
<212> TYPE: PRT
<213> ORGANISM: Artificial Sequence
<220> FEATURE:
<223> OTHER INFORMATION: synthetic construct heavy chain CDR2

<400> SEQUENCE: 31

Ile Ser Tyr Asp Gly Asn Asp Lys
1               5

<210> SEQ ID NO 32
<211> LENGTH: 8
<212> TYPE: PRT
<213> ORGANISM: Artificial Sequence
<220> FEATURE:
<223> OTHER INFORMATION: synthetic construct heavy chain CDR2

<400> SEQUENCE: 32

Ile Ser Tyr Asp Gly Ser Asn Lys
1               5

```
<210> SEQ ID NO 33
<211> LENGTH: 8
<212> TYPE: PRT
<213> ORGANISM: Artificial Sequence
<220> FEATURE:
<223> OTHER INFORMATION: synthetic construct heavy chain CDR2

<400> SEQUENCE: 33

Ile Ser Trp Asn Ser Gly Arg Ile
1               5

<210> SEQ ID NO 34
<211> LENGTH: 8
<212> TYPE: PRT
<213> ORGANISM: Artificial Sequence
<220> FEATURE:
<223> OTHER INFORMATION: synthetic construct heavy chain CDR2

<400> SEQUENCE: 34

Ile Ser Trp Asn Ser Gly Thr Ile
1               5

<210> SEQ ID NO 35
<211> LENGTH: 8
<212> TYPE: PRT
<213> ORGANISM: Artificial Sequence
<220> FEATURE:
<223> OTHER INFORMATION: synthetic construct heavy chain CDR2

<400> SEQUENCE: 35

Ile Ile Pro Leu Phe Ser Thr Ala
1               5

<210> SEQ ID NO 36
<211> LENGTH: 8
<212> TYPE: PRT
<213> ORGANISM: Artificial Sequence
<220> FEATURE:
<223> OTHER INFORMATION: synthetic construct heavy chain CDR2

<400> SEQUENCE: 36

Ile Ile Pro Ile Phe Gly Ser Ala
1               5

<210> SEQ ID NO 37
<211> LENGTH: 8
<212> TYPE: PRT
<213> ORGANISM: Artificial Sequence
<220> FEATURE:
<223> OTHER INFORMATION: synthetic construct heavy chain CDR2

<400> SEQUENCE: 37

Ile Ser Ala Ser Gly Asn Ser Ile
1               5

<210> SEQ ID NO 38
<211> LENGTH: 8
<212> TYPE: PRT
<213> ORGANISM: Artificial Sequence
<220> FEATURE:
<223> OTHER INFORMATION: synthetic construct heavy chain CDR2

<400> SEQUENCE: 38

Ile Asn Pro Ser Asp Gly Ser Ala
1               5
```

<210> SEQ ID NO 39
<211> LENGTH: 8
<212> TYPE: PRT
<213> ORGANISM: Artificial Sequence
<220> FEATURE:
<223> OTHER INFORMATION: synthetic construct heavy chain CDR2

<400> SEQUENCE: 39

Ile Ser Trp Asn Ser Asn Asn Ile
1               5

<210> SEQ ID NO 40
<211> LENGTH: 8
<212> TYPE: PRT
<213> ORGANISM: Artificial Sequence
<220> FEATURE:
<223> OTHER INFORMATION: synthetic construct heavy chain CDR2

<400> SEQUENCE: 40

Leu His Ala Asp Ser Gly Lys Thr
1               5

<210> SEQ ID NO 41
<211> LENGTH: 8
<212> TYPE: PRT
<213> ORGANISM: Artificial Sequence
<220> FEATURE:
<223> OTHER INFORMATION: synthetic construct heavy chain CDR2

<400> SEQUENCE: 41

Ile Phe Ser Gly Gly Thr Thr Lys
1               5

<210> SEQ ID NO 42
<211> LENGTH: 8
<212> TYPE: PRT
<213> ORGANISM: Artificial Sequence
<220> FEATURE:
<223> OTHER INFORMATION: synthetic construct heavy chain CDR2

<400> SEQUENCE: 42

Val Ile Pro Thr Leu Gly Leu Thr
1               5

<210> SEQ ID NO 43
<211> LENGTH: 8
<212> TYPE: PRT
<213> ORGANISM: Artificial Sequence
<220> FEATURE:
<223> OTHER INFORMATION: synthetic construct heavy chain CDR2

<400> SEQUENCE: 43

Ile Ser Tyr Asp Gly Ser Lys Ile
1               5

<210> SEQ ID NO 44
<211> LENGTH: 8
<212> TYPE: PRT
<213> ORGANISM: Artificial Sequence
<220> FEATURE:
<223> OTHER INFORMATION: synthetic construct heavy chain CDR2

<400> SEQUENCE: 44

Ile Ser Trp Asn Ser His Asn Ile
1               5

<210> SEQ ID NO 45

<211> LENGTH: 8
<212> TYPE: PRT
<213> ORGANISM: Artificial Sequence
<220> FEATURE:
<223> OTHER INFORMATION: synthetic construct heavy chain CDR2

<400> SEQUENCE: 45

Ile Lys Gln Asp Gly Ser Glu Lys
1               5

<210> SEQ ID NO 46
<211> LENGTH: 8
<212> TYPE: PRT
<213> ORGANISM: Artificial Sequence
<220> FEATURE:
<223> OTHER INFORMATION: synthetic construct heavy chain CDR2

<400> SEQUENCE: 46

Ile Asn Pro Gly Asn Gly His Thr
1               5

<210> SEQ ID NO 47
<211> LENGTH: 8
<212> TYPE: PRT
<213> ORGANISM: Artificial Sequence
<220> FEATURE:
<223> OTHER INFORMATION: synthetic construct heavy chain CDR2

<400> SEQUENCE: 47

Ile Ser Trp Asn Ser Gly Thr Pro
1               5

<210> SEQ ID NO 48
<211> LENGTH: 8
<212> TYPE: PRT
<213> ORGANISM: Artificial Sequence
<220> FEATURE:
<223> OTHER INFORMATION: synthetic construct heavy chain CDR2

<400> SEQUENCE: 48

Ile Arg Ser Lys Ala Tyr Gly Glu
1               5

<210> SEQ ID NO 49
<211> LENGTH: 8
<212> TYPE: PRT
<213> ORGANISM: Artificial Sequence
<220> FEATURE:
<223> OTHER INFORMATION: synthetic construct heavy chain CDR2

<400> SEQUENCE: 49

Ile Ser Tyr Asp Gly Gln Asp Lys
1               5

<210> SEQ ID NO 50
<211> LENGTH: 8
<212> TYPE: PRT
<213> ORGANISM: Artificial Sequence
<220> FEATURE:
<223> OTHER INFORMATION: synthetic construct heavy chain CDR2

<400> SEQUENCE: 50

Ile Ser Tyr Asp Gly Arg His Lys
1               5

<210> SEQ ID NO 51
<211> LENGTH: 8

```
<212> TYPE: PRT
<213> ORGANISM: Artificial Sequence
<220> FEATURE:
<223> OTHER INFORMATION: synthetic construct heavy chain CDR2

<400> SEQUENCE: 51

Ile Ser Tyr Asp Gly Gln His Lys
1               5

<210> SEQ ID NO 52
<211> LENGTH: 8
<212> TYPE: PRT
<213> ORGANISM: Artificial Sequence
<220> FEATURE:
<223> OTHER INFORMATION: synthetic construct heavy chain CDR2

<400> SEQUENCE: 52

Ile Ser Tyr Asp Gly Ala His Lys
1               5

<210> SEQ ID NO 53
<211> LENGTH: 8
<212> TYPE: PRT
<213> ORGANISM: Artificial Sequence
<220> FEATURE:
<223> OTHER INFORMATION: synthetic construct heavy chain CDR2

<400> SEQUENCE: 53

Ile Ser Tyr Asp Gly Gln Tyr Lys
1               5

<210> SEQ ID NO 54
<211> LENGTH: 8
<212> TYPE: PRT
<213> ORGANISM: Artificial Sequence
<220> FEATURE:
<223> OTHER INFORMATION: synthetic construct heavy chain CDR2

<400> SEQUENCE: 54

Ile Ser Tyr Asp Gly Arg Tyr Lys
1               5

<210> SEQ ID NO 55
<211> LENGTH: 8
<212> TYPE: PRT
<213> ORGANISM: Artificial Sequence
<220> FEATURE:
<223> OTHER INFORMATION: synthetic construct heavy chain CDR2

<400> SEQUENCE: 55

Ile Ser Tyr Asp Gly Ser His Lys
1               5

<210> SEQ ID NO 56
<211> LENGTH: 8
<212> TYPE: PRT
<213> ORGANISM: Artificial Sequence
<220> FEATURE:
<223> OTHER INFORMATION: synthetic construct heavy chain CDR2

<400> SEQUENCE: 56

Ile Ser His Asp Gly Asn Asp Lys
1               5

<210> SEQ ID NO 57
<211> LENGTH: 7
<212> TYPE: PRT
```

```
<213> ORGANISM: Artificial Sequence
<220> FEATURE:
<223> OTHER INFORMATION: synthetic construct heavy chain CDR3

<400> SEQUENCE: 57

Val Pro Thr Thr Phe Glu Tyr
1               5

<210> SEQ ID NO 58
<211> LENGTH: 7
<212> TYPE: PRT
<213> ORGANISM: Artificial Sequence
<220> FEATURE:
<223> OTHER INFORMATION: synthetic construct heavy chain CDR3

<400> SEQUENCE: 58

Thr Thr Thr Thr Phe Asp Ser
1               5

<210> SEQ ID NO 59
<211> LENGTH: 10
<212> TYPE: PRT
<213> ORGANISM: Artificial Sequence
<220> FEATURE:
<223> OTHER INFORMATION: synthetic construct heavy chain CDR3

<400> SEQUENCE: 59

Ala Arg Ser Gln Gln Gln Ile Leu Asp Tyr
1               5                   10

<210> SEQ ID NO 60
<211> LENGTH: 10
<212> TYPE: PRT
<213> ORGANISM: Artificial Sequence
<220> FEATURE:
<223> OTHER INFORMATION: synthetic construct heavy chain CDR3

<400> SEQUENCE: 60

Ala Arg Ser Ile Arg Gln Ile Leu Asp Tyr
1               5                   10

<210> SEQ ID NO 61
<211> LENGTH: 13
<212> TYPE: PRT
<213> ORGANISM: Artificial Sequence
<220> FEATURE:
<223> OTHER INFORMATION: synthetic construct heavy chain CDR3
<220> FEATURE:
<221> NAME/KEY: misc_feature
<222> LOCATION: (6)..(6)
<223> OTHER INFORMATION: Xaa can be any naturally occurring amino acid

<400> SEQUENCE: 61

Ala Arg Ser Leu Pro Xaa Ser Arg Ser Arg Leu Asp Val
1               5                   10

<210> SEQ ID NO 62
<211> LENGTH: 14
<212> TYPE: PRT
<213> ORGANISM: Artificial Sequence
<220> FEATURE:
<223> OTHER INFORMATION: synthetic construct heavy chain CDR3
<220> FEATURE:
<221> NAME/KEY: misc_feature
<222> LOCATION: (4)..(4)
<223> OTHER INFORMATION: Xaa can be any naturally occurring amino acid

<400> SEQUENCE: 62
```

Ala Arg Ala Xaa Thr Ser Pro Leu Asp Met Ser Leu Asp Tyr
1               5                   10

<210> SEQ ID NO 63
<211> LENGTH: 15
<212> TYPE: PRT
<213> ORGANISM: Artificial Sequence
<220> FEATURE:
<223> OTHER INFORMATION: synthetic construct heavy chain CDR3

<400> SEQUENCE: 63

Ala Arg Leu Leu His Gln Met Asn Glu His Glu Phe Met Asp Val
1               5                   10                  15

<210> SEQ ID NO 64
<211> LENGTH: 17
<212> TYPE: PRT
<213> ORGANISM: Artificial Sequence
<220> FEATURE:
<223> OTHER INFORMATION: synthetic construct heavy chain CDR3

<400> SEQUENCE: 64

Ala Lys His Lys Gly Leu Pro Phe Asp Trp Ser Pro Asp Gly Phe Asp
1               5                   10                  15

Thr

<210> SEQ ID NO 65
<211> LENGTH: 10
<212> TYPE: PRT
<213> ORGANISM: Artificial Sequence
<220> FEATURE:
<223> OTHER INFORMATION: synthetic construct heavy chain CDR3

<400> SEQUENCE: 65

Ala Arg Thr Ile Glu Gly Ala Phe Asp Ile
1               5                   10

<210> SEQ ID NO 66
<211> LENGTH: 11
<212> TYPE: PRT
<213> ORGANISM: Artificial Sequence
<220> FEATURE:
<223> OTHER INFORMATION: synthetic construct heavy chain CDR3

<400> SEQUENCE: 66

Val Thr Ser Gly Pro Phe Gly Glu Phe Arg Asn
1               5                   10

<210> SEQ ID NO 67
<211> LENGTH: 15
<212> TYPE: PRT
<213> ORGANISM: Artificial Sequence
<220> FEATURE:
<223> OTHER INFORMATION: synthetic construct heavy chain CDR3

<400> SEQUENCE: 67

Ala Arg Leu Met His Thr Phe Ser Val Gln Tyr Phe Leu Asp Val
1               5                   10                  15

<210> SEQ ID NO 68
<211> LENGTH: 19
<212> TYPE: PRT
<213> ORGANISM: Artificial Sequence
<220> FEATURE:
<223> OTHER INFORMATION: synthetic construct heavy chain CDR3

<400> SEQUENCE: 68

```
Ala Arg Asp Gly Asn Tyr Tyr Asp Ser Arg Gly Tyr Tyr Tyr Asp Thr
1               5                   10                  15

Phe Asp Met

<210> SEQ ID NO 69
<211> LENGTH: 10
<212> TYPE: PRT
<213> ORGANISM: Artificial Sequence
<220> FEATURE:
<223> OTHER INFORMATION: synthetic construct heavy chain CDR3

<400> SEQUENCE: 69

Ala Arg Gly Ala Leu Thr Pro Leu Asp Val
1               5                   10

<210> SEQ ID NO 70
<211> LENGTH: 9
<212> TYPE: PRT
<213> ORGANISM: Artificial Sequence
<220> FEATURE:
<223> OTHER INFORMATION: synthetic construct heavy chain CDR3

<400> SEQUENCE: 70

Ala Arg Gly Thr His Trp Leu Asp Ser
1               5

<210> SEQ ID NO 71
<211> LENGTH: 17
<212> TYPE: PRT
<213> ORGANISM: Artificial Sequence
<220> FEATURE:
<223> OTHER INFORMATION: synthetic construct heavy chain CDR3

<400> SEQUENCE: 71

Ala Arg Glu Glu Gln Phe Leu Ile Ala Leu Ala Gly Arg Tyr Phe Asp
1               5                   10                  15

Tyr

<210> SEQ ID NO 72
<211> LENGTH: 11
<212> TYPE: PRT
<213> ORGANISM: Artificial Sequence
<220> FEATURE:
<223> OTHER INFORMATION: synthetic construct heavy chain CDR3

<400> SEQUENCE: 72

Ala Arg Gly Tyr Gly Ser Gly Ala Phe Asp Ile
1               5                   10

<210> SEQ ID NO 73
<211> LENGTH: 11
<212> TYPE: PRT
<213> ORGANISM: Artificial Sequence
<220> FEATURE:
<223> OTHER INFORMATION: synthetic construct heavy chain CDR3

<400> SEQUENCE: 73

Ala Arg Ile Gly Tyr Lys Asp Ala Phe Asp Ile
1               5                   10

<210> SEQ ID NO 74
<211> LENGTH: 9
<212> TYPE: PRT
<213> ORGANISM: Artificial Sequence
<220> FEATURE:
```

<223> OTHER INFORMATION: synthetic construct heavy chain CDR3

<400> SEQUENCE: 74

Ser Thr Ser Gly Leu Gly Val His Ala
1               5

<210> SEQ ID NO 75
<211> LENGTH: 11
<212> TYPE: PRT
<213> ORGANISM: Artificial Sequence
<220> FEATURE:
<223> OTHER INFORMATION: synthetic construct heavy chain CDR3

<400> SEQUENCE: 75

Ala Arg Asp Ser Phe Gly Gly His Leu Asp Leu
1               5                   10

<210> SEQ ID NO 76
<211> LENGTH: 14
<212> TYPE: PRT
<213> ORGANISM: Artificial Sequence
<220> FEATURE:
<223> OTHER INFORMATION: synthetic construct heavy chain CDR3

<400> SEQUENCE: 76

Ala Arg Glu Gly Asp Gly Ser Tyr Trp Gly Tyr Phe Asp Ser
1               5                   10

<210> SEQ ID NO 77
<211> LENGTH: 14
<212> TYPE: PRT
<213> ORGANISM: Artificial Sequence
<220> FEATURE:
<223> OTHER INFORMATION: synthetic construct heavy chain CDR3

<400> SEQUENCE: 77

Ala Arg Gly His Asn Tyr Leu Asp Ser Ser Tyr Tyr Asp Tyr
1               5                   10

<210> SEQ ID NO 78
<211> LENGTH: 18
<212> TYPE: PRT
<213> ORGANISM: Artificial Sequence
<220> FEATURE:
<223> OTHER INFORMATION: synthetic construct heavy chain CDR3

<400> SEQUENCE: 78

Ala Ser Val Ser Tyr Cys Ser Gly Gly Ser Cys Tyr Gln Gly Thr Phe
1               5                   10                  15

Asp Tyr

<210> SEQ ID NO 79
<211> LENGTH: 7
<212> TYPE: PRT
<213> ORGANISM: Artificial Sequence
<220> FEATURE:
<223> OTHER INFORMATION: synthetic construct heavy chain CDR3

<400> SEQUENCE: 79

Ala Arg Thr Thr Phe Asp Tyr
1               5

<210> SEQ ID NO 80
<211> LENGTH: 25
<212> TYPE: PRT
<213> ORGANISM: Artificial Sequence -continued

```
<220> FEATURE:
<223> OTHER INFORMATION: synthetic construct heavy chain variable region
      FR1

<400> SEQUENCE: 80

Gln Val Gln Leu Val Glu Ser Gly Gly Gly Val Val Gln Pro Gly Arg
1               5                   10                  15

Ser Leu Arg Leu Ser Cys Ala Ala Ser
            20                  25

<210> SEQ ID NO 81
<211> LENGTH: 25
<212> TYPE: PRT
<213> ORGANISM: Artificial Sequence
<220> FEATURE:
<223> OTHER INFORMATION: synthetic construct heavy chain variable region
      FR1

<400> SEQUENCE: 81

Gln Val Gln Leu Val Glu Ser Gly Gly Gly Leu Val Gln Pro Gly Arg
1               5                   10                  15

Ser Leu Arg Leu Ser Cys Ala Ala Ser
            20                  25

<210> SEQ ID NO 82
<211> LENGTH: 25
<212> TYPE: PRT
<213> ORGANISM: Artificial Sequence
<220> FEATURE:
<223> OTHER INFORMATION: synthetic construct heavy chain variable region
      FR1

<400> SEQUENCE: 82

Gln Val Gln Leu Val Glu Ser Gly Gly Gly Leu Val Lys Pro Gly Gly
1               5                   10                  15

Ser Leu Arg Leu Ser Cys Ala Ala Ser
            20                  25

<210> SEQ ID NO 83
<211> LENGTH: 25
<212> TYPE: PRT
<213> ORGANISM: Artificial Sequence
<220> FEATURE:
<223> OTHER INFORMATION: synthetic construct heavy chain variable region
      FR1

<400> SEQUENCE: 83

Gln Met Gln Leu Val Glu Ser Gly Gly Asn Leu Val Gln Pro Gly Arg
1               5                   10                  15

Ser Leu Arg Leu Ser Cys Ala Ala Ser
            20                  25

<210> SEQ ID NO 84
<211> LENGTH: 25
<212> TYPE: PRT
<213> ORGANISM: Artificial Sequence
<220> FEATURE:
<223> OTHER INFORMATION: synthetic construct heavy chain variable region
      FR1

<400> SEQUENCE: 84

Gln Val Gln Leu Val Gln Ser Gly Ala Glu Val Lys Lys Pro Gly Ser
1               5                   10                  15

Ser Val Lys Val Ser Cys Lys Ala Ser
            20                  25
```

<210> SEQ ID NO 85
<211> LENGTH: 25
<212> TYPE: PRT
<213> ORGANISM: Artificial Sequence
<220> FEATURE:
<223> OTHER INFORMATION: synthetic construct heavy chain variable region
      FR1

<400> SEQUENCE: 85

Gln Met Gln Leu Val Glu Ser Gly Gly Gly Val Val Gln Pro Gly Arg
1               5                   10                  15

Ser Leu Arg Leu Ser Cys Ala Ala Ser
            20                  25

<210> SEQ ID NO 86
<211> LENGTH: 25
<212> TYPE: PRT
<213> ORGANISM: Artificial Sequence
<220> FEATURE:
<223> OTHER INFORMATION: synthetic construct heavy chain variable region
      FR1

<400> SEQUENCE: 86

Gln Val Gln Leu Val Gln Ser Gly Ala Glu Val Lys Lys Pro Gly Ala
1               5                   10                  15

Ser Val Lys Leu Ser Cys Lys Ala Ser
            20                  25

<210> SEQ ID NO 87
<211> LENGTH: 25
<212> TYPE: PRT
<213> ORGANISM: Artificial Sequence
<220> FEATURE:
<223> OTHER INFORMATION: synthetic construct heavy chain variable region
      FR1

<400> SEQUENCE: 87

Gln Met Gln Leu Val Glu Ser Gly Gly Gly Leu Val Gln Pro Gly Arg
1               5                   10                  15

Ser Leu Arg Leu Ser Cys Ala Ala Ser
            20                  25

<210> SEQ ID NO 88
<211> LENGTH: 25
<212> TYPE: PRT
<213> ORGANISM: Artificial Sequence
<220> FEATURE:
<223> OTHER INFORMATION: synthetic construct heavy chain variable region
      FR1

<400> SEQUENCE: 88

Gln Met Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 89
<211> LENGTH: 25
<212> TYPE: PRT
<213> ORGANISM: Artificial Sequence
<220> FEATURE:
<223> OTHER INFORMATION: synthetic construct heavy chain variable region
      FR1

<400> SEQUENCE: 89

```
Gln Val Gln Leu Val Gln Ser Gly Gly Gly Leu Ile Gln Pro Gly Gly
1               5                   10                  15

Ser Leu Arg Leu Ser Cys Ala Ala Ser
            20                  25

<210> SEQ ID NO 90
<211> LENGTH: 25
<212> TYPE: PRT
<213> ORGANISM: Artificial Sequence
<220> FEATURE:
<223> OTHER INFORMATION: synthetic construct heavy chain variable region
      FR1

<400> SEQUENCE: 90

Gln Met Gln Leu Val Gln Ser Gly Ala Glu Val Lys Lys Pro Gly Ser
1               5                   10                  15

Ser Val Lys Val Ser Cys Lys Ala Ser
            20                  25

<210> SEQ ID NO 91
<211> LENGTH: 25
<212> TYPE: PRT
<213> ORGANISM: Artificial Sequence
<220> FEATURE:
<223> OTHER INFORMATION: synthetic construct heavy chain variable region
      FR1

<400> SEQUENCE: 91

Gln Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 92
<211> LENGTH: 25
<212> TYPE: PRT
<213> ORGANISM: Artificial Sequence
<220> FEATURE:
<223> OTHER INFORMATION: synthetic construct heavy chain variable region
      FR1

<400> SEQUENCE: 92

Gln Val Gln Leu Val Glu Ser Gly Ala Glu Val Lys Lys Pro Gly Ala
1               5                   10                  15

Ser Val Lys Leu Ser Cys Lys Ala Ser
            20                  25

<210> SEQ ID NO 93
<211> LENGTH: 25
<212> TYPE: PRT
<213> ORGANISM: Artificial Sequence
<220> FEATURE:
<223> OTHER INFORMATION: synthetic construct heavy chain variable region
      FR1

<400> SEQUENCE: 93

Gln Val Gln Leu Val Gln Ser Gly Gly Asn Leu Val Gln Pro Gly Arg
1               5                   10                  15

Ser Leu Arg Leu Ser Cys Ala Ala Ser
            20                  25

<210> SEQ ID NO 94
<211> LENGTH: 25
<212> TYPE: PRT
```

<213> ORGANISM: Artificial Sequence
<220> FEATURE:
<223> OTHER INFORMATION: synthetic construct heavy chain variable region
      FR1

<400> SEQUENCE: 94

Gln Val Gln Leu Val Glu Ser Gly Gly Asp Leu Val Lys Pro Gly Arg
1               5                   10                  15

Ser Leu Arg Leu Ser Cys Thr Gly Ser
            20                  25

<210> SEQ ID NO 95
<211> LENGTH: 25
<212> TYPE: PRT
<213> ORGANISM: Artificial Sequence
<220> FEATURE:
<223> OTHER INFORMATION: synthetic construct heavy chain variable region
      FR1

<400> SEQUENCE: 95

Gln Val Gln Leu Val Gln Ser Gly Gly Gly Val Val Gln Pro Gly Arg
1               5                   10                  15

Ser Leu Arg Leu Ser Cys Ala Ala Ser
            20                  25

<210> SEQ ID NO 96
<211> LENGTH: 17
<212> TYPE: PRT
<213> ORGANISM: Artificial Sequence
<220> FEATURE:
<223> OTHER INFORMATION: synthetic construct heavy chain variable region
      FR2

<400> SEQUENCE: 96

Met His Trp Val Arg Gln Val Pro Gly Lys Gly Leu Glu Trp Val Ala
1               5                   10                  15

Val

<210> SEQ ID NO 97
<211> LENGTH: 17
<212> TYPE: PRT
<213> ORGANISM: Artificial Sequence
<220> FEATURE:
<223> OTHER INFORMATION: synthetic construct heavy chain variable region
      FR2

<400> SEQUENCE: 97

Met His Trp Val Arg Gln Ala Pro Gly Lys Gly Leu Glu Trp Val Ala
1               5                   10                  15

Val

<210> SEQ ID NO 98
<211> LENGTH: 17
<212> TYPE: PRT
<213> ORGANISM: Artificial Sequence
<220> FEATURE:
<223> OTHER INFORMATION: synthetic construct heavy chain variable region
      FR2

<400> SEQUENCE: 98

Met His Trp Val Arg Gln Val Pro Gly Lys Gly Leu Glu Trp Val Ser
1               5                   10                  15

Gly

```
<210> SEQ ID NO 99
<211> LENGTH: 17
<212> TYPE: PRT
<213> ORGANISM: Artificial Sequence
<220> FEATURE:
<223> OTHER INFORMATION: synthetic construct heavy chain variable region
      FR2

<400> SEQUENCE: 99

Met His Trp Val Arg Gln Ala Pro Gly Lys Gly Leu Glu Trp Val Ser
1               5                   10                  15

Ser

<210> SEQ ID NO 100
<211> LENGTH: 17
<212> TYPE: PRT
<213> ORGANISM: Artificial Sequence
<220> FEATURE:
<223> OTHER INFORMATION: synthetic construct heavy chain variable region
      FR2

<400> SEQUENCE: 100

Ile Ser Trp Val Arg Gln Ala Pro Gly Gln Gly Leu Glu Trp Met Gly
1               5                   10                  15

Gly

<210> SEQ ID NO 101
<211> LENGTH: 17
<212> TYPE: PRT
<213> ORGANISM: Artificial Sequence
<220> FEATURE:
<223> OTHER INFORMATION: synthetic construct heavy chain variable region
      FR2

<400> SEQUENCE: 101

Val Ser Trp Val Arg Gln Ala Pro Gly Glu Gly Leu Glu Trp Met Ala
1               5                   10                  15

Asp

<210> SEQ ID NO 102
<211> LENGTH: 17
<212> TYPE: PRT
<213> ORGANISM: Artificial Sequence
<220> FEATURE:
<223> OTHER INFORMATION: synthetic construct heavy chain variable region
      FR2

<400> SEQUENCE: 102

Met Ser Trp Ile Arg Gln Ala Pro Gly Lys Gly Leu Glu Trp Val Ser
1               5                   10                  15

Asp

<210> SEQ ID NO 103
<211> LENGTH: 17
<212> TYPE: PRT
<213> ORGANISM: Artificial Sequence
<220> FEATURE:
<223> OTHER INFORMATION: synthetic construct heavy chain variable region
      FR2

<400> SEQUENCE: 103

Val His Trp Val Arg Gln Ala Pro Gly Gln Gly Leu Glu Trp Met Gly
1               5                   10                  15

Ile
```

```
<210> SEQ ID NO 104
<211> LENGTH: 17
<212> TYPE: PRT
<213> ORGANISM: Artificial Sequence
<220> FEATURE:
<223> OTHER INFORMATION: synthetic construct heavy chain variable region
      FR2

<400> SEQUENCE: 104

Met His Trp Val Arg Gln Ala Pro Gly Gln Gly Leu Glu Trp Val Ser
1               5                   10                  15
Gly

<210> SEQ ID NO 105
<211> LENGTH: 17
<212> TYPE: PRT
<213> ORGANISM: Artificial Sequence
<220> FEATURE:
<223> OTHER INFORMATION: synthetic construct heavy chain variable region
      FR2

<400> SEQUENCE: 105

Ile Asn Trp Val Arg Gln Ala Ser Gly Gln Ala Pro Glu Trp Met Gly
1               5                   10                  15
Trp

<210> SEQ ID NO 106
<211> LENGTH: 17
<212> TYPE: PRT
<213> ORGANISM: Artificial Sequence
<220> FEATURE:
<223> OTHER INFORMATION: synthetic construct heavy chain variable region
      FR2

<400> SEQUENCE: 106

Met Asn Trp Val Arg Gln Thr Pro Gly Lys Gly Pro Glu Trp Val Ser
1               5                   10                  15
Leu

<210> SEQ ID NO 107
<211> LENGTH: 17
<212> TYPE: PRT
<213> ORGANISM: Artificial Sequence
<220> FEATURE:
<223> OTHER INFORMATION: synthetic construct heavy chain variable region
      FR2

<400> SEQUENCE: 107

Ile Asn Trp Val Arg Gln Ala Pro Gly Gln Gly Leu Glu Trp Met Gly
1               5                   10                  15
Arg

<210> SEQ ID NO 108
<211> LENGTH: 17
<212> TYPE: PRT
<213> ORGANISM: Artificial Sequence
<220> FEATURE:
<223> OTHER INFORMATION: synthetic construct heavy chain variable region
      FR2

<400> SEQUENCE: 108

Met His Trp Val Arg Gln Pro Pro Gly Lys Gly Leu Glu Trp Val Ser
1               5                   10                  15
Ser
```

```
<210> SEQ ID NO 109
<211> LENGTH: 17
<212> TYPE: PRT
<213> ORGANISM: Artificial Sequence
<220> FEATURE:
<223> OTHER INFORMATION: synthetic construct heavy chain variable region
      FR2

<400> SEQUENCE: 109

Met Thr Trp Val Arg Gln Ala Pro Gly Lys Gly Leu Glu Trp Val Ala
1               5                   10                  15
Asn

<210> SEQ ID NO 110
<211> LENGTH: 17
<212> TYPE: PRT
<213> ORGANISM: Artificial Sequence
<220> FEATURE:
<223> OTHER INFORMATION: synthetic construct heavy chain variable region
      FR2

<400> SEQUENCE: 110

Met His Trp Val Arg Gln Ala Pro Gly Gln Arg Leu Glu Trp Met Gly
1               5                   10                  15
Glu

<210> SEQ ID NO 111
<211> LENGTH: 17
<212> TYPE: PRT
<213> ORGANISM: Artificial Sequence
<220> FEATURE:
<223> OTHER INFORMATION: synthetic construct heavy chain variable region
      FR2

<400> SEQUENCE: 111

Met His Trp Val Arg Gln Ala Pro Gly Lys Gly Leu Glu Trp Val Ser
1               5                   10                  15
Gly

<210> SEQ ID NO 112
<211> LENGTH: 17
<212> TYPE: PRT
<213> ORGANISM: Artificial Sequence
<220> FEATURE:
<223> OTHER INFORMATION: synthetic construct heavy chain variable region
      FR2

<400> SEQUENCE: 112

Leu Thr Trp Val Arg Gln Ile Pro Gly Lys Gly Leu Glu Trp Val Gly
1               5                   10                  15
Phe

<210> SEQ ID NO 113
<211> LENGTH: 17
<212> TYPE: PRT
<213> ORGANISM: Artificial Sequence
<220> FEATURE:
<223> OTHER INFORMATION: synthetic construct heavy chain variable region
      FR2

<400> SEQUENCE: 113

Met His Trp Val Arg Gln Ala Pro Gly Lys Gly Leu Glu Trp Val Thr
1               5                   10                  15
```

Val

<210> SEQ ID NO 114
<211> LENGTH: 38
<212> TYPE: PRT
<213> ORGANISM: Artificial Sequence
<220> FEATURE:
<223> OTHER INFORMATION: synthetic construct heavy chain variable region
      FR3

<400> SEQUENCE: 114

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 115
<211> LENGTH: 38
<212> TYPE: PRT
<213> ORGANISM: Artificial Sequence
<220> FEATURE:
<223> OTHER INFORMATION: synthetic construct heavy chain variable region
      FR3

<400> SEQUENCE: 115

Tyr Tyr Ala Asp Ser Val Lys Gly Arg Phe Thr Ile Ser Arg Asp Asn
1               5                   10                  15

Pro Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 116
<211> LENGTH: 38
<212> TYPE: PRT
<213> ORGANISM: Artificial Sequence
<220> FEATURE:
<223> OTHER INFORMATION: synthetic construct heavy chain variable region
      FR3

<400> SEQUENCE: 116

Val Tyr Ala Asp Ser Met Lys Gly Arg Phe Thr Ile Ser Arg Asp Asn
1               5                   10                  15

Ala Lys Asn Ser Leu Tyr Leu Gln Met Asn Ser Leu Arg Ala Glu Asp
            20                  25                  30

Thr Ala Val Tyr Tyr Cys
        35

<210> SEQ ID NO 117
<211> LENGTH: 38
<212> TYPE: PRT
<213> ORGANISM: Artificial Sequence
<220> FEATURE:
<223> OTHER INFORMATION: synthetic construct heavy chain variable region
      FR3

<400> SEQUENCE: 117

Gly Tyr Ala Asp Ser Val Lys Gly Arg Phe Thr Ile Ser Arg Asp Asn
1               5                   10                  15

Ala Lys Asn Ser Leu Tyr Leu Gln Met Asn Ser Leu Arg Ser Glu Asp
            20                  25                  30

Thr Ala Val Tyr Tyr Cys
        35

<210> SEQ ID NO 118
<211> LENGTH: 38
<212> TYPE: PRT
<213> ORGANISM: Artificial Sequence
<220> FEATURE:
<223> OTHER INFORMATION: synthetic construct heavy chain variable region
      FR3

<400> SEQUENCE: 118

His Ser Ala Gln Lys Phe Gln Gly Arg Val Thr Ile Thr Ala Asp Glu
1               5                   10                  15

Ser Ser Ser Thr Ala Tyr Met Glu Leu Ser Ser Leu Arg Ser Glu Asp
            20                  25                  30

Thr Ala Val Tyr Tyr Cys
        35

<210> SEQ ID NO 119
<211> LENGTH: 38
<212> TYPE: PRT
<213> ORGANISM: Artificial Sequence
<220> FEATURE:
<223> OTHER INFORMATION: synthetic construct heavy chain variable region
      FR3

<400> SEQUENCE: 119

Asn Tyr Ala Gln Lys Phe Gln Gly Arg Leu Thr Leu Thr Ala Asp Val
1               5                   10                  15

Ser Thr Ser Thr Ala Tyr Met Glu Leu Ser Ser Leu Arg Ser Glu Asp
            20                  25                  30

Thr Ala Val Tyr Tyr Cys
        35

<210> SEQ ID NO 120
<211> LENGTH: 38
<212> TYPE: PRT
<213> ORGANISM: Artificial Sequence
<220> FEATURE:
<223> OTHER INFORMATION: synthetic construct heavy chain variable region
      FR3

<400> SEQUENCE: 120

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Arg Leu Arg Ser Glu Asp
            20                  25                  30

Thr Ala Val Tyr Tyr Cys
        35

<210> SEQ ID NO 121
<211> LENGTH: 38
<212> TYPE: PRT
<213> ORGANISM: Artificial Sequence
<220> FEATURE:
<223> OTHER INFORMATION: synthetic construct heavy chain variable region
      FR3

<400> SEQUENCE: 121

Tyr Tyr Ala Asp Ser Val Lys Arg Arg Phe Thr Ile Ser Arg Asp Asn
1               5                   10                  15

Ser Lys Asn Ser Leu Tyr Leu Gln Met Asn Ser Leu Arg Ala Glu Asp
            20                  25                  30

```
Thr Ala Val Tyr Tyr Cys
        35

<210> SEQ ID NO 122
<211> LENGTH: 38
<212> TYPE: PRT
<213> ORGANISM: Artificial Sequence
<220> FEATURE:
<223> OTHER INFORMATION: synthetic construct heavy chain variable region
      FR3

<400> SEQUENCE: 122

Thr Tyr Ala Gln Lys Phe Gln Gly Arg Val Thr Met Thr Ser Asp Thr
1               5                   10                  15

Ser Thr Ser Ser Val Tyr Met Glu Leu Ser Ser Leu Arg Ser Glu Asp
            20                  25                  30

Thr Ala Val Tyr Tyr Cys
        35

<210> SEQ ID NO 123
<211> LENGTH: 38
<212> TYPE: PRT
<213> ORGANISM: Artificial Sequence
<220> FEATURE:
<223> OTHER INFORMATION: synthetic construct heavy chain variable region
      FR3

<400> SEQUENCE: 123

Lys Tyr Ala Asp Ser Val Lys Gly Arg Phe Thr Ile Ser Arg Asp Asn
1               5                   10                  15

Ser Lys Asn Ser Leu Tyr Leu Gln Met Asn Ser Leu Arg Ala Glu Asp
            20                  25                  30

Thr Ala Val Tyr Tyr Cys
        35

<210> SEQ ID NO 124
<211> LENGTH: 38
<212> TYPE: PRT
<213> ORGANISM: Artificial Sequence
<220> FEATURE:
<223> OTHER INFORMATION: synthetic construct heavy chain variable region
      FR3

<400> SEQUENCE: 124

Gly Tyr Ala Gln Thr Phe Gln Gly Arg Val Thr Met Thr Arg Asp Thr
1               5                   10                  15

Ser Ile Asp Thr Ala Tyr Leu Glu Leu Ser Ser Leu Arg Ser Glu Asp
            20                  25                  30

Thr Ala Val Tyr Tyr Cys
        35

<210> SEQ ID NO 125
<211> LENGTH: 38
<212> TYPE: PRT
<213> ORGANISM: Artificial Sequence
<220> FEATURE:
<223> OTHER INFORMATION: synthetic construct heavy chain variable region
      FR3

<400> SEQUENCE: 125

Tyr Lys Asp Ser Val Lys Gly Arg Phe Thr Ile Ser Arg Asp Asn Ser
1               5                   10                  15

Lys Asn Thr Leu Tyr Leu Gln Met Asn Ser Leu Arg Ala Glu Asp Thr
```

```
                20                  25                  30

Ala Val Tyr Tyr Cys Ala
        35

<210> SEQ ID NO 126
<211> LENGTH: 38
<212> TYPE: PRT
<213> ORGANISM: Artificial Sequence
<220> FEATURE:
<223> OTHER INFORMATION: synthetic construct heavy chain variable region
      FR3

<400> SEQUENCE: 126

Thr Tyr Ala Gln Asn Phe Gln Asp Thr Val Thr Ile Ile Ala Asp Lys
1               5                   10                  15

Ser Thr Asn Thr Ala Tyr Met Glu Leu Lys Asn Leu Arg Ser Glu Asp
                20                  25                  30

Thr Ala Val Tyr Tyr Cys
        35

<210> SEQ ID NO 127
<211> LENGTH: 38
<212> TYPE: PRT
<213> ORGANISM: Artificial Sequence
<220> FEATURE:
<223> OTHER INFORMATION: synthetic construct heavy chain variable region
      FR3

<400> SEQUENCE: 127

Tyr Tyr Ala Asp Ser Val Lys Gly Arg Phe Thr Val Ser Arg Asp Asn
1               5                   10                  15

Ser Lys Asn Thr Leu Tyr Leu Gln Met Asn Ser Leu Arg Ala Glu Asp
                20                  25                  30

Thr Ala Val Tyr Tyr Cys
        35

<210> SEQ ID NO 128
<211> LENGTH: 38
<212> TYPE: PRT
<213> ORGANISM: Artificial Sequence
<220> FEATURE:
<223> OTHER INFORMATION: synthetic construct heavy chain variable region
      FR3

<400> SEQUENCE: 128

Ala Tyr Ala Asp Ser Val Lys Gly Arg Phe Thr Ile Ser Arg Asp Asn
1               5                   10                  15

Ser Lys Asn Ser Leu Tyr Leu Gln Met Asn Ser Leu Arg Ala Glu Asp
                20                  25                  30

Thr Ala Val Tyr Tyr Cys
        35

<210> SEQ ID NO 129
<211> LENGTH: 38
<212> TYPE: PRT
<213> ORGANISM: Artificial Sequence
<220> FEATURE:
<223> OTHER INFORMATION: synthetic construct heavy chain variable region
      FR3

<400> SEQUENCE: 129

Tyr Tyr Val Asp Ser Val Lys Gly Arg Phe Thr Ile Ser Arg Asp Asn
1               5                   10                  15
```

Ala Lys Asn Ser Leu Tyr Leu Gln Met Asn Ser Leu Arg Ala Glu Asp
            20                  25                  30

Thr Ala Val Tyr Tyr Cys
        35

<210> SEQ ID NO 130
<211> LENGTH: 38
<212> TYPE: PRT
<213> ORGANISM: Artificial Sequence
<220> FEATURE:
<223> OTHER INFORMATION: synthetic construct heavy chain variable region
      FR3

<400> SEQUENCE: 130

Asn Tyr Asn Glu Lys Phe Lys Ser Arg Val Thr Ile Thr Val Asp Lys
1               5                   10                  15

Ser Ala Ser Thr Ala Tyr Met Glu Leu Ser Ser Leu Arg Ser Glu Asp
            20                  25                  30

Thr Ala Val Tyr Tyr Cys
        35

<210> SEQ ID NO 131
<211> LENGTH: 38
<212> TYPE: PRT
<213> ORGANISM: Artificial Sequence
<220> FEATURE:
<223> OTHER INFORMATION: synthetic construct heavy chain variable region
      FR3

<400> SEQUENCE: 131

Gly Tyr Ala Asp Ser Val Gln Gly Arg Phe Thr Ile Ser Arg Asp Asn
1               5                   10                  15

Ala Lys Asn Ser Leu Tyr Leu Gln Met Asn Ser Leu Arg Ala Glu Asp
            20                  25                  30

Thr Ala Val Tyr Tyr Cys
        35

<210> SEQ ID NO 132
<211> LENGTH: 38
<212> TYPE: PRT
<213> ORGANISM: Artificial Sequence
<220> FEATURE:
<223> OTHER INFORMATION: synthetic construct heavy chain variable region
      FR3

<400> SEQUENCE: 132

Thr Thr Glu Tyr Ala Ala Ser Val Lys Gly Arg Phe Thr Ile Ser Arg
1               5                   10                  15

Asp Asp Ser Lys Ser Ile Ala Tyr Leu Gln Met Asn Ser Leu Arg Ala
            20                  25                  30

Glu Asp Thr Ala Val Tyr
        35

<210> SEQ ID NO 133
<211> LENGTH: 38
<212> TYPE: PRT
<213> ORGANISM: Artificial Sequence
<220> FEATURE:
<223> OTHER INFORMATION: synthetic construct heavy chain variable region
      FR3

<400> SEQUENCE: 133

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ser Glu Asp
            20                  25                  30

Thr Ala Val Tyr Tyr Cys
        35

<210> SEQ ID NO 134
<211> LENGTH: 38
<212> TYPE: PRT
<213> ORGANISM: Artificial Sequence
<220> FEATURE:
<223> OTHER INFORMATION: synthetic construct heavy chain variable region
      FR3

<400> SEQUENCE: 134

Tyr Tyr Ala Asp Ser Val Lys Gly Arg Phe Thr Ile Ser Arg Asp Asn
1               5                   10                  15

Ser Lys Asn Met Leu Tyr Leu Glu Met Asn Ser Leu Arg Ala Glu Asp
            20                  25                  30

Thr Ala Val Tyr Tyr Cys
        35

<210> SEQ ID NO 135
<211> LENGTH: 11
<212> TYPE: PRT
<213> ORGANISM: Artificial Sequence
<220> FEATURE:
<223> OTHER INFORMATION: synthetic construct heavy chain variable region
      FR4

<400> SEQUENCE: 135

Trp Gly Gln Gly Ser Gln Val Thr Val Ser Ser
1               5                   10

<210> SEQ ID NO 136
<211> LENGTH: 11
<212> TYPE: PRT
<213> ORGANISM: Artificial Sequence
<220> FEATURE:
<223> OTHER INFORMATION: synthetic construct heavy chain variable region
      FR4

<400> SEQUENCE: 136

Trp Gly Arg Gly Thr Leu Val Thr Val Ser Ser
1               5                   10

<210> SEQ ID NO 137
<211> LENGTH: 11
<212> TYPE: PRT
<213> ORGANISM: Artificial Sequence
<220> FEATURE:
<223> OTHER INFORMATION: synthetic construct heavy chain variable region
      FR4

<400> SEQUENCE: 137

Trp Gly Gln Gly Thr Leu Val Thr Val Ser Ser
1               5                   10

<210> SEQ ID NO 138
<211> LENGTH: 11
<212> TYPE: PRT
<213> ORGANISM: Artificial Sequence
<220> FEATURE:
<223> OTHER INFORMATION: synthetic construct heavy chain variable region
      FR4

<400> SEQUENCE: 138

-continued

Trp Gly Gln Gly Thr Thr Val Thr Val Ser Ser
1               5                   10

<210> SEQ ID NO 139
<211> LENGTH: 11
<212> TYPE: PRT
<213> ORGANISM: Artificial Sequence
<220> FEATURE:
<223> OTHER INFORMATION: synthetic construct heavy chain variable region
      FR4

<400> SEQUENCE: 139

Trp Gly Gln Gly Thr Met Val Thr Val Ser Ser
1               5                   10

<210> SEQ ID NO 140
<211> LENGTH: 11
<212> TYPE: PRT
<213> ORGANISM: Artificial Sequence
<220> FEATURE:
<223> OTHER INFORMATION: synthetic construct heavy chain variable region
      FR4

<400> SEQUENCE: 140

Trp Gly Gln Gly Thr Leu Ile Thr Val Ser Ser
1               5                   10

<210> SEQ ID NO 141
<211> LENGTH: 11
<212> TYPE: PRT
<213> ORGANISM: Artificial Sequence
<220> FEATURE:
<223> OTHER INFORMATION: synthetic construct heavy chain variable region
      FR4

<400> SEQUENCE: 141

Trp Gly Leu Gly Thr Leu Val Thr Val Ser Ser
1               5                   10

<210> SEQ ID NO 142
<211> LENGTH: 11
<212> TYPE: PRT
<213> ORGANISM: Artificial Sequence
<220> FEATURE:
<223> OTHER INFORMATION: synthetic construct heavy chain variable region
      FR4

<400> SEQUENCE: 142

Trp Gly Gln Gly Thr Pro Val Thr Val Ser Ser
1               5                   10

<210> SEQ ID NO 143
<211> LENGTH: 11
<212> TYPE: PRT
<213> ORGANISM: Artificial Sequence
<220> FEATURE:
<223> OTHER INFORMATION: synthetic construct heavy chain variable region
      FR4

<400> SEQUENCE: 143

Trp Gly Gln Gly Thr Met Ile Thr Val Ser Ser
1               5                   10

<210> SEQ ID NO 144
<211> LENGTH: 11
<212> TYPE: PRT
<213> ORGANISM: Artificial Sequence

```
<220> FEATURE:
<223> OTHER INFORMATION: synthetic construct heavy chain variable region
      FR4

<400> SEQUENCE: 144

Trp Gly Gln Gly Thr Pro Ile Thr Val Ser Ser
1               5                   10

<210> SEQ ID NO 145
<211> LENGTH: 11
<212> TYPE: PRT
<213> ORGANISM: Artificial Sequence
<220> FEATURE:
<223> OTHER INFORMATION: synthetic construct heavy chain variable region
      FR4

<400> SEQUENCE: 145

Trp Ser Gln Gly Thr Leu Val Thr Val Ser Ser
1               5                   10

<210> SEQ ID NO 146
<211> LENGTH: 114
<212> TYPE: PRT
<213> ORGANISM: Artificial Sequence
<220> FEATURE:
<223> OTHER INFORMATION: synthetic construct heavy chain variable region

<400> SEQUENCE: 146

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Val Pro Gly Lys Gly Leu Glu Trp Val
        35                  40                  45

Ala Val Ile Ser Tyr Asp Gly Asn Asp Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Pro Thr Thr Phe Glu Tyr Trp Gly Gln Gly Ser Gln Val Thr Val
            100                 105                 110

Ser Ser

<210> SEQ ID NO 147
<211> LENGTH: 114
<212> TYPE: PRT
<213> ORGANISM: Artificial Sequence
<220> FEATURE:
<223> OTHER INFORMATION: synthetic construct heavy chain variable region

<400> SEQUENCE: 147

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Pro Lys Asn Thr Leu Tyr
```

```
                65                   70                  75                  80
Leu Gln Met Asn Ser Leu Arg Ala Glu Asp Thr Ala Val Tyr Tyr Cys
                        85                  90                  95

Thr Thr Thr Thr Phe Asp Ser Trp Gly Arg Gly Thr Leu Val Thr Val
                100                 105                 110

Ser Ser

<210> SEQ ID NO 148
<211> LENGTH: 117
<212> TYPE: PRT
<213> ORGANISM: Artificial Sequence
<220> FEATURE:
<223> OTHER INFORMATION: synthetic construct heavy chain variable region

<400> SEQUENCE: 148

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
                20                  25                  30

Ala Met His Trp Val Arg Gln Val Pro Gly Lys Gly Leu Glu Trp Val
            35                  40                  45

Ser Gly Ile Ser Trp Asn Ser Gly Arg Ile Val Tyr Ala Asp Ser Met
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Gln Gln Gln Ile Leu Asp Tyr Trp Gly Gln Gly Thr Leu
                100                 105                 110

Val Thr Val Ser Ser
            115

<210> SEQ ID NO 149
<211> LENGTH: 117
<212> TYPE: PRT
<213> ORGANISM: Artificial Sequence
<220> FEATURE:
<223> OTHER INFORMATION: synthetic construct heavy chain variable region

<400> SEQUENCE: 149

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Asp Tyr
                20                  25                  30

Ala Met His Trp Val Arg Gln Val Pro Gly Lys Gly Leu Glu Trp Val
            35                  40                  45

Ser Gly Ile Ser Trp Asn Ser Gly Arg Ile Val Tyr Ala Asp Ser Met
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Ile Arg Gln Ile Leu Asp Tyr Trp Gly Gln Gly Thr Leu
                100                 105                 110

Val Thr Val Ser Ser
            115
```

-continued

```
<210> SEQ ID NO 150
<211> LENGTH: 120
<212> TYPE: PRT
<213> ORGANISM: Artificial Sequence
<220> FEATURE:
<223> OTHER INFORMATION: synthetic construct heavy chain variable region
<220> FEATURE:
<221> NAME/KEY: misc_feature
<222> LOCATION: (102)..(102)
<223> OTHER INFORMATION: Xaa can be any naturally occurring amino acid

<400> SEQUENCE: 150
```

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
            20                  25                  30

Ala Met His Trp Val Arg Gln Val Pro Gly Lys Gly Leu Glu Trp Val
        35                  40                  45

Ser Gly Ile Ser Trp Asn Ser Gly Arg Ile Val Tyr Ala Asp Ser Met
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Pro Xaa Ser Arg Ser Arg Leu Asp Val Trp Gly Gln
            100                 105                 110

Gly Thr Leu Val Thr Val Ser Ser
        115                 120

```
<210> SEQ ID NO 151
<211> LENGTH: 121
<212> TYPE: PRT
<213> ORGANISM: Artificial Sequence
<220> FEATURE:
<223> OTHER INFORMATION: synthetic construct heavy chain variable region
<220> FEATURE:
<221> NAME/KEY: misc_feature
<222> LOCATION: (100)..(100)
<223> OTHER INFORMATION: Xaa can be any naturally occurring amino acid

<400> SEQUENCE: 151
```

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
            20                  25                  30

Ala Met His Trp Val Arg Gln Val Pro Gly Lys Gly Leu Glu Trp Val
        35                  40                  45

Ser Gly Ile Ser Trp Asn Ser Gly Arg Ile Val Tyr Ala Asp Ser Met
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ala Xaa Thr Ser Pro Leu Asp Met Ser Leu Asp Tyr Trp Gly
            100                 105                 110

Gln Gly Thr Leu Val Thr Val Ser Ser
        115                 120

```
<210> SEQ ID NO 152
<211> LENGTH: 122
<212> TYPE: PRT
```

<213> ORGANISM: Artificial Sequence
<220> FEATURE:
<223> OTHER INFORMATION: synthetic construct heavy chain variable region

<400> SEQUENCE: 152

Gln Met Gln Leu Val Glu Ser Gly Gly Asn Leu Val Gln Pro Gly Arg
1               5                   10                  15

Ser Leu Arg Leu Ser Cys Ala Ala Ser Gly Phe Thr Phe Asp Asp Tyr
            20                  25                  30

Gly Met His Trp Val Arg Gln Ala Pro Gly Lys Gly Leu Glu Trp Val
        35                  40                  45

Ser Ser Ile Ser Trp Asn Ser Gly Thr Ile Gly Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ser Glu Asp Thr Ala Val Tyr Tyr Cys
                85                  90                  95

Ala Arg Leu Leu His Gln Met Asn Glu His Gly Phe Met Asp Val Trp
            100                 105                 110

Gly Gln Gly Thr Thr Val Thr Val Ser Ser
        115                 120

<210> SEQ ID NO 153
<211> LENGTH: 124
<212> TYPE: PRT
<213> ORGANISM: Artificial Sequence
<220> FEATURE:
<223> OTHER INFORMATION: synthetic construct heavy chain variable region

<400> SEQUENCE: 153

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Leu Phe Ser Thr Ala His Ser Ala Gln Lys Phe
50                  55                  60

Gln Gly Arg Val Thr Ile Thr Ala Asp Glu Ser Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Lys His Lys Gly Leu Pro Phe Asp Trp Ser Pro Asp Gly Phe Asp
            100                 105                 110

Thr Trp Gly Gln Gly Thr Met Val Thr Val Ser Ser
        115                 120

<210> SEQ ID NO 154
<211> LENGTH: 117
<212> TYPE: PRT
<213> ORGANISM: Artificial Sequence
<220> FEATURE:
<223> OTHER INFORMATION: synthetic construct heavy chain variable region

<400> SEQUENCE: 154

Gln Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Thr Arg Asn
            20                  25                  30

```
Ala Val Ser Trp Val Arg Gln Ala Pro Gly Glu Gly Leu Glu Trp Met
            35                  40                  45

Ala Asp Ile Ile Pro Ile Phe Gly Ser Ala Asn Tyr Ala Gln Lys Phe
 50                  55                  60

Gln Gly Arg Leu Thr Leu Thr Ala Asp Val Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Thr Ile Glu Gly Ala Phe Asp Ile Trp Gly Gln Gly Thr Met
                100                 105                 110

Val Thr Val Ser Ser
            115

<210> SEQ ID NO 155
<211> LENGTH: 114
<212> TYPE: PRT
<213> ORGANISM: Artificial Sequence
<220> FEATURE:
<223> OTHER INFORMATION: synthetic construct heavy chain variable region

<400> SEQUENCE: 155

Gln Met Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
             20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Arg Leu Arg Ser Glu Asp Thr Ala Val Tyr Tyr Cys
                 85                  90                  95

Thr Thr Thr Thr Phe Asp Ser Trp Gly Gln Gly Thr Leu Ile Thr Val
                100                 105                 110

Ser Ser

<210> SEQ ID NO 156
<211> LENGTH: 118
<212> TYPE: PRT
<213> ORGANISM: Artificial Sequence
<220> FEATURE:
<223> OTHER INFORMATION: synthetic construct heavy chain variable region

<400> SEQUENCE: 156

Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
             20                  25                  30

Tyr Met Ser Trp Ile Arg Gln Ala Pro Gly Lys Gly Leu Glu Trp Val
            35                  40                  45

Ser Asp Ile Ser Ala Ser Gly Asn Ser Ile Tyr Tyr Ala Asp Ser Val
 50                  55                  60

Lys Arg Arg Phe Thr Ile Ser Arg Asp Asn Ser Lys Asn Ser Leu Tyr
 65                  70                  75                  80

Leu Gln Met Asn Ser Leu Arg Ala Glu Asp Thr Ala Val Tyr Tyr Cys
                 85                  90                  95
```

Val Thr Ser Gly Pro Phe Gly Glu Phe Arg Asn Trp Gly Leu Gly Thr
                100                 105                 110

Leu Val Thr Val Ser Ser
        115

<210> SEQ ID NO 157
<211> LENGTH: 122
<212> TYPE: PRT
<213> ORGANISM: Artificial Sequence
<220> FEATURE:
<223> OTHER INFORMATION: synthetic construct heavy chain variable region

<400> SEQUENCE: 157

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Met His Thr Phe Ser Val Gln Tyr Phe Leu Asp Val Trp
            100                 105                 110

Gly Gln Gly Thr Thr Val Thr Val Ser Ser
        115                 120

<210> SEQ ID NO 158
<211> LENGTH: 114
<212> TYPE: PRT
<213> ORGANISM: Artificial Sequence
<220> FEATURE:
<223> OTHER INFORMATION: synthetic construct heavy chain variable region

<400> SEQUENCE: 158

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Val Pro Gly Lys Gly Leu Glu Trp Val
        35                  40                  45

Ala Val Ile Ser Tyr Asp Gly Asn Asp Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Pro Thr Thr Phe Glu Tyr Trp Gly Gln Gly Ser Gln Val Thr Val
            100                 105                 110

Ser Ser

<210> SEQ ID NO 159
<211> LENGTH: 126
<212> TYPE: PRT
<213> ORGANISM: Artificial Sequence

```
<220> FEATURE:
<223> OTHER INFORMATION: synthetic construct heavy chain variable region

<400> SEQUENCE: 159

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Asn Ser Tyr
                20                  25                  30

Tyr Val His Trp Val Arg Gln Ala Pro Gly Gln Gly Leu Glu Trp Met
            35                  40                  45

Gly Ile Ile Asn Pro Ser Asp Gly Ser Ala Thr Tyr Ala Gln Lys Phe
    50                  55                  60

Gln Gly Arg Val Thr Met Thr Ser Asp Thr Ser Thr Ser Val Tyr
65                  70                  75                  80

Met Glu Leu Ser Ser Leu Arg Ser Glu Asp Thr Ala Val Tyr Tyr Cys
                85                  90                  95

Ala Arg Asp Gly Asn Tyr Tyr Asp Ser Arg Gly Tyr Tyr Tyr Asp Thr
            100                 105                 110

Phe Asp Met Trp Gly Gln Gly Thr Leu Ile Thr Val Ser Ser
        115                 120                 125

<210> SEQ ID NO 160
<211> LENGTH: 117
<212> TYPE: PRT
<213> ORGANISM: Artificial Sequence
<220> FEATURE:
<223> OTHER INFORMATION: synthetic construct heavy chain variable region

<400> SEQUENCE: 160

Gln Met Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Gln Gly Leu Glu Trp Val
            35                  40                  45

Ser Gly Ile Ser Trp Asn Ser Asn Ile Lys Tyr Ala Asp Ser Val
    50                  55                  60

Lys Gly Arg Phe Thr Ile Ser Arg Asp Asn Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Leu Thr Pro Leu Asp Val Trp Gly Gln Gly Thr Pro
            100                 105                 110

Val Thr Val Ser Ser
        115

<210> SEQ ID NO 161
<211> LENGTH: 116
<212> TYPE: PRT
<213> ORGANISM: Artificial Sequence
<220> FEATURE:
<223> OTHER INFORMATION: synthetic construct heavy chain variable region

<400> SEQUENCE: 161

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30
```

```
Asp Ile Asn Trp Val Arg Gln Ala Ser Gly Gln Ala Pro Glu Trp Met
            35                  40                  45

Gly Trp Leu His Ala Asp Ser Gly Lys Thr Gly Tyr Ala Gln Thr Phe
 50                  55                  60

Gln Gly Arg Val Thr Met Thr Arg Asp Thr Ser Ile Asp Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Gly Thr His Trp Leu Asp Ser Trp Gly Gln Gly Thr Leu Val
            100                 105                 110

Thr Val Ser Ser
        115

<210> SEQ ID NO 162
<211> LENGTH: 123
<212> TYPE: PRT
<213> ORGANISM: Artificial Sequence
<220> FEATURE:
<223> OTHER INFORMATION: synthetic construct heavy chain variable region

<400> SEQUENCE: 162

Gln Val Gln Leu Val Gln Ser Gly Gly Gly Leu Ile Gln Pro Gly Gly
 1               5                  10                  15

Ser Leu Arg Leu Ser Cys Ala Ala Ser Gly Phe Thr Val Ser Arg Asn
             20                  25                  30

Ser Met Asn Trp Val Arg Gln Thr Pro Gly Lys Gly Pro Glu Trp Val
            35                  40                  45

Ser Leu Ile Phe Ser Gly Gly Thr Thr Lys Tyr Lys Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Glu Glu Gln Phe Leu Ile Ala Leu Ala Gly Arg Tyr Phe Asp Tyr
            100                 105                 110

Trp Gly Gln Gly Thr Leu Val Thr Val Ser Ser
        115                 120

<210> SEQ ID NO 163
<211> LENGTH: 118
<212> TYPE: PRT
<213> ORGANISM: Artificial Sequence
<220> FEATURE:
<223> OTHER INFORMATION: synthetic construct heavy chain variable region

<400> SEQUENCE: 163

Gln Met Gln Leu Val Gln Ser Gly Ala Glu Val Lys Lys Pro Gly Ser
 1               5                  10                  15

Ser Val Lys Val Ser Cys Lys Ala Ser Gly Asp Thr Phe Thr Arg Tyr
             20                  25                  30

Ile Ile Asn Trp Val Arg Gln Ala Pro Gly Gln Gly Leu Glu Trp Met
            35                  40                  45

Gly Arg Val Ile Pro Thr Leu Gly Leu Thr Thr Tyr Ala Gln Asn Phe
 50                  55                  60

Gln Asp Thr Val Thr Ile Ile Ala Asp Lys Ser Thr Asn Thr Ala Tyr
 65                  70                  75                  80

Met Glu Leu Lys Asn Leu Arg Ser Glu Asp Thr Ala Val Tyr Tyr Cys
                 85                  90                  95
```

Ala Arg Gly Tyr Gly Ser Gly Ala Phe Asp Ile Trp Gly Gln Gly Thr
            100                 105                 110

Met Ile Thr Val Ser Ser
        115

<210> SEQ ID NO 164
<211> LENGTH: 118
<212> TYPE: PRT
<213> ORGANISM: Artificial Sequence
<220> FEATURE:
<223> OTHER INFORMATION: synthetic construct heavy chain variable region

<400> SEQUENCE: 164

Gln Met Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser His Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Lys Ile Tyr Tyr Ala Asp Ser Val
    50                  55                  60

Lys Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Gly Tyr Lys Asp Ala Phe Asp Ile Trp Gly Gln Gly Thr
            100                 105                 110

Met Val Thr Val Ser Ser
        115

<210> SEQ ID NO 165
<211> LENGTH: 114
<212> TYPE: PRT
<213> ORGANISM: Artificial Sequence
<220> FEATURE:
<223> OTHER INFORMATION: synthetic construct heavy chain variable region

<400> SEQUENCE: 165

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Pro Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Thr Thr Thr Phe Asp Ser Trp Gly Arg Gly Thr Leu Val Thr Val
            100                 105                 110

Ser Ser

<210> SEQ ID NO 166
<211> LENGTH: 116
<212> TYPE: PRT
<213> ORGANISM: Artificial Sequence

```
<220> FEATURE:
<223> OTHER INFORMATION: synthetic construct heavy chain variable region

<400> SEQUENCE: 166

Gln Met Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Glu Asp Tyr
            20                  25                  30

Ala Met His Trp Val Arg Gln Pro Pro Gly Lys Gly Leu Glu Trp Val
        35                  40                  45

Ser Ser Ile Ser Trp Asn Ser His Asn Ile Ala Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Val Tyr Tyr Cys
                85                  90                  95

Ser Thr Ser Gly Leu Gly Val His Ala Trp Gly Gln Gly Thr Met Val
            100                 105                 110

Thr Val Ser Ser
        115

<210> SEQ ID NO 167
<211> LENGTH: 118
<212> TYPE: PRT
<213> ORGANISM: Artificial Sequence
<220> FEATURE:
<223> OTHER INFORMATION: synthetic construct heavy chain variable region

<400> SEQUENCE: 167

Gln Val Gln Leu Val Glu Ser Gly Gly Gly Leu Val Gln Pro Gly Gly
1               5                   10                  15

Ser Leu Arg Leu Ser Cys Ala Ala Ser Gly Leu Ser Phe Ser Ser Tyr
            20                  25                  30

Trp Met Thr Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Phe Gly Gly His Leu Asp Leu Trp Gly Gln Gly Thr
            100                 105                 110

Leu Val Thr Val Ser Ser
        115

<210> SEQ ID NO 168
<211> LENGTH: 121
<212> TYPE: PRT
<213> ORGANISM: Artificial Sequence
<220> FEATURE:
<223> OTHER INFORMATION: synthetic construct heavy chain variable region

<400> SEQUENCE: 168

Gln Val Gln Leu Val Glu Ser Gly Ala Glu Val Lys Lys Pro Gly Ala
1               5                   10                  15

Ser Val Lys Leu Ser Cys Lys Ala Ser Gly Tyr Thr Phe Ser Ser Tyr
            20                  25                  30
```

```
Trp Met His Trp Val Arg Gln Ala Pro Gly Gln Arg Leu Glu Trp Met
        35                  40                  45
Gly Glu Ile Asn Pro Gly Asn Gly His Thr Asn Tyr Asn Glu Lys Phe
    50                  55                  60
Lys Ser Arg Val Thr Ile Thr Val Asp Lys Ser Ala Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Glu Gly Asp Gly Ser Tyr Trp Gly Tyr Phe Asp Ser Trp Gly
                100                 105                 110
Gln Gly Thr Pro Ile Thr Val Ser Ser
        115                 120
```

<210> SEQ ID NO 169
<211> LENGTH: 121
<212> TYPE: PRT
<213> ORGANISM: Artificial Sequence
<220> FEATURE:
<223> OTHER INFORMATION: synthetic construct heavy chain variable region

<400> SEQUENCE: 169

```
Gln Val Gln Leu Val Gln Ser Gly Gly Asn Leu Val Gln Pro Gly Arg
1               5                   10                  15
Ser Leu Arg Leu Ser Cys Ala Ala Ser Gly Phe Thr Phe Asp Asp Tyr
                20                  25                  30
Ala Met His Trp Val Arg Gln Ala Pro Gly Lys Gly Leu Glu Trp Val
        35                  40                  45
Ser Gly Ile Ser Trp Asn Ser Gly Thr Pro Gly Tyr Ala Asp Ser Val
    50                  55                  60
Gln Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Gly His Asn Tyr Leu Asp Ser Ser Tyr Tyr Asp Tyr Trp Gly
                100                 105                 110
Gln Gly Thr Leu Val Thr Val Ser Ser
        115                 120
```

<210> SEQ ID NO 170
<211> LENGTH: 127
<212> TYPE: PRT
<213> ORGANISM: Artificial Sequence
<220> FEATURE:
<223> OTHER INFORMATION: synthetic construct heavy chain variable region

<400> SEQUENCE: 170

```
Gln Val Gln Leu Val Glu Ser Gly Gly Asp Leu Val Lys Pro Gly Arg
1               5                   10                  15
Ser Leu Arg Leu Ser Cys Thr Gly Ser Gly Phe Thr Phe Gly Asp His
                20                  25                  30
Pro Leu Thr Trp Val Arg Gln Ile Pro Gly Lys Gly Leu Glu Trp Val
        35                  40                  45
Gly Phe Ile Arg Ser Lys Ala Tyr Gly Glu Thr Glu Tyr Ala Ala
    50                  55                  60
Ser Val Lys Gly Arg Phe Thr Ile Ser Arg Asp Asp Ser Lys Ser Ile
65                  70                  75                  80
Ala Tyr Leu Gln Met Asn Ser Leu Arg Ala Glu Asp Thr Ala Val Tyr
                85                  90                  95
```

```
Tyr Cys Ala Ser Val Ser Tyr Cys Ser Gly Gly Ser Cys Tyr Gln Gly
            100                 105                 110

Thr Phe Asp Tyr Trp Gly Gln Gly Thr Leu Val Thr Val Ser Ser
        115                 120                 125

<210> SEQ ID NO 171
<211> LENGTH: 114
<212> TYPE: PRT
<213> ORGANISM: Artificial Sequence
<220> FEATURE:
<223> OTHER INFORMATION: synthetic construct heavy chain variable region

<400> SEQUENCE: 171

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Leu Arg Tyr
            20                  25                  30

Ala Met His Trp Val Arg Gln Ala Pro Gly Lys Gly Leu Glu Trp Val
        35                  40                  45

Ala Val Ile Ser Tyr Asp Gly Gln Asp Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Thr Thr Thr Phe Asp Ser Trp Gly Arg Gly Thr Leu Val Thr Val
            100                 105                 110

Ser Ser

<210> SEQ ID NO 172
<211> LENGTH: 114
<212> TYPE: PRT
<213> ORGANISM: Artificial Sequence
<220> FEATURE:
<223> OTHER INFORMATION: synthetic construct heavy chain variable region

<400> SEQUENCE: 172

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Lys Asn Asn
            20                  25                  30

Ala Met His Trp Val Arg Gln Ala Pro Gly Lys Gly Leu Glu Trp Val
        35                  40                  45

Ala Val Ile Ser Tyr Asp Gly Arg His Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Thr Thr Thr Phe Asp Ser Trp Gly Gln Gly Thr Leu Val Thr Val
            100                 105                 110

Ser Ser

<210> SEQ ID NO 173
<211> LENGTH: 114
<212> TYPE: PRT
<213> ORGANISM: Artificial Sequence
<220> FEATURE:
```

<223> OTHER INFORMATION: synthetic construct heavy chain variable region

<400> SEQUENCE: 173

```
Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Arg Asn Tyr
            20                  25                  30
Ala Met His Trp Val Arg Gln Ala Pro Gly Lys Gly Leu Glu Trp Val
        35                  40                  45
Ala Val Ile Ser Tyr Asp Gly Gln His Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Thr Thr Thr Thr Phe Asp Ser Trp Ser Gln Gly Thr Leu Val Thr Val
                100                 105                 110
Ser Ser
```

<210> SEQ ID NO 174
<211> LENGTH: 114
<212> TYPE: PRT
<213> ORGANISM: Artificial Sequence
<220> FEATURE:
<223> OTHER INFORMATION: synthetic construct heavy chain variable region

<400> SEQUENCE: 174

```
Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Pro Ile Tyr
            20                  25                  30
Ala Met His Trp Val Arg Gln Ala Pro Gly Lys Gly Leu Glu Trp Val
        35                  40                  45
Ala Val Ile Ser Tyr Asp Gly Ala His Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Thr Thr Thr Thr Phe Asp Ser Trp Gly Gln Gly Thr Leu Val Thr Val
                100                 105                 110
Ser Ser
```

<210> SEQ ID NO 175
<211> LENGTH: 114
<212> TYPE: PRT
<213> ORGANISM: Artificial Sequence
<220> FEATURE:
<223> OTHER INFORMATION: synthetic construct heavy chain variable region

<400> SEQUENCE: 175

```
Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Lys Thr Tyr
            20                  25                  30
Ala Met His Trp Val Arg Gln Ala Pro Gly Lys Gly Leu Glu Trp Val
        35                  40                  45
```

```
Ala Val Ile Ser Tyr Asp Gly Gln His Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Thr Thr Thr Phe Asp Ser Trp Gly Gln Gly Thr Leu Val Thr Val
                100                 105                 110

Ser Ser
```

<210> SEQ ID NO 176
<211> LENGTH: 114
<212> TYPE: PRT
<213> ORGANISM: Artificial Sequence
<220> FEATURE:
<223> OTHER INFORMATION: synthetic construct heavy chain variable region

<400> SEQUENCE: 176

```
Gln Val Gln Leu Val Glu Ser Gly Gly Val Val Gln Pro Gly Arg
 1               5                  10                  15

Ser Leu Arg Leu Ser Cys Ala Ala Ser Gly Phe Thr Phe Lys Tyr Tyr
                 20                  25                  30

Ala Met His Trp Val Arg Gln Ala Pro Gly Lys Gly Leu Glu Trp Val
            35                  40                  45

Thr Val Ile Ser Tyr Asp Gly Gln Tyr Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Thr Thr Thr Phe Asp Ser Trp Gly Gln Gly Thr Leu Val Thr Val
                100                 105                 110

Ser Ser
```

<210> SEQ ID NO 177
<211> LENGTH: 114
<212> TYPE: PRT
<213> ORGANISM: Artificial Sequence
<220> FEATURE:
<223> OTHER INFORMATION: synthetic construct heavy chain variable region

<400> SEQUENCE: 177

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Arg Ser Tyr
                 20                  25                  30

Ala Met His Trp Val Arg Gln Ala Pro Gly Lys Gly Leu Glu Trp Val
            35                  40                  45

Ala Val Ile Ser Tyr Asp Gly Gln Asp Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Thr Thr Thr Phe Asp Ser Trp Gly Gln Gly Thr Leu Val Thr Val
                100                 105                 110

Ser Ser
```

<210> SEQ ID NO 178
<211> LENGTH: 114
<212> TYPE: PRT
<213> ORGANISM: Artificial Sequence
<220> FEATURE:
<223> OTHER INFORMATION: synthetic construct heavy chain variable region

<400> SEQUENCE: 178

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Leu Arg Tyr
            20                  25                  30

Ala Met His Trp Val Arg Gln Ala Pro Gly Lys Gly Leu Glu Trp Val
        35                  40                  45

Ala Val Ile Ser Tyr Asp Gly Arg Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Thr Thr Thr Phe Asp Ser Trp Gly Gln Gly Thr Leu Val Thr Val
            100                 105                 110

Ser Ser

<210> SEQ ID NO 179
<211> LENGTH: 114
<212> TYPE: PRT
<213> ORGANISM: Artificial Sequence
<220> FEATURE:
<223> OTHER INFORMATION: synthetic construct heavy chain variable region

<400> SEQUENCE: 179

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Leu Val Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser His Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Thr Thr Thr Phe Asp Ser Trp Gly Gln Gly Thr Leu Val Thr Val
            100                 105                 110

Ser Ser

<210> SEQ ID NO 180
<211> LENGTH: 114
<212> TYPE: PRT
<213> ORGANISM: Artificial Sequence
<220> FEATURE:
<223> OTHER INFORMATION: synthetic construct heavy chain variable region

<400> SEQUENCE: 180

Gln Val Gln Leu Val Glu Ser Gly Gly Gly Val Val Gln Pro Gly Arg
1               5                   10                  15

```
Ser Leu Arg Leu Ser Cys Ala Ala Ser Gly Phe Thr Phe Lys Thr Tyr
            20                  25                  30

Ala Met His Trp Val Arg Gln Ala Pro Gly Lys Gly Leu Glu Trp Val
            35                  40                  45

Ala Val Ile Ser Tyr Asp Gly Gln His Lys Tyr Tyr Ala Asp Ser Val
        50                  55                  60

Lys Gly Arg Phe Thr Ile Ser Arg Asp Asn Ser Lys Asn Thr Leu Tyr
65                      70                  75                  80

Leu Gln Met Asn Ser Leu Arg Ala Glu Asp Thr Ala Val Tyr Tyr Cys
                    85                  90                  95

Thr Thr Thr Thr Phe Asp Ser Trp Gly Gln Gly Thr Leu Val Thr Val
                100                 105                 110

Ser Ser

<210> SEQ ID NO 181
<211> LENGTH: 114
<212> TYPE: PRT
<213> ORGANISM: Artificial Sequence
<220> FEATURE:
<223> OTHER INFORMATION: synthetic construct heavy chain variable region

<400> SEQUENCE: 181

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Val Pro Gly Lys Gly Leu Glu Trp Val
            35                  40                  45

Ala Val Ile Ser Tyr Asp Gly Asn Asp Lys Tyr Tyr Ala Asp Ser Val
        50                  55                  60

Lys Gly Arg Phe Thr Ile Ser Arg Asp Asn Ser Lys Asn Thr Leu Tyr
65                      70                  75                  80

Leu Gln Met Asn Ser Leu Arg Ala Glu Asp Thr Ala Val Tyr Tyr Cys
                    85                  90                  95

Val Pro Thr Thr Phe Glu Tyr Trp Gly Gln Gly Ser Val Thr Val
                100                 105                 110

Ser Ser

<210> SEQ ID NO 182
<211> LENGTH: 114
<212> TYPE: PRT
<213> ORGANISM: Artificial Sequence
<220> FEATURE:
<223> OTHER INFORMATION: synthetic construct heavy chain variable region

<400> SEQUENCE: 182

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
            35                  40                  45

Ala Val Ile Ser Tyr Asp Gly Asn Asp Lys Tyr Tyr Ala Asp Ser Val
        50                  55                  60

Lys Gly Arg Phe Thr Ile Ser Arg Asp Asn Ser Lys Asn Thr Leu Tyr
65                      70                  75                  80
```

Leu Gln Met Asn Ser Leu Arg Ala Glu Asp Thr Ala Val Tyr Tyr Cys
                85                  90                  95

Val Pro Thr Thr Phe Glu Tyr Trp Gly Gln Gly Thr Leu Val Thr Val
            100                 105                 110

Ser Ser

<210> SEQ ID NO 183
<211> LENGTH: 114
<212> TYPE: PRT
<213> ORGANISM: Artificial Sequence
<220> FEATURE:
<223> OTHER INFORMATION: synthetic construct heavy chain variable region

<400> SEQUENCE: 183

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Leu Tyr
            20                  25                  30

Ala Met His Trp Val Arg Gln Ala Pro Gly Lys Gly Leu Glu Trp Val
        35                  40                  45

Ala Val Ile Ser His Asp Gly Asn Asp Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Pro Thr Thr Phe Glu Tyr Trp Gly Gln Gly Thr Leu Val Thr Val
            100                 105                 110

Ser Ser

<210> SEQ ID NO 184
<211> LENGTH: 114
<212> TYPE: PRT
<213> ORGANISM: Artificial Sequence
<220> FEATURE:
<223> OTHER INFORMATION: synthetic construct heavy chain variable region

<400> SEQUENCE: 184

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Phe Tyr
            20                  25                  30

Ala Met His Trp Val Arg Gln Ala Pro Gly Lys Gly Leu Glu Trp Val
        35                  40                  45

Ala Val Ile Ser Tyr Asp Gly Asn Asp Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Pro Thr Thr Phe Glu Tyr Trp Gly Gln Gly Thr Leu Val Thr Val
            100                 105                 110

Ser Ser

<210> SEQ ID NO 185
<211> LENGTH: 114
<212> TYPE: PRT
<213> ORGANISM: Artificial Sequence

```
<220> FEATURE:
<223> OTHER INFORMATION: synthetic construct heavy chain variable region

<400> SEQUENCE: 185

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Thr Tyr
            20                  25                  30

Ala Met His Trp Val Arg Gln Ala Pro Gly Lys Gly Leu Glu Trp Val
        35                  40                  45

Ala Val Ile Ser Tyr Asp Gly Asn Asp Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Pro Thr Thr Phe Glu Tyr Trp Gly Gln Gly Thr Leu Val Thr Val
            100                 105                 110

Ser Ser

<210> SEQ ID NO 186
<211> LENGTH: 114
<212> TYPE: PRT
<213> ORGANISM: Artificial Sequence
<220> FEATURE:
<223> OTHER INFORMATION: synthetic construct heavy chain variable region

<400> SEQUENCE: 186

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Val Tyr
            20                  25                  30

Ala Met His Trp Val Arg Gln Ala Pro Gly Lys Gly Leu Glu Trp Val
        35                  40                  45

Ala Val Ile Ser Tyr Asp Gly Asn Asp Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Pro Thr Thr Phe Glu Tyr Trp Gly Gln Gly Thr Leu Val Thr Val
            100                 105                 110

Ser Ser

<210> SEQ ID NO 187
<211> LENGTH: 114
<212> TYPE: PRT
<213> ORGANISM: Artificial Sequence
<220> FEATURE:
<223> OTHER INFORMATION: synthetic construct heavy chain variable region

<400> SEQUENCE: 187

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Met Arg Tyr
            20                  25                  30

Ala Met His Trp Val Arg Gln Ala Pro Gly Lys Gly Leu Glu Trp Val
        35                  40                  45
```

```
Ala Val Ile Ser Tyr Asp Gly Asn Asp Lys Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Val Pro Thr Thr Phe Glu Tyr Trp Gly Gln Gly Thr Leu Val Thr Val
               100                 105                 110

Ser Ser
```

<210> SEQ ID NO 188
<211> LENGTH: 114
<212> TYPE: PRT
<213> ORGANISM: Artificial Sequence
<220> FEATURE:
<223> OTHER INFORMATION: synthetic construct heavy chain variable region

<400> SEQUENCE: 188

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Thr Tyr
                20                  25                  30

Ala Met His Trp Val Arg Gln Ala Pro Gly Lys Gly Leu Glu Trp Val
            35                  40                  45

Ala Val Ile Ser Tyr Asp Gly Asn Asp Lys Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Val Pro Thr Thr Phe Glu Tyr Trp Gly Gln Gly Thr Leu Val Thr Val
               100                 105                 110

Ser Ser
```

<210> SEQ ID NO 189
<211> LENGTH: 114
<212> TYPE: PRT
<213> ORGANISM: Artificial Sequence
<220> FEATURE:
<223> OTHER INFORMATION: synthetic construct heavy chain variable region

<400> SEQUENCE: 189

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Thr Thr Thr Thr Phe Asp Ser Trp Gly Gln Gly Thr Leu Val Thr Val
               100                 105                 110
```

Ser Ser

<210> SEQ ID NO 190
<211> LENGTH: 114
<212> TYPE: PRT
<213> ORGANISM: Artificial Sequence
<220> FEATURE:
<223> OTHER INFORMATION: synthetic construct heavy chain variable region

<400> SEQUENCE: 190

```
Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Thr Phe Asp Tyr Trp Gly Gln Gly Thr Leu Ile Thr Val
            100                 105                 110

Ser Ser
```

<210> SEQ ID NO 191
<211> LENGTH: 114
<212> TYPE: PRT
<213> ORGANISM: Artificial Sequence
<220> FEATURE:
<223> OTHER INFORMATION: synthetic construct heavy chain variable region

<400> SEQUENCE: 191

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Pro Thr Thr Phe Glu Tyr Trp Gly Gln Gly Ser Gln Val Thr Val
            100                 105                 110

Ser Ser
```

<210> SEQ ID NO 192
<211> LENGTH: 114
<212> TYPE: PRT
<213> ORGANISM: Artificial Sequence
<220> FEATURE:
<223> OTHER INFORMATION: synthetic construct heavy chain variable region

<400> SEQUENCE: 192

```
Gln Val Gln Leu Val Glu Ser Gly Gly Gly Val Val Gln Pro Gly Arg
```

```
                 1               5                  10                  15
Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ser Glu Asp Thr Ala Val Tyr Tyr Cys
                85                  90                  95

Val Pro Thr Thr Phe Glu Tyr Trp Gly Gln Gly Ser Gln Val Thr Val
            100                 105                 110

Ser Ser
```

<210> SEQ ID NO 193
<211> LENGTH: 114
<212> TYPE: PRT
<213> ORGANISM: Artificial Sequence
<220> FEATURE:
<223> OTHER INFORMATION: synthetic construct heavy chain variable region

<400> SEQUENCE: 193

```
Gln Val Gln Leu Val Glu Ser Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Met Leu Tyr
 65                 70                  75                  80

Leu Glu Met Asn Ser Leu Arg Ala Glu Asp Thr Ala Val Tyr Tyr Cys
                85                  90                  95

Val Pro Thr Thr Phe Glu Tyr Trp Gly Gln Gly Ser Gln Val Thr Val
            100                 105                 110

Ser Ser
```

<210> SEQ ID NO 194
<211> LENGTH: 23
<212> TYPE: DNA
<213> ORGANISM: Artificial Sequence
<220> FEATURE:
<223> OTHER INFORMATION: PD1-F primer

<400> SEQUENCE: 194
ccaggatggt tcttagactc ccc                                           23

<210> SEQ ID NO 195
<211> LENGTH: 20
<212> TYPE: DNA
<213> ORGANISM: Artificial Sequence
<220> FEATURE:
<223> OTHER INFORMATION: PD1-R primer

<400> SEQUENCE: 195
caccagggtt tggaactggc                                               20

<210> SEQ ID NO 196
<211> LENGTH: 232
<212> TYPE: PRT
<213> ORGANISM: Artificial Sequence
<220> FEATURE:
<223> OTHER INFORMATION: synthetic construct human Fc

<400> SEQUENCE: 196

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 197
<211> LENGTH: 233
<212> TYPE: PRT
<213> ORGANISM: Artificial Sequence
<220> FEATURE:
<223> OTHER INFORMATION: synthetic construct mouse Fc

<400> SEQUENCE: 197

```
Glu Pro Arg Gly Pro Thr Ile Lys Pro Cys Pro Pro Cys Lys Cys Pro
1               5                   10                  15

Ala Pro Asn Leu Leu Gly Gly Pro Ser Val Phe Ile Phe Pro Pro Lys
            20                  25                  30

Ile Lys Asp Val Leu Met Ile Ser Leu Ser Pro Ile Val Thr Cys Val
        35                  40                  45

Val Val Asp Val Ser Glu Asp Asp Pro Asp Val Gln Ile Ser Trp Phe
    50                  55                  60

Val Asn Asn Val Glu Val His Thr Ala Gln Thr Gln Thr His Arg Glu
65                  70                  75                  80
```

```
Asp Tyr Asn Ser Thr Leu Arg Val Val Ser Ala Leu Pro Ile Gln His
                85                  90                  95

Gln Asp Trp Met Ser Gly Lys Glu Phe Lys Cys Lys Val Asn Asn Lys
            100                 105                 110

Asp Leu Pro Ala Pro Ile Glu Arg Thr Ile Ser Lys Pro Lys Gly Ser
        115                 120                 125

Val Arg Ala Pro Gln Val Tyr Val Leu Pro Pro Glu Glu Glu Met
    130                 135                 140

Thr Lys Lys Gln Val Thr Leu Thr Cys Met Val Thr Asp Phe Met Pro
145                 150                 155                 160

Glu Asp Ile Tyr Val Glu Trp Thr Asn Asn Gly Lys Thr Glu Leu Asn
                165                 170                 175

Tyr Lys Asn Thr Glu Pro Val Leu Asp Ser Asp Gly Ser Tyr Phe Met
            180                 185                 190

Tyr Ser Lys Leu Arg Val Glu Lys Lys Asn Trp Val Glu Arg Asn Ser
        195                 200                 205

Tyr Ser Cys Ser Val Val His Glu Gly Leu His Asn His Thr Thr
    210                 215                 220

Lys Ser Phe Ser Arg Thr Pro Gly Lys
225                 230

<210> SEQ ID NO 198
<211> LENGTH: 6
<212> TYPE: PRT
<213> ORGANISM: Artificial Sequence
<220> FEATURE:
<223> OTHER INFORMATION: synthetic construct light chain CDR1

<400> SEQUENCE: 198

Arg Asp Ile Ser Arg Trp
1               5

<210> SEQ ID NO 199
<211> LENGTH: 5
<212> TYPE: PRT
<213> ORGANISM: Artificial Sequence
<220> FEATURE:
<223> OTHER INFORMATION: synthetic construct light chain CDR1

<400> SEQUENCE: 199

Gln Ser Leu Val His
1               5

<210> SEQ ID NO 200
<211> LENGTH: 6
<212> TYPE: PRT
<213> ORGANISM: Artificial Sequence
<220> FEATURE:
<223> OTHER INFORMATION: synthetic construct light chain CDR1

<400> SEQUENCE: 200

Gln Ala Ile Ser Asn Trp
1               5

<210> SEQ ID NO 201
<211> LENGTH: 6
<212> TYPE: PRT
<213> ORGANISM: Artificial Sequence
<220> FEATURE:
<223> OTHER INFORMATION: synthetic construct light chain CDR1

<400> SEQUENCE: 201
```

Ala Leu Ser Lys Gln Tyr
1               5

<210> SEQ ID NO 202
<211> LENGTH: 8
<212> TYPE: PRT
<213> ORGANISM: Artificial Sequence
<220> FEATURE:
<223> OTHER INFORMATION: synthetic construct light chain CDR1

<400> SEQUENCE: 202

Thr Ser Asn Ile Gly Thr Asn Ala
1               5

<210> SEQ ID NO 203
<211> LENGTH: 9
<212> TYPE: PRT
<213> ORGANISM: Artificial Sequence
<220> FEATURE:
<223> OTHER INFORMATION: synthetic construct light chain CDR1

<400> SEQUENCE: 203

Ser Ser Asn Ile Gly Ala Gly Tyr Asp
1               5

<210> SEQ ID NO 204
<211> LENGTH: 6
<212> TYPE: PRT
<213> ORGANISM: Artificial Sequence
<220> FEATURE:
<223> OTHER INFORMATION: synthetic construct light chain CDR1

<400> SEQUENCE: 204

Gln Gly Ile Val Ser Trp
1               5

<210> SEQ ID NO 205
<211> LENGTH: 12
<212> TYPE: PRT
<213> ORGANISM: Artificial Sequence
<220> FEATURE:
<223> OTHER INFORMATION: synthetic construct light chain CDR1

<400> SEQUENCE: 205

Gln Ser Leu Leu Asp Ser Glu Asp Gly Asn Thr Tyr
1               5                   10

<210> SEQ ID NO 206
<211> LENGTH: 6
<212> TYPE: PRT
<213> ORGANISM: Artificial Sequence
<220> FEATURE:
<223> OTHER INFORMATION: synthetic construct light chain CDR1

<400> SEQUENCE: 206

Gln Gly Ile Ser Ser Tyr
1               5

<210> SEQ ID NO 207
<211> LENGTH: 8
<212> TYPE: PRT
<213> ORGANISM: Artificial Sequence
<220> FEATURE:
<223> OTHER INFORMATION: synthetic construct light chain CDR1

<400> SEQUENCE: 207

Thr Phe Asn Ile Gly Thr Thr Thr
1               5

<210> SEQ ID NO 208
<211> LENGTH: 12
<212> TYPE: PRT
<213> ORGANISM: Artificial Sequence
<220> FEATURE:
<223> OTHER INFORMATION: synthetic construct light chain CDR1

<400> SEQUENCE: 208

Gln Ser Leu Leu Asp Ser Asp Asp Gly Lys Thr Tyr
1               5                   10

<210> SEQ ID NO 209
<211> LENGTH: 6
<212> TYPE: PRT
<213> ORGANISM: Artificial Sequence
<220> FEATURE:
<223> OTHER INFORMATION: synthetic construct light chain CDR1

<400> SEQUENCE: 209

Ser Leu Arg Thr Tyr Tyr
1               5

<210> SEQ ID NO 210
<211> LENGTH: 6
<212> TYPE: PRT
<213> ORGANISM: Artificial Sequence
<220> FEATURE:
<223> OTHER INFORMATION: synthetic construct light chain CDR1

<400> SEQUENCE: 210

Asn Leu Arg Thr Lys Tyr
1               5

<210> SEQ ID NO 211
<211> LENGTH: 9
<212> TYPE: PRT
<213> ORGANISM: Artificial Sequence
<220> FEATURE:
<223> OTHER INFORMATION: synthetic construct light chain CDR1

<400> SEQUENCE: 211

Ser Ser Asp Val Gly Gly Tyr Asn Tyr
1               5

<210> SEQ ID NO 212
<211> LENGTH: 9
<212> TYPE: PRT
<213> ORGANISM: Artificial Sequence
<220> FEATURE:
<223> OTHER INFORMATION: synthetic construct light chain CDR1

<400> SEQUENCE: 212

Arg Ser Asn Phe Gly Ala Gly His Asp
1               5

<210> SEQ ID NO 213
<211> LENGTH: 12
<212> TYPE: PRT
<213> ORGANISM: Artificial Sequence
<220> FEATURE:
<223> OTHER INFORMATION: synthetic construct light chain CDR1

<400> SEQUENCE: 213

Gln Ser Leu Leu Asp Ser His Asp Gly Asn Thr Tyr

<210> SEQ ID NO 214
<211> LENGTH: 8
<212> TYPE: PRT
<213> ORGANISM: Artificial Sequence
<220> FEATURE:
<223> OTHER INFORMATION: synthetic construct light chain CDR1

<400> SEQUENCE: 214

Ser Ser Asn Ile Gly Ile Asn Thr
1               5

<210> SEQ ID NO 215
<211> LENGTH: 12
<212> TYPE: PRT
<213> ORGANISM: Artificial Sequence
<220> FEATURE:
<223> OTHER INFORMATION: synthetic construct light chain CDR1

<400> SEQUENCE: 215

Gln Ser Leu Phe Asp Ser Asp Asp Gly Asn Thr Tyr
1               5                   10

<210> SEQ ID NO 216
<211> LENGTH: 11
<212> TYPE: PRT
<213> ORGANISM: Artificial Sequence
<220> FEATURE:
<223> OTHER INFORMATION: synthetic construct light chain CDR1

<400> SEQUENCE: 216

Gln Ser Leu Leu Tyr Ile Asp Gly Glu Thr Tyr
1               5                   10

<210> SEQ ID NO 217
<211> LENGTH: 11
<212> TYPE: PRT
<213> ORGANISM: Artificial Sequence
<220> FEATURE:
<223> OTHER INFORMATION: synthetic construct light chain CDR1

<400> SEQUENCE: 217

Gln Ser Leu Leu His Ser Asn Gly Asn Asn Tyr
1               5                   10

<210> SEQ ID NO 218
<211> LENGTH: 6
<212> TYPE: PRT
<213> ORGANISM: Artificial Sequence
<220> FEATURE:
<223> OTHER INFORMATION: synthetic construct light chain CDR1

<400> SEQUENCE: 218

Ala Leu Ser Lys Glu Tyr
1               5

<210> SEQ ID NO 219
<211> LENGTH: 6
<212> TYPE: PRT
<213> ORGANISM: Artificial Sequence
<220> FEATURE:
<223> OTHER INFORMATION: synthetic construct light chain CDR1

<400> SEQUENCE: 219

Gln Ser Val Thr Ser Asp
1               5

<210> SEQ ID NO 220
<211> LENGTH: 12
<212> TYPE: PRT
<213> ORGANISM: Artificial Sequence
<220> FEATURE:
<223> OTHER INFORMATION: synthetic construct light chain CDR1

<400> SEQUENCE: 220

Gln Ser Leu Leu Asp Ser Asp Gly Asn Thr Tyr
1               5                   10

<210> SEQ ID NO 221
<211> LENGTH: 12
<212> TYPE: PRT
<213> ORGANISM: Artificial Sequence
<220> FEATURE:
<223> OTHER INFORMATION: synthetic construct light chain CDR1

<400> SEQUENCE: 221

Gln Ser Leu Leu Asp Arg Asp Gly Gly His Thr Tyr
1               5                   10

<210> SEQ ID NO 222
<211> LENGTH: 12
<212> TYPE: PRT
<213> ORGANISM: Artificial Sequence
<220> FEATURE:
<223> OTHER INFORMATION: synthetic construct light chain CDR1

<400> SEQUENCE: 222

Gln Ser Leu Leu Asp Arg Gly Gly Gly His Thr Tyr
1               5                   10

<210> SEQ ID NO 223
<211> LENGTH: 9
<212> TYPE: PRT
<213> ORGANISM: Artificial Sequence
<220> FEATURE:
<223> OTHER INFORMATION: synthetic construct light chain CDR3

<400> SEQUENCE: 223

Gln Gln Gly Lys Ser Phe Pro Tyr Thr
1               5

<210> SEQ ID NO 224
<211> LENGTH: 9
<212> TYPE: PRT
<213> ORGANISM: Artificial Sequence
<220> FEATURE:
<223> OTHER INFORMATION: synthetic construct light chain CDR3

<400> SEQUENCE: 224

Met Gln Ser Thr Gln Phe Pro Tyr Thr
1               5

<210> SEQ ID NO 225
<211> LENGTH: 9
<212> TYPE: PRT
<213> ORGANISM: Artificial Sequence
<220> FEATURE:
<223> OTHER INFORMATION: synthetic construct light chain CDR3

<400> SEQUENCE: 225

Gln Gln Thr Asp Ser Phe Pro Leu Thr
1               5

```
<210> SEQ ID NO 226
<211> LENGTH: 12
<212> TYPE: PRT
<213> ORGANISM: Artificial Sequence
<220> FEATURE:
<223> OTHER INFORMATION: synthetic construct light chain CDR3

<400> SEQUENCE: 226

Gln Ser Ile Thr Asp Lys Ser Gly Thr Asp Val Ile
1               5                   10

<210> SEQ ID NO 227
<211> LENGTH: 11
<212> TYPE: PRT
<213> ORGANISM: Artificial Sequence
<220> FEATURE:
<223> OTHER INFORMATION: synthetic construct light chain CDR3

<400> SEQUENCE: 227

Ala Ala Trp Asp Asp Ser Leu Asn Gly Trp Val
1               5                   10

<210> SEQ ID NO 228
<211> LENGTH: 11
<212> TYPE: PRT
<213> ORGANISM: Artificial Sequence
<220> FEATURE:
<223> OTHER INFORMATION: synthetic construct light chain CDR3

<400> SEQUENCE: 228

Gln Ser Tyr Asp Ser Ser Leu Ser Gly Tyr Val
1               5                   10

<210> SEQ ID NO 229
<211> LENGTH: 9
<212> TYPE: PRT
<213> ORGANISM: Artificial Sequence
<220> FEATURE:
<223> OTHER INFORMATION: synthetic construct light chain CDR3

<400> SEQUENCE: 229

Gln Gln Ala Asp Ser Phe Pro Leu Thr
1               5

<210> SEQ ID NO 230
<211> LENGTH: 9
<212> TYPE: PRT
<213> ORGANISM: Artificial Sequence
<220> FEATURE:
<223> OTHER INFORMATION: synthetic construct light chain CDR3

<400> SEQUENCE: 230

Leu Gln Arg Met Gly Phe Pro Tyr Thr
1               5

<210> SEQ ID NO 231
<211> LENGTH: 9
<212> TYPE: PRT
<213> ORGANISM: Artificial Sequence
<220> FEATURE:
<223> OTHER INFORMATION: synthetic construct light chain CDR3

<400> SEQUENCE: 231

Gln Gln Ser Tyr Thr Ser Pro Arg Thr
1               5
```

```
<210> SEQ ID NO 232
<211> LENGTH: 11
<212> TYPE: PRT
<213> ORGANISM: Artificial Sequence
<220> FEATURE:
<223> OTHER INFORMATION: synthetic construct light chain CDR3

<400> SEQUENCE: 232

Ala Ala Trp Asp Asp Ser Leu Asn Ala Trp Leu
1               5                   10

<210> SEQ ID NO 233
<211> LENGTH: 9
<212> TYPE: PRT
<213> ORGANISM: Artificial Sequence
<220> FEATURE:
<223> OTHER INFORMATION: synthetic construct light chain CDR3

<400> SEQUENCE: 233

Met Gln Arg Val Glu Phe Pro Phe Thr
1               5

<210> SEQ ID NO 234
<211> LENGTH: 11
<212> TYPE: PRT
<213> ORGANISM: Artificial Sequence
<220> FEATURE:
<223> OTHER INFORMATION: synthetic construct light chain CDR3

<400> SEQUENCE: 234

Asn Ser Arg Asp Ser Ser Gly Lys Ser Leu Val
1               5                   10

<210> SEQ ID NO 235
<211> LENGTH: 11
<212> TYPE: PRT
<213> ORGANISM: Artificial Sequence
<220> FEATURE:
<223> OTHER INFORMATION: synthetic construct light chain CDR3

<400> SEQUENCE: 235

Met Thr Trp Asp Val Asp Thr Thr Ser Met Ile
1               5                   10

<210> SEQ ID NO 236
<211> LENGTH: 10
<212> TYPE: PRT
<213> ORGANISM: Artificial Sequence
<220> FEATURE:
<223> OTHER INFORMATION: synthetic construct light chain CDR3

<400> SEQUENCE: 236

Ser Ser Phe Thr Ser Ser Ser Thr Val Val
1               5                   10

<210> SEQ ID NO 237
<211> LENGTH: 11
<212> TYPE: PRT
<213> ORGANISM: Artificial Sequence
<220> FEATURE:
<223> OTHER INFORMATION: synthetic construct light chain CDR3

<400> SEQUENCE: 237

Gln Ser Tyr Asp Ser Ser Leu Ser Ala Trp Gly
1               5                   10

<210> SEQ ID NO 238
```

```
<211> LENGTH: 9
<212> TYPE: PRT
<213> ORGANISM: Artificial Sequence
<220> FEATURE:
<223> OTHER INFORMATION: synthetic construct light chain CDR3

<400> SEQUENCE: 238

Met Gln Arg Ile Asp Phe Pro Tyr Thr
1               5

<210> SEQ ID NO 239
<211> LENGTH: 11
<212> TYPE: PRT
<213> ORGANISM: Artificial Sequence
<220> FEATURE:
<223> OTHER INFORMATION: synthetic construct light chain CDR3

<400> SEQUENCE: 239

Ala Ser Trp Asp Asp Thr Leu Asn Gly Trp Val
1               5                   10

<210> SEQ ID NO 240
<211> LENGTH: 10
<212> TYPE: PRT
<213> ORGANISM: Artificial Sequence
<220> FEATURE:
<223> OTHER INFORMATION: synthetic construct light chain CDR3

<400> SEQUENCE: 240

Ser Ser Phe Ala Arg Asn Ser Asn Tyr Val
1               5                   10

<210> SEQ ID NO 241
<211> LENGTH: 9
<212> TYPE: PRT
<213> ORGANISM: Artificial Sequence
<220> FEATURE:
<223> OTHER INFORMATION: synthetic construct light chain CDR3

<400> SEQUENCE: 241

Met Gln Gly Ile His Leu Pro Leu Thr
1               5

<210> SEQ ID NO 242
<211> LENGTH: 9
<212> TYPE: PRT
<213> ORGANISM: Artificial Sequence
<220> FEATURE:
<223> OTHER INFORMATION: synthetic construct light chain CDR3

<400> SEQUENCE: 242

Met Gln Gly Leu Gln Ile Pro Ser Thr
1               5

<210> SEQ ID NO 243
<211> LENGTH: 11
<212> TYPE: PRT
<213> ORGANISM: Artificial Sequence
<220> FEATURE:
<223> OTHER INFORMATION: synthetic construct light chain CDR3

<400> SEQUENCE: 243

Gln Ser Val Asp Ser Ser Asp Thr Ser Val Val
1               5                   10

<210> SEQ ID NO 244
<211> LENGTH: 9
```

```
<212> TYPE: PRT
<213> ORGANISM: Artificial Sequence
<220> FEATURE:
<223> OTHER INFORMATION: synthetic construct light chain CDR3

<400> SEQUENCE: 244

Gln Gln Tyr Asn Asn Trp Pro Leu Thr
1               5

<210> SEQ ID NO 245
<211> LENGTH: 9
<212> TYPE: PRT
<213> ORGANISM: Artificial Sequence
<220> FEATURE:
<223> OTHER INFORMATION: synthetic construct light chain CDR3

<400> SEQUENCE: 245

Met Gln Arg Ile Glu Phe Pro Tyr Thr
1               5

<210> SEQ ID NO 246
<211> LENGTH: 9
<212> TYPE: PRT
<213> ORGANISM: Artificial Sequence
<220> FEATURE:
<223> OTHER INFORMATION: synthetic construct light chain CDR3

<400> SEQUENCE: 246

Met Gln Arg Val Glu Phe Pro Tyr Thr
1               5

<210> SEQ ID NO 247
<211> LENGTH: 9
<212> TYPE: PRT
<213> ORGANISM: Artificial Sequence
<220> FEATURE:
<223> OTHER INFORMATION: synthetic construct light chain CDR3

<400> SEQUENCE: 247

Met Gln Arg Ile Glu Phe Pro Phe Thr
1               5

<210> SEQ ID NO 248
<211> LENGTH: 9
<212> TYPE: PRT
<213> ORGANISM: Artificial Sequence
<220> FEATURE:
<223> OTHER INFORMATION: synthetic construct light chain CDR3

<400> SEQUENCE: 248

Met Gln Arg Arg Asp Phe Pro Phe Thr
1               5

<210> SEQ ID NO 249
<211> LENGTH: 9
<212> TYPE: PRT
<213> ORGANISM: Artificial Sequence
<220> FEATURE:
<223> OTHER INFORMATION: synthetic construct light chain CDR3

<400> SEQUENCE: 249

Met Gln Arg Lys Glu Phe Pro Leu Thr
1               5

<210> SEQ ID NO 250
<211> LENGTH: 9
<212> TYPE: PRT
```

```
<213> ORGANISM: Artificial Sequence
<220> FEATURE:
<223> OTHER INFORMATION: synthetic construct light chain CDR3

<400> SEQUENCE: 250

Met Gln Arg Ile His Phe Pro Leu Thr
1               5

<210> SEQ ID NO 251
<211> LENGTH: 26
<212> TYPE: PRT
<213> ORGANISM: Artificial Sequence
<220> FEATURE:
<223> OTHER INFORMATION: synthetic construct light chain variable region
      FR1

<400> SEQUENCE: 251

Asp Ile Gln Met Thr Gln Ser Pro Ser Ser Val Ser Ala Ser Val Gly
1               5                   10                  15

Asp Arg Val Thr Ile Thr Cys Arg Ala Ser
            20                  25

<210> SEQ ID NO 252
<211> LENGTH: 26
<212> TYPE: PRT
<213> ORGANISM: Artificial Sequence
<220> FEATURE:
<223> OTHER INFORMATION: synthetic construct light chain variable region
      FR1

<400> SEQUENCE: 252

Asp Ile Val Met Thr Gln Thr Pro Leu Ser Ser Pro Val Thr Leu Gly
1               5                   10                  15

Gln Pro Ala Ser Ile Ser Cys Arg Ser Ser
            20                  25

<210> SEQ ID NO 253
<211> LENGTH: 26
<212> TYPE: PRT
<213> ORGANISM: Artificial Sequence
<220> FEATURE:
<223> OTHER INFORMATION: synthetic construct light chain variable region
      FR1

<400> SEQUENCE: 253

Asp Ile Gln Met Thr Gln Ser Pro Ser Ser Val Ser Ala Ser Leu Gly
1               5                   10                  15

Asp Arg Val Thr Ile Thr Cys Arg Ala Ser
            20                  25

<210> SEQ ID NO 254
<211> LENGTH: 25
<212> TYPE: PRT
<213> ORGANISM: Artificial Sequence
<220> FEATURE:
<223> OTHER INFORMATION: synthetic construct light chain variable region
      FR1

<400> SEQUENCE: 254

Ser Tyr Glu Leu Thr Gln Ser Pro Ser Val Ser Met Ser Pro Gly Gln
1               5                   10                  15

Thr Ala Arg Ile Thr Cys Ser Gly Asp
            20                  25

<210> SEQ ID NO 255
```

```
<211> LENGTH: 25
<212> TYPE: PRT
<213> ORGANISM: Artificial Sequence
<220> FEATURE:
<223> OTHER INFORMATION: synthetic construct light chain variable region
      FR1

<400> SEQUENCE: 255

Gln Leu Val Leu Thr Gln Pro Ser Ser Met Ser Glu Ala Pro Gly Gln
1               5                   10                  15

Arg Val Thr Ile Ser Cys Ser Gly Gly
            20                  25

<210> SEQ ID NO 256
<211> LENGTH: 25
<212> TYPE: PRT
<213> ORGANISM: Artificial Sequence
<220> FEATURE:
<223> OTHER INFORMATION: synthetic construct light chain variable region
      FR1

<400> SEQUENCE: 256

Gln Phe Val Leu Thr Gln Pro Pro Ser Val Ser Gly Ala Pro Gly Gln
1               5                   10                  15

Arg Val Ile Ile Ser Cys Thr Gly Ser
            20                  25

<210> SEQ ID NO 257
<211> LENGTH: 26
<212> TYPE: PRT
<213> ORGANISM: Artificial Sequence
<220> FEATURE:
<223> OTHER INFORMATION: synthetic construct light chain variable region
      FR1

<400> SEQUENCE: 257

Asp Ile Val Met Thr Gln Thr Pro Leu Ser Leu Pro Val Thr Pro Gly
1               5                   10                  15

Glu Ala Ala Ser Ile Ser Cys Arg Ser Ser
            20                  25

<210> SEQ ID NO 258
<211> LENGTH: 26
<212> TYPE: PRT
<213> ORGANISM: Artificial Sequence
<220> FEATURE:
<223> OTHER INFORMATION: synthetic construct light chain variable region
      FR1

<400> SEQUENCE: 258

Asp Ile Gln Met Thr Gln Ser Pro Ser Ser Leu Ser Ala Ser Val Gly
1               5                   10                  15

Asp Arg Val Thr Thr Thr Cys Arg Ala Ser
            20                  25

<210> SEQ ID NO 259
<211> LENGTH: 25
<212> TYPE: PRT
<213> ORGANISM: Artificial Sequence
<220> FEATURE:
<223> OTHER INFORMATION: synthetic construct light chain variable region
      FR1

<400> SEQUENCE: 259

Gln Phe Val Leu Thr Gln Ser Pro Ser Ala Ser Gly Thr Pro Gly Gln
1               5                   10                  15
```

Asn Ile Val Ile Ser Cys Ser Ala Ser
            20                  25

<210> SEQ ID NO 260
<211> LENGTH: 25
<212> TYPE: PRT
<213> ORGANISM: Artificial Sequence
<220> FEATURE:
<223> OTHER INFORMATION: synthetic construct light chain variable region
      FR1

<400> SEQUENCE: 260

Ser Tyr Glu Leu Thr Gln Asp Pro Ala Val Ser Val Ala Leu Gly Gln
1               5                   10                  15

Thr Val Arg Ile Thr Cys Gln Gly Asp
            20                  25

<210> SEQ ID NO 261
<211> LENGTH: 25
<212> TYPE: PRT
<213> ORGANISM: Artificial Sequence
<220> FEATURE:
<223> OTHER INFORMATION: synthetic construct light chain variable region
      FR1

<400> SEQUENCE: 261

Ser Tyr Glu Leu Thr Gln Ala Pro Ser Leu Ser Val Ser Pro Gly Gln
1               5                   10                  15

Thr Ala Asn Ile Ile Cys Ser Gly Asp
            20                  25

<210> SEQ ID NO 262
<211> LENGTH: 25
<212> TYPE: PRT
<213> ORGANISM: Artificial Sequence
<220> FEATURE:
<223> OTHER INFORMATION: synthetic construct light chain variable region
      FR1

<400> SEQUENCE: 262

Gln Ser Ala Leu Thr Gln Pro Ala Ser Val Ser Gly Ser Pro Gly Gln
1               5                   10                  15

Ser Ile Thr Ile Ser Cys Thr Gly Thr
            20                  25

<210> SEQ ID NO 263
<211> LENGTH: 25
<212> TYPE: PRT
<213> ORGANISM: Artificial Sequence
<220> FEATURE:
<223> OTHER INFORMATION: synthetic construct light chain variable region
      FR1

<400> SEQUENCE: 263

Gln Phe Val Leu Thr Gln Pro Pro Ser Val Ser Gly Ala Pro Gly Gln
1               5                   10                  15

Arg Val Thr Ile Ser Cys Thr Gly Ser
            20                  25

<210> SEQ ID NO 264
<211> LENGTH: 26
<212> TYPE: PRT
<213> ORGANISM: Artificial Sequence
<220> FEATURE:
<223> OTHER INFORMATION: synthetic construct light chain variable region

```
                        FR1

<400> SEQUENCE: 264

Asp Ile Val Met Thr Gln Thr Pro Leu Ser Leu Pro Val Thr Pro Gly
1               5                   10                  15

Glu Pro Ala Ser Ile Ser Cys Arg Ser Ser
            20                  25

<210> SEQ ID NO 265
<211> LENGTH: 25
<212> TYPE: PRT
<213> ORGANISM: Artificial Sequence
<220> FEATURE:
<223> OTHER INFORMATION: synthetic construct light chain variable region
      FR1

<400> SEQUENCE: 265

Asn Phe Met Leu Thr Gln Pro Pro Ser Thr Ser Gly Thr Pro Gly Gln
1               5                   10                  15

Arg Val Thr Ile Ser Cys Ser Gly Arg
            20                  25

<210> SEQ ID NO 266
<211> LENGTH: 26
<212> TYPE: PRT
<213> ORGANISM: Artificial Sequence
<220> FEATURE:
<223> OTHER INFORMATION: synthetic construct light chain variable region
      FR1

<400> SEQUENCE: 266

Asp Ile Val Met Thr Gln Ser Pro Leu Ser Leu Pro Val Thr Pro Gly
1               5                   10                  15

Glu Pro Ala Ser Ile Ser Cys Arg Ser Ser
            20                  25

<210> SEQ ID NO 267
<211> LENGTH: 25
<212> TYPE: PRT
<213> ORGANISM: Artificial Sequence
<220> FEATURE:
<223> OTHER INFORMATION: synthetic construct light chain variable region
      FR1

<400> SEQUENCE: 267

Gln Ser Ala Leu Thr Gln Pro Pro Ser Ala Ser Gly Ser Pro Gly Gln
1               5                   10                  15

Ser Val Thr Ile Ser Cys Thr Gly Thr
            20                  25

<210> SEQ ID NO 268
<211> LENGTH: 26
<212> TYPE: PRT
<213> ORGANISM: Artificial Sequence
<220> FEATURE:
<223> OTHER INFORMATION: synthetic construct light chain variable region
      FR1

<400> SEQUENCE: 268

Asp Ile Val Met Thr Gln Thr Pro Leu Ser Leu Ser Val Thr Pro Gly
1               5                   10                  15

Gln Pro Ala Ser Ile Ser Cys Lys Ser Ser
            20                  25
```

```
<210> SEQ ID NO 269
<211> LENGTH: 25
<212> TYPE: PRT
<213> ORGANISM: Artificial Sequence
<220> FEATURE:
<223> OTHER INFORMATION: synthetic construct light chain variable region
      FR1

<400> SEQUENCE: 269

Ser Tyr Glu Leu Thr Gln Pro Leu Ser Leu Ser Val Ala Pro Gly Gln
1               5                   10                  15

Thr Ala Arg Ile Thr Cys Ser Gly Asp
            20                  25

<210> SEQ ID NO 270
<211> LENGTH: 26
<212> TYPE: PRT
<213> ORGANISM: Artificial Sequence
<220> FEATURE:
<223> OTHER INFORMATION: synthetic construct light chain variable region
      FR1

<400> SEQUENCE: 270

Asp Ile Gln Met Thr Gln Ser Pro Ala Ile Leu Ser Leu Ser Pro Gly
1               5                   10                  15

Glu Arg Ala Thr Leu Ser Cys Arg Ala Ser
            20                  25

<210> SEQ ID NO 271
<211> LENGTH: 26
<212> TYPE: PRT
<213> ORGANISM: Artificial Sequence
<220> FEATURE:
<223> OTHER INFORMATION: synthetic construct light chain variable region
      FR1

<400> SEQUENCE: 271

Asp Ile Val Met Thr Gln Thr Pro His Ser Leu Pro Val Thr Pro Gly
1               5                   10                  15

Glu Pro Ala Ser Ile Ser Cys Arg Ser Ser
            20                  25

<210> SEQ ID NO 272
<211> LENGTH: 26
<212> TYPE: PRT
<213> ORGANISM: Artificial Sequence
<220> FEATURE:
<223> OTHER INFORMATION: synthetic construct light chain variable region
      FR1

<400> SEQUENCE: 272

Asp Ile Val Met Thr Gln Ser Pro Leu Ser Leu Pro Val Thr Pro Gly
1               5                   10                  15

Glu Ala Ala Ser Ile Ser Cys Arg Ser Ser
            20                  25

<210> SEQ ID NO 273
<211> LENGTH: 26
<212> TYPE: PRT
<213> ORGANISM: Artificial Sequence
<220> FEATURE:
<223> OTHER INFORMATION: synthetic construct light chain variable region
      FR1

<400> SEQUENCE: 273

Asp Ile Val Met Thr Gln Thr Pro Leu Ser Pro Pro Val Thr Pro Gly
```

```
1               5                   10                  15
Glu Pro Ala Ser Ile Ser Cys Arg Ser Ser
            20                  25

<210> SEQ ID NO 274
<211> LENGTH: 26
<212> TYPE: PRT
<213> ORGANISM: Artificial Sequence
<220> FEATURE:
<223> OTHER INFORMATION: synthetic construct light chain variable region
      FR1

<400> SEQUENCE: 274

Asp Ile Val Met Thr Gln Thr Pro Leu Ser Leu Pro Val Met Pro Gly
1               5                   10                  15
Glu Ala Ala Ser Ile Ser Cys Arg Ser Ser
            20                  25

<210> SEQ ID NO 275
<211> LENGTH: 26
<212> TYPE: PRT
<213> ORGANISM: Artificial Sequence
<220> FEATURE:
<223> OTHER INFORMATION: synthetic construct light chain variable region
      FR1

<400> SEQUENCE: 275

Asp Ile Val Met Thr Gln Thr Pro Leu Ser Leu Ser Val Thr Pro Gly
1               5                   10                  15
Glu Pro Ala Ser Ile Ser Cys Arg Ser Ser
            20                  25

<210> SEQ ID NO 276
<211> LENGTH: 17
<212> TYPE: PRT
<213> ORGANISM: Artificial Sequence
<220> FEATURE:
<223> OTHER INFORMATION: synthetic construct light chain variable region
      FR2

<400> SEQUENCE: 276

Leu Ala Trp Tyr Gln Gln Lys Pro Gly Glu Ala Pro Lys Leu Leu Ile
1               5                   10                  15
Tyr

<210> SEQ ID NO 277
<211> LENGTH: 17
<212> TYPE: PRT
<213> ORGANISM: Artificial Sequence
<220> FEATURE:
<223> OTHER INFORMATION: synthetic construct light chain variable region
      FR2

<400> SEQUENCE: 277

Leu Asn Trp Phe His Gln Arg Pro Gly Gln Pro Pro Arg Leu Leu Ile
1               5                   10                  15
His

<210> SEQ ID NO 278
<211> LENGTH: 17
<212> TYPE: PRT
<213> ORGANISM: Artificial Sequence
<220> FEATURE:
<223> OTHER INFORMATION: synthetic construct light chain variable region
      FR2
```

```
<400> SEQUENCE: 278

Leu Thr Trp Tyr Gln Gln Lys Pro Gly Lys Ala Pro Lys Leu Leu Ile
1               5                   10                  15

Tyr

<210> SEQ ID NO 279
<211> LENGTH: 17
<212> TYPE: PRT
<213> ORGANISM: Artificial Sequence
<220> FEATURE:
<223> OTHER INFORMATION: synthetic construct light chain variable region
      FR2

<400> SEQUENCE: 279

Ala Ser Trp Tyr Gln Leu Lys Pro Gly Gln Ala Pro Val Val Val Met
1               5                   10                  15

Tyr

<210> SEQ ID NO 280
<211> LENGTH: 17
<212> TYPE: PRT
<213> ORGANISM: Artificial Sequence
<220> FEATURE:
<223> OTHER INFORMATION: synthetic construct light chain variable region
      FR2

<400> SEQUENCE: 280

Val Asn Trp Tyr Gln Gln Pro Pro Gly Lys Ala Pro Thr Leu Leu Ile
1               5                   10                  15

Tyr

<210> SEQ ID NO 281
<211> LENGTH: 17
<212> TYPE: PRT
<213> ORGANISM: Artificial Sequence
<220> FEATURE:
<223> OTHER INFORMATION: synthetic construct light chain variable region
      FR2

<400> SEQUENCE: 281

Val His Trp Tyr Gln Gln Leu Pro Gly Thr Ala Pro Lys Val Leu Ile
1               5                   10                  15

Tyr

<210> SEQ ID NO 282
<211> LENGTH: 17
<212> TYPE: PRT
<213> ORGANISM: Artificial Sequence
<220> FEATURE:
<223> OTHER INFORMATION: synthetic construct light chain variable region
      FR2

<400> SEQUENCE: 282

Leu Ala Trp Tyr Gln Gln Lys Pro Gly Lys Ala Pro Arg Leu Leu Ile
1               5                   10                  15

Tyr

<210> SEQ ID NO 283
<211> LENGTH: 17
<212> TYPE: PRT
<213> ORGANISM: Artificial Sequence
<220> FEATURE:
<223> OTHER INFORMATION: synthetic construct light chain variable region
```

```
            FR2

<400> SEQUENCE: 283

Leu Asp Trp Tyr Leu Gln Lys Pro Gly Gln Ser Pro Gln Leu Leu Ile
1               5                   10                  15

Tyr

<210> SEQ ID NO 284
<211> LENGTH: 17
<212> TYPE: PRT
<213> ORGANISM: Artificial Sequence
<220> FEATURE:
<223> OTHER INFORMATION: synthetic construct light chain variable region
      FR2

<400> SEQUENCE: 284

Leu Ala Trp Tyr Gln Gln Lys Pro Gly Lys Ala Pro Lys Leu Leu Ile
1               5                   10                  15

Tyr

<210> SEQ ID NO 285
<211> LENGTH: 17
<212> TYPE: PRT
<213> ORGANISM: Artificial Sequence
<220> FEATURE:
<223> OTHER INFORMATION: synthetic construct light chain variable region
      FR2

<400> SEQUENCE: 285

Val Asn Trp Tyr Gln Arg Leu Pro Gly Thr Ala Pro Lys Leu Leu Ile
1               5                   10                  15

Tyr

<210> SEQ ID NO 286
<211> LENGTH: 17
<212> TYPE: PRT
<213> ORGANISM: Artificial Sequence
<220> FEATURE:
<223> OTHER INFORMATION: synthetic construct light chain variable region
      FR2

<400> SEQUENCE: 286

Ala Ser Trp Tyr Gln Gln Lys Pro Gly Gln Ala Pro Ile Leu Val Ile
1               5                   10                  15

Tyr

<210> SEQ ID NO 287
<211> LENGTH: 17
<212> TYPE: PRT
<213> ORGANISM: Artificial Sequence
<220> FEATURE:
<223> OTHER INFORMATION: synthetic construct light chain variable region
      FR2

<400> SEQUENCE: 287

Val Ser Trp Tyr Gln Gln Lys Pro Gly Gln Ser Pro Leu Leu Val Ile
1               5                   10                  15

Tyr

<210> SEQ ID NO 288
<211> LENGTH: 17
<212> TYPE: PRT
<213> ORGANISM: Artificial Sequence
<220> FEATURE:
```

<223> OTHER INFORMATION: synthetic construct light chain variable region
      FR2

<400> SEQUENCE: 288

Val Ser Trp Tyr Gln Gln His Pro Gly Lys Ala Pro Lys Leu Met Ile
1               5                   10                  15
Tyr

<210> SEQ ID NO 289
<211> LENGTH: 17
<212> TYPE: PRT
<213> ORGANISM: Artificial Sequence
<220> FEATURE:
<223> OTHER INFORMATION: synthetic construct light chain variable region
      FR2

<400> SEQUENCE: 289

Val His Trp Cys Gln Gln Leu Pro Gly Thr Ala Pro Lys Leu Leu Ile
1               5                   10                  15
Tyr

<210> SEQ ID NO 290
<211> LENGTH: 17
<212> TYPE: PRT
<213> ORGANISM: Artificial Sequence
<220> FEATURE:
<223> OTHER INFORMATION: synthetic construct light chain variable region
      FR2

<400> SEQUENCE: 290

Val Thr Trp Tyr Gln Gln Leu Pro Gly Thr Ala Pro Lys Val Leu Met
1               5                   10                  15
Tyr

<210> SEQ ID NO 291
<211> LENGTH: 17
<212> TYPE: PRT
<213> ORGANISM: Artificial Sequence
<220> FEATURE:
<223> OTHER INFORMATION: synthetic construct light chain variable region
      FR2

<400> SEQUENCE: 291

Leu Phe Trp Tyr Leu Gln Lys Pro Gly Gln Ser Pro Gln Leu Leu Ile
1               5                   10                  15
Tyr

<210> SEQ ID NO 292
<211> LENGTH: 17
<212> TYPE: PRT
<213> ORGANISM: Artificial Sequence
<220> FEATURE:
<223> OTHER INFORMATION: synthetic construct light chain variable region
      FR2

<400> SEQUENCE: 292

Ser Tyr Trp Tyr Gln Gln Lys Pro Gly Gln Ala Pro Val Leu Val Met
1               5                   10                  15
Tyr

<210> SEQ ID NO 293
<211> LENGTH: 17
<212> TYPE: PRT
<213> ORGANISM: Artificial Sequence

```
<220> FEATURE:
<223> OTHER INFORMATION: synthetic construct light chain variable region
      FR2

<400> SEQUENCE: 293

Val Ala Trp Tyr Gln His Ile Arg Gly Gln Ala Pro Arg Leu Leu Ile
1               5                   10                  15

Tyr

<210> SEQ ID NO 294
<211> LENGTH: 17
<212> TYPE: PRT
<213> ORGANISM: Artificial Sequence
<220> FEATURE:
<223> OTHER INFORMATION: synthetic construct light chain variable region
      FR2

<400> SEQUENCE: 294

Val Asp Trp Tyr Leu Gln Lys Pro Gly Gln Ser Pro Arg Leu Leu Ile
1               5                   10                  15

Tyr

<210> SEQ ID NO 295
<211> LENGTH: 17
<212> TYPE: PRT
<213> ORGANISM: Artificial Sequence
<220> FEATURE:
<223> OTHER INFORMATION: synthetic construct light chain variable region
      FR2

<400> SEQUENCE: 295

Leu Asp Trp Tyr Leu Gln Arg Pro Gly Gln Ser Pro Gln Leu Leu Ile
1               5                   10                  15

Tyr

<210> SEQ ID NO 296
<211> LENGTH: 17
<212> TYPE: PRT
<213> ORGANISM: Artificial Sequence
<220> FEATURE:
<223> OTHER INFORMATION: synthetic construct light chain variable region
      FR2

<400> SEQUENCE: 296

Leu Asp Trp Tyr Leu Gln Lys Pro Gly Gln Ser Pro Arg Leu Leu Ile
1               5                   10                  15

Tyr

<210> SEQ ID NO 297
<211> LENGTH: 36
<212> TYPE: PRT
<213> ORGANISM: Artificial Sequence
<220> FEATURE:
<223> OTHER INFORMATION: synthetic construct light chain variable region
      FR3

<400> SEQUENCE: 297

Ser Leu Arg Ser Gly Val Ser Ser Arg Phe Ser Gly Ser Gly Ser Gly
1               5                   10                  15

Thr Asp Phe Thr Leu Thr Ile Ser Ser Leu Gln Pro Glu Asp Phe Ala
                20                  25                  30

Thr Tyr Phe Cys
            35
```

```
<210> SEQ ID NO 298
<211> LENGTH: 36
<212> TYPE: PRT
<213> ORGANISM: Artificial Sequence
<220> FEATURE:
<223> OTHER INFORMATION: synthetic construct light chain variable region
      FR3

<400> SEQUENCE: 298

Asn Arg Val Ser Gly Val Pro Asp Arg Phe Ser Gly Ser Gly Ala Gly
1               5                   10                  15

Thr Asp Phe Thr Leu Lys Ile Ser Arg Val Glu Ala Glu Asp Val Gly
            20                  25                  30

Val Tyr Tyr Cys
            35

<210> SEQ ID NO 299
<211> LENGTH: 36
<212> TYPE: PRT
<213> ORGANISM: Artificial Sequence
<220> FEATURE:
<223> OTHER INFORMATION: synthetic construct light chain variable region
      FR3

<400> SEQUENCE: 299

Ser Leu Gln Ser Gly Val Pro Ser Arg Phe Ser Gly Ser Gly Ser Gly
1               5                   10                  15

Thr Asp Phe Thr Leu Thr Ile Ser Ser Leu Gln Pro Glu Asp Val Ala
            20                  25                  30

Thr Tyr Tyr Cys
            35

<210> SEQ ID NO 300
<211> LENGTH: 36
<212> TYPE: PRT
<213> ORGANISM: Artificial Sequence
<220> FEATURE:
<223> OTHER INFORMATION: synthetic construct light chain variable region
      FR3

<400> SEQUENCE: 300

Glu Arg Pro Ser Gly Ile Pro Asp Arg Phe Ser Gly Ser Ser Ser Gly
1               5                   10                  15

Thr Thr Val Thr Leu Thr Ile Ser Gly Val Gln Ala Glu Asp Gly Ala
            20                  25                  30

Asp Tyr Tyr Cys
            35

<210> SEQ ID NO 301
<211> LENGTH: 36
<212> TYPE: PRT
<213> ORGANISM: Artificial Sequence
<220> FEATURE:
<223> OTHER INFORMATION: synthetic construct light chain variable region
      FR3

<400> SEQUENCE: 301

Arg Leu Thr Ser Gly Val Ser Asp Arg Phe Ser Gly Ser Lys Ser Gly
1               5                   10                  15

Thr Ser Ala Ser Leu Ala Ile Ser Arg Leu Gln Ser Glu Asp Glu Ala
            20                  25                  30

Asp Tyr Tyr Cys
            35
```

```
<210> SEQ ID NO 302
<211> LENGTH: 36
<212> TYPE: PRT
<213> ORGANISM: Artificial Sequence
<220> FEATURE:
<223> OTHER INFORMATION: synthetic construct light chain variable region
      FR3

<400> SEQUENCE: 302

Asp Arg Pro Ser Gly Val Pro Asp Arg Phe Ser Ala Ser Lys Ser Ala
1               5                   10                  15

Thr Ser Ala Ser Leu Ala Ile Thr Gly Leu Gln Ala Glu Asp Glu Ala
            20                  25                  30

Asp Tyr Tyr Cys
        35

<210> SEQ ID NO 303
<211> LENGTH: 36
<212> TYPE: PRT
<213> ORGANISM: Artificial Sequence
<220> FEATURE:
<223> OTHER INFORMATION: synthetic construct light chain variable region
      FR3

<400> SEQUENCE: 303

Asp Leu Glu Thr Gly Val Pro Ser Arg Phe Ser Gly Ser Gly Ser Gly
1               5                   10                  15

Thr Asp Phe Thr Leu Thr Ile Ser Ser Leu Gln Pro Glu Asp Val Ala
            20                  25                  30

Thr Tyr Tyr Cys
        35

<210> SEQ ID NO 304
<211> LENGTH: 36
<212> TYPE: PRT
<213> ORGANISM: Artificial Sequence
<220> FEATURE:
<223> OTHER INFORMATION: synthetic construct light chain variable region
      FR3

<400> SEQUENCE: 304

His Arg Ala Ser Gly Val Pro Asp Arg Phe Ser Gly Ser Gly Ser Gly
1               5                   10                  15

Thr Asp Phe Thr Leu Lys Ile Ser Arg Val Ala Ala Glu Asp Val Gly
            20                  25                  30

Leu Tyr Tyr Cys
        35

<210> SEQ ID NO 305
<211> LENGTH: 36
<212> TYPE: PRT
<213> ORGANISM: Artificial Sequence
<220> FEATURE:
<223> OTHER INFORMATION: synthetic construct light chain variable region
      FR3

<400> SEQUENCE: 305

Thr Leu Gln Ser Gly Val Pro Ser Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Phe Cys
```

```
<210> SEQ ID NO 306
<211> LENGTH: 36
<212> TYPE: PRT
<213> ORGANISM: Artificial Sequence
<220> FEATURE:
<223> OTHER INFORMATION: synthetic construct light chain variable region
      FR3

<400> SEQUENCE: 306

Gln Arg Pro Ser Gly Val Pro Asp Arg Phe Ser Gly Ser Lys Ser Gly
1               5                   10                  15

Thr Ser Ala Ser Leu Ala Ile Ser Gly Leu Gln Ser Glu Asp Glu Ala
            20                  25                  30

Asp Tyr Tyr Cys
        35

<210> SEQ ID NO 307
<211> LENGTH: 36
<212> TYPE: PRT
<213> ORGANISM: Artificial Sequence
<220> FEATURE:
<223> OTHER INFORMATION: synthetic construct light chain variable region
      FR3

<400> SEQUENCE: 307

Tyr Arg Ala Ser Gly Val Pro Asp Arg Phe Ser Gly Ser Gly Ser Gly
1               5                   10                  15

Thr Glu Phe Asn Leu Arg Ile Ser Arg Val Glu Ala Glu Asp Val Gly
            20                  25                  30

Ile Tyr Tyr Cys
        35

<210> SEQ ID NO 308
<211> LENGTH: 36
<212> TYPE: PRT
<213> ORGANISM: Artificial Sequence
<220> FEATURE:
<223> OTHER INFORMATION: synthetic construct light chain variable region
      FR3

<400> SEQUENCE: 308

Asn Arg Pro Ser Gly Ile Pro Asp Arg Phe Ser Gly Ser Ser Ser Gly
1               5                   10                  15

Asn Thr Ala Ser Leu Thr Ile Thr Ala Ala Gln Ala Glu Asp Glu Ala
            20                  25                  30

Asp Tyr Tyr Cys
        35

<210> SEQ ID NO 309
<211> LENGTH: 36
<212> TYPE: PRT
<213> ORGANISM: Artificial Sequence
<220> FEATURE:
<223> OTHER INFORMATION: synthetic construct light chain variable region
      FR3

<400> SEQUENCE: 309

Arg Arg Pro Ser Gly Ile Pro Ala Arg Phe Ser Gly Ser Asn Ser Gly
1               5                   10                  15

Asn Thr Ala Thr Leu Thr Ile Ser Gly Thr Gln Thr Arg Asp Glu Ser
            20                  25                  30
```

Thr Tyr Tyr Cys
        35

<210> SEQ ID NO 310
<211> LENGTH: 36
<212> TYPE: PRT
<213> ORGANISM: Artificial Sequence
<220> FEATURE:
<223> OTHER INFORMATION: synthetic construct light chain variable region
      FR3

<400> SEQUENCE: 310

Lys Arg Pro Ser Gly Val Ser Asn Arg Phe Ser Gly Ser Lys Ser Gly
1               5                   10                  15

Asn Thr Ala Ser Leu Thr Ile Ser Gly Leu Gln Ala Glu Asp Glu Ala
            20                  25                  30

Asp Tyr Tyr Cys
        35

<210> SEQ ID NO 311
<211> LENGTH: 36
<212> TYPE: PRT
<213> ORGANISM: Artificial Sequence
<220> FEATURE:
<223> OTHER INFORMATION: synthetic construct light chain variable region
      FR3

<400> SEQUENCE: 311

Asn Arg Pro Ser Gly Val Pro Asp Arg Phe Ser Gly Ser Lys Ser Gly
1               5                   10                  15

Thr Ser Ala Ser Leu Ala Ile Thr Gly Leu Gln Ala Glu Asp Glu Ala
            20                  25                  30

Glu Tyr Tyr Cys
        35

<210> SEQ ID NO 312
<211> LENGTH: 36
<212> TYPE: PRT
<213> ORGANISM: Artificial Sequence
<220> FEATURE:
<223> OTHER INFORMATION: synthetic construct light chain variable region
      FR3

<400> SEQUENCE: 312

His Arg Ala Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Val Gly
            20                  25                  30

Leu Tyr Tyr Cys
        35

<210> SEQ ID NO 313
<211> LENGTH: 36
<212> TYPE: PRT
<213> ORGANISM: Artificial Sequence
<220> FEATURE:
<223> OTHER INFORMATION: synthetic construct light chain variable region
      FR3

<400> SEQUENCE: 313

Gln Arg Pro Ser Gly Val Pro Asp Arg Phe Ser Gly Ser Arg Ser Gly
1               5                   10                  15

Ile Ser Ala Ser Leu Ala Ile Ser Gly Leu Gln Ser Glu Asp Glu Ala
            20                  25                  30

Asp Tyr Tyr Cys
        35

<210> SEQ ID NO 314
<211> LENGTH: 36
<212> TYPE: PRT
<213> ORGANISM: Artificial Sequence
<220> FEATURE:
<223> OTHER INFORMATION: synthetic construct light chain variable region
      FR3

<400> SEQUENCE: 314

His Arg Ala Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Val Gly
            20                  25                  30

Ile Tyr Tyr Cys
        35

<210> SEQ ID NO 315
<211> LENGTH: 36
<212> TYPE: PRT
<213> ORGANISM: Artificial Sequence
<220> FEATURE:
<223> OTHER INFORMATION: synthetic construct light chain variable region
      FR3

<400> SEQUENCE: 315

Lys Arg Pro Ser Gly Val Pro Asp Arg Phe Ser Gly Ser Lys Ser Gly
1               5                   10                  15

Asn Thr Ala Ser Leu Thr Val Ser Gly Leu Gln Pro Glu Asp Glu Ala
            20                  25                  30

Asp Tyr Tyr Cys
        35

<210> SEQ ID NO 316
<211> LENGTH: 36
<212> TYPE: PRT
<213> ORGANISM: Artificial Sequence
<220> FEATURE:
<223> OTHER INFORMATION: synthetic construct light chain variable region
      FR3

<400> SEQUENCE: 316

Ser Arg Phe Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Val Gly
            20                  25                  30

Val Tyr Tyr Cys
        35

<210> SEQ ID NO 317
<211> LENGTH: 36
<212> TYPE: PRT
<213> ORGANISM: Artificial Sequence
<220> FEATURE:
<223> OTHER INFORMATION: synthetic construct light chain variable region
      FR3

<400> SEQUENCE: 317

Tyr Arg Ala Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Val Gly

```
                20                  25                  30

Leu Tyr Tyr Cys
        35

<210> SEQ ID NO 318
<211> LENGTH: 36
<212> TYPE: PRT
<213> ORGANISM: Artificial Sequence
<220> FEATURE:
<223> OTHER INFORMATION: synthetic construct light chain variable region
      FR3

<400> SEQUENCE: 318

Glu Arg Pro Ser Gly Ile Pro Glu Arg Phe Ser Gly Ser Ser Ser Gly
1               5                   10                  15

Thr Thr Val Thr Leu Thr Ile Ser Gly Val Gln Ala Glu Asp Glu Ala
            20                  25                  30

Asp Tyr Tyr Cys
        35

<210> SEQ ID NO 319
<211> LENGTH: 36
<212> TYPE: PRT
<213> ORGANISM: Artificial Sequence
<220> FEATURE:
<223> OTHER INFORMATION: synthetic construct light chain variable region
      FR3

<400> SEQUENCE: 319

Asn Arg Ala Ser Gly Ile Pro Ala Arg Phe Ser Gly Gly Gly Ser Gly
1               5                   10                  15

Thr Glu Phe Thr Leu Thr Ile Ser Ser Leu Glu Pro Glu Asp Phe Ala
            20                  25                  30

Val Tyr Tyr Cys
        35

<210> SEQ ID NO 320
<211> LENGTH: 36
<212> TYPE: PRT
<213> ORGANISM: Artificial Sequence
<220> FEATURE:
<223> OTHER INFORMATION: synthetic construct light chain variable region
      FR3

<400> SEQUENCE: 320

His Arg Ala Ser Gly Val Pro Asp Arg Phe Ser Gly Ser Gly Ser Gly
1               5                   10                  15

Thr Glu Phe Asn Leu Arg Ile Ser Arg Val Glu Ala Glu Asp Val Gly
            20                  25                  30

Ile Tyr Tyr Cys
        35

<210> SEQ ID NO 321
<211> LENGTH: 36
<212> TYPE: PRT
<213> ORGANISM: Artificial Sequence
<220> FEATURE:
<223> OTHER INFORMATION: synthetic construct light chain variable region
      FR3

<400> SEQUENCE: 321

Tyr Arg Ala Ser Gly Val Pro Asp Arg Phe Ser Gly Ser Gly Ser Gly
1               5                   10                  15
```

Thr Asp Phe Thr Leu Lys Ile Ser Arg Val Glu Ala Glu Asp Val Gly
            20                  25                  30

Val Tyr Tyr Cys
        35

<210> SEQ ID NO 322
<211> LENGTH: 36
<212> TYPE: PRT
<213> ORGANISM: Artificial Sequence
<220> FEATURE:
<223> OTHER INFORMATION: synthetic construct light chain variable region
      FR3

<400> SEQUENCE: 322

His Arg Ala Leu Gly Val Pro Asp Arg Phe Ser Gly Ser Gly Ser Gly
1               5                   10                  15

Thr Asp Phe Thr Leu Lys Ile Ser Arg Val Glu Ala Glu Asp Ser Gly
            20                  25                  30

Ile Tyr Tyr Cys
        35

<210> SEQ ID NO 323
<211> LENGTH: 36
<212> TYPE: PRT
<213> ORGANISM: Artificial Sequence
<220> FEATURE:
<223> OTHER INFORMATION: synthetic construct light chain variable region
      FR3

<400> SEQUENCE: 323

His Arg Ala Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Ser Gly
            20                  25                  30

Ile Tyr Tyr Cys
        35

<210> SEQ ID NO 324
<211> LENGTH: 36
<212> TYPE: PRT
<213> ORGANISM: Artificial Sequence
<220> FEATURE:
<223> OTHER INFORMATION: synthetic construct light chain variable region
      FR3

<400> SEQUENCE: 324

His Arg Ala Leu Gly Val Pro Asp Arg Phe Ser Gly Ser Gly Ser Gly
1               5                   10                  15

Thr Asp Phe Thr Leu Lys Ile Ser Arg Val Glu Ala Asp Asp Val Gly
            20                  25                  30

Leu Tyr Tyr Cys
        35

<210> SEQ ID NO 325
<211> LENGTH: 36
<212> TYPE: PRT
<213> ORGANISM: Artificial Sequence
<220> FEATURE:
<223> OTHER INFORMATION: synthetic construct light chain variable region
      FR3

<400> SEQUENCE: 325

His Arg Ala Ser Gly Val Pro Gly Arg Phe Ser Gly Ser Gly Ser Gly
1               5                   10                  15

```
Thr Glu Phe Asn Leu Arg Ile Ser Arg Val Glu Ala Glu Asp Val Gly
             20                  25                  30

Ile Tyr Tyr Cys
         35

<210> SEQ ID NO 326
<211> LENGTH: 36
<212> TYPE: PRT
<213> ORGANISM: Artificial Sequence
<220> FEATURE:
<223> OTHER INFORMATION: synthetic construct light chain variable region
      FR3

<400> SEQUENCE: 326

His Arg Ala Leu Gly Val Pro Asp Arg Phe Ser Gly Ser Gly Ser Gly
1               5                   10                  15

Thr Asp Phe Thr Leu Lys Ile Ser Arg Val Ala Ala Glu Asp Val Gly
             20                  25                  30

Leu Tyr Tyr Cys
         35

<210> SEQ ID NO 327
<211> LENGTH: 36
<212> TYPE: PRT
<213> ORGANISM: Artificial Sequence
<220> FEATURE:
<223> OTHER INFORMATION: synthetic construct light chain variable region
      FR3

<400> SEQUENCE: 327

His Arg Ala Ser Gly Val Pro Asp Arg Phe Ser Gly Ser Gly Ser Gly
1               5                   10                  15

Thr Asp Phe Thr Leu Glu Ile Ser Arg Val Glu Ala Glu Asp Val Gly
             20                  25                  30

Val Tyr Tyr Cys
         35

<210> SEQ ID NO 328
<211> LENGTH: 36
<212> TYPE: PRT
<213> ORGANISM: Artificial Sequence
<220> FEATURE:
<223> OTHER INFORMATION: synthetic construct light chain variable region
      FR3

<400> SEQUENCE: 328

His Arg Ala Leu Gly Val Pro Asp Arg Phe Ser Gly Ser Gly Ser Gly
1               5                   10                  15

Thr Asp Phe Thr Leu Lys Ile Ser Arg Val Glu Ala Asp Asn Val Gly
             20                  25                  30

Leu Tyr Tyr Cys
         35

<210> SEQ ID NO 329
<211> LENGTH: 36
<212> TYPE: PRT
<213> ORGANISM: Artificial Sequence
<220> FEATURE:
<223> OTHER INFORMATION: synthetic construct light chain variable region
      FR3

<400> SEQUENCE: 329

His Arg Ala Ser Gly Val Ser Asp Arg Phe Ser Gly Ser Gly Ser Gly
```

```
1               5                   10                  15
Thr Asp Phe Thr Leu Lys Ile Ser Arg Val Glu Ala Glu Asp Ser Gly
                20                  25                  30

Ile Tyr Tyr Cys
        35

<210> SEQ ID NO 330
<211> LENGTH: 36
<212> TYPE: PRT
<213> ORGANISM: Artificial Sequence
<220> FEATURE:
<223> OTHER INFORMATION: synthetic construct light chain variable region
      FR3

<400> SEQUENCE: 330

His Arg Ala Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Val Gly
                20                  25                  30

Val Tyr Tyr Cys
        35

<210> SEQ ID NO 331
<211> LENGTH: 36
<212> TYPE: PRT
<213> ORGANISM: Artificial Sequence
<220> FEATURE:
<223> OTHER INFORMATION: synthetic construct light chain variable region
      FR3

<400> SEQUENCE: 331

His Arg Ala Ser Gly Val Pro Asp Arg Phe Ser Gly Ser Gly Ser Gly
1               5                   10                  15

Thr Asp Phe Thr Leu Lys Ile Ser Arg Val Ala Ala Glu Asp Val Gly
                20                  25                  30

Ile Tyr Tyr Cys
        35

<210> SEQ ID NO 332
<211> LENGTH: 36
<212> TYPE: PRT
<213> ORGANISM: Artificial Sequence
<220> FEATURE:
<223> OTHER INFORMATION: synthetic construct light chain variable region
      FR3

<400> SEQUENCE: 332

His Arg Ala Ser Gly Val Pro Asp Arg Phe Ser Gly Ser Gly Ser Gly
1               5                   10                  15

Thr Asp Phe Thr Leu Lys Ile Ser Arg Val Glu Ala Asp Asp Val Gly
                20                  25                  30

Ile Tyr Tyr Cys
        35

<210> SEQ ID NO 333
<211> LENGTH: 36
<212> TYPE: PRT
<213> ORGANISM: Artificial Sequence
<220> FEATURE:
<223> OTHER INFORMATION: synthetic construct light chain variable region
      FR3

<400> SEQUENCE: 333
```

His Arg Ala Ser Gly Val Ser Asp Arg Phe Ser Gly Ser Gly Ser Gly
1               5                   10                  15

Thr Asp Phe Thr Leu Glu Ile Ser Arg Val Glu Ala Glu Asp Val Gly
                20                  25                  30

Val Tyr Tyr Cys
        35

<210> SEQ ID NO 334
<211> LENGTH: 36
<212> TYPE: PRT
<213> ORGANISM: Artificial Sequence
<220> FEATURE:
<223> OTHER INFORMATION: synthetic construct light chain variable region
      FR3

<400> SEQUENCE: 334

Tyr Arg Ala Ser Gly Val Pro Asp Arg Phe Ser Gly Ser Gly Ser Gly
1               5                   10                  15

Thr Asp Phe Thr Leu Lys Ile Ser Arg Val Ala Ala Glu Asp Val Gly
                20                  25                  30

Ile Tyr Tyr Cys
        35

<210> SEQ ID NO 335
<211> LENGTH: 36
<212> TYPE: PRT
<213> ORGANISM: Artificial Sequence
<220> FEATURE:
<223> OTHER INFORMATION: synthetic construct light chain variable region
      FR3

<400> SEQUENCE: 335

His Arg Ala Ser Gly Val Pro Asp Arg Phe Ser Gly Ser Gly Ser Gly
1               5                   10                  15

Thr Asp Phe Thr Leu Lys Ile Thr Arg Val Glu Ala Glu Asp Val Gly
                20                  25                  30

Val Tyr Tyr Cys
        35

<210> SEQ ID NO 336
<211> LENGTH: 36
<212> TYPE: PRT
<213> ORGANISM: Artificial Sequence
<220> FEATURE:
<223> OTHER INFORMATION: synthetic construct light chain variable region
      FR3

<400> SEQUENCE: 336

His Arg Ala Ser Gly Val Pro Asp Arg Phe Ser Gly Arg Gly Ser His
1               5                   10                  15

Thr Asp Phe Thr Leu Thr Ile Ser Ser Val Glu Ala Glu Asp Val Gly
                20                  25                  30

Val Tyr Tyr Cys
        35

<210> SEQ ID NO 337
<211> LENGTH: 10
<212> TYPE: PRT
<213> ORGANISM: Artificial Sequence
<220> FEATURE:
<223> OTHER INFORMATION: synthetic construct light chain variable region
      FR4

<400> SEQUENCE: 337

```
Phe Gly Gln Gly Thr Lys Val Asp Ile Lys
1               5                   10

<210> SEQ ID NO 338
<211> LENGTH: 10
<212> TYPE: PRT
<213> ORGANISM: Artificial Sequence
<220> FEATURE:
<223> OTHER INFORMATION: synthetic construct light chain variable region
      FR4

<400> SEQUENCE: 338

Phe Gly Gly Gly Thr Lys Val Asp Ile Lys
1               5                   10

<210> SEQ ID NO 339
<211> LENGTH: 10
<212> TYPE: PRT
<213> ORGANISM: Artificial Sequence
<220> FEATURE:
<223> OTHER INFORMATION: synthetic construct light chain variable region
      FR4

<400> SEQUENCE: 339

Phe Gly Gly Gly Thr Lys Leu Thr Val Leu
1               5                   10

<210> SEQ ID NO 340
<211> LENGTH: 10
<212> TYPE: PRT
<213> ORGANISM: Artificial Sequence
<220> FEATURE:
<223> OTHER INFORMATION: synthetic construct light chain variable region
      FR4

<400> SEQUENCE: 340

Phe Gly Thr Gly Thr Lys Val Thr Val Leu
1               5                   10

<210> SEQ ID NO 341
<211> LENGTH: 10
<212> TYPE: PRT
<213> ORGANISM: Artificial Sequence
<220> FEATURE:
<223> OTHER INFORMATION: synthetic construct light chain variable region
      FR4

<400> SEQUENCE: 341

Phe Gly Gly Gly Thr Lys Val Glu Ile Lys
1               5                   10

<210> SEQ ID NO 342
<211> LENGTH: 10
<212> TYPE: PRT
<213> ORGANISM: Artificial Sequence
<220> FEATURE:
<223> OTHER INFORMATION: synthetic construct light chain variable region
      FR4

<400> SEQUENCE: 342

Phe Gly Gln Gly Thr Lys Leu Asp Ile Lys
1               5                   10

<210> SEQ ID NO 343
<211> LENGTH: 10
<212> TYPE: PRT
<213> ORGANISM: Artificial Sequence
```

```
<220> FEATURE:
<223> OTHER INFORMATION: synthetic construct light chain variable region
      FR4

<400> SEQUENCE: 343

Val Arg Arg Arg Asp Gln Ala Asp Arg Pro
1               5                   10

<210> SEQ ID NO 344
<211> LENGTH: 10
<212> TYPE: PRT
<213> ORGANISM: Artificial Sequence
<220> FEATURE:
<223> OTHER INFORMATION: synthetic construct light chain variable region
      FR4

<400> SEQUENCE: 344

Phe Gly Gln Gly Thr Lys Val Glu Ile Lys
1               5                   10

<210> SEQ ID NO 345
<211> LENGTH: 10
<212> TYPE: PRT
<213> ORGANISM: Artificial Sequence
<220> FEATURE:
<223> OTHER INFORMATION: synthetic construct light chain variable region
      FR4

<400> SEQUENCE: 345

Phe Gly Gln Gly Thr Arg Leu Glu Ile Lys
1               5                   10

<210> SEQ ID NO 346
<211> LENGTH: 10
<212> TYPE: PRT
<213> ORGANISM: Artificial Sequence
<220> FEATURE:
<223> OTHER INFORMATION: synthetic construct light chain variable region
      FR4

<400> SEQUENCE: 346

Phe Gly Pro Gly Thr Lys Val Asp Ile Lys
1               5                   10

<210> SEQ ID NO 347
<211> LENGTH: 10
<212> TYPE: PRT
<213> ORGANISM: Artificial Sequence
<220> FEATURE:
<223> OTHER INFORMATION: synthetic construct light chain variable region
      FR4

<400> SEQUENCE: 347

Phe Gly Gln Gly Thr Lys Leu Glu Ile Lys
1               5                   10

<210> SEQ ID NO 348
<211> LENGTH: 10
<212> TYPE: PRT
<213> ORGANISM: Artificial Sequence
<220> FEATURE:
<223> OTHER INFORMATION: synthetic construct light chain variable region
      FR4

<400> SEQUENCE: 348

Phe Gly Pro Gly Thr Lys Leu Glu Ile Lys
1               5                   10
```

<210> SEQ ID NO 349
<211> LENGTH: 107
<212> TYPE: PRT
<213> ORGANISM: Artificial Sequence
<220> FEATURE:
<223> OTHER INFORMATION: synthetic construct light chain variable region

<400> SEQUENCE: 349

```
Asp Ile Gln Met Thr Gln Ser Pro Ser Ser Val Ser Ala Ser Val Gly
1               5                   10                  15

Asp Arg Val Thr Ile Thr Cys Arg Ala Ser Arg Asp Ile Ser Arg Trp
            20                  25                  30

Leu Ala Trp Tyr Gln Gln Lys Pro Gly Glu Ala Pro Lys Leu Leu Ile
        35                  40                  45

Tyr Gly Ala Ser Ser Leu Arg Ser Gly Val Ser Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Gly Lys Ser Phe Pro Tyr
                85                  90                  95

Thr Phe Gly Gln Gly Thr Lys Val Asp Ile Lys
            100                 105
```

<210> SEQ ID NO 350
<211> LENGTH: 106
<212> TYPE: PRT
<213> ORGANISM: Artificial Sequence
<220> FEATURE:
<223> OTHER INFORMATION: synthetic construct light chain variable region

<400> SEQUENCE: 350

```
Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Leu
            20                  25                  30

Asn Trp Phe His Gln Arg Pro Gly Gln Pro Pro Arg Leu Leu Ile His
        35                  40                  45

Lys Ile Ser Asn Arg Val Ser Gly Val Pro Asp Arg Phe Ser Gly Ser
50                  55                  60

Gly Ala Gly Thr Asp Phe Thr Leu Lys Ile Ser Arg Val Glu Ala Glu
65                  70                  75                  80

Asp Val Gly Val Tyr Tyr Cys Met Gln Ser Thr Gln Phe Pro Tyr Thr
                85                  90                  95

Phe Gly Gln Gly Thr Lys Val Asp Ile Lys
            100                 105
```

<210> SEQ ID NO 351
<211> LENGTH: 107
<212> TYPE: PRT
<213> ORGANISM: Artificial Sequence
<220> FEATURE:
<223> OTHER INFORMATION: synthetic construct light chain variable region

<400> SEQUENCE: 351

```
Asp Ile Gln Met Thr Gln Ser Pro Ser Ser Val Ser Ala Ser Leu Gly
1               5                   10                  15

Asp Arg Val Thr Ile Thr Cys Arg Ala Ser Gln Ala Ile Ser Asn Trp
            20                  25                  30

Leu Thr Trp Tyr Gln Gln Lys Pro Gly Lys Ala Pro Lys Leu Leu Ile
```

```
                35                  40                  45
Tyr Ala Thr Ser Ser Leu Gln Ser Gly Val Pro Ser Arg Phe Ser Gly
            50                  55                  60
Ser Gly Ser Gly Thr Asp Phe Thr Leu Thr Ile Ser Ser Leu Gln Pro
65                  70                  75                  80
Glu Asp Val Ala Thr Tyr Tyr Cys Gln Gln Thr Asp Ser Phe Pro Leu
                85                  90                  95
Thr Phe Gly Gly Gly Thr Lys Val Asp Ile Lys
            100                 105
```

<210> SEQ ID NO 352
<211> LENGTH: 109
<212> TYPE: PRT
<213> ORGANISM: Artificial Sequence
<220> FEATURE:
<223> OTHER INFORMATION: synthetic construct light chain variable region

<400> SEQUENCE: 352

```
Ser Tyr Glu Leu Thr Gln Ser Pro Ser Val Ser Met Ser Pro Gly Gln
1               5                   10                  15
Thr Ala Arg Ile Thr Cys Ser Gly Asp Ala Leu Ser Lys Gln Tyr Ala
            20                  25                  30
Ser Trp Tyr Gln Leu Lys Pro Gly Gln Ala Pro Val Val Val Met Tyr
        35                  40                  45
Lys Asp Thr Glu Arg Pro Ser Gly Ile Pro Asp Arg Phe Ser Gly Ser
    50                  55                  60
Ser Ser Gly Thr Thr Val Thr Leu Thr Ile Ser Gly Val Gln Ala Glu
65                  70                  75                  80
Asp Gly Ala Asp Tyr Tyr Cys Gln Ser Ile Thr Asp Lys Ser Gly Thr
                85                  90                  95
Asp Val Ile Phe Gly Gly Gly Thr Lys Leu Thr Val Leu
            100                 105
```

<210> SEQ ID NO 353
<211> LENGTH: 110
<212> TYPE: PRT
<213> ORGANISM: Artificial Sequence
<220> FEATURE:
<223> OTHER INFORMATION: synthetic construct light chain variable region

<400> SEQUENCE: 353

```
Gln Leu Val Leu Thr Gln Pro Ser Ser Met Ser Glu Ala Pro Gly Gln
1               5                   10                  15
Arg Val Thr Ile Ser Cys Ser Gly Gly Thr Ser Asn Ile Gly Thr Asn
            20                  25                  30
Ala Val Asn Trp Tyr Gln Gln Pro Pro Gly Lys Ala Pro Thr Leu Leu
        35                  40                  45
Ile Tyr Tyr Asp Asp Arg Leu Thr Ser Gly Val Ser Asp Arg Phe Ser
    50                  55                  60
Gly Ser Lys Ser Gly Thr Ser Ala Ser Leu Ala Ile Ser Arg Leu Gln
65                  70                  75                  80
Ser Glu Asp Glu Ala Asp Tyr Tyr Cys Ala Ala Trp Asp Asp Ser Leu
                85                  90                  95
Asn Gly Trp Val Phe Gly Gly Gly Thr Lys Leu Thr Val Leu
            100                 105                 110
```

<210> SEQ ID NO 354
<211> LENGTH: 111

```
<212> TYPE: PRT
<213> ORGANISM: Artificial Sequence
<220> FEATURE:
<223> OTHER INFORMATION: synthetic construct light chain variable region

<400> SEQUENCE: 354

Gln Phe Val Leu Thr Gln Pro Pro Ser Val Ser Gly Ala Pro Gly Gln
1               5                   10                  15

Arg Val Ile Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Val
        35                  40                  45

Leu Ile Tyr Gly Asn Ser Asp Arg Pro Ser Gly Val Pro Asp Arg Phe
    50                  55                  60

Ser Ala Ser Lys Ser Ala Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu
            100                 105                 110

<210> SEQ ID NO 355
<211> LENGTH: 107
<212> TYPE: PRT
<213> ORGANISM: Artificial Sequence
<220> FEATURE:
<223> OTHER INFORMATION: synthetic construct light chain variable region

<400> SEQUENCE: 355

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Val Ser Trp
            20                  25                  30

Leu Ala Trp Tyr Gln Gln Lys Pro Gly Lys Ala Pro Arg Leu Leu Ile
        35                  40                  45

Tyr Arg Ala Ser Asp Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Ala Asp Ser Phe Pro Leu
                85                  90                  95

Thr Phe Gly Gly Gly Thr Lys Val Glu Ile Lys
            100                 105

<210> SEQ ID NO 356
<211> LENGTH: 113
<212> TYPE: PRT
<213> ORGANISM: Artificial Sequence
<220> FEATURE:
<223> OTHER INFORMATION: synthetic construct light chain variable region

<400> SEQUENCE: 356

Asp Ile Val Met Thr Gln Thr Pro Leu Ser Leu Pro Val Thr Pro Gly
1               5                   10                  15

Glu Ala Ala Ser Ile Ser Cys Arg Ser Ser Gln Ser Leu Leu Asp Ser
            20                  25                  30

Glu Asp Gly Asn Thr Tyr Leu Asp Trp Tyr Leu Gln Lys Pro Gly Gln
        35                  40                  45

Ser Pro Gln Leu Leu Ile Tyr Thr Leu Ser His Arg Ala Ser Gly Val
```

```
                    50                  55                  60

Pro Asp Arg Phe Ser Gly Ser Gly Ser Gly Thr Asp Phe Thr Leu Lys
 65                  70                  75                  80

Ile Ser Arg Val Ala Ala Glu Asp Val Gly Leu Tyr Tyr Cys Leu Gln
                     85                  90                  95

Arg Met Gly Phe Pro Tyr Thr Phe Gly Gln Gly Thr Lys Leu Asp Ile
                    100                 105                 110

Lys

<210> SEQ ID NO 357
<211> LENGTH: 107
<212> TYPE: PRT
<213> ORGANISM: Artificial Sequence
<220> FEATURE:
<223> OTHER INFORMATION: synthetic construct light chain variable region

<400> SEQUENCE: 357

Asp Ile Gln Met Thr Gln Ser Pro Ser Ser Leu Ser Ala Ser Val Gly
 1               5                  10                  15

Asp Arg Val Thr Thr Thr Cys Arg Ala Ser Gln Gly Ile Ser Ser Tyr
                20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Phe Cys Gln Gln Ser Tyr Thr Ser Pro Arg
                 85                  90                  95

Thr Phe Gly Gln Gly Thr Lys Leu Asp Ile Lys
                100                 105

<210> SEQ ID NO 358
<211> LENGTH: 110
<212> TYPE: PRT
<213> ORGANISM: Artificial Sequence
<220> FEATURE:
<223> OTHER INFORMATION: synthetic construct light chain variable region

<400> SEQUENCE: 358

Gln Phe Val Leu Thr Gln Ser Pro Ser Ala Ser Gly Thr Pro Gly Gln
 1               5                  10                  15

Asn Ile Val Ile Ser Cys Ser Ala Ser Thr Phe Asn Ile Gly Thr Thr
                20                  25                  30

Thr Val Asn Trp Tyr Gln Arg Leu Pro Gly Thr Ala Pro Lys Leu Leu
            35                  40                  45

Ile Tyr Asn Tyr Asp Gln Arg Pro Ser Gly Val Pro Asp Arg Phe Ser
     50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Ala Trp Leu Phe Gly Gly Gly Thr Lys Leu Thr Val Leu
                100                 105                 110

<210> SEQ ID NO 359
<211> LENGTH: 113
<212> TYPE: PRT
```

<213> ORGANISM: Artificial Sequence
<220> FEATURE:
<223> OTHER INFORMATION: synthetic construct light chain variable region

<400> SEQUENCE: 359

Asp Ile Val Met Thr Gln Thr Pro Leu Ser Leu Pro Val Thr Pro Gly
1               5                   10                  15

Glu Ala Ala Ser Ile Ser Cys Arg Ser Gln Ser Leu Leu Asp Ser
            20                  25                  30

Asp Asp Gly Lys Thr Tyr Leu Asp Trp Tyr Leu Gln Lys Pro Gly Gln
        35                  40                  45

Ser Pro Gln Leu Leu Ile Tyr Thr Leu Ser Tyr Arg Ala Ser Gly Val
    50                  55                  60

Pro Asp Arg Phe Ser Gly Ser Gly Ser Gly Thr Glu Phe Asn Leu Arg
65                  70                  75                  80

Ile Ser Arg Val Glu Ala Glu Asp Val Gly Ile Tyr Tyr Cys Met Gln
                85                  90                  95

Arg Val Glu Phe Pro Thr Phe Gly Gln Gly Thr Lys Leu Asp Ile
            100                 105                 110

Lys

<210> SEQ ID NO 360
<211> LENGTH: 108
<212> TYPE: PRT
<213> ORGANISM: Artificial Sequence
<220> FEATURE:
<223> OTHER INFORMATION: synthetic construct light chain variable region

<400> SEQUENCE: 360

Ser Tyr Glu Leu Thr Gln Asp Pro Ala Val Ser Val Ala Leu Gly Gln
1               5                   10                  15

Thr Val Arg Ile Thr Cys Gln Gly Asp Ser Leu Arg Thr Tyr Tyr Ala
            20                  25                  30

Ser Trp Tyr Gln Gln Lys Pro Gly Gln Ala Pro Ile Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Ala Ala Gln Ala Glu
65                  70                  75                  80

Asp Glu Ala Asp Tyr Tyr Cys Asn Ser Arg Asp Ser Ser Gly Lys Ser
                85                  90                  95

Leu Val Phe Gly Gly Gly Thr Lys Leu Thr Val Leu
            100                 105

<210> SEQ ID NO 361
<211> LENGTH: 108
<212> TYPE: PRT
<213> ORGANISM: Artificial Sequence
<220> FEATURE:
<223> OTHER INFORMATION: synthetic construct light chain variable region

<400> SEQUENCE: 361

Ser Tyr Glu Leu Thr Gln Ala Pro Ser Leu Ser Val Ser Pro Gly Gln
1               5                   10                  15

Thr Ala Asn Ile Ile Cys Ser Gly Asp Asn Leu Arg Thr Lys Tyr Val
            20                  25                  30

Ser Trp Tyr Gln Gln Lys Pro Gly Gln Ser Pro Leu Leu Val Ile Tyr
        35                  40                  45

```
Gln Asp Thr Arg Arg Pro Ser Gly Ile Pro Ala Arg Phe Ser Gly Ser
 50                  55                  60

Asn Ser Gly Asn Thr Ala Thr Leu Thr Ile Ser Gly Thr Gln Thr Arg
 65                  70                  75                  80

Asp Glu Ser Thr Tyr Tyr Cys Met Thr Trp Asp Val Asp Thr Ser
                 85                  90                  95

Met Ile Phe Gly Gly Gly Thr Lys Leu Thr Val Leu
                100                 105
```

<210> SEQ ID NO 362
<211> LENGTH: 110
<212> TYPE: PRT
<213> ORGANISM: Artificial Sequence
<220> FEATURE:
<223> OTHER INFORMATION: synthetic construct light chain variable region

<400> SEQUENCE: 362

```
Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
                 20                  25                  30

Asn Tyr Val Ser Trp Tyr Gln Gln His Pro Gly Lys Ala Pro Lys Leu
             35                  40                  45

Met Ile Tyr Asp Val Ser Lys Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Phe Thr Ser Ser
                 85                  90                  95

Ser Thr Val Val Phe Gly Gly Gly Thr Lys Leu Thr Val Leu
                100                 105                 110
```

<210> SEQ ID NO 363
<211> LENGTH: 111
<212> TYPE: PRT
<213> ORGANISM: Artificial Sequence
<220> FEATURE:
<223> OTHER INFORMATION: synthetic construct light chain variable region

<400> SEQUENCE: 363

```
Gln Phe Val Leu Thr Gln Pro Pro Ser Val Ser Gly Ala Pro Gly Gln
 1               5                  10                  15

Arg Val Thr Ile Ser Cys Thr Gly Ser Arg Ser Asn Phe Gly Ala Gly
                 20                  25                  30

His Asp Val His Trp Cys Gln Gln Leu Pro Gly Thr Ala Pro Lys Leu
             35                  40                  45

Leu Ile Tyr Gly Asn Asn Asn Arg Pro Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ala Glu Asp Glu Ala Glu Tyr Tyr Cys Gln Ser Tyr Asp Ser Ser
                 85                  90                  95

Leu Ser Ala Trp Gly Val Arg Arg Asp Gln Ala Asp Arg Pro
                100                 105                 110
```

<210> SEQ ID NO 364
<211> LENGTH: 113
<212> TYPE: PRT
<213> ORGANISM: Artificial Sequence
<220> FEATURE:
<223> OTHER INFORMATION: synthetic construct light chain variable region

<400> SEQUENCE: 364

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

His Asp Gly Asn Thr Tyr Leu Asp Trp Tyr Leu Gln Lys Pro Gly Gln
        35                  40                  45

Ser Pro Gln Leu Leu Ile Tyr Thr Leu Ser His Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Leu Tyr Tyr Cys Met Gln
                85                  90                  95

Arg Ile Asp Phe Pro Tyr Thr Phe Gly Gln Gly Thr Lys Val Glu Ile
            100                 105                 110

Lys

<210> SEQ ID NO 365
<211> LENGTH: 110
<212> TYPE: PRT
<213> ORGANISM: Artificial Sequence
<220> FEATURE:
<223> OTHER INFORMATION: synthetic construct light chain variable region

<400> SEQUENCE: 365

Asn Phe Met Leu Thr Gln Pro Pro Ser Thr Ser Gly Thr Pro Gly Gln
1               5                   10                  15

Arg Val Thr Ile Ser Cys Ser Gly Arg Ser Ser Asn Ile Gly Ile Asn
            20                  25                  30

Thr Val Thr Trp Tyr Gln Gln Leu Pro Gly Thr Ala Pro Lys Val Leu
        35                  40                  45

Met Tyr Arg Asp Asp Gln Arg Pro Ser Gly Val Pro Asp Arg Phe Ser
    50                  55                  60

Gly Ser Arg Ser Gly Ile Ser Ala Ser Leu Ala Ile Ser Gly Leu Gln
65                  70                  75                  80

Ser Glu Asp Glu Ala Asp Tyr Tyr Cys Ala Ser Trp Asp Asp Thr Leu
                85                  90                  95

Asn Gly Trp Val Phe Gly Gly Gly Thr Lys Leu Thr Val Leu
            100                 105                 110

<210> SEQ ID NO 366
<211> LENGTH: 113
<212> TYPE: PRT
<213> ORGANISM: Artificial Sequence
<220> FEATURE:
<223> OTHER INFORMATION: synthetic construct light chain variable region

<400> SEQUENCE: 366

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Phe Asp Ser
            20                  25                  30

Asp Asp Gly Asn Thr Tyr Leu Asp Trp Tyr Leu Gln Lys Pro Gly Gln
        35                  40                  45

Ser Pro Gln Leu Leu Ile Tyr Thr Leu Ser His Arg Ala Ser Gly Val

```
                50                  55                  60
Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Ile Tyr Tyr Cys Leu Gln
                 85                  90                  95

Arg Met Gly Phe Pro Tyr Thr Phe Gly Gln Gly Thr Lys Val Glu Ile
                100                 105                 110

Lys

<210> SEQ ID NO 367
<211> LENGTH: 110
<212> TYPE: PRT
<213> ORGANISM: Artificial Sequence
<220> FEATURE:
<223> OTHER INFORMATION: synthetic construct light chain variable region

<400> SEQUENCE: 367

Gln Ser Ala Leu Thr Gln Pro Pro Ser Ala Ser Gly Ser Pro Gly Gln
 1               5                  10                  15

Ser Val Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
             35                  40                  45

Met Ile Tyr Glu Val Ser Lys Arg Pro Ser Gly Val Pro Asp Arg Phe
 50                  55                  60

Ser Gly Ser Lys Ser Gly Asn Thr Ala Ser Leu Thr Val Ser Gly Leu
 65                  70                  75                  80

Gln Pro Glu Asp Glu Ala Asp Tyr Tyr Cys Ser Ser Phe Ala Arg Asn
                 85                  90                  95

Ser Asn Tyr Val Phe Gly Thr Gly Thr Lys Val Thr Val Leu
                100                 105                 110

<210> SEQ ID NO 368
<211> LENGTH: 112
<212> TYPE: PRT
<213> ORGANISM: Artificial Sequence
<220> FEATURE:
<223> OTHER INFORMATION: synthetic construct light chain variable region

<400> SEQUENCE: 368

Asp Ile Val Met Thr Gln Thr Pro Leu Ser Leu Ser Val Thr Pro Gly
 1               5                  10                  15

Gln Pro Ala Ser Ile Ser Cys Lys Ser Ser Gln Ser Leu Leu Tyr Ile
                20                  25                  30

Asp Gly Glu Thr Tyr Leu Phe Trp Tyr Leu Gln Lys Pro Gly Gln Ser
             35                  40                  45

Pro Gln Leu Leu Ile Tyr Glu Val Ser Ser Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Ile His Leu Pro Leu Thr Phe Gly Gln Gly Thr Arg Leu Glu Ile Lys
                100                 105                 110

<210> SEQ ID NO 369
<211> LENGTH: 112
<212> TYPE: PRT
```

<213> ORGANISM: Artificial Sequence
<220> FEATURE:
<223> OTHER INFORMATION: synthetic construct light chain variable region

<400> SEQUENCE: 369

Asp Ile Val Met Thr Gln Thr Pro Leu Ser Leu Pro Val Thr Pro Gly
1               5                   10                  15

Glu Pro Ala Ser Ile Ser Cys Arg Ser Gln Ser Leu Leu His Ser
            20                  25                  30

Asn Gly Asn Asn Tyr Leu Asp Trp Tyr Leu Gln Lys Pro Gly Gln Ser
        35                  40                  45

Pro Gln Leu Leu Ile Tyr Leu Gly Ser Tyr Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Leu Tyr Tyr Cys Met Gln Gly
                85                  90                  95

Leu Gln Ile Pro Ser Thr Phe Pro Gly Thr Lys Val Asp Ile Lys
            100                 105                 110

<210> SEQ ID NO 370
<211> LENGTH: 108
<212> TYPE: PRT
<213> ORGANISM: Artificial Sequence
<220> FEATURE:
<223> OTHER INFORMATION: synthetic construct light chain variable region

<400> SEQUENCE: 370

Ser Tyr Glu Leu Thr Gln Pro Leu Ser Leu Ser Val Ala Pro Gly Gln
1               5                   10                  15

Thr Ala Arg Ile Thr Cys Ser Gly Asp Ala Leu Ser Lys Glu Tyr Ser
            20                  25                  30

Tyr Trp Tyr Gln Gln Lys Pro Gly Gln Ala Pro Val Leu Val Met Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Val Asp Ser Ser Asp Thr Ser
                85                  90                  95

Val Val Phe Gly Gly Gly Thr Lys Leu Thr Val Leu
            100                 105

<210> SEQ ID NO 371
<211> LENGTH: 107
<212> TYPE: PRT
<213> ORGANISM: Artificial Sequence
<220> FEATURE:
<223> OTHER INFORMATION: synthetic construct light chain variable region

<400> SEQUENCE: 371

Asp Ile Gln Met Thr Gln Ser Pro Ala Ile Leu Ser Leu Ser Pro Gly
1               5                   10                  15

Glu Arg Ala Thr Leu Ser Cys Arg Ala Ser Gln Ser Val Thr Ser Asp
            20                  25                  30

Val Ala Trp Tyr Gln His Ile Arg Gly Gln Ala Pro Arg Leu Leu Ile
        35                  40                  45

Tyr Asp Ala Ser Asn Arg Ala Ser Gly Ile Pro Ala Arg Phe Ser Gly
    50                  55                  60

```
Gly Gly Ser Gly Thr Glu Phe Thr Leu Thr Ile Ser Ser Leu Glu Pro
 65                  70                  75                  80

Glu Asp Phe Ala Val Tyr Tyr Cys Gln Gln Tyr Asn Asn Trp Pro Leu
                 85                  90                  95

Thr Phe Gly Gly Gly Thr Lys Val Glu Ile Lys
                100                 105
```

<210> SEQ ID NO 372
<211> LENGTH: 113
<212> TYPE: PRT
<213> ORGANISM: Artificial Sequence
<220> FEATURE:
<223> OTHER INFORMATION: synthetic construct light chain variable region

<400> SEQUENCE: 372

```
Asp Ile Val Met Thr Gln Thr Pro Leu Ser Leu Pro Val Thr Pro Gly
 1               5                  10                  15

Glu Pro Ala Ser Ile Ser Cys Arg Ser Ser Gln Ser Leu Leu Asp Ser
                 20                  25                  30

Asp Gly Asn Thr Tyr Leu Asp Trp Tyr Leu Gln Lys Pro Gly Gln
             35                  40                  45

Ser Pro Gln Leu Leu Ile Tyr Thr Leu Ser His Arg Ala Ser Gly Val
         50                  55                  60

Pro Asp Arg Phe Ser Gly Ser Gly Ser Gly Thr Glu Phe Asn Leu Arg
 65                  70                  75                  80

Ile Ser Arg Val Glu Ala Glu Asp Val Gly Ile Tyr Tyr Cys Met Gln
                 85                  90                  95

Arg Val Glu Phe Pro Phe Thr Phe Gly Gln Gly Thr Lys Leu Glu Ile
                100                 105                 110

Lys
```

<210> SEQ ID NO 373
<211> LENGTH: 113
<212> TYPE: PRT
<213> ORGANISM: Artificial Sequence
<220> FEATURE:
<223> OTHER INFORMATION: synthetic construct light chain variable region

<400> SEQUENCE: 373

```
Asp Ile Val Met Thr Gln Thr Pro Leu Ser Leu Pro Val Thr Pro Gly
 1               5                  10                  15

Glu Pro Ala Ser Ile Ser Cys Arg Ser Ser Gln Ser Leu Phe Asp Ser
                 20                  25                  30

Asp Gly Asn Thr Tyr Leu Asp Trp Tyr Leu Gln Lys Pro Gly Gln
             35                  40                  45

Ser Pro Gln Leu Leu Ile Tyr Thr Leu Ser Tyr Arg Ala Ser Gly Val
         50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Met Gln
                 85                  90                  95

Arg Val Glu Phe Pro Phe Thr Phe Gly Gln Gly Thr Lys Val Glu Ile
                100                 105                 110

Lys
```

<210> SEQ ID NO 374
<211> LENGTH: 113

<212> TYPE: PRT
<213> ORGANISM: Artificial Sequence
<220> FEATURE:
<223> OTHER INFORMATION: synthetic construct light chain variable region

<400> SEQUENCE: 374

```
Asp Ile Val Met Thr Gln Thr Pro His Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Glu Asp Gly Asn Thr Tyr Leu Asp Trp Tyr Leu Gln Lys Pro Gly Gln
        35                  40                  45

Ser Pro Gln Leu Leu Ile Tyr Thr Leu Ser His Arg Ala Leu Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Ser Gly Ile Tyr Tyr Cys Met Gln
                85                  90                  95

Arg Ile Glu Phe Pro Tyr Thr Phe Gly Gln Gly Thr Lys Leu Glu Ile
            100                 105                 110

Lys
```

<210> SEQ ID NO 375
<211> LENGTH: 113
<212> TYPE: PRT
<213> ORGANISM: Artificial Sequence
<220> FEATURE:
<223> OTHER INFORMATION: synthetic construct light chain variable region

<400> SEQUENCE: 375

```
Asp Ile Val Met Thr Gln Ser Pro Leu Ser Leu Pro Val Thr Pro Gly
1               5                   10                  15

Glu Ala Ala Ser Ile Ser Cys Arg Ser Ser Gln Ser Leu Leu Asp Ser
            20                  25                  30

Glu Asp Gly Asn Thr Tyr Leu Asp Trp Tyr Leu Gln Lys Pro Gly Gln
        35                  40                  45

Ser Pro Gln Leu Leu Ile Tyr Thr Leu Ser His Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Ser Gly Ile Tyr Tyr Cys Met Gln
                85                  90                  95

Arg Val Glu Phe Pro Tyr Thr Phe Gly Gln Gly Thr Lys Leu Asp Ile
            100                 105                 110

Lys
```

<210> SEQ ID NO 376
<211> LENGTH: 113
<212> TYPE: PRT
<213> ORGANISM: Artificial Sequence
<220> FEATURE:
<223> OTHER INFORMATION: synthetic construct light chain variable region

<400> SEQUENCE: 376

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Arg
            20                  25                  30
```

Asp Gly Gly His Thr Tyr Val Asp Trp Tyr Leu Gln Lys Pro Gly Gln
            35                  40                  45

Ser Pro Arg Leu Leu Ile Tyr Thr Leu Ser His Arg Ala Leu Gly Val
 50                  55                  60

Pro Asp Arg Phe Ser Gly Ser Gly Ser Gly Thr Asp Phe Thr Leu Lys
 65                  70                  75                  80

Ile Ser Arg Val Glu Ala Asp Asp Val Gly Leu Tyr Tyr Cys Met Gln
                 85                  90                  95

Arg Ile Glu Phe Pro Phe Thr Phe Gly Gln Gly Thr Lys Val Glu Ile
                100                 105                 110

Lys

<210> SEQ ID NO 377
<211> LENGTH: 113
<212> TYPE: PRT
<213> ORGANISM: Artificial Sequence
<220> FEATURE:
<223> OTHER INFORMATION: synthetic construct light chain variable region

<400> SEQUENCE: 377

Asp Ile Val Met Thr Gln Thr Pro Leu Ser Leu Pro Val Thr Pro Gly
 1               5                  10                  15

Glu Ala Ala Ser Ile Ser Cys Arg Ser Ser Gln Ser Leu Leu Asp Ser
                 20                  25                  30

Glu Asp Gly Asn Thr Tyr Leu Asp Trp Tyr Leu Gln Arg Pro Gly Gln
            35                  40                  45

Ser Pro Gln Leu Leu Ile Tyr Thr Leu Ser His Arg Ala Ser Gly Val
 50                  55                  60

Pro Gly Arg Phe Ser Gly Ser Gly Ser Gly Thr Glu Phe Asn Leu Arg
 65                  70                  75                  80

Ile Ser Arg Val Glu Ala Glu Asp Val Gly Ile Tyr Tyr Cys Met Gln
                 85                  90                  95

Arg Val Glu Phe Pro Phe Thr Phe Gly Gln Gly Thr Lys Val Glu Ile
                100                 105                 110

Lys

<210> SEQ ID NO 378
<211> LENGTH: 113
<212> TYPE: PRT
<213> ORGANISM: Artificial Sequence
<220> FEATURE:
<223> OTHER INFORMATION: synthetic construct light chain variable region

<400> SEQUENCE: 378

Asp Ile Val Met Thr Gln Thr Pro Leu Ser Leu Pro Val Thr Pro Gly
 1               5                  10                  15

Glu Pro Ala Ser Ile Ser Cys Arg Ser Ser Gln Ser Leu Phe Asp Ser
                 20                  25                  30

Asp Asp Gly Asn Thr Tyr Leu Asp Trp Tyr Leu Gln Lys Pro Gly Gln
            35                  40                  45

Ser Pro Arg Leu Leu Ile Tyr Thr Leu Ser His Arg Ala Leu Gly Val
 50                  55                  60

Pro Asp Arg Phe Ser Gly Ser Gly Ser Gly Thr Asp Phe Thr Leu Lys
 65                  70                  75                  80

Ile Ser Arg Val Ala Ala Glu Asp Val Gly Leu Tyr Tyr Cys Leu Gln
                 85                  90                  95

Arg Met Gly Phe Pro Tyr Thr Phe Gly Gln Gly Thr Lys Leu Glu Ile

Lys

<210> SEQ ID NO 379
<211> LENGTH: 113
<212> TYPE: PRT
<213> ORGANISM: Artificial Sequence
<220> FEATURE:
<223> OTHER INFORMATION: synthetic construct light chain variable region

<400> SEQUENCE: 379

```
Asp Ile Val Met Thr Gln Thr Pro Leu Ser Leu Pro Val Thr Pro Gly
1               5                   10                  15

Glu Ala Ala Ser Ile Ser Cys Arg Ser Ser Gln Ser Leu Leu Asp Ser
            20                  25                  30

Glu Asp Gly Asn Thr Tyr Leu Asp Trp Tyr Leu Gln Lys Pro Gly Gln
        35                  40                  45

Ser Pro Gln Leu Leu Ile Tyr Thr Leu Ser His Arg Ala Ser Gly Val
    50                  55                  60

Pro Asp Arg Phe Ser Gly Ser Gly Ser Gly Thr Asp Phe Thr Leu Glu
65                  70                  75                  80

Ile Ser Arg Val Glu Ala Glu Asp Val Gly Val Tyr Tyr Cys Met Gln
                85                  90                  95

Arg Arg Asp Phe Pro Phe Thr Phe Gly Gln Gly Thr Lys Val Asp Ile
            100                 105                 110
```

Lys

<210> SEQ ID NO 380
<211> LENGTH: 113
<212> TYPE: PRT
<213> ORGANISM: Artificial Sequence
<220> FEATURE:
<223> OTHER INFORMATION: synthetic construct light chain variable region

<400> SEQUENCE: 380

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asp Asp Gly Asn Thr Tyr Leu Asp Trp Tyr Leu Gln Lys Pro Gly Gln
        35                  40                  45

Ser Pro Gln Leu Leu Ile Tyr Thr Leu Ser His Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Ala Ala Glu Asp Val Gly Leu Tyr Tyr Cys Met Gln
                85                  90                  95

Arg Val Glu Phe Pro Phe Thr Phe Gly Gln Gly Thr Lys Leu Asp Ile
            100                 105                 110
```

Lys

<210> SEQ ID NO 381
<211> LENGTH: 113
<212> TYPE: PRT
<213> ORGANISM: Artificial Sequence
<220> FEATURE:
<223> OTHER INFORMATION: synthetic construct light chain variable region

<400> SEQUENCE: 381

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Arg
            20                  25                  30

Asp Gly Gly His Thr Tyr Val Asp Trp Tyr Leu Gln Lys Pro Gly Gln
        35                  40                  45

Ser Pro Arg Leu Leu Ile Tyr Thr Leu Ser His Arg Ala Leu Gly Val
50                  55                  60

Pro Asp Arg Phe Ser Gly Ser Gly Ser Gly Thr Asp Phe Thr Leu Lys
65                  70                  75                  80

Ile Ser Arg Val Glu Ala Asp Asn Val Gly Leu Tyr Tyr Cys Met Gln
                85                  90                  95

Arg Ile Glu Phe Pro Phe Thr Phe Gly Gln Gly Thr Lys Val Glu Ile
            100                 105                 110

Lys

<210> SEQ ID NO 382
<211> LENGTH: 113
<212> TYPE: PRT
<213> ORGANISM: Artificial Sequence
<220> FEATURE:
<223> OTHER INFORMATION: synthetic construct light chain variable region

<400> SEQUENCE: 382

Asp Ile Val Met Thr Gln Thr Pro Leu Ser Leu Pro Val Thr Pro Gly
1               5                   10                  15

Glu Ala Ala Ser Ile Ser Cys Arg Ser Ser Gln Ser Leu Leu Asp Ser
            20                  25                  30

Glu Asp Gly Asn Thr Tyr Leu Asp Trp Tyr Leu Gln Lys Pro Gly Gln
        35                  40                  45

Ser Pro Gln Leu Leu Ile Tyr Thr Leu Ser His Arg Ala Ser Gly Val
50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Ile Tyr Tyr Cys Met Gln
                85                  90                  95

Arg Val Glu Phe Pro Phe Thr Phe Gly Gln Gly Thr Lys Val Glu Ile
            100                 105                 110

Lys

<210> SEQ ID NO 383
<211> LENGTH: 113
<212> TYPE: PRT
<213> ORGANISM: Artificial Sequence
<220> FEATURE:
<223> OTHER INFORMATION: synthetic construct light chain variable region

<400> SEQUENCE: 383

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Glu Asp Gly Asn Thr Tyr Leu Asp Trp Tyr Leu Gln Lys Pro Gly Gln
        35                  40                  45

Ser Pro Gln Leu Leu Ile Tyr Thr Leu Ser His Arg Ala Ser Gly Val
50                  55                  60

```
Pro Asp Arg Phe Ser Gly Ser Gly Ser Gly Thr Asp Phe Thr Leu Glu
 65                  70                  75                  80

Ile Ser Arg Val Glu Ala Glu Asp Val Gly Val Tyr Tyr Cys Met Gln
                 85                  90                  95

Arg Val Glu Phe Pro Phe Thr Phe Gly Gln Gly Thr Lys Leu Asp Ile
            100                 105                 110

Lys

<210> SEQ ID NO 384
<211> LENGTH: 113
<212> TYPE: PRT
<213> ORGANISM: Artificial Sequence
<220> FEATURE:
<223> OTHER INFORMATION: synthetic construct light chain variable region

<400> SEQUENCE: 384

Asp Ile Val Met Thr Gln Thr Pro Leu Ser Leu Pro Val Thr Pro Gly
 1               5                  10                  15

Glu Pro Ala Ser Ile Ser Cys Arg Ser Ser Gln Ser Leu Phe Asp Ser
                 20                  25                  30

Asp Asp Gly Asn Thr Tyr Leu Asp Trp Tyr Leu Gln Lys Pro Gly Gln
             35                  40                  45

Ser Pro Gln Leu Leu Ile Tyr Thr Leu Ser His Arg Ala Ser Gly Val
     50                  55                  60

Ser Asp Arg Phe Ser Gly Ser Gly Ser Gly Thr Asp Phe Thr Leu Lys
 65                  70                  75                  80

Ile Ser Arg Val Glu Ala Glu Asp Ser Gly Ile Tyr Tyr Cys Met Gln
                 85                  90                  95

Arg Val Glu Phe Pro Phe Thr Phe Gly Gln Gly Thr Lys Leu Asp Ile
            100                 105                 110

Lys

<210> SEQ ID NO 385
<211> LENGTH: 113
<212> TYPE: PRT
<213> ORGANISM: Artificial Sequence
<220> FEATURE:
<223> OTHER INFORMATION: synthetic construct light chain variable region

<400> SEQUENCE: 385

Asp Ile Val Met Thr Gln Thr Pro Leu Ser Leu Pro Val Thr Pro Gly
 1               5                  10                  15

Glu Ala Ala Ser Ile Ser Cys Arg Ser Ser Gln Ser Leu Leu Asp Ser
                 20                  25                  30

Glu Asp Gly Asn Thr Tyr Leu Asp Trp Tyr Leu Gln Lys Pro Gly Gln
             35                  40                  45

Ser Pro Gln Leu Leu Ile Tyr Thr Leu Ser His Arg Ala Ser Gly Val
     50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Met Gln
                 85                  90                  95

Arg Val Glu Phe Pro Phe Thr Phe Gly Gln Gly Thr Lys Leu Glu Ile
            100                 105                 110

Lys

<210> SEQ ID NO 386
```

```
<211> LENGTH: 113
<212> TYPE: PRT
<213> ORGANISM: Artificial Sequence
<220> FEATURE:
<223> OTHER INFORMATION: synthetic construct light chain variable region

<400> SEQUENCE: 386

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asp Asp Gly Asn Thr Tyr Leu Asp Trp Tyr Leu Gln Lys Pro Gly Gln
        35                  40                  45

Ser Pro Gln Leu Leu Ile Tyr Thr Leu Ser His Arg Ala Ser Gly Val
    50                  55                  60

Pro Gly Arg Phe Ser Gly Ser Gly Ser Gly Thr Glu Phe Asn Leu Arg
65                  70                  75                  80

Ile Ser Arg Val Glu Ala Glu Asp Val Gly Ile Tyr Tyr Cys Met Gln
                85                  90                  95

Arg Val Glu Phe Pro Phe Thr Phe Gly Gln Gly Thr Lys Leu Glu Ile
            100                 105                 110

Lys

<210> SEQ ID NO 387
<211> LENGTH: 113
<212> TYPE: PRT
<213> ORGANISM: Artificial Sequence
<220> FEATURE:
<223> OTHER INFORMATION: synthetic construct light chain variable region

<400> SEQUENCE: 387

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asp Asp Gly Asn Thr Tyr Leu Asp Trp Tyr Leu Gln Lys Pro Gly Gln
        35                  40                  45

Ser Pro Gln Leu Leu Ile Tyr Thr Leu Ser His Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Ile Tyr Tyr Cys Met Gln
                85                  90                  95

Arg Val Glu Phe Pro Phe Thr Phe Gly Gln Gly Thr Lys Leu Asp Ile
            100                 105                 110

Lys

<210> SEQ ID NO 388
<211> LENGTH: 113
<212> TYPE: PRT
<213> ORGANISM: Artificial Sequence
<220> FEATURE:
<223> OTHER INFORMATION: synthetic construct light chain variable region

<400> SEQUENCE: 388

Asp Ile Val Met Thr Gln Thr Pro Leu Ser Leu Pro Val Thr Pro Gly
1               5                   10                  15

Glu Ala Ala Ser Ile Ser Cys Arg Ser Ser Gln Ser Leu Leu Asp Ser
            20                  25                  30
```

```
Glu Asp Gly Asn Thr Tyr Leu Asp Trp Tyr Leu Gln Lys Pro Gly Gln
            35                  40                  45

Ser Pro Gln Leu Leu Ile Tyr Thr Leu Ser His Arg Ala Ser Gly Val
        50                  55                  60

Pro Asp Arg Phe Ser Gly Ser Gly Ser Gly Thr Asp Phe Thr Leu Lys
65                  70                  75                  80

Ile Ser Arg Val Ala Ala Glu Asp Val Gly Ile Tyr Tyr Cys Met Gln
                85                  90                  95

Arg Val Glu Phe Pro Phe Thr Phe Gly Gln Gly Thr Lys Leu Glu Ile
            100                 105                 110

Lys
```

<210> SEQ ID NO 389
<211> LENGTH: 113
<212> TYPE: PRT
<213> ORGANISM: Artificial Sequence
<220> FEATURE:
<223> OTHER INFORMATION: synthetic construct light chain variable region

<400> SEQUENCE: 389

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Glu Asp Gly Asn Thr Tyr Leu Asp Trp Tyr Leu Gln Lys Pro Gly Gln
            35                  40                  45

Ser Pro Gln Leu Leu Ile Tyr Thr Leu Ser His Arg Ala Ser Gly Val
        50                  55                  60

Pro Asp Arg Phe Ser Gly Ser Gly Ser Gly Thr Glu Phe Asn Leu Arg
65                  70                  75                  80

Ile Ser Arg Val Glu Ala Glu Asp Val Gly Ile Tyr Tyr Cys Met Gln
                85                  90                  95

Arg Val Glu Phe Pro Phe Thr Phe Gly Gln Gly Thr Lys Val Asp Ile
            100                 105                 110

Lys
```

<210> SEQ ID NO 390
<211> LENGTH: 113
<212> TYPE: PRT
<213> ORGANISM: Artificial Sequence
<220> FEATURE:
<223> OTHER INFORMATION: synthetic construct light chain variable region

<400> SEQUENCE: 390

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Phe Asp Ser
            20                  25                  30

Asp Asp Gly Asn Thr Tyr Leu Asp Trp Tyr Leu Gln Lys Pro Gly Gln
            35                  40                  45

Ser Pro Gln Leu Leu Ile Tyr Thr Leu Ser His Arg Ala Ser Gly Val
        50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Leu Tyr Tyr Cys Met Gln
                85                  90                  95
```

Arg Val Glu Phe Pro Phe Thr Phe Gly Gln Gly Thr Lys Leu Glu Ile
            100                 105                 110
Lys

<210> SEQ ID NO 391
<211> LENGTH: 113
<212> TYPE: PRT
<213> ORGANISM: Artificial Sequence
<220> FEATURE:
<223> OTHER INFORMATION: synthetic construct light chain variable region

<400> SEQUENCE: 391

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Glu Asp Gly Asn Thr Tyr Leu Asp Trp Tyr Leu Gln Lys Pro Gly Gln
        35                  40                  45

Ser Pro Gln Leu Leu Ile Tyr Thr Leu Ser His Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Arg Ile Asp Phe Pro Tyr Thr Phe Gly Gln Gly Thr Lys Leu Asp Ile
            100                 105                 110
Lys

<210> SEQ ID NO 392
<211> LENGTH: 113
<212> TYPE: PRT
<213> ORGANISM: Artificial Sequence
<220> FEATURE:
<223> OTHER INFORMATION: synthetic construct light chain variable region

<400> SEQUENCE: 392

Asp Ile Val Met Thr Gln Thr Pro Leu Ser Pro Pro Val Thr Pro Gly
1               5                   10                  15

Glu Pro Ala Ser Ile Ser Cys Arg Ser Ser Gln Ser Leu Leu Asp Ser
            20                  25                  30

Asp Asp Gly Asn Thr Tyr Leu Asp Trp Tyr Leu Gln Lys Pro Gly Gln
        35                  40                  45

Ser Pro Gln Leu Leu Ile Tyr Thr Leu Ser His Arg Ala Ser Gly Val
    50                  55                  60

Pro Asp Arg Phe Ser Gly Ser Gly Ser Gly Thr Asp Phe Thr Leu Glu
65                  70                  75                  80

Ile Ser Arg Val Glu Ala Glu Asp Val Gly Val Tyr Tyr Cys Met Gln
                85                  90                  95

Arg Arg Asp Phe Pro Thr Phe Gly Gln Gly Thr Lys Leu Asp Ile
            100                 105                 110
Lys

<210> SEQ ID NO 393
<211> LENGTH: 113
<212> TYPE: PRT
<213> ORGANISM: Artificial Sequence
<220> FEATURE:
<223> OTHER INFORMATION: synthetic construct light chain variable region

```
<400> SEQUENCE: 393

Asp Ile Val Met Thr Gln Thr Pro Leu Ser Leu Pro Val Met Pro Gly
1               5                   10                  15

Glu Ala Ala Ser Ile Ser Cys Arg Ser Ser Gln Ser Leu Leu Asp Ser
            20                  25                  30

Glu Asp Gly Asn Thr Tyr Leu Asp Trp Tyr Leu Gln Lys Pro Gly Gln
        35                  40                  45

Ser Pro Gln Leu Leu Ile Tyr Thr Leu Ser His Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Asp Asp Val Gly Ile Tyr Tyr Cys Met Gln
                85                  90                  95

Arg Val Glu Phe Pro Phe Thr Phe Gly Gln Gly Thr Lys Val Glu Ile
                100                 105                 110

Lys

<210> SEQ ID NO 394
<211> LENGTH: 113
<212> TYPE: PRT
<213> ORGANISM: Artificial Sequence
<220> FEATURE:
<223> OTHER INFORMATION: synthetic construct light chain variable region

<400> SEQUENCE: 394

Asp Ile Val Met Thr Gln Thr Pro Leu Ser Leu Pro Val Thr Pro Gly
1               5                   10                  15

Glu Ala Ala Ser Ile Ser Cys Arg Ser Ser Gln Ser Leu Leu Asp Ser
            20                  25                  30

Glu Asp Gly Asn Thr Tyr Leu Asp Trp Tyr Leu Gln Lys Pro Gly Gln
        35                  40                  45

Ser Pro Gln Leu Leu Ile Tyr Thr Leu Ser His Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Ile Tyr Tyr Cys Met Gln
                85                  90                  95

Arg Val Glu Phe Pro Phe Thr Phe Gly Gln Gly Thr Lys Val Glu Ile
                100                 105                 110

Lys

<210> SEQ ID NO 395
<211> LENGTH: 113
<212> TYPE: PRT
<213> ORGANISM: Artificial Sequence
<220> FEATURE:
<223> OTHER INFORMATION: synthetic construct light chain variable region

<400> SEQUENCE: 395

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Glu Asp Gly Asn Thr Tyr Leu Asp Trp Tyr Leu Gln Lys Pro Gly Gln
        35                  40                  45

Ser Pro Gln Leu Leu Ile Tyr Thr Leu Ser His Arg Ala Ser Gly Val
    50                  55                  60
```

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Arg Val Glu Phe Pro Phe Thr Phe Gly Gln Gly Thr Lys Leu Asp Ile
            100                 105                 110

Lys

<210> SEQ ID NO 396
<211> LENGTH: 113
<212> TYPE: PRT
<213> ORGANISM: Artificial Sequence
<220> FEATURE:
<223> OTHER INFORMATION: synthetic construct light chain variable region

<400> SEQUENCE: 396

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asp Asp Gly Asn Thr Tyr Leu Asp Trp Tyr Leu Gln Lys Pro Gly Gln
        35                  40                  45

Ser Pro Gln Leu Leu Ile Tyr Thr Leu Ser His Arg Ala Ser Gly Val
    50                  55                  60

Ser Asp Arg Phe Ser Gly Ser Gly Ser Gly Thr Asp Phe Thr Leu Glu
65                  70                  75                  80

Ile Ser Arg Val Glu Ala Glu Asp Val Gly Val Tyr Tyr Cys Met Gln
                85                  90                  95

Arg Arg Asp Phe Pro Phe Thr Phe Gly Gln Gly Thr Lys Val Glu Ile
            100                 105                 110

Lys

<210> SEQ ID NO 397
<211> LENGTH: 113
<212> TYPE: PRT
<213> ORGANISM: Artificial Sequence
<220> FEATURE:
<223> OTHER INFORMATION: synthetic construct light chain variable region

<400> SEQUENCE: 397

Asp Ile Val Met Thr Gln Thr Pro Leu Ser Leu Pro Val Thr Pro Gly
1               5                   10                  15

Glu Ala Ala Ser Ile Ser Cys Arg Ser Ser Gln Ser Leu Leu Asp Ser
            20                  25                  30

Glu Asp Gly Asn Thr Tyr Leu Asp Trp Tyr Leu Gln Lys Pro Gly Gln
        35                  40                  45

Ser Pro Gln Leu Leu Ile Tyr Thr Leu Ser His Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Ile Tyr Tyr Cys Met Gln
                85                  90                  95

Arg Val Glu Phe Pro Phe Thr Phe Gly Gln Gly Thr Lys Leu Glu Ile
            100                 105                 110

Lys

<210> SEQ ID NO 398
<211> LENGTH: 113
<212> TYPE: PRT
<213> ORGANISM: Artificial Sequence
<220> FEATURE:
<223> OTHER INFORMATION: synthetic construct light chain variable region

<400> SEQUENCE: 398

```
Asp Ile Val Met Thr Gln Thr Pro Leu Ser Leu Pro Val Thr Pro Gly
1               5                   10                  15
Glu Pro Ala Ser Ile Ser Cys Arg Ser Ser Gln Ser Leu Phe Asp Ser
            20                  25                  30
Asp Asp Gly Asn Thr Tyr Leu Asp Trp Tyr Leu Gln Lys Pro Gly Gln
        35                  40                  45
Ser Pro Gln Leu Leu Ile Tyr Thr Leu Ser Tyr Arg Ala Ser Gly Val
    50                  55                  60
Pro Asp Arg Phe Ser Gly Ser Gly Ser Gly Thr Asp Phe Thr Leu Lys
65                  70                  75                  80
Ile Ser Arg Val Ala Ala Glu Asp Val Gly Ile Tyr Tyr Cys Met Gln
                85                  90                  95
Arg Val Glu Phe Pro Phe Thr Phe Gly Gln Gly Thr Lys Val Asp Ile
            100                 105                 110
Lys
```

<210> SEQ ID NO 399
<211> LENGTH: 113
<212> TYPE: PRT
<213> ORGANISM: Artificial Sequence
<220> FEATURE:
<223> OTHER INFORMATION: synthetic construct light chain variable region

<400> SEQUENCE: 399

```
Asp Ile Val Met Thr Gln Thr Pro Leu Ser Leu Pro Val Thr Pro Gly
1               5                   10                  15
Glu Ala Ala Ser Ile Ser Cys Arg Ser Ser Gln Ser Leu Leu Asp Ser
            20                  25                  30
Glu Asp Gly Asn Thr Tyr Leu Asp Trp Tyr Leu Gln Lys Pro Gly Gln
        35                  40                  45
Ser Pro Gln Leu Leu Ile Tyr Thr Leu Ser His Arg Ala Ser Gly Val
    50                  55                  60
Pro Asp Arg Phe Ser Gly Ser Gly Ser Gly Thr Asp Phe Thr Leu Lys
65                  70                  75                  80
Ile Thr Arg Val Glu Ala Glu Asp Val Gly Val Tyr Tyr Cys Met Gln
                85                  90                  95
Arg Ile Glu Phe Pro Tyr Thr Phe Gly Gln Gly Thr Lys Leu Glu Ile
            100                 105                 110
Lys
```

<210> SEQ ID NO 400
<211> LENGTH: 113
<212> TYPE: PRT
<213> ORGANISM: Artificial Sequence
<220> FEATURE:
<223> OTHER INFORMATION: synthetic construct light chain variable region

<400> SEQUENCE: 400

```
Asp Ile Val Met Thr Gln Thr Pro Leu Ser Leu Pro Val Thr Pro Gly
1               5                   10                  15
Glu Pro Ala Ser Ile Ser Cys Arg Ser Ser Gln Ser Leu Leu Asp Arg
```

```
                20              25              30
Gly Gly Gly His Thr Tyr Leu Asp Trp Tyr Leu Gln Lys Pro Gly Gln
            35              40              45

Ser Pro Gln Leu Leu Ile Tyr Thr Leu Ser His Arg Ala Ser Gly Val
        50              55              60

Pro Asp Arg Phe Ser Gly Ser Gly Ser Gly Thr Asp Phe Thr Leu Lys
65              70              75              80

Ile Ser Arg Val Glu Ala Glu Asp Val Gly Ile Tyr Tyr Cys Met Gln
                85              90              95

Arg Lys Glu Phe Pro Leu Thr Phe Gly Pro Gly Thr Lys Leu Glu Ile
            100             105             110

Lys

<210> SEQ ID NO 401
<211> LENGTH: 113
<212> TYPE: PRT
<213> ORGANISM: Artificial Sequence
<220> FEATURE:
<223> OTHER INFORMATION: synthetic construct light chain variable region

<400> SEQUENCE: 401

Asp Ile Val Met Thr Gln Thr Pro Leu Ser Leu Ser Val Thr Pro Gly
1               5               10              15

Glu Pro Ala Ser Ile Ser Cys Arg Ser Ser Gln Ser Leu Leu Asp Ser
            20              25              30

Asp Asp Gly Asn Thr Tyr Leu Asp Trp Tyr Leu Gln Lys Pro Gly Gln
            35              40              45

Ser Pro Gln Leu Leu Ile Tyr Thr Leu Ser His Arg Ala Ser Gly Val
        50              55              60

Pro Asp Arg Phe Ser Gly Arg Gly Ser His Thr Asp Phe Thr Leu Thr
65              70              75              80

Ile Ser Ser Val Glu Ala Glu Asp Val Gly Val Tyr Tyr Cys Met Gln
                85              90              95

Arg Ile His Phe Pro Leu Thr Phe Gly Gln Gly Thr Arg Leu Glu Ile
            100             105             110

Lys
```